US012674190B2

(12) United States Patent (10) Patent No.: US 12,674,190 B2
Sedlak et al. (45) Date of Patent: Jul. 7, 2026

(54) SYSTEMS, COMPOSITIONS, AND METHODS FOR TARGET ENTITY DETECTION

(71) Applicant: Mercy BioAnalytics, Inc., Natick, MA (US)

(72) Inventors: Joseph Charles Sedlak, Cambridge, MA (US); Laura Teresa Bortolin, Newtonville, MA (US); Daniel Parker Salem, Somerville, MA (US)

(73) Assignee: Mercy BioAnalytics, Inc., Waltham, MA (US)

( * ) Notice: Subject to any disclaimer, the term of this patent is extended or adjusted under 35 U.S.C. 154(b) by 420 days.

(21) Appl. No.: 17/204,773

(22) Filed: Mar. 17, 2021

(65) Prior Publication Data

US 2021/0214806 A1 Jul. 15, 2021

Related U.S. Application Data

(63) Continuation of application No. 16/805,637, filed on Feb. 28, 2020, now Pat. No. 11,085,089.

(60) Provisional application No. 62/962,722, filed on Jan. 17, 2020, provisional application No. 62/812,878, filed on Mar. 1, 2019.

(51) Int. Cl.
| | |
|---|---|
| *C12Q 1/6804* | (2018.01) |
| *C12Q 1/6816* | (2018.01) |
| *C12Q 1/6862* | (2018.01) |
| *C12Q 1/6886* | (2018.01) |
| *G01N 33/543* | (2006.01) |
| *G01N 33/575* | (2026.01) |
| *G01N 30/02* | (2006.01) |

(52) U.S. Cl.
CPC ......... *C12Q 1/6804* (2013.01); *C12Q 1/6816* (2013.01); *C12Q 1/6862* (2013.01); *C12Q 1/6886* (2013.01); *G01N 33/54306* (2013.01); *G01N 33/5758* (2026.01); *C12Q 2600/112* (2013.01); *C12Q 2600/118* (2013.01); *C12Q 2600/156* (2013.01); *C12Q 2600/166* (2013.01); *G01N 2030/027* (2013.01)

(58) Field of Classification Search
None
See application file for complete search history.

(56) References Cited

U.S. PATENT DOCUMENTS

| | | | |
|---|---|---|---|
| 5,605,804 | A | 2/1997 | Allard et al. |
| 7,306,904 | B2 | 12/2007 | Landegren et al. |
| 7,892,760 | B2 | 2/2011 | Birse et al. |
| 7,914,987 | B2 | 3/2011 | Fredriksson et al. |
| 7,932,060 | B2 | 4/2011 | Nadeau et al. |
| 8,013,134 | B2 | 9/2011 | Fredriksson |
| 8,268,554 | B2 | 9/2012 | Schallmeiner |
| 8,372,605 | B2 | 2/2013 | Nadeau et al. |
| 8,481,698 | B2 | 7/2013 | Lieberman et al. |
| 8,758,991 | B2 | 6/2014 | Klein et al. |
| 9,029,086 | B2 | 5/2015 | Moghaddam |
| 9,086,412 | B2 | 7/2015 | Taylor et al. |
| 9,499,858 | B2 | 11/2016 | Nadeau et al. |
| 9,777,315 | B2 | 10/2017 | Fredriksson et al. |
| 10,174,361 | B2 | 1/2019 | Skog et al. |
| 10,174,366 | B2 | 1/2019 | Landegren et al. |
| 10,301,681 | B2 | 5/2019 | Skog et al. |
| 10,465,235 | B2 | 11/2019 | Gullberg et al. |
| 11,085,089 | B2 | 8/2021 | Sedlak et al. |
| 2002/0064779 | A1 | 5/2002 | Landegren et al. |
| 2003/0118987 | A1 | 6/2003 | Cantor et al. |
| 2007/0275375 | A1 | 11/2007 | Van Eijk |
| 2011/0223585 | A1 | 9/2011 | Gullberg et al. |
| 2013/0196316 | A1 | 8/2013 | Moghaddam |
| 2013/0288249 | A1 | 10/2013 | Gullberg et al. |
| 2013/0295574 | A1 | 11/2013 | Skog et al. |
| 2015/0176073 | A1 | 6/2015 | Skog |
| 2015/0252428 | A1 | 9/2015 | Comper et al. |
| 2015/0353920 | A1 | 12/2015 | Enderle et al. |
| 2016/0202248 | A1* | 7/2016 | Lee ...................... G01N 33/531 506/9 |
| 2016/0237422 | A1 | 8/2016 | Comper et al. |
| 2016/0319361 | A1* | 11/2016 | Spetzler .............. C12Q 1/6886 |

(Continued)

FOREIGN PATENT DOCUMENTS

| | | | |
|---|---|---|---|
| EP | | 2714925 A1 | 4/2014 |
| EP | | 3102698 A1 | 12/2016 |

(Continued)

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Assarsson, E. et al., Homogenous 96-Plex PEA Immunoassay Exhibiting High Sensitivity, Specificity, and Excellent Scalability, PLOS, 9(4):e95192 (2004).
Balaj, L. et al., Tumour microvesicles contain retrotransposon elements and amplified oncogene sequences, Nature communications, 2:180 (2011).
Bebelman, M. P. et al., Biogenesis and function of extracellular vesicles in cancer, Pharmacology & Therapeutics, 188:1-11 (2018).
Bellucci, A. et al., The "in situ" Proximity Ligation Assay to Probe Protein-Protein Interactions in Intact Tissues, Methods Mol. Biol., 1174:397-405 (2014).

(Continued)

*Primary Examiner* — Katherine D Salmon
(74) *Attorney, Agent, or Firm* — Thomas C. Meyers; Sullivan & Worcester LLP

(57) ABSTRACT

The present disclosure provides technologies for target entity detection. One aspect of the present disclosure provides technologies for detection (e.g., early detection) of a disease, disorder, or condition (e.g., cancer). In another aspect, technologies provided herein are useful for selecting and/or monitoring and/or evaluating efficacy of, a treatment administered to a subject in need thereof, e.g., a subject determined to have or susceptible to cancer. In some embodiments, technologies provided herein are useful for development of companion diagnostics, e.g., by measuring tumor burdens and changes in tumor burdens in conjunction with therapeutics.

10 Claims, 33 Drawing Sheets

Specification includes a Sequence Listing.

(56) References Cited

U.S. PATENT DOCUMENTS

| | | | |
|---|---|---|---|
| 2016/0369321 A1 | 12/2016 | Landegren et al. | |
| 2017/0009278 A1 | 1/2017 | Soderberg et al. | |
| 2017/0014450 A1 | 1/2017 | Joyce et al. | |
| 2017/0253916 A1 | 9/2017 | Schorey et al. | |
| 2018/0066262 A1* | 3/2018 | Domenyuk ........ | G01N 33/5005 |
| 2018/0100189 A1 | 4/2018 | Fredriksson et al. | |
| 2018/0312901 A1 | 11/2018 | Fredriksson et al. | |
| 2019/0376128 A1* | 12/2019 | Skog ................... | C12Q 1/6851 |
| 2020/0164284 A1 | 5/2020 | Gho et al. | |
| 2020/0171084 A1 | 6/2020 | Joyce et al. | |
| 2020/0299780 A1 | 9/2020 | Sedlak et al. | |
| 2020/0362334 A1* | 11/2020 | Regev ................. | C12N 15/113 |
| 2021/0382043 A1 | 12/2021 | Routenberg et al. | |
| 2022/0155304 A1 | 5/2022 | Sedlak et al. | |

FOREIGN PATENT DOCUMENTS

| | | |
|---|---|---|
| WO | WO-2003/044231 A1 | 5/2003 |
| WO | WO-2004/094456 A2 | 11/2004 |
| WO | WO-2007/107743 A1 | 9/2007 |
| WO | WO-2007/127848 A1 | 11/2007 |
| WO | WO-2012/064993 A1 | 5/2012 |
| WO | WO-2012/104261 A1 | 8/2012 |
| WO | WO-2012/155014 A1 | 11/2012 |
| WO | WO-2012/160083 A1 | 11/2012 |
| WO | WO-2013/071239 A1 | 5/2013 |
| WO | WO-2014/015149 A2 | 1/2014 |
| WO | WO-2014/055775 A1 | 4/2014 |
| WO | WO-2014/076209 A1 | 5/2014 |
| WO | WO-2014/076214 A1 | 5/2014 |
| WO | WO-2014/107571 A1 | 7/2014 |
| WO | WO-2015/021158 A1 | 2/2015 |
| WO | WO-2015/047186 A1 | 4/2015 |
| WO | WO-2015/118029 A1 | 8/2015 |
| WO | WO-2015/130956 A2 | 9/2015 |
| WO | WO-2015/175856 A1 | 11/2015 |
| WO | WO-2015/193427 A1 | 12/2015 |
| WO | WO-2016/093838 A1 | 6/2016 |
| WO | WO-2017/053516 A1 | 3/2017 |
| WO | WO-2017/068116 A1 | 4/2017 |
| WO | WO-2018/119455 A1 | 6/2018 |
| WO | WO-2019/014486 A1 | 1/2019 |
| WO | WO-2019/018537 A1 | 1/2019 |
| WO | WO-2019/022542 A2 | 1/2019 |
| WO | WO-2019/066501 A1 | 4/2019 |
| WO | WO-2019/103548 A2 | 5/2019 |
| WO | WO-2019/222708 A2 | 11/2019 |
| WO | WO-2019/236853 A1 | 12/2019 |
| WO | WO-2019/238944 A1 | 12/2019 |
| WO | WO-2020/086751 A1 | 4/2020 |
| WO | WO-2020/106853 A1 | 5/2020 |
| WO | WO-2020/180741 A1 | 9/2020 |
| WO | WO-2021/146659 A1 | 7/2021 |

OTHER PUBLICATIONS

Chuo, S. T-Y, et al., Imaging extracellular vesicles: current and emerging methods, Journal of Biomedical Sciences, 25: 91 (2018).

Darmanis, S. et al., Sensitive plasma protein analysis by microparticle-based proximity ligation assays, Molecular & cellular proteomics, 9(2): 327-335 (2010).

Darmanis, S. et al., Self-assembly of proximity probes for flexible and modular proximity ligation assays, BioTechniques, 43(4):443-450 (2007).

Foroni, C. et al., When Less Is More: Specific Capture and Analysis of Tumor Exosomes in Plasma Increases the Sensitivity of Liquid Biopsy for Comprehensive Detection of Multiple Androgen Receptor Phenotypes in Advanced Prostate Cancer Patients, Biomedicines, 8(131):1-14 (2021).

Gullberg, M. et al., Cytokine detection by antibody-based proximity ligation, PNAS, 101(22):8420-8424 (2004).

Ibsen, S. D. et al., Rapid Isolation and Detection of Exosomes and Associated Biomarkers from Plasma, ACS Nano., 11(7): 6641-6651 (2017).

Im, H. et al, Label-free detection and molecular profiling of exosomes with a nano-plasmonic sensor, Nature biotechnology, 32(5): 490-5 (2014).

International Search Report for PCT/US20/20529, 5 pages (mailed Jun. 29, 2020).

Jeong, S. et al., Integrated magneto-electrochemical sensor for exosome analysis, ACS nano, 10(2):1802-1809 (2016).

Kosaka et al., Exploiting the message from cancer, the diagnostic value of extracellular vesicles for clinical applications, Experimental and Molecular Medicine, 51:31 (2019).

Lewis, J. M. et al., Integrated analysis of exosomal protein biomarkers on alternating current electrokinetic chips enables rapid detection of pancreatic cancer in patient blood, American Chemical Society, 12:3311-3320 (2018).

Liu, W. et al., Target-induced proximity ligation triggers recombinase polymerase amplification and transcription-mediated amplification to detect tumor-derived exosomes in nasopharyngeal carcinoma with high sensitivity, Biosensors and Bioelectronics, 102:204-210 (2018).

Lof, L. et al., Detecting individual extracellular vesicles using a multicolor in situ proximity ligation assay with flow cytometric readout, Nature, 6:3458 (2016).

Melo, S. A. et al., Glypican-1 identifies cancer exosomes and detects early pancreatic cancer, Nature, 523:177-200 (2015).

Shao, H. et al., New technologies for analysis of extracellular vesicles, Chemical reviews, 118(4): 1917-1950 (2018).

Soderberg, O. et al., Direct Observation of Individual Endogenous Protein Complexes in Situ by Proximity Ligation, Nat. Methods, 3(12):995-1000 (2006).

Song, I. H. et al., Enzyme-guided DNA sewing architecture, Scientific Reports, 5:17722 (2015).

Tavoosidana, G. et al., Multiple recognition assay reveals prostasomes as promising plasma biomarkers for prostate cancer, PNAS, 108(21):8809-8814 (2011).

Written Opinion for PCT/US20/20529, 18 pages (mailed Jun. 29, 2020).

Wu, D. et al., Profiling surface proteins on individual exosomes using a proximity barcoding assay, Nature Communications, 10:3854 (2019).

Wu, K. et al., Extracellular vesicles as emerging targets in cancer: recent development from bench to bedside, Biochim Biophys Acta., 1868(2):538-563 (2017).

Yang, K. S. et al., Multiparametric plasma EV profiling facilitates diagnosis of pancreatic malignancy, Science Translational Medicine, 9:1-10 (2017).

Yoshioka, Y. et al., Ultra-sensitive liquid biopsy of circulating extracellular vesicles using ExoScreen, Nature Communications, 5:3591 (2014).

Yu, W. et al., Exosome-based Liquid Biopsies in Cancer: Opportunities and Challenges, Annals of Oncology (2021).

Hinestrosa, J. P. et al., Early-stage multi-cancer detection using an extracellular vesicle protein-based blood test, Comm. Med., 2(29):1-9 (2022).

Koliha, N. et al., A novel multiplex bead-based platform highlights the diversity of extracellular vesicles, Journal of Extracellular Vesicles, 5: 29975 (2016).

Lundberg, M. et al., Homogeneous antibody-based proximity extension assays provide sensitive and specific detection of low-abundant proteins in human blood, Nucleic Acids Research, 39(15):e102 (2011).

Lundberg, M. et al., Multiplexed Homogeneous Proximity Ligation Assays for High-throughput Protein Biomarker Research in Serological Material*m1, Mol & Cell Proteomics, 10.4:1-10 (2011).

Lof et al.: "Detection of Extracellular Vesicles Using Proximity Ligation Assay with Flow Cytometry Readout-ExoPLA", Current Protocols in Cytometry, (Year: 2017), 81, 4.8.1-4.8.10.

Schallmeiner et al.: "Sensitive protein detection via triple-binder proximity ligation assays", Nature Methods, (Year: 2006), vol. 4, No. 2, pp. 135-137.

(56)          References Cited

OTHER PUBLICATIONS

He et al.: "Integrated immunoisolation and protein analysis of circulating exosomes using microfluidic technology", Lab Chip, (Year: 2014), vol. 14, pp. 3773-3780.
Skog et al.: "Glioblastoma microvesicles transport RNA and protein that promote tumour growth and provide diagnostic biomarkers", Nature Cell Biology, (Year: 2008), vol. 10, No. 12, pp. 1470-1476.
Greenwood et al.: "Proximity assays for sensitive quantification of proteins", Biomolecular Detection and Quantification, (Year: 2015), vol. 4, pp. 10-16.

* cited by examiner

FIGURE 3
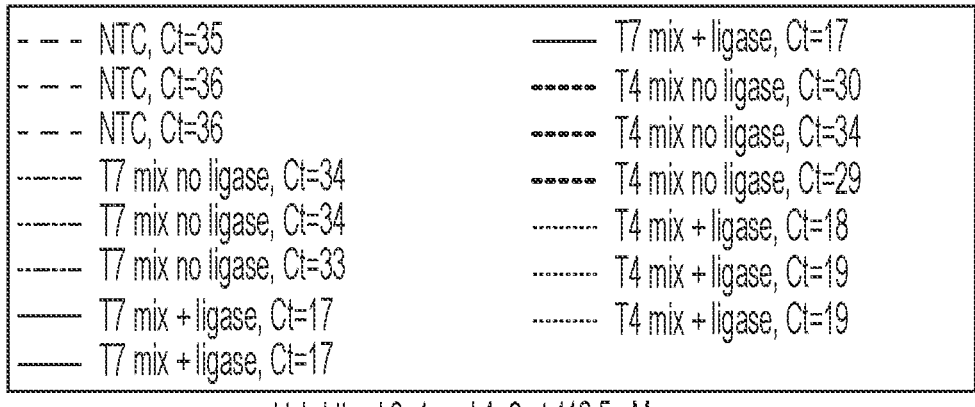
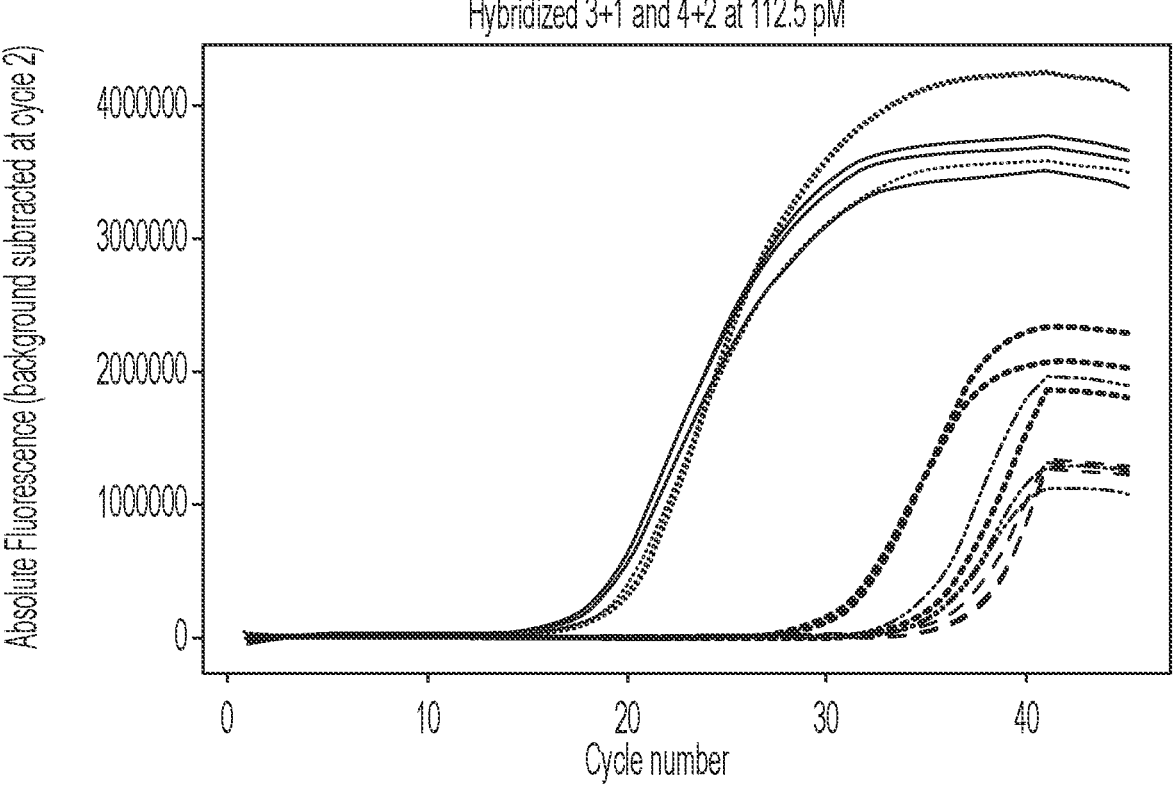

FIGURE 4

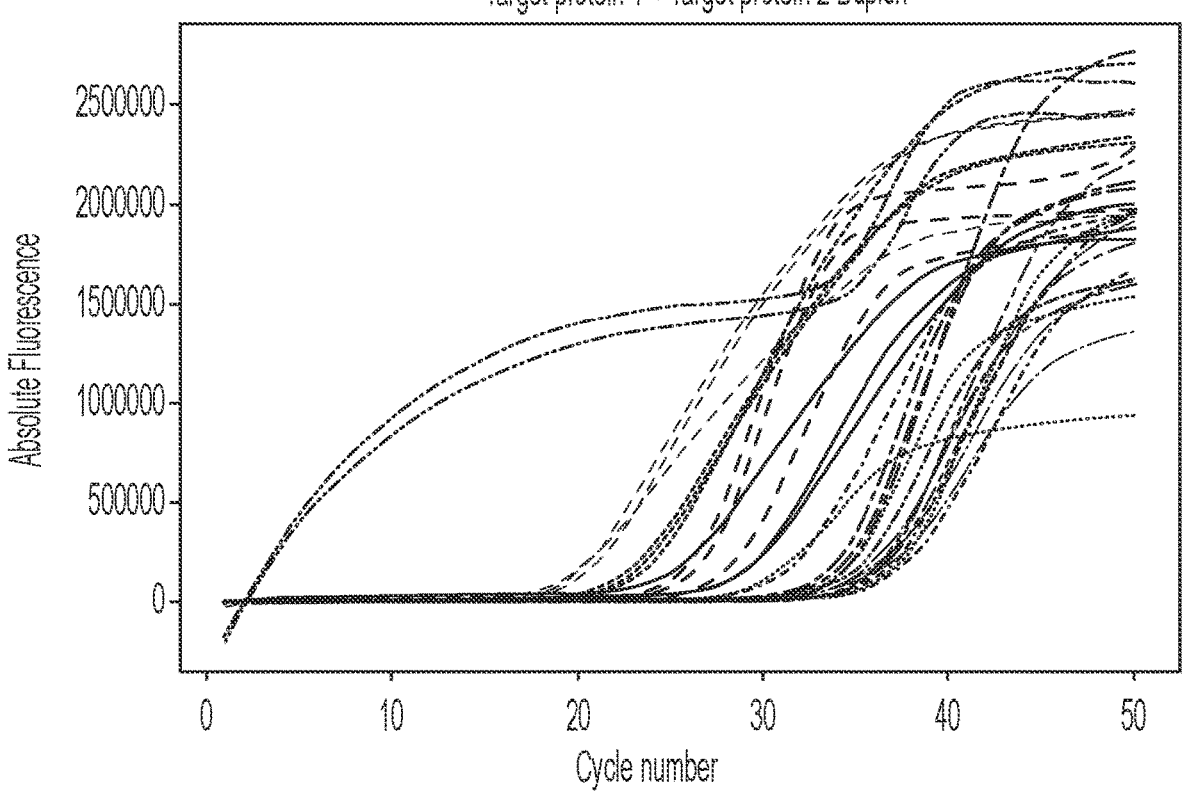

| | |
|---|---|
| − − NTC, Ct=26 | −−−−− SKMEL1 1 ug/mL Ab, Ct=21 |
| − − NTC, Ct=25 | −−−−− SKMEL1 1 ug/mL Ab, Ct=21 |
| − − NTC, Ct=25 | −−−−− SKMEL1 1 ug/mL Ab, Ct=22 |
| −−−−− T84 no Ab, Ct=nan | −−− SKMEL1 10 ng/mL Ab, Ct=33 |
| −−−−− T84 no Ab, Ct=nan | −−− SKMEL1 10 ng/mL Ab, Ct=33 |
| −−−−− T84 no Ab, Ct=33 | −−− SKMEL1 10 ng/mL Ab, Ct=32 |
| ——— T84 1 ug/mL Ab, Ct=23 | −−− MeWo no Ab, Ct=35 |
| ——— T84 1 ug/mL Ab, Ct=27 | −−− MeWo no Ab, Ct=34 |
| ——— T84 1 ug/mL Ab, Ct=27 | −−− MeWo no Ab, Ct=35 |
| −·− T84 10 ng/mL Ab, Ct=35 | − − − MeWo 1 ug/mL Ab, Ct=18 |
| −·− T84 10 ng/mL Ab, Ct=34 | − − − MeWo 1 ug/mL Ab, Ct=18 |
| −·− T84 10 ng/mL Ab, Ct=34 | − − − MeWo 1 ug/mL Ab, Ct=19 |
| ······· SKMEL1 no Ab, Ct=28 | −−−− MeWo 10 ng/mL Ab, Ct=35 |
| ······· SKMEL1 no Ab, Ct=33 | −−−− MeWo 10 ng/mL Ab, Ct=30 |
| ······· SKMEL1 no Ab, Ct=36 | −−−− MeWo 10 ng/mL Ab, Ct=36 |

Target protein 1 + Target protein 2 Duplex

FIGURE 6
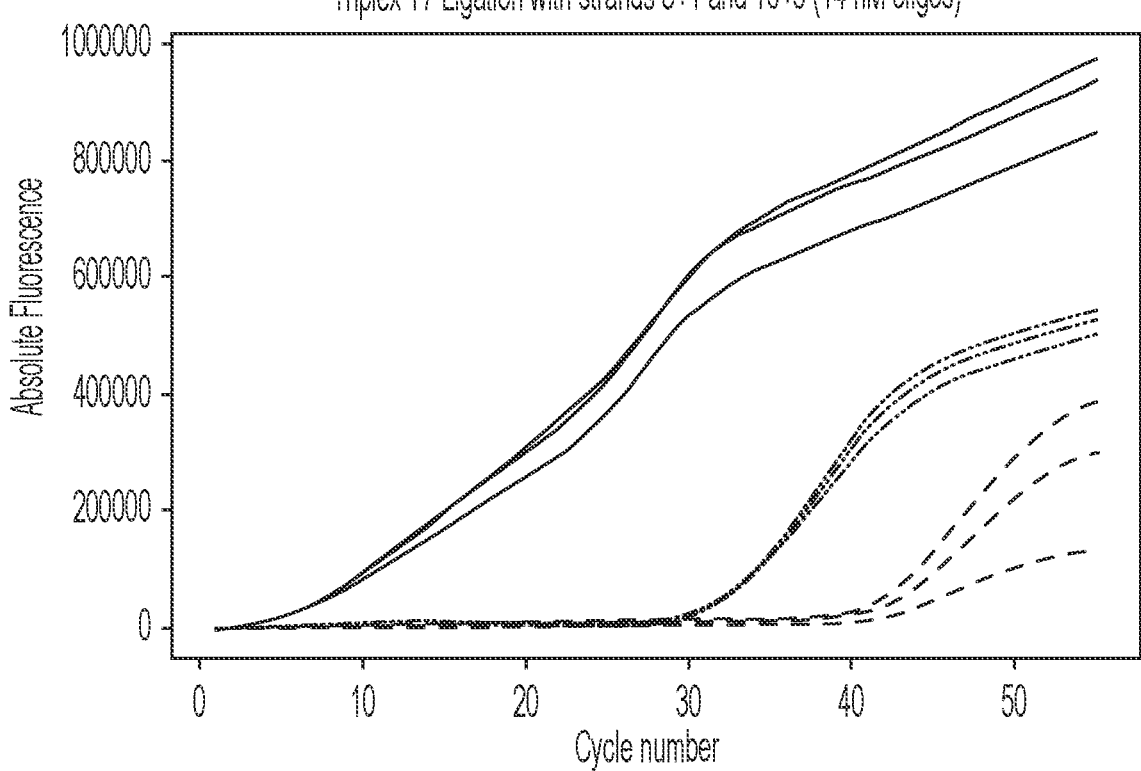
Triplex T7 Ligation with strands 8+1 and 10+9 (14 nM oligos)

FIGURE 7
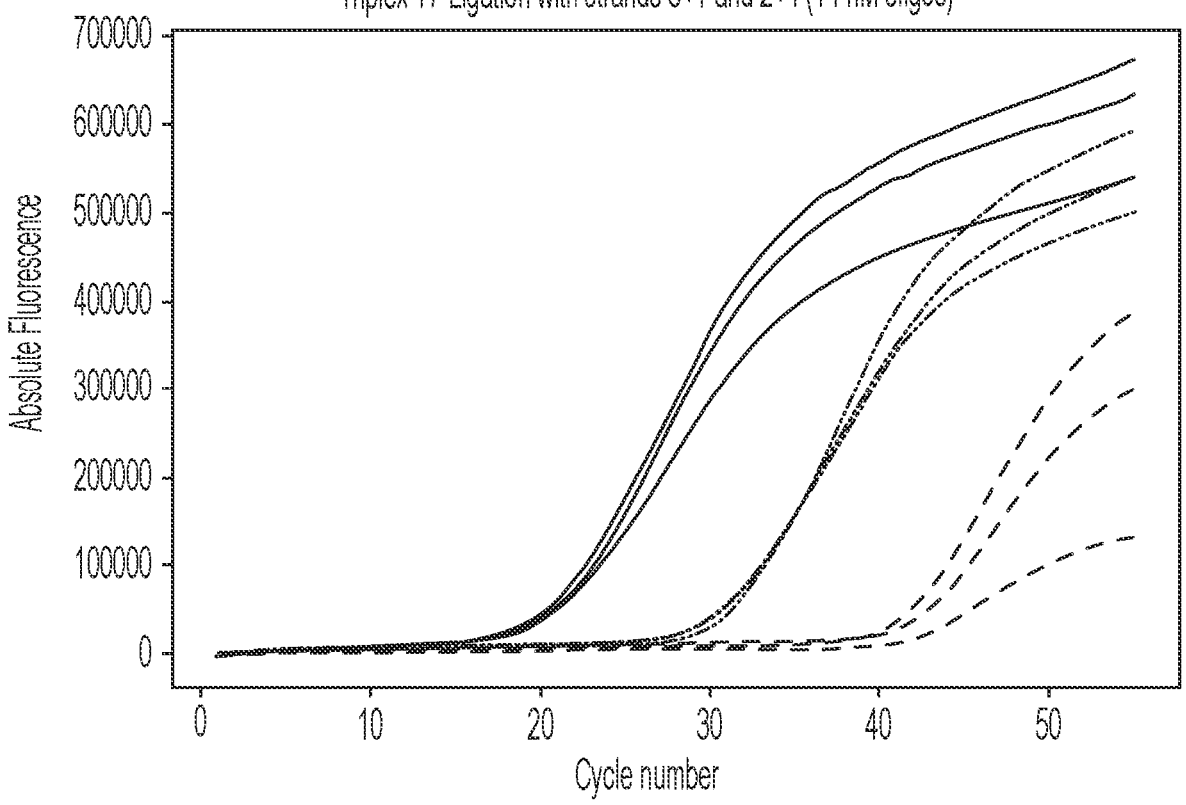

FIGURE 8
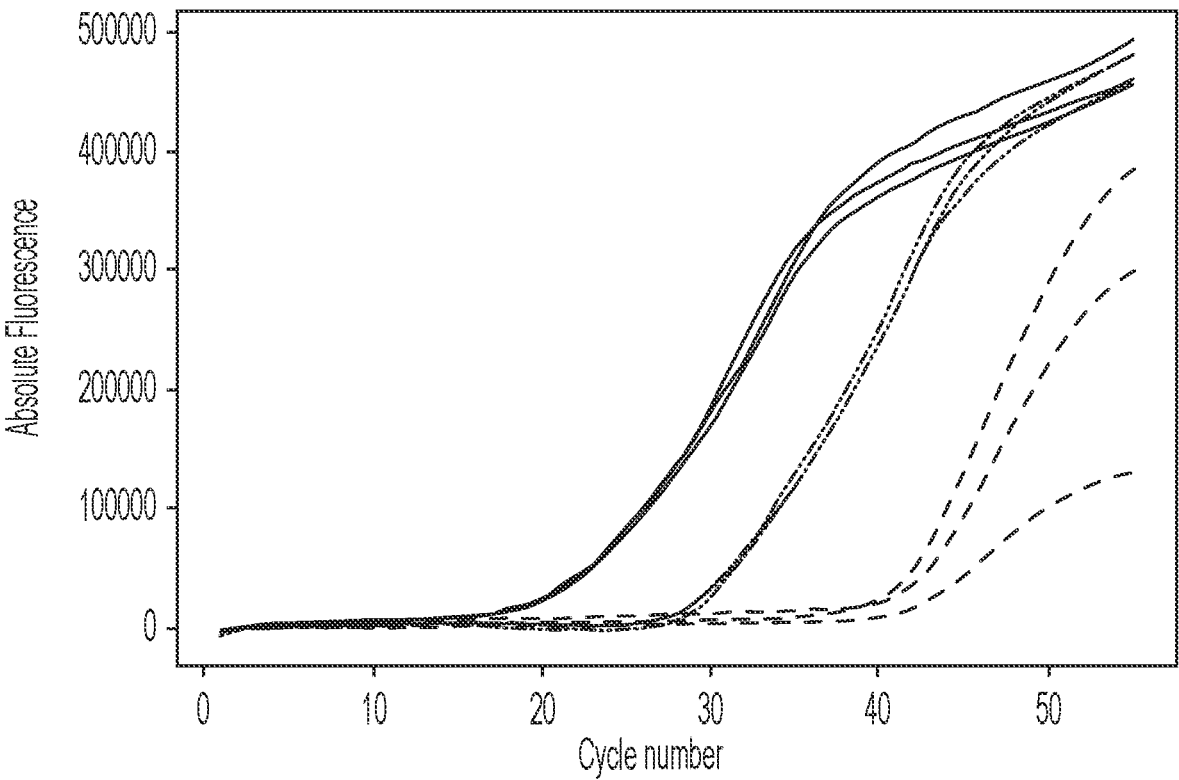

FIGURE 9
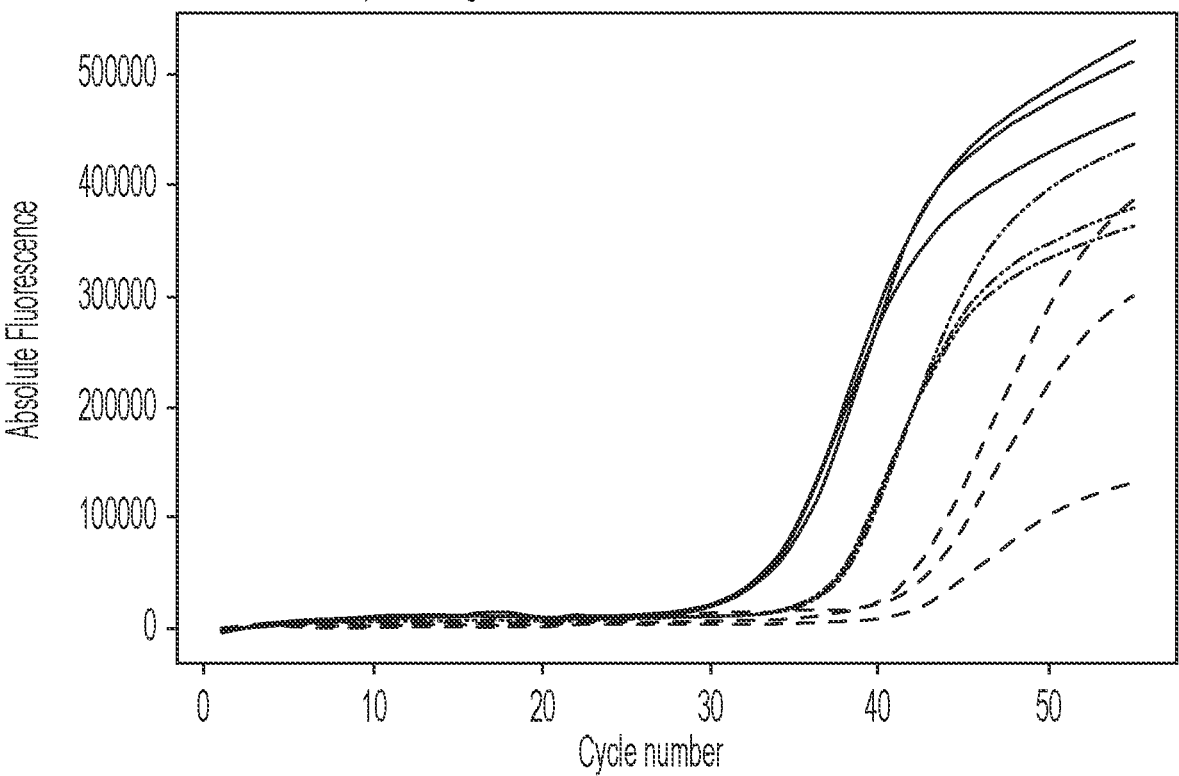
Triplex T7 Ligation with strands 2+4 and 10+9 (14 nM oligos)

FIGURE 12

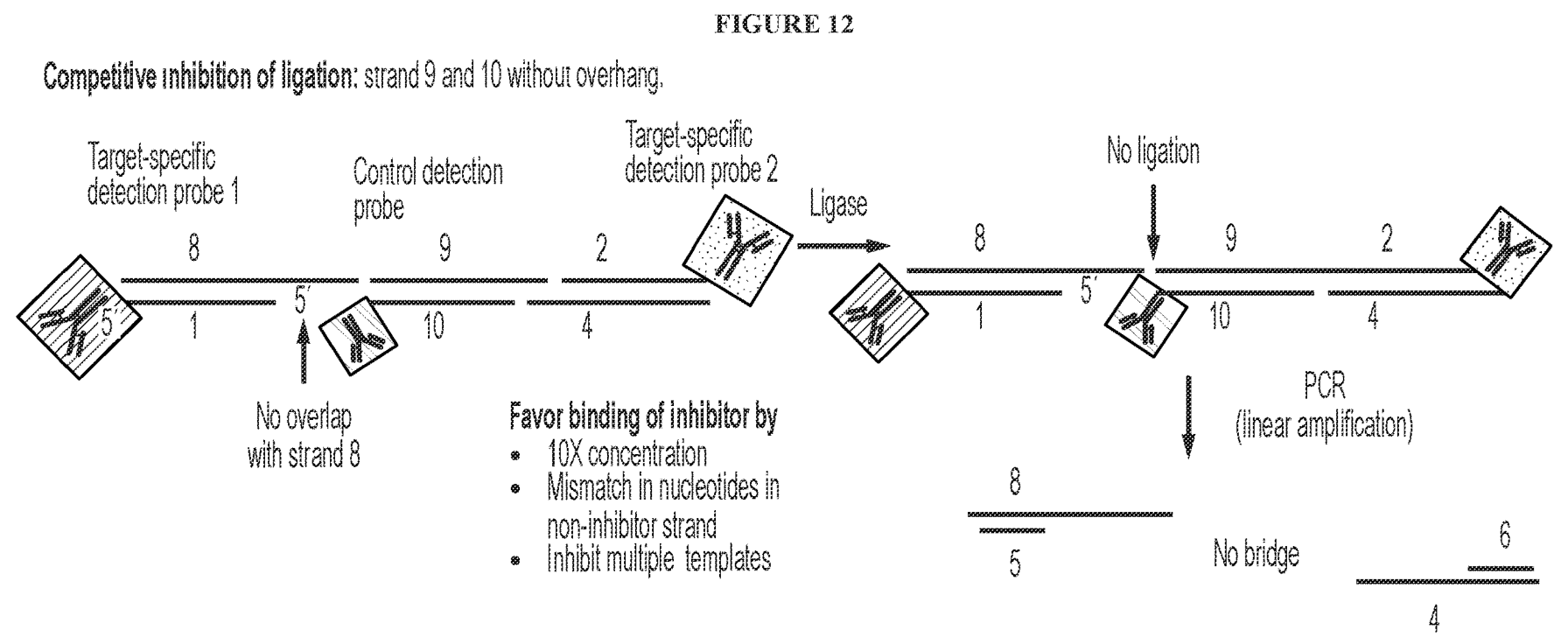

Competitive inhibition of ligation: strand 9 and 10 without overhang.

Target-specific detection probe 1

Control detection probe

Target-specific detection probe 2

No overlap with strand 8

Ligase

No ligation

PCR (linear amplification)

No bridge

Favor binding of inhibitor by
* 10X concentration
* Mismatch in nucleotides in non-inhibitor strand
* Inhibit multiple templates

| ----- MeWo EVs, Cts=22.4, 22 | – – Negative control w/ Abs, Cts=35.3, 35 |
| ----- MeWo EVs, Cts=22.2, 22 | – – Negative control w/ Abs, Cts=36.5, 36 |
| ----- MeWo EVs, Cts=22.3, 22 | – – Negative control w/ Abs, Cts=36.4, 36 |
| – — T84 EVs, Cts=28.7, 28 | ----- NTC, Cts=43.3, 42 |
| – — T84 EVs, Cts=28.6, 28 | ----- NTC, Cts=43.0, 42 |
| – — T84 EVs, Cts=28.8, 28 | ----- NTC, Cts=44.1, 43 |

Duplex on MeWo and T84 cell line EVs

FIGURE 13B
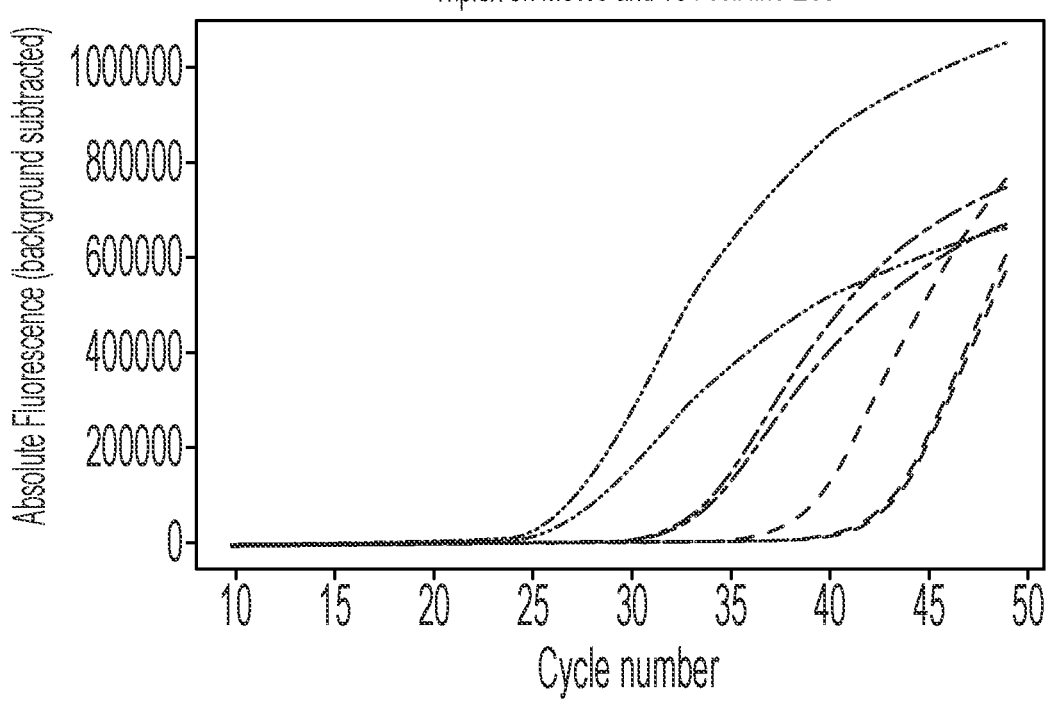

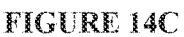
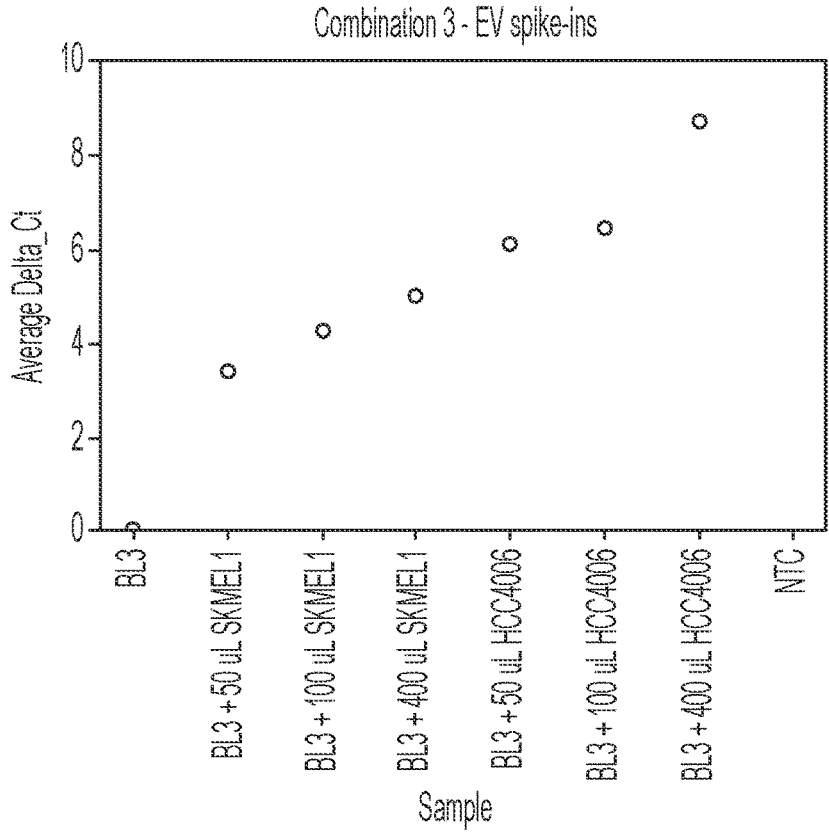
FIGURE 14C
Combination 3 - EV spike-ins
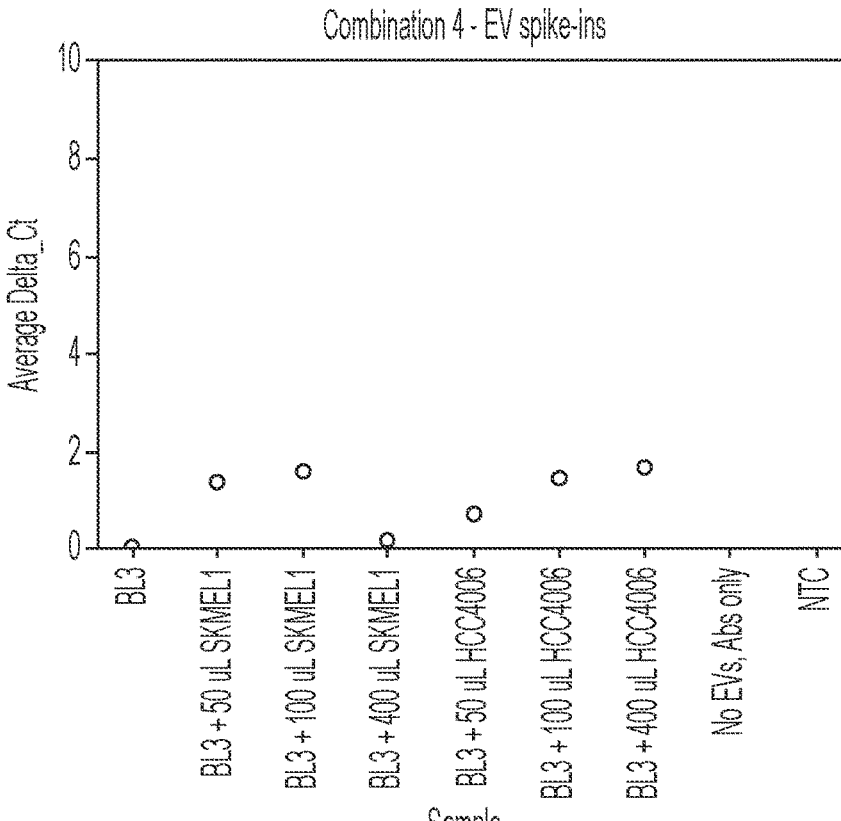
FIGURE 14D
Combination 4 - EV spike-ins Combination 3 Receiver operating characteristic curve

FIGURE 18

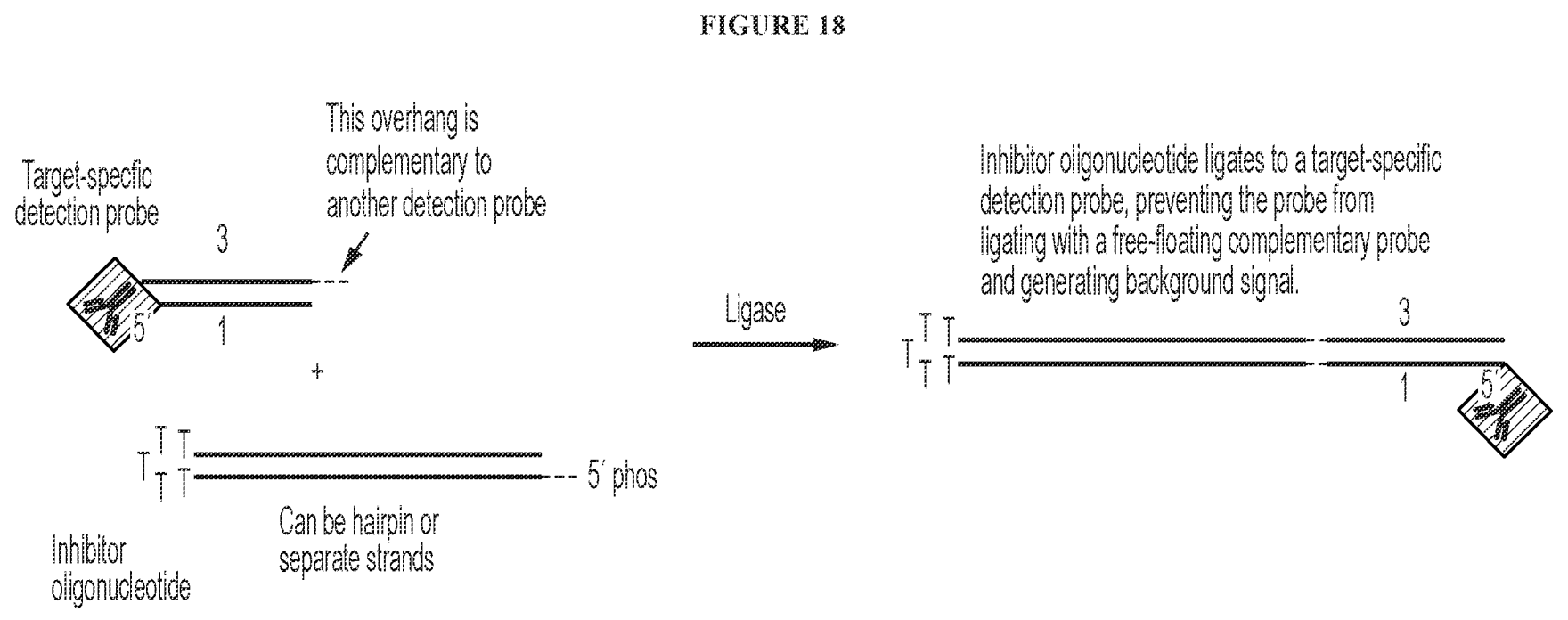

Inhibitor oligonucleotide ligates to a target-specific detection probe, preventing the probe from ligating with a free-floating complementary probe and generating background signal.

Ligase

Target-specific detection probe

This overhang is complementary to another detection probe

5' phos

Can be hairpin or separate strands

Inhibitor oligonucleotide

FIGURE 19
A
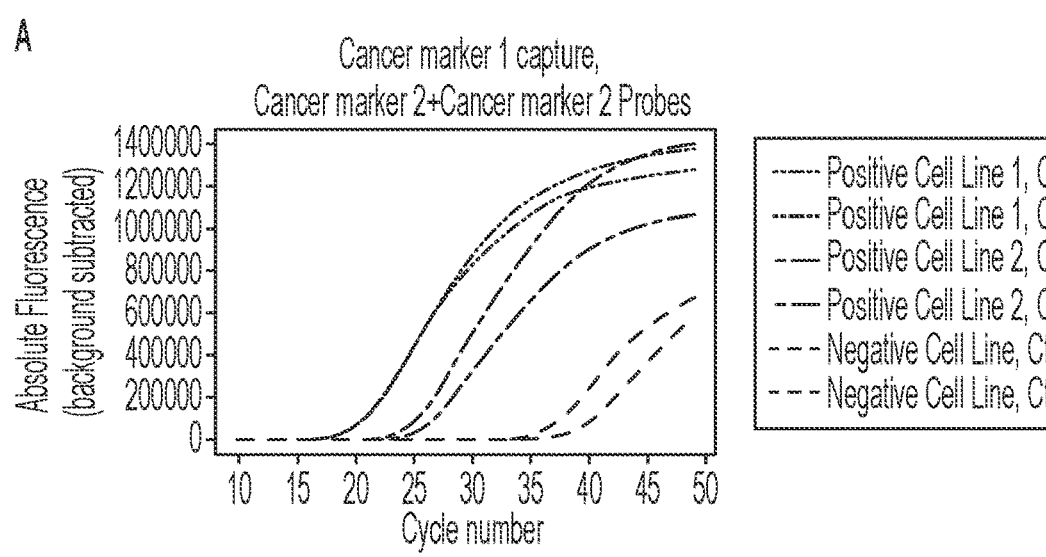
| Cell Line | Cancer marker 1 Expression | Cancer marker 2 Expression | Avg Ct |
|---|---|---|---|
| Positive Cell Line 1 | +++ | +++ | 20.8 |
| Positive Cell Line 2 | + | + | 26.0 |
| Negative Cell Line | – | – | 38.5 |
B
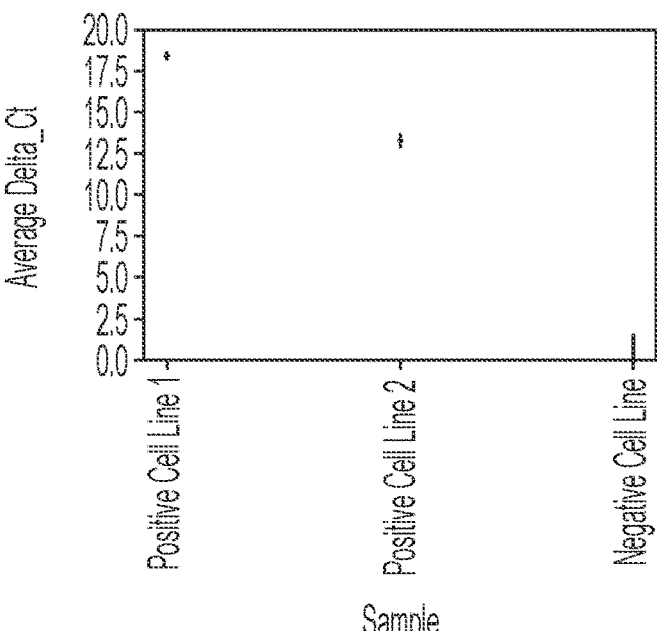

FIGURE 24

----    1e9 T84, Long, Cts=34.1
----    1e9 T84, Long, Cts=34.3
----    1e9 T84, Long, Cts=34.1
---    1e9 T84, Medium, Cts=32.9
---    1e9 T84, Medium, Cts=32.9
---    1e9 T84, Medium, Cts=33.1
-- --    1e9 T84, Short, Cts=31.1
-- --    1e9 T84, Short, Cts=31.7
-- --    1e9 T84, Short, Cts=32.4
·---    1e9 HCC4006, Long, Cts=33.2
·---    1e9 HCC4006, Long, Cts=32.5
·---    1e9 HCC4006, Long, Cts=32.4
——    1e9 HCC4006, Medium, Cts=31.9
——    1e9 HCC4006, Medium, Cts=31.9
——    1e9 HCC4006, Medium, Cts=31.8
– –    1e9 HCC4006, Short, Cts=30.4
– –    1e9 HCC4006, Short, Cts=30.1
– –    1e9 HCC4006, Short, Cts=30.5
——    No EVs, Long, Cts=35.9
——    No EVs, Long, Cts=36.5
——    No EVs, Long, Cts=36.5
----    No EVs, Medium, Cts=35.1
----    No EVs, Medium, Cts=36.2
----    No EVs, Medium, Cts=35.9
——    No EVs, Short, Cts=36.1
-·-·    No EVs, Short, Cts=35.3
——    No EVs, Short, Cts=35.9

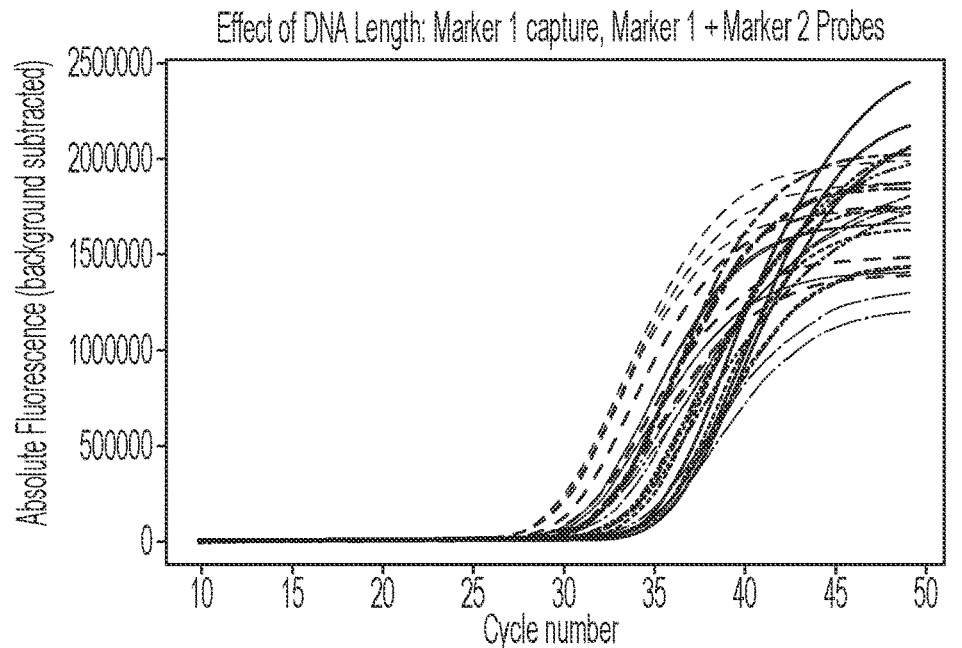

Effect of DNA Length: Marker 1 capture, Marker 1 + Marker 2 Probes

FIGURE 25

Effect of DNA Length: Marker 1 capture, Marker 1 + Marker 2 Probes

FIGURE 26
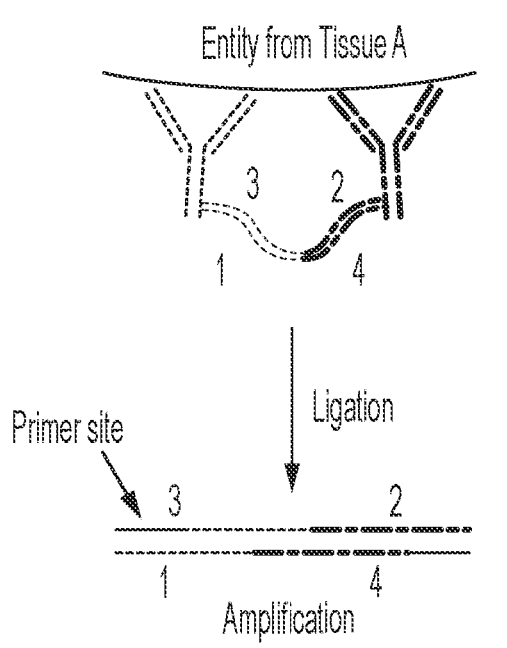
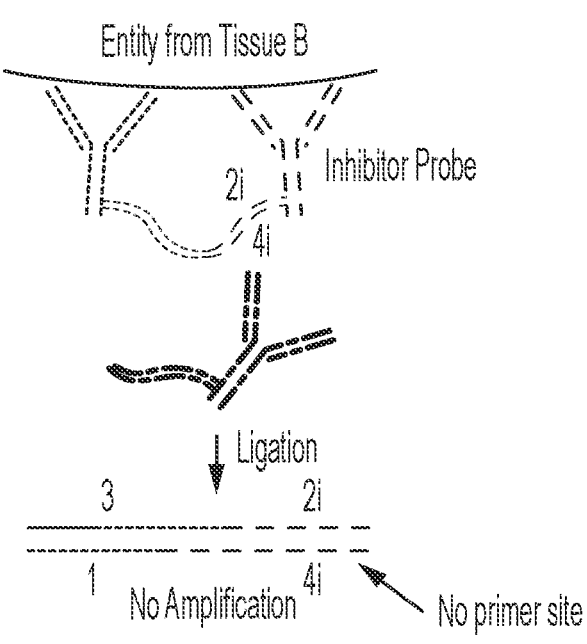

FIGURE 27

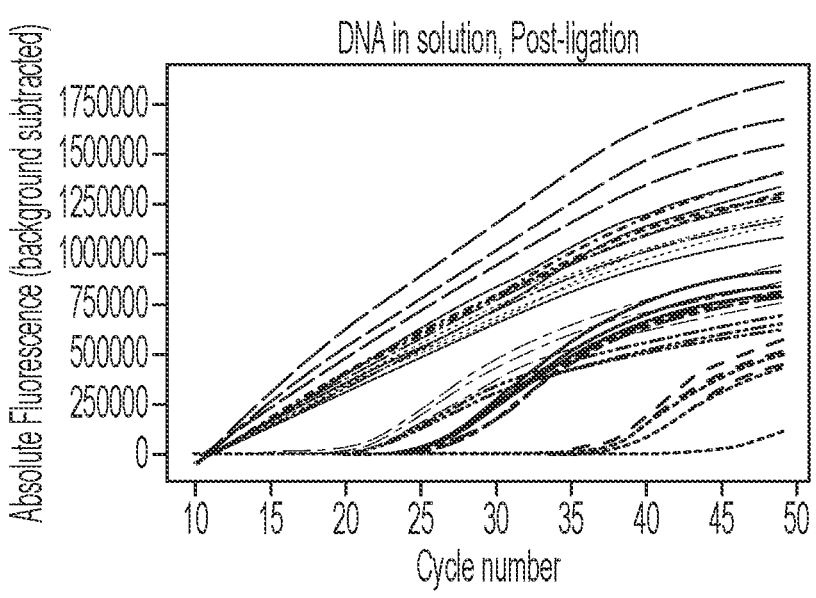

| | | | |
|---|---|---|---|
| ----- (1+3), Cts=22.0 | ------- (1i+3i)+(2i+i4), Cts=46.8 |
| ------- (1+3), Cts=22.0 | ------ (1i+3i)+(2i+i4), Cts=38.6 |
| ------- (1+3), Cts=22.5 | ----- (1i+3i)+(2i+i4), Cts=37.8 |
| ---- (2+4), Cts=26.9 | --- (1+3)+(2+4)+(1i+3i), Cts=9.8 |
| --- (2+4), Cts=26.7 | --- (1+3)+(2+4)+(1i+3i), Cts=10.2 |
| ---- (2+4), Cts=26.8 | --- (1+3)+(2+4)+(1i+3i), Cts=10.0 |
| -- -- (1i+3i), Cts=37.8 | -- -- (1+3)+(2+4)+(2i+4i), Cts=9.7 |
| -- -- (1i+3i), Cts=36.6 | -- -- (1+3)+(2+4)+(2i+4i), Cts=9.5 |
| -- -- (1i+3i), Cts=37.3 | -- -- (1+3)+(2+4)+(2i+4i), Cts=10.5 |
| --- (2i+4i), Cts=37.9 | —— (1+3)+(2+4)+2*(1i+3i), Cts=10.2 |
| --- (2i+4i), Cts=38.4 | —— (1+3)+(2+4)+2*(1i+3i), Cts=11.2 |
| --- (2i+4i), Cts=38.1 | —— (1+3)+(2+4)+2*(1i+3i), Cts=11.0 |
| —— (1+3)+(2+4), Cts=9.1 | ----- (1+3)+(2+4)+2*(2i+4i), Cts=10.7 |
| —— (1+3)+(2+4), Cts=9.5 | ----- (1+3)+(2+4)+2*(2i+4i), Cts=10.9 |
| —— (1+3)+(2+4), Cts=8.3 | ----- (1+3)+(2+4)+2*(2i+4i), Cts=11.8 |
| --- (1+3)+(2i+4i), Cts=21.8 | ······· (1+3)+(2+4)+(1i+3i)+(2i+4i), Cts=11.2 |
| ······· (1+3)+(2i+4i), Cts=22.1 | ······· (1+3)+(2+4)+(1i+3i)+(2i+4i), Cts=9.0 |
| --- (1+3)+(2i+4i), Cts=21.5 | ······· (1+3)+(2+4)+(1i+3i)+(2i+4i), Cts=10.7 |
| —— (1i+3i)+(2+4), Cts=25.5 | |
| —— (1i+3i)+(2+4), Cts=26.4 | |
| —— (1i+3i)+(2+4), Cts=25.7 | |

DNA in solution, Post-ligation

SEQUENCE LISTING

<160> NUMBER OF SEQ ID NOS: 50

<210> SEQ ID NO 1
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cagtctgact caccactcgt taatcgtcgc tgctaccctt gacatccgtg actggctaga      60
cagaggtgt                                                             69

<210> SEQ ID NO 2
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caccagacct acgaagtcca tagccttgcc tgattagcca ctgtccagtt tggctcctgg      60
tctcactag                                                             69

<210> SEQ ID NO 3
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagtacacct ctgtctagcc agtcacggat gtcaagggta gcagcgacga ttaacgagtg      60
gtgagtcaga ctg                                                        73

<210> SEQ ID NO 4
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actcctagtg agaccaggag ccaaactgga cagtggctaa tcaggcaagg ctatggactt      60
cgtaggtctg gtg                                                        73

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cagtctgact caccactcgt                                                 20

<210> SEQ ID NO 6
<211> LENGTH: 20
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 6
caccagacct acgaagtcca                                               20

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttttttttt tttttttttt ttttttt                                      27

<210> SEQ ID NO 8
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttccaactat tttttacac ctctgtctag ccagtcacgg atgtcaaggg tagcagcgac     60
gattaacgag tggtgagtca gactg                                         85

<210> SEQ ID NO 9
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccaactattt ttttacacct ctgtctagcc agtcacggat gtcaagggta gcagcgacga     60
ttaacgagtg gtgagtcaga ctg                                           83

<210> SEQ ID NO 10
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctattttttt acacctctgt ctagccagtc acggatgtca agggtagcag cgacgattaa     60
cgagtggtga gtcagactg                                                79

<210> SEQ ID NO 11
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttccaactat ttacacctct gtctagccag tcacggatgt caagggtagc agcgacgatt     60
```
aacgagtggt gagtcagact g                                                                        81

<210> SEQ ID NO 12
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccaactattt acacctctgt ctagccagtc acggatgtca agggtagcag cgacgattaa      60
cgagtggtga gtcagactg                                                                            79

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctatttacac ctctgtctag ccagtcacgg atgtcaaggg tagcagcgac gattaacgag      60
tggtgagtca gactg                                                                                75

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gagtgtgagg atgtcagtgt gtctc                                                                     25

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gagtgtgagg atgtcagtgt gtctctt                                                                   27

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gagtgtgagg atgtcagtgt gtctcttcca a                                                              31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 17
atagttggaa gagacacact gacatcctca c                                    31

<210> SEQ ID NO 18
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagtctgaca cagcagtcgt taatcgtcgc tgctaccctt gacatccgtg actggctaga      60
cagaggtgt                                                             69

<210> SEQ ID NO 19
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gacctgacct acagtgacca tagccttgcc tgattagcca ctgtccagtt tggctcctgg      60
tctcactag                                                             69

<210> SEQ ID NO 20
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagtacacct ctgtctagcc agtcacggat gtcaagggta gcagcgacga ttaacgactg      60
ctgtgtcaga ctg                                                        73

<210> SEQ ID NO 21
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
actcctagtg agaccaggag ccaaactgga cagtggctaa tcaggcaagg ctatggtcac      60
tgtaggtcag gtc                                                        73

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagtctgaca cagcagtcgt                                                 20

```
<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gacctgacct acagtgacca                                                    20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
agaggtgtac tcctagtgag a                                                  21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
caccagacct acgaagtcca                                                    20

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagtctgact caccactcgt gactggctag acagaggtgt                              40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caccagacct acgaagtcca ttggctcctg gtctcactag                              40

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gagtacacct ctgtctagcc agtcacgagt ggtgagtcag actg                         44
```

<210> SEQ ID NO 29
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
actcctagtg agaccaggag ccaatggact tcgtaggtct ggtg                    44

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagtctgaca cagcagtcgt gactggctag acagaggtgt                         40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gacctgacct acagtgacca ttggctcctg gtctcactag                         40

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagtacacct ctgtctagcc agtcacgact gctgtgtcag actg                    44

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
actcctagtg agaccaggag ccaatggtca ctgtaggtca ggtc                    44

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gagtacgagt ggtgagtcag actg                                          24

<210> SEQ ID NO 35

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
actctggact tcgtaggtct ggtg                                           24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gagtacgact gctgtgtcag actg                                           24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
actctggtca ctgtaggtca ggtc                                           24

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cagtctgaca cagcagtcgt                                                20

<210> SEQ ID NO 39
<211> LENGTH: 69
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gcacacacct catcgtcttg taatcgtcgc tgctaccctt gacatccgtg actggctaga    60
cagaggtgt                                                            69

<210> SEQ ID NO 40
<211> LENGTH: 69
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cacaatctcg accacgcaag tagccttgcc tgattagcca ctgtccagtt tggctcctgg    60
tctcactag                                                            69
```

-continued

```
<210> SEQ ID NO 41
<211> LENGTH: 73
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
gagtacacct ctgtctagcc agtcacggat gtcaagggta gcagcgacga ttacaagacg      60
atgaggtgtg tgc                                                         73

<210> SEQ ID NO 42
<211> LENGTH: 73
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
actcctagtg agaccaggag ccaaactgga cagtggctaa tcaggcaagg ctacttgcgt      60
ggtcgagatt gtg                                                         73

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
gcacacacct catcgtcttg gactggctag acagaggtgt                            40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
cacaatctcg accacgcaag ttggctcctg gtctcactag                            40

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gagtacacct ctgtctagcc agtccaagac gatgaggtgt gtgc                       44

<210> SEQ ID NO 46
<211> LENGTH: 44
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 46
actcctagtg agaccaggag ccaacttgcg tggtcgagat tgtg                    44

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
gcacacacct catcgtcttg                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
cacaatctcg accacgcaag                                               20

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
gagtcaagac gatgaggtgt gtgc                                          24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
actccttgcg tggtcgagat tgtg                                          24
```

SYSTEMS, COMPOSITIONS, AND METHODS FOR TARGET ENTITY DETECTION

CROSS-REFERENCE TO RELATED APPLICATIONS

This application is a continuation of U.S. application Ser. No. 16/805,637 filed Feb. 28, 2020, which claims the benefit of U.S. Provisional Application No. 62/812,878 filed Mar. 1, 2019, and U.S. Provisional Application No. 62/962,722 filed Jan. 17, 2020, the contents of each of which are hereby incorporated herein in their entirety.

SEQUENCE LISTING

The instant application contains a Sequence Listing which has been submitted electronically in ASCII format and is hereby incorporated by reference in its entirety. Said ASCII copy, created on Apr. 20, 2020, is named 2013276-0030_SL.txt and is 13,348 bytes in size.

BACKGROUND

Early detection of cancer greatly increases the chance of successful treatment. However, many cancers still lack effective screening recommendations. Typical challenges for cancer-screening tests include limited sensitivity and specificity. A high rate of false-positive results can be of particular concern, as it can create difficult management decisions for clinicians and patients who would not want to unnecessarily administer (or receive) anti-cancer therapy that may potentially have undesirable side effects. Conversely, a high rate of false-negative results fails to satisfy the purpose of the screening test, as patients who need therapy are missed, resulting in a treatment delay and consequently a reduced possibility of success.

SUMMARY

The present disclosure, among other things, provides insights and technologies for achieving effective cancer screening. In some embodiments, provided technologies are effective for detection of early-stage cancers. In some embodiments, provided technologies are effective even when applied to populations comprising or consisting of asymptomatic individuals (e.g., due to sufficiently high sensitivity and/or low rates of false-positive and/or false-negative results). In some embodiments, provided technologies are effective when applied to populations comprising or consisting of individuals (e.g., asymptomatic individuals) without hereditary risk in developing cancer. In some embodiments, provided technologies may be or include one or more compositions (e.g., molecular entities or complexes, systems, cells, collections, combinations, kits, etc.) and/or methods (e.g., of making, using, assessing, etc.), as will be clear to one skilled in the art reading the disclosure provided herein.

In some embodiments, the present disclosure identifies the source of a problem with certain prior technologies including, for example, certain conventional approaches to cancer detection and diagnosis. For example, the present disclosure appreciates that many conventional diagnostic assays, e.g., based on cell-free nucleic acids, circulating tumor cells, proteins, serum proteins, and/or bulk analysis of extracellular vesicles, can be time-consuming, costly, and/or lacking sensitivity and/or specificity sufficient to provide a reliable and comprehensive diagnostic assessment. In some embodiments, the present disclosure provides technologies (including systems, compositions, and methods) that solve such problems, among other things, by developing a target entity detection approach based on interaction and/or co-localization of molecules or epitopes on individual target entities (e.g., biological entities).

In some embodiments, the present disclosure, among other things, provides insights that screening of asymptotic individuals, e.g., regular screening prior to or otherwise in absence of developed symptom(s), can be beneficial, and even important for effective management (e.g., successful treatment) of cancer. Alternatively or additionally, in some embodiments, the present disclosure further provides insights that screening (e.g., regular screening) for different types of cancer (e.g., for a plurality of different cancers) can be beneficial, and even important for effective management (e.g., successful treatment) of cancer. In some embodiments, the present disclosure provides cancer screening systems that can be implemented, for example, to detect cancer, including early-stage cancer, in some embodiments in asymptomatic individuals (e.g., without hereditary risks in cancer). In some embodiments, provided technologies are implemented to achieve regular screening of asymptomatic individuals (e.g., without hereditary risks in cancer) and/or for multiple cancers. The present disclosure provides, for example, compositions (e.g., reagents, kits, components, etc.), and methods of providing and/or using them, including strategies that involve regular testing of one or more individuals (e.g., asymptomatic individuals). The present disclosure defines usefulness of such systems, and provides compositions and methods for implementing them.

In some embodiments, provided technologies achieve detection (e.g., early detection, e.g., in asymptomatic individual(s) and/or population(s)) of one or more features (e.g., incidence, progression, responsiveness to therapy, recurrence, etc.) of cancer and/or a plurality of cancers, with sensitivity and/or specificity (e.g., rate of false-positive and/or false-negative results) appropriate to permit useful application of provided technologies to single-time and/or regular (e.g., periodic) assessment. In some embodiments, provided technologies are useful in conjunction with individuals' periodic physical examination. In some embodiments, provided technologies are useful in conjunction with treatment regimen(s); in some embodiments, provided technologies may improve one or more characteristics (e.g., rate of success according to an accepted parameter) of such treatment regimen(s).

In some aspects, provided are technologies for use in detecting an entity of interest (e.g., a biological or chemical entity, such as a cell, an extracellular vesicle, or an analyte, etc.) comprising at least two or more targets (e.g., molecular targets), which in some embodiments such at least two or more targets may be the same, while in some embodiments, such at least two or more targets may be distinct. In some embodiments, the present disclosure provides systems comprising a plurality (e.g., at least two, at least three, or more) of detection probes each for a specific such target. In some embodiments, a provided system may comprise two or more (e.g., 3, 4, 5, 6, 7, 8, 9, 10, 11, 12, 13, 14, 15, 16, 17, 18, 19, 20 or more) detection probes. In some embodiments, individual detection probes may be directed at different targets. In some embodiments, two or more individual detection probes may be directed at the same target. In some embodiments, a provided system comprises two or more different detection probes directed at different targets, and optionally may include at least one additional detection probe also directed at a target to which another detection probe is directed. In some embodiments, a provided system comprises a plurality of subsets of detection probes, each subset of which comprises two or more detection probes directed at the same target.

Typically, a detection probe as provided and/or utilized herein comprises a target binding moiety and an oligonucleotide domain coupled to the target binding moiety, the oligonucleotide domain comprising a double-stranded portion and a single-stranded overhang extended from at least one end of the oligonucleotide domain. In many embodiments, at least a portion of a single-stranded overhang is designed such that it is complementary to a single-stranded overhang of a second detection probe, thus forming a double-stranded complex with a second detection probe through hybridization of the complementary single-stranded overhangs. In many embodiments, an oligonucleotide domain of a detection probe is configured to have a length such that when a first detection probe and a second detection probe bind to their respective targets on the same entity of interest (e.g., on a particular biological entity of interest), the first single-stranded overhang and the second single-stranded overhang are in sufficiently close proximity to permit hybridization.

In some embodiments involving detection probes as described and/or utilized herein, the corresponding oligonucleotide domain has a single-stranded overhang of at least 4 to 15 nucleotides in length. In some embodiments, a single-stranded overhang has a nucleotide sequence preferentially selected for ligation by a specific nucleic acid ligase of interest (e.g., a DNA ligase such as a T4 or T7 ligase). For example, such a single-stranded overhang may have a nucleotide sequence of GAGT.

In some embodiments involving detection probes as described and/or utilized herein, the length of the corresponding oligonucleotide domain can vary with, e.g., physical characteristics of an entity of interest (e.g., a biological entity of interest), and/or selection and localization of targets (e.g., molecular targets) in an entity of interest (e.g., a biological entity of interest). For example, when a biological entity is or comprises an extracellular vesicle (e.g., an exosome), the oligonucleotide domain of detection probes can each independently have a length, for example, of about 20 nm to about 200 nm such that their respective single-stranded overhangs are in sufficiently close proximity to anneal to each other when the corresponding detection probes are bound to the same extracellular vesicle.

In some embodiments involving at least one set of two (i.e., at least one pair of) detection probes in a system as described and/or utilized herein, oligonucleotide domains of such detection probes are configured such that when single-stranded overhangs of a first detection probe and a second detection probe anneal to each other to form a double-stranded complex, each respective target binding moiety is located at each end of the double-stranded complex. In some embodiments of such a double-stranded complex, both strands of the double-stranded complex are ligatable in the presence of a nucleic acid ligase, e.g., for amplification and/or detection.

In some embodiments involving at least three or more (n≥3) detection probes in a system as described and/or utilized herein, when single-stranded overhangs of detection probes anneal to each respective partner(s) to form a double-stranded complex, at least (n−2) target binding moiety/moieties is/are present at internal position(s) of the double-stranded complex. In some embodiments of such a double-stranded complex, it is desirable to have internal target binding moieties present in a single strand of the double-stranded complex such that another strand of the double-stranded complex is free of any internal target binding moieties and is thus ligatable in the presence of a nucleic acid ligase, e.g., for amplification and/or detection.

In some embodiments, the present disclosure utilizes a set of detection probes (e.g., two or more detection probes) that together are specific for a cancer (e.g., a particular cancer and/or stage of cancer as described herein), though one or more individual such probes may be directed to a target that itself is not specific to the cancer. For example, in some embodiments, a useful set of detection probes may comprise at least one detection probe directed to a target specific for the relevant cancer (i.e., a cancer-specific target), and may further comprise at least one detection probe directed to a target that is not necessarily or completely specific for the relevant cancer (e.g., that may also be found on some or all cells that are not cancerous, are not of the particular cancer, and/or are not of the particular stage of interest). That is, as will be appreciated by those skilled in the art reading the present specification, so long as the set of detection probes utilized in accordance with the present invention is or comprises a plurality of individual detection probes that together are specific for the relevant target biological entities of interest (e.g., cancer cells of interest or extracellular vesicles secreted by cancer cells) (i.e., sufficiently distinguish the relevant target biological entities (e.g., cancer cells of interest or extracellular vesicles secreted by cancer cells) for detection from other biological entities not of interest for detection), the set is useful in accordance with certain embodiments of the present invention.

In some embodiments where a strand of a double-stranded complex comprises at least one or more internal target binding moieties, the strand comprises a gap between an end of an oligonucleotide strand of a detection probe to which the internal target binding moiety is coupled and an end of an oligonucleotide strand of another detection probe. In some embodiments, the size of a gap within a strand of a double-stranded complex is large enough such that the strand becomes non-ligatable in the presence of a nucleic acid ligase. In some embodiments, the gap may be at least 2 to 8 nucleotides in size. In some embodiments, the gap is about 6 nucleotides in size.

In some embodiments involving detection probes as described and/or utilized herein, a target-binding moiety is or comprises an antibody agent directed at a specific target (e.g., a specific molecular target). In some embodiments, a target-binding moiety is or comprises an aptamer for a specific target (e.g., a specific molecular target). For example, in some embodiments, a target-binding moiety of a detection probe can be or comprise an antibody agent against a cancer-associated target such as a cancer-associated epitope. For example, in some embodiments, a cancer-associated target can be or comprise a target that is associated with more than one cancer (i.e., at least two or more cancers). In some embodiments, a cancer-associated can be or comprise a generic target that is typically associated with cancers. In some embodiments, a cancer-associated target can be or comprise a target that is associated with cancers of a specific tissue. In some embodiments, a cancer-associated target can be or comprise a target that is specific to a particular cancer.

In some embodiments involving detection probes as described and/or utilized herein, a target-binding moiety of a detection probe may be directed to a tissue-specific target (e.g., present in a normal healthy tissue and/or a diseased tissue such as a tumor). In some embodiments, a target-binding moiety may be directed to a target that is specifically associated with a normal healthy condition of a subject.

In some embodiments involving detection probes as described and/or utilized herein, an oligonucleotide domain is coupled to a target binding moiety by a means of covalent attachment (e.g., via a bond and/or a linker). Methods to covalently couple an oligonucleotide to various agents, e.g., peptides, nucleic acids, or antibodies, are known in the art and can be used to couple an oligonucleotide domain to a target binding moiety to form a detection probe as provided and/or utilized herein.

In some embodiments, a system appropriate for use in accordance with the present disclosure can comprise a control probe (e.g., in addition to target-specific detection probes). For example, in some embodiments, a control probe is configured to bind to a control reference such that its binding to an entity of interest (e.g., a biological entity of interest) inhibits or precludes generation of a detection signal (e.g., by inhibiting or precluding ligation of two or more detection probes and/or amplification of a template such as a template resulting from ligation of two or more detection probes).

In some embodiments, technologies described herein are useful, among other things, in detecting one or more entities of interest (e.g., one or more biological and/or chemical entities) in a sample (e.g., in a biological, environmental, or other sample), through interaction with two or more targets (e.g., molecular targets, which may, in some embodiments, represent different sites on a single molecular target, complex, agent, etc., or, more commonly, may be on different molecular targets). Those skilled in the art, reading the present disclosure will recognize that provided technologies are useful for a wide variety of applications and/or purposes. Such a skilled person will further appreciate that certain particular embodiments described herein relate to methods of using a plurality (e.g., at least 2, at least 3, or more) of detection probes as described and/or utilized herein. In some embodiments, a method comprises contacting an entity of interest (e.g., a biological entity) in a sample with a set of detection probes appropriate for use in accordance with the present disclosure.

In some embodiments, a method provided herein can comprise immobilizing an entity of interest (e.g., a biological entity) to be assayed on a solid substrate. An exemplary solid substrate may be or comprise a bead or a surface. In some embodiments, a solid substrate may be or comprise a capture surface (e.g., an entity capture surface) of an assay chamber, including, e.g., a bead, filter, matrix, membrane, plate, tube, and/or well.

In some embodiments, a method provided herein comprises allowing a set of detection probes (e.g., as described and/or utilized herein) to bind to one or more entities of interest (e.g., one or more biological entities) in a sample such that detection probes bind to respective targets (e.g., molecular targets), if present, in the entities of interest (e.g., biological entities) to form one or more double-stranded complexes. In some embodiments, a double-stranded complex is formed by direct hybridization or annealing of complementary single-stranded overhangs of detection probes bound to an entity of interest (e.g., a biological entity). Therefore, in at least some embodiments, no connector oligonucleotides are necessary to indirectly connect oligonucleotide domains of detection probes; in some embodiments, such connector oligonucleotides are not utilized. Accordingly, in some embodiments, a method provided herein does not comprise, after an entity of interest (e.g., a biological entity) is contacted with a plurality of detection probes, adding a connector oligonucleotide that is capable of binding to at least a portion of an oligonucleotide domain of a first detection probe and at least a portion of an oligonucleotide domain of a second detection probe.

A double-stranded complex (resulted from contacting an entity of interest (e.g., a biological entity) with detection probes, e.g., as described and/or utilized herein) can be contacted with a nucleic acid ligase to generate a ligated template comprising at least an oligonucleotide strand of a first detection probe and an oligonucleotide strand of a second detection probe. Detection of such a ligated template provides information as to whether an entity of interest (e.g., a biological entity) in a sample is positive or negative for targets to which detection probes are directed. For example, a detectable level (e.g., a level that is above a reference level, e.g., by at least 10% or more, where in some embodiments, a reference level may be a level observed in a negative control sample, such as a sample in which an entity of interest comprising such targets is absent) of such a ligated template is indicative of a tested entity of interest (e.g., a biological entity) comprising targets (e.g., molecular targets) of interest, whereas a non-detectable level (e.g., a level that is below the threshold of a detectable level) of such a ligated template indicates that at least one of targets (e.g., molecular targets) of interest is absent from a tested entity of interest (e.g., a biological entity).

A ligated template can be detected by an appropriate nucleic acid detection method known in the art. For example, in some embodiments, a ligated template is detected by performing amplification of the ligated template, optionally followed by detection of the presence of the amplification product. An exemplary nucleic acid detection method involves quantitative polymerase chain reaction.

Technologies provided herein can be applied to a sample of interest comprising an entity of interest (e.g., a biological or chemical entity, such as an extracellular vesicle and/or an analyte) to be assayed. For example, in some embodiments, a sample may be or comprise a biological sample. In some embodiments, a sample may be or comprise an environmental sample. In some embodiments, a sample may be or comprise a primary sample. In some embodiments, a sample may be or comprise a processed sample. For example, in some embodiments, a sample may be processed to isolate one or more entities of interest to be assayed.

In some embodiments where a sample comprises or is a biological sample, such a sample can be derived from a plasma or blood sample of a subject (e.g., a human subject) in need of such an assay. In some embodiments, a biological sample can be or comprise a primary sample (e.g., a tissue or tumor sample) from a subject (e.g., a human subject) in need of such an assay. In some embodiments, a biological sample can be processed to separate one or more entities of interest from non-target entities of interest, and/or to enrich one or more entities of interest. In some embodiments, an entity of interest present in a sample may be or comprise a biological entity, e.g., a cell or an extracellular vesicle (e.g., an exosome). In some embodiments, such a biological entity may be processed or contacted with a chemical reagent, e.g., to stabilize and/or crosslink targets to be assayed in the biological entity and/or to reduce non-specific binding with detection probes. In some embodiments, a biological entity is or comprises a cell, which may be optionally processed, e.g., with a chemical reagent for stabilizing and/or cross-linking targets (e.g., molecular targets) and/or for reducing non-specific binding. In some embodiments, a biological entity is or comprises an extracellular vesicle (e.g., an exosome), which may be optionally processed, e.g., with a chemical reagent for stabilizing and/or crosslinking targets (e.g., molecular targets) and/or for reducing non-specific binding.

In some embodiments, the present disclosure, among other things, provide technologies (including systems, compositions, and methods) that solve problems associated with conventional cancer diagnostics, e.g., based on cell-free nucleic acids, serum proteins, and/or bulk analysis of extracellular vesicles, by detecting co-localization of a target biomarker signature of cancer in individual extracellular vesicles, which comprises at least one extracellular vesicle-associated membrane-bound polypeptide and at least one target biomarker selected from the group consisting of surface protein biomarkers, internal protein biomarkers, and RNA biomarkers. In some embodiments, the present disclosure provides technologies (including systems, compositions, and methods) that solve such problems, among other things, by detecting such target biomarker signature of cancer using a target entity detection approach (e.g., ones described herein) which is based on interaction and/or co-localization of at least two or more target entities (e.g., a target biomarker signature) in individual extracellular vesicles.

In some aspects, provided are technologies for use in classifying a subject (e.g., an asymptomatic subject) as having or being susceptible to cancer. In some embodiments, the present disclosure provides methods or assays for classifying a subject (e.g., an asymptomatic subject) as having or being susceptible to cancer. In some embodiments, a provided method or assay comprises (a) detecting, in a blood-derived sample from a subject in need thereof, extracellular vesicles expressing a target biomarker signature of cancer, the target biomarker signature comprising: at least one extracellular vesicle-associated membrane-bound polypeptide and at least one target biomarker selected from the group consisting of: surface protein biomarkers, intravesicular protein biomarkers, and intravesicular RNA biomarkers; (b) comparing sample information indicative of level of the target biomarker signature-expressing extracellular vesicles in the blood-derived sample to reference information including a reference threshold level; and (c) classifying the subject as having or being susceptible to cancer when the blood-derived sample shows an elevated level of target biomarker signature-expressing extracellular vesicles relative to the reference threshold level.

In some embodiments, an extracellular vesicle-associated membrane-bound polypeptide for use in a target biomarker signature of cancer used and/or described herein may be or comprise a tumor-specific biomarker and/or a tissue-specific biomarker. In some embodiments, such an extracellular vesicle-associated membrane-bound polypeptide may be or comprise a non-specific marker, e.g., it is present in one or more non-target tumors, and/or in one or more non-target tissues.

In some embodiments, a target biomarker signature of cancer may comprise an extracellular vesicle-associated membrane-bound polypeptide and at least one additional target surface protein biomarker.

In some embodiments, a target biomarker signature of cancer may comprise an extracellular vesicle-associated membrane-bound polypeptide and at least one target intravesicular RNA (e.g., mRNA) biomarker.

In some embodiments, a target biomarker signature of cancer may comprise an extracellular vesicle-associated membrane-bound polypeptide (e.g., ones described herein) and at least one additional target intravesicular protein biomarker.

In some embodiments, a reference threshold level for use in a provided method or assay described herein is determined by levels of target biomarker signature-expressing extracellular vesicles observed in comparable samples from a population of non-cancer subjects.

In some embodiments, an extracellular vesicle-associated membrane-bound polypeptide included in a target biomarker signature may be detected using antibody-based agents. In some embodiments, such an extracellular vesicle-associated membrane-bound polypeptide may be detected using a capture assay comprising an antibody-based agent. For example, in some embodiments, a capture assay for detecting the presence of an extracellular vesicle-associated membrane-bound polypeptide in an extracellular vesicle may involve contacting a blood-derived sample comprising extracellular vesicles with a capture agent directed to such an extracellular vesicle-associated membrane-bound polypeptide. In some embodiments, such a capture agent may comprise a binding moiety directed to an extracellular vesicle-associated membrane-bound polypeptide (e.g., ones described herein), which may be optionally conjugated to a solid substrate. Without limitations, an exemplary capture agent for an extracellular vesicle-associated membrane-bound polypeptide may be or comprise a solid substrate (e.g., a magnetic bead) and a binding moiety (e.g., an antibody agent) directed to an extracellular vesicle-associated membrane-bound polypeptide.

In some embodiments, a target biomarker included in a target biomarker signature may be detected using appropriate methods known in the art, which may vary with types of analytes to be detected (e.g., surface proteins, intravesicular proteins, intravesicular RNA (e.g., mRNA)). For example, a person skilled in the art, reading the present disclosure, will appreciate that a surface protein biomarker and/or an intravesicular protein biomarker may be detected using antibody-based agents in some embodiments, while in some embodiments, an intravesicular RNA (e.g., mRNA) biomarker may be detected using nucleic acid-based agents, e.g., using quantitative reverse transcription PCR.

For example, in some embodiments where a target biomarker is or comprises a surface protein biomarker and/or an intravesicular protein marker, such a target biomarker may be detected involving a proximity ligation assay, e.g., following a capture assay (e.g., ones as described herein) to capture extracellular vesicles that express an extracellular vesicle-associated membrane-bound polypeptide (e.g., ones as used and/or described herein). In some embodiments, such a proximity ligation assay may comprise contacting a blood-derived sample comprising extracellular vesicles with a set of detection probes, each directed to a target biomarker, which set comprises at least two distinct detection probes, so that a combination comprising the extracellular vesicles and the set of detection probes is generated, wherein the two detection probes each comprise: (i) a binding moiety directed to a surface protein biomarker and/or an intravesicular protein biomarker; and (ii) an oligonucleotide domain coupled to the binding moiety, the oligonucleotide domain comprising a double-stranded portion and a single-stranded overhang portion extended from one end of the oligonucleotide domain. Such single-stranded overhang portions of the detection probes are characterized in that they can hybridize to each other when the detection probes are bound to the same extracellular vesicle. Such a combination comprising the extracellular vesicles and the set of detection probes is then maintained under conditions that permit binding of the set of detection probes to their respective targets on the extracellular vesicles such that the detection probes can bind to the same extracellular vesicle to form a double-stranded complex. Such a double-stranded complex can be detected by contacting the double-stranded complex with a nucleic acid ligase to generate a ligated template; and detecting the ligated template. The presence of such a ligated template is indicative of presence of extracellular vesicles that are positive for a target biomarker signature of cancer. While such a proximity ligation assay may perform better, e.g., with higher specificity and/or sensitivity than other existing proximity ligation assays, a person skilled in the art reading the present disclosure will appreciate that other forms of proximity ligation assays that are known in the art may be used instead.

In some embodiments where a target biomarker is or comprises an intravesicular RNA (e.g., mRNA) marker, such a target biomarker may be detected involving a nucleic acid detection assay. In some embodiments, an exemplary nucleic acid detection assay may be or comprise reverse-transcription PCR.

In some embodiments where a target biomarker is or comprises an intravesicular biomarker (e.g., an intravesicular protein biomarker and/or an intravesicular RNA (e.g., mRNA) biomarker), such a target biomarker may be detected involving, prior to a detection assay (e.g., a proximity ligation assay as described herein), a sample treatment (e.g., fixation and/or permeabilization) to expose intravesicular biomarker(s) for subsequent detection.

The present disclosure, among other things, recognizes that detection of a single cancer-associated serum protein or biomarker or a plurality of cancer-associated biomarkers based on a bulk sample (e.g., a bulk sample of extracellular vesicles), rather than at a resolution of a single extracellular vesicle, typically does not provide sufficient specificity and/or sensitivity in determination of whether a subject from whom the sample is obtained is likely to be suffering from or susceptible to cancer. The present disclosure, among other things, provides technologies, including systems, compositions, and/or methods, that solve such problems, including, for example, by specifically requiring that individual target entities (e.g., individual biological entities such as individual extracellular vesicles) for detection be characterized by presence of a combination of targets (e.g., molecular targets). In some embodiments, such a combination of targets may be a target biomarker signature comprising a combination of at least one or more extracellular vesicle-associated membrane-bound polypeptides and at least one or more target biomarkers. In particular embodiments, the present disclosure teaches technologies that require such individual entities (e.g., biological entities such as extracellular vesicles) be characterized by presence (e.g., by expression) of a combination of targets (e.g., molecular targets) that is cancer specific (i.e., "target biomarker signature" of the relevant cancer), while biological entities (e.g., extracellular vesicles) that do not comprise the targeted combination (e.g., target biomarker signature) do not produce a detectable signal (e.g., a level that is above a reference level, e.g., by at least 10% or more, where in some embodiments, a reference level may be a level observed in a negative control sample, such as a sample in which individual biological entities (e.g., individual extracellular vesicles) comprising such a targeted combination (e.g., a target biomarker signature) are absent).

Accordingly, in some embodiments, technologies provided herein can be useful for detection of incidence or recurrence of cancer in a subject and/or across a population of subjects. In some embodiments, a combination of targets (e.g., a target biomarker signature) may be selected for cancer detection. In some embodiments, a combination of targets (e.g., a target biomarker signature) may be selected for detection of a specific cancer or its stage and/or subtype thereof. In some embodiments, a combination of biomarkers (e.g., a target biomarker signature) may be detected by a plurality of (e.g., at least two or more) pairwise or orthogonal combinations of detection probes, wherein each pair of detection probes may be directed to at least one distinct target. In some embodiments, a combination of biomarkers (e.g., a target biomarker signature) may be detected by a set of detection probes that each are designed to hybridize to one another to form a linear complex. In some embodiments, a plurality of (e.g., at least two or more) combinations of biomarkers may be selected for cancer detection. In some embodiments, a plurality of (e.g., at least two or more) combinations of biomarkers may be selected for detection of a specific cancer or its stage and/or subtype thereof. In some embodiments, a plurality of (e.g., at least two or more) orthogonal combinations of biomarkers may be selected for cancer detection. In some embodiments, a plurality of (e.g., at least two or more) orthogonal combinations of biomarkers may be selected for detection of a specific cancer or its stage and/or subtype thereof. In some embodiments, a plurality of (e.g., at least two or more) target biomarker signatures may be selected for cancer detection. In some embodiments, a plurality of (e.g., at least two or more) target biomarker signatures may be selected for detection of a specific cancer or its stage and/or subtype thereof. In some embodiments, technologies provided herein can be used periodically (e.g., every year) to screen a human subject or across a population of human subjects for early-stage cancer or cancer recurrence.

In some embodiments, a combination (e.g., a set) of detection probes may be selected for a system or a method (e.g., ones described herein) for detection of a specific cancer. In some embodiments, a combination (e.g., a set) of detection probes is selected for a system or a method (e.g., ones described herein) for detection of one or more cancers. In some embodiments, a combination (e.g., a set) of detection probes may include a plurality of (e.g., at least two or more) pairwise or orthogonal combinations of detection probes, wherein each pair of detection probes may be directed to at least one distinct target. In some embodiments, detection probes in a combination (e.g., a set) may be each designed to hybridize to one another to form a linear complex. In some embodiments, examples of cancers that can be detected by technologies provided herein include, but are not limited to acute lymphocytic leukemia, acute myeloid leukemia, bile duct cancer, bladder cancer, brain cancer, breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer.

In some embodiments, a subject that is amenable to technologies provided herein for detection of incidence or recurrence of cancer may be an asymptomatic human subject and/or across an asymptomatic population. Such an asymptomatic subject may be a subject who has a family history of cancer, who has been previously treated for cancer, who is at risk of cancer recurrence after cancer treatment, who is in remission after cancer treatment, and/or who has been previously or periodically screened for the presence of at least one cancer biomarker. Alternatively, in some embodiments, an asymptomatic subject may be a subject who has not been previously screened for cancer, who has not been diagnosed for cancer, and/or who has not previously received cancer therapy.

In some embodiments, a subject or population of subjects may be selected based on one or more characteristics such as age, race, genetic history, medical history, personal history (e.g., smoking, alcohol, drugs, carcinogenic agents, diet, obesity, physical activity, sun exposure, radiation exposure, exposure to infectious agents such as viruses, and/or occupational hazard).

In some embodiments, technologies provided herein can be useful for selecting therapy for a subject who is suffering from or susceptible to cancer. In some embodiments, a cancer therapy and/or an adjunct therapy can be selected in light of findings based on technologies provided herein.

In some embodiments, technologies provided herein can be useful for monitoring and/or evaluating efficacy of therapy administered to a subject (e.g., a cancer subject).

In some embodiments, the present disclosure provides technologies for managing patient care, e.g., for one or more individual subjects and/or across a population of subjects. To give but a few examples, in some embodiments, the present disclosure provides technologies that may be utilized in screening (e.g., temporally or incidentally motivated screening and/or non-temporally or incidentally motivated screening, e.g., periodic screening such as annual, semi-annual, bi-annual, or with some other frequency). For example, in some embodiments, provided technologies for use in temporally motivated screening can be useful for screening one or more individual subjects or across a population of subjects (e.g., asymptomatic subjects) who are of a certain age or age group, e.g., older than a certain age (e.g., over 20, 25, 30, 35, 40, 45, 50, 55, 60, 65, 70, or older). In some embodiments, provided technologies for use in incidentally motivated screening can be useful for screening individual subjects who may have experienced an incident or event that motivates screening for cancer as described herein. For example, in some embodiments, an incidental motivation relating to determination of one or more indicators of cancer or susceptibility thereto may be or comprise, e.g., an incident based on their family history (e.g., a close relative such as blood-related relative was previously diagnosed for cancer), identification of one or more risk factors for cancer (e.g., smoking, alcohol, diet, obesity, occupational hazard, etc.) and/or prior incidental findings from genetic tests (e.g., genome sequencing), and/or imaging diagnostic tests (e.g., ultrasound, computerized tomography (CT) and/or magnetic resonance imaging (MRI) scans), development of one or more signs or symptoms characteristic of cancer (e.g., a persistent cough potentially indicative of lung cancer; a lump in breast tissue potentially indicative of breast cancer; gastrointestinal (GI) tract bleeding potentially indicative of GI cancer, or abnormal bleeding during a woman's period potentially indicative of ovarian cancer, etc.).

In some embodiments, provided technologies for managing patient care can inform treatment and/or payment (e.g., reimbursement for treatment) decisions and/or actions. For example, in some embodiments, provided technologies can provide determination of whether individual subjects have one or more indicators of incidence or recurrence of a disease or disorder (e.g., cancer), thereby informing physicians and/or patients when to initiate therapy in light of such findings. Additionally or alternatively, in some embodiments, provided technologies can inform physicians and/or patients of treatment selection, e.g., based on findings of specific responsiveness biomarkers (e.g., cancer responsiveness biomarkers). In some embodiments, provided technologies can provide determination of whether individual subjects are responsive to current treatment, e.g., based on findings of changes in one or more levels of molecular targets associated with a disease, disorder, or condition (e.g., cancer), thereby informing physicians and/or patients of efficacy of such therapy and/or decisions to maintain or alter therapy in light of such findings.

In some embodiments, provided technologies can inform decision making relating to whether health insurance providers reimburse (or not), e.g., for (1) screening itself (e.g., reimbursement available only for periodic/regular screening or available only for temporally and/or incidentally motivated screening); and/or for (2) initiating, maintaining, and/or altering therapy in light of findings by provided technologies. For example, in some embodiments, the present disclosure provides methods relating to (a) receiving results of a screening as described herein and also receiving a request for reimbursement of the screening and/or of a particular therapeutic regimen; (b) approving reimbursement of the screening if it was performed on a subject according to an appropriate schedule or response to a relevant incident and/or approving reimbursement of the therapeutic regimen if it represents appropriate treatment in light of the received screening results; and, optionally (c) implementing the reimbursement or providing notification that reimbursement is refused. In some embodiments, a therapeutic regimen is appropriate in light of received screening results if the received screening results detect a biomarker that represents an approved biomarker for the relevant therapeutic regimen (e.g., as may be noted in a prescribing information label and/or via an approved companion diagnostic). Alternatively or additionally, the present disclosure contemplates reporting systems (e.g., implemented via appropriate electronic device(s) and/or communications system(s)) that permit or facilitate reporting and/or processing of screening results, and/or of reimbursement decisions as described herein.

Some aspects provided herein relate to systems and kits for use in provided technologies. In some embodiments, a system or kit comprises at least one set of detection probes (e.g., as described and/or utilized herein), each directed to a target. In some embodiments, a set of detection probes in a provided system or kit comprises two or more (e.g., 3, 4, 5, 6, 7, 8, 9, 10, 11, 12, 13, 14, 15, 16, 17, 18, 19, 20 or more) detection probes. In some embodiments, individual detection probes may be directed at different targets. In some embodiments, two or more individual detection probes may be directed to the same target. In some embodiments, a provided system or kit comprises two or more different detection probes directed at different targets, and optionally may include at least one additional detection probe also directed at a target to which another detection probe is directed.

Some aspects provided herein relate to systems and kits for use in provided technologies relating to biomarker detection and/or characterization. In some embodiments, a system or kit may comprise detection agents for a target biomarker signature of a disease or disorder (e.g., cancer). In some embodiments, such a system or kit may comprise a capture agent for an extracellular vesicle-associated membrane-bound polypeptide present in extracellular vesicles associated with a disease or disorder (e.g., cancer); and (b) at least one or more detection agents directed to one or more target biomarkers of a target biomarker signature of such a disease or disorder (e.g., cancer), which may be or comprise additional surface protein biomarker(s), intravesicular protein biomarker(s), and/or intravesicular RNA (e.g., mRNA) biomarker(s).

In some embodiments, a capture agent included in a system and/or kit may comprise a binding moiety directed to an extracellular vesicle-associated membrane-bound polypeptide. In some embodiments, such a binding moiety may be conjugated to a solid substrate, which in some embodiments may be or comprise a solid substrate. In some embodiments, such a solid substrate may be or comprise a magnetic bead. In some embodiments, an exemplary capture agent included in a provided system and/or kit may be or comprise a solid substrate (e.g., a magnetic bead) and an antibody agent directed to an extracellular vesicle-associated membrane-bound polypeptide conjugated thereto.

In some embodiments where a target biomarker includes a surface protein biomarker and/or an intravesicular protein biomarker, a system and/or kit may include detection agents for performing a proximity ligation assay (e.g., ones as described herein). In some embodiments, such detection agents for performing a proximity ligation assay may comprise a set of detection probes, each directed to a target biomarker of a target biomarker signature, which set comprises at least two detection probes, wherein the two detection probes each comprise: (i) a polypeptide-binding moiety directed to a target biomarker; and (ii) an oligonucleotide domain coupled to the binding moiety, the oligonucleotide domain comprising a double-stranded portion and a single-stranded overhang portion extended from one end of the oligonucleotide domain, wherein the single-stranded overhang portions of the detection probes are characterized in that they can hybridize to each other when the detection probes are bound to the same extracellular vesicle.

In some embodiments, a provided system and/or kit may comprise a plurality (e.g., 2, 3, 4, 5, or more) of sets of detection probes, each set of which comprises two or more (e.g., 3, 4, 5, 6, 7, 8, 9, 10, 11, 12, 13, 14, 15, 16, 17, 18, 19, 20 or more) detection probes. In some embodiments, each set may be directed to detection for a different disease, disorder, or condition. In some embodiments, two or more sets may be directed to detection for the same disease, disorder, or condition. In some embodiments, at least one or more sets (e.g., at least one, at least two, at least three, at least four, at least five, or more) of detection probes may be directed to detection for cancer. For example, in some embodiments, each set may be directed to detection for a different cancer (e.g., different cancer types associated with the same or different tissues). In some embodiments, two or more sets may be directed to detection of the same cancer. In some embodiments, a provided system and/kit may comprise at least one set of detection probes for detection of one cancer and at least one set of detection probes for detection of a different cancer (e.g., pancreatic cancer). In some embodiments, two or more detection probes may be directed to different subtypes and/or categories of cancer. In some embodiments, two or more sets may be directed to detection of cancer of different stages. In some embodiments, two or more sets may be directed to detection of cancer of the same stage.

In some embodiments, detection probes in a provided kit may be provided as a single mixture in a container. In some embodiments, multiple sets of detection probes may be provided as individual mixtures in separate containers. In some embodiments, each detection probe is provided individually in a separate container.

In some embodiments where a target biomarker includes an intravesicular RNA (e.g., mRNA) biomarker, such a system and/or kit may include detection agents for performing a nucleic acid detection assay. In some embodiments, such a system and/or kit may include detection agents for performing a quantitative reverse-transcription PCR, for example, which may comprise primers directed to intravesicular RNA (e.g., mRNA) target(s).

In some embodiments, a provided system and/or kit may comprise at least one chemical reagent, e.g., to process a sample and/or entities of interest (e.g., extracellular vesicles) therein. In some embodiments, a provided system and/or kit may comprise at least one chemical reagent to process entities of interest (e.g., biological entities of interest such as extracellular vesicles) in a sample, including, e.g., but not limited to a fixation agent, a permeabilization agent, and/or a blocking agent. In some embodiments, a provided system and/or kit may comprise a nucleic acid ligase and/or a nucleic acid polymerase. In some embodiments, a provided system and/or kit may comprise one or more primers and/or probes. In some embodiments, a provided system and/or kit may comprise one or more pairs of primers, for example for PCR, e.g., quantitative PCR (qPCR) reactions. In some embodiments, a provided system and/or kit may comprise one or more probes such as, for example, hydrolysis probes which may in some embodiments be designed to increase the specificity of qPCR (e.g., TaqMan probes). In some embodiments, a provided system and/or kit may comprise one or more multiplexing probes, for example as may be useful when simultaneous or parallel qPCR reactions are employed (e.g., to facilitate or improve readout).

In some embodiments, a provided system and/or kit can be used for screening (e.g., regular screening) and/or other assessment of individuals (e.g., asymptomatic or symptomatic subjects) for detection (e.g., early detection) of a disease or disorder (e.g., cancer). In some embodiments, a provided system and/or kit can be used for screening and/or other assessment of individuals susceptible to a disease or disorder (e.g., cancer) (e.g., individuals with a known genetic, environmental, or experiential risk, etc.). In some embodiments, provided system and/or kits can be used for monitoring recurrence of a disease or disorder (e.g., cancer) in a subject who has been previously treated. In some embodiments, provided systems and/or kits can be used as a companion diagnostic in combination with a therapy for a subject who is suffering from a disease or disorder (e.g., cancer). In some embodiments, provided systems and/or kits can be used for monitoring or evaluating efficacy of a therapy administered to a subject who is suffering from a disease or disorder (e.g., cancer). In some embodiments, provided systems and/or kits can be used for selecting a therapy for a subject who is suffering from a disease or disorder (e.g., cancer). In some embodiments, provided systems and/or kits can be used for making a therapy decision and/or selecting a therapy for a subject with one or more symptoms (e.g., non-specific symptoms) associated with a disease or disorder (e.g., cancer).

In some embodiments, a set of detection probes provided and/or utilized in a kit or system may be selected for screening (e.g., regular screening) or diagnosis of a specific cancer (including, e.g., but not limited to acute lymphocytic leukemia, acute myeloid leukemia, bile duct cancer, bladder cancer, brain cancer, breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer).

In some embodiments, a provided kit or system may comprise a plurality of sets of detection probes, each set comprising at least two or more detection probes for detection of a different cancer. For example, such a kit can be used to screen (e.g., regularly screen) a subject or across a population of subjects for various cancers (including, e.g., but not limited to acute lymphocytic leukemia, acute myeloid leukemia, bile duct cancer, bladder cancer, brain cancer, breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer) in a single assay.

Double-stranded complexes formed by at least two or more detection probes (e.g., as described and/or utilized herein) bound to an entity of interest (e.g., a chemical or biological entity, such as an extracellular vesicle or an analyte) is also within the scope of disclosure.

Complexes formed by performing methods described herein and/or using systems and/or kits described herein are also within the scope of disclosure. For example, in some embodiments, a complex comprising: (a) an extracellular vesicle expressing a target biomarker signature, at least two of which include at least one extracellular vesicle-associated membrane-bound polypeptide and at least one target biomarker selected from the group consisting of: surface protein biomarkers, intravesicular protein biomarkers, and intravesicular RNA biomarkers, wherein the extracellular vesicle is immobilized onto a solid substrate comprising a binding moiety directed to such a extracellular vesicle-associated membrane-bound polypeptide. Such a complex further comprises at least two detection probes directed to at least one target biomarker of the target biomarker signature present in the extracellular vesicle, wherein each detection probe is bound to such a target biomarker and each comprises: (i) a binding directed to the target biomarker; and (ii) an oligonucleotide domain coupled to the binding moiety, the oligonucleotide domain comprising a double-stranded portion and a single-stranded overhang portion extended from one end of the oligonucleotide domain, wherein the single-stranded overhang portions of the detection probes are hybridized to each other.

These, and other aspects encompassed by the present disclosure, are described in more detail below and in the claims.

BRIEF DESCRIPTION OF THE DRAWINGS

FIG. 2A shows, in some embodiments, a target entity detection assay using a combination of detection probes, which combination is specific for detection of cancer. In some embodiments, a duplex system including a first detection probe for a target protein 1 (e.g., cancer marker 1) and a second detection probe for a target protein 2 (e.g., cancer marker 2) are added to a sample comprising a biological entity (e.g., extracellular vesicle or analyte). In some embodiments, detection probes each comprise a target binding moiety (e.g., an antibody agent against a target protein) coupled to an oligonucleotide domain, which comprises a double-stranded portion and a single-stranded overhang extended from one end of the oligonucleotide domain. A detection signal is generated when distinct target binding moieties (e.g., antibody agents against target protein 1 and target protein 2, respectively) of the first and second detection probes are localized to the same biological entity (e.g., an extracellular vesicle or analyte) in close proximity such that the corresponding single-stranded overhangs hybridize to each other, thus allowing ligation of their oligonucleotide domains to occur. For example, a control entity (e.g., a biological entity from a healthy subject sample) does not express one or both of target protein 1 (e.g., cancer marker 1) and target protein 2 (e.g., cancer marker 2), so no detection of signal can be generated. However, when a biological entity from a cancer sample expresses target protein 1 and target protein 2, and the target proteins are present within a short enough distance of each other in the same biological entity (e.g., extracellular vesicle), a detection signal is generated. FIG. 2B shows a non-limiting example of a double-stranded complex comprising a first detection probe and a second detection probe connected to each other through direct hybridization of their respective single-stranded overhangs.

FIG. 3 is a graph showing qPCR detection of a ligated template with and without a DNA ligase (e.g., T4 or T7 ligase).

FIG. 4 is a graph showing qPCR detection of a ligated template in different cell samples (e.g., cancer cell samples such as T84, MeWo, or SK-MEL-1 cell samples).

FIG. 6 is a graph showing qPCR detection of a ligated product when the corresponding oligonucleotide domains of all three distinct detection probes are present.

FIG. 7 is a graph showing qPCR detection of a ligated product when two (e.g., for Target 1 and Target 3) of three detection probes are present.

FIG. 8 is a graph showing qPCR detection of a ligated product when two (e.g., for Target 1 and Target 2) of three detection probes are present.

FIG. 9 is a graph showing qPCR detection of a ligated product when two (e.g., for Target 2 and Target 3) of three detection probes are present.

FIG. 12 is a schematic diagram illustrating a target entity detection assay of an exemplary embodiment described herein involving competitive inhibition of ligation. As shown in FIG. 11, when a control probe is localized with other target-specific detection probes to the same biological entity, no ligation product can be formed. In some embodiments, a control probe is designed such that (i) it is arranged between two target-specific detection probes; and (ii) one end of the control probe is a blunt end and is thus not ligatable with other detection probes. Additionally or alternatively, a control probe can have a dideoxynucleotide at one end of a strand such that it is not ligatable.

FIGS. 13A-13B are graphs showing qPCR detection of ligated templates in samples comprising melanoma cell line (MeWo)-derived extracellular vesicles, colorectal cancer cell line (T84)-derived extracellular vesicles, and no templates (negative controls). FIG. 13A shows the experimental data obtained from an exemplary duplex system (e.g., as described herein). FIG. 13B shows the experimental data obtained from an exemplary triplex system (e.g., as described herein).

FIGS. 14A-14D are graphs showing average delta Ct values (using healthy patient samples as the baseline) obtained from assaying extracellular vesicles in plasma samples spiked with a known amount of cancer cell line-derived extracellular vesicles using an exemplary duplex detection assay with detection probes directed to a specific set of biomarkers as indicated in Table 4. FIG. 14A shows data based on use of detection probes directed to Target marker A and Target marker B (Combination 1). FIG. 14B shows data based on use of detection probes directed to Target marker E and Target marker F (Combination 2). FIG. 14C shows data based on use of detection probes directed to Target marker E and Target marker A (Combination 3). FIG. 14D shows data based on use of detection probes directed to Target marker G and Target marker F (Combination 4).

FIG. 15A shows average delta Ct values (using healthy patient sample A as the baseline). FIG. 15B shows normalized signal, calculated as $2^{delta\_Ct}$. FIG. 15C shows a receiver operating characteristic (ROC) curve, with a threshold of the mean healthy normalized signal plus three standard deviations, classifying samples as healthy or stage IV lung adenocarcinoma.

FIG. 16A shows average delta Ct values (using healthy patient sample A as the baseline). FIG. 16B shows normalized signal, calculated as $2^{delta\_Ct}$. FIG. 16C shows a receiver operating characteristic (ROC) curve, with a threshold of the mean healthy normalized signal plus three standard deviations, classifying samples as healthy or stage IV lung adenocarcinoma.

FIG. 18 is a schematic diagram showing an exemplary inhibitor oligonucleotide that can be used to reduce or inhibit a non-specific ligated template from generating a detectable signal, thereby reducing background signal.

FIG. 19 show experimental data from qPCR detection of a ligated sample, e.g., using the assay illustrated in FIG. 1 or FIGS. 2A-2B, in different cell line-derived extracellular vesicle samples. In some embodiments, a target entity detection assay includes agents for capturing extracellular vesicles based on a cancer marker 1 ("cancer marker 1 capture") and an exemplary duplex system, for example, involving at least two detection probes each comprising a binding moiety directed to a cancer marker 2 (e.g., anti-cancer marker 2 antibody) coupled to a distinct oligonucleotide domain, which comprises a double-stranded portion and a single-stranded overhang extended from one end of the oligonucleotide domain ("cancer marker 2+cancer marker 2 antibody probes"). Panel A shows a graph of qPCR data comparing detection of biomarker-positive cancer cell-line EVs (positive cell line) over biomarker-negative cancer cell line EVs (negative cell line). Panel B shows corresponding average delta Ct values using a negative control cell line (e.g., biomarker-negative cancer cell line) as the baseline.

FIG. 24 is a graph showing raw qPCR data that illustrate the effect of oligonucleotide length on assay signal. Cell line EVs were captured using anti-Target 1-functionalized magnetic beads and signal was generated using anti-Target 1 and anti-Target 2 detection probes for an exemplary duplex target entity detection system described herein.

FIG. 25 is a graph showing average delta Ct values (using healthy plasma sample as the baseline) obtained from assaying cell line EVs using an exemplary duplex detection assay with detection probes directed to Combination 1 as indicated in Table 6.

FIG. 26 is a schematic diagram illustrating a target entity detection assay of an exemplary embodiment described herein. In some embodiments, a target entity detection assay utilizes a combination of detection probes, which combination in some embodiments is specific for a target, for example, for detection of a target entity from a tissue of interest (Tissue A as shown in FIG. 26). In some embodiments, such a combination of detection probes includes at least two or more target-specific detection probes, each directed to a target present in an entity of interest (which in some embodiments may be the same target, or in some embodiments may be a distinct target). In some embodiments, detection probes each comprise a target-binding moiety (e.g., an antibody agent or aptamer) coupled to an oligonucleotide domain, which comprises a double-stranded portion and a single-stranded overhang extended from one end of the oligonucleotide domain. In some embodiments, such a target entity detection assay further comprises at least one or more at least one or more control probes, e.g., an inhibitor probe that is designed to reduce cross-reactivity with non-targets. For example, in some embodiments, an inhibitor probe is designed such that its binding to a non-target entity, while allowing ligation with another probe, e.g., a detection probe, inhibits or precludes amplification of a ligated template. For example, as shown in FIG. 26, in some embodiments, an inhibitor probe may be directed to a non-target, e.g., a marker that is not associated with a target tissue, or a marker that is not associated with a disease, disorder, or condition (e.g., cancer) to be diagnosed. In some such embodiments, an inhibitor probe is similar to a detection probe as described herein such that when a detection probe and an inhibitor probe are in close proximity, their single-stranded overhangs are hybridized with each other, thus allowing ligation. However, unlike a detection probe described herein, at least one strand of the oligonucleotide domain of such an inhibitor probe does not have a primer site, thus prohibiting amplification of any ligated template that may be formed as a result of interaction between a detection probe and an inhibitor probe. In some embodiments, a combination of detection probes and inhibitor probe(s) is added to a sample comprising a biological entity (e.g., extracellular vesicle or analyte). A detection signal is generated when all target-specific detection probes (e.g., directed to Target 1 from Tissue A, Target 2 from Tissue A), but not an inhibitor probe, are localized to the same biological entity (e.g., an extracellular vesicle or analyte) in close proximity. The corresponding single-stranded overhangs of target-specific detection probes hybridize to form a double-stranded complex, and ligation of at least one strand of the resulting double-stranded complex occurs, thereby allowing a ligated product to be detected. In the presence of an inhibitor probe binding to a non-target entity (e.g., a biological entity from a different tissue), no detection signal can be generated because the inhibitor probe inhibits amplification of a template. In some embodiments, inclusion of such an inhibitor probe can selectively remove false positives, thereby improving specificity of detection.

FIG. 27 is a graph showing raw qPCR data from 13 different combinations of templates as indicated.

CERTAIN DEFINITIONS

Figure 1:
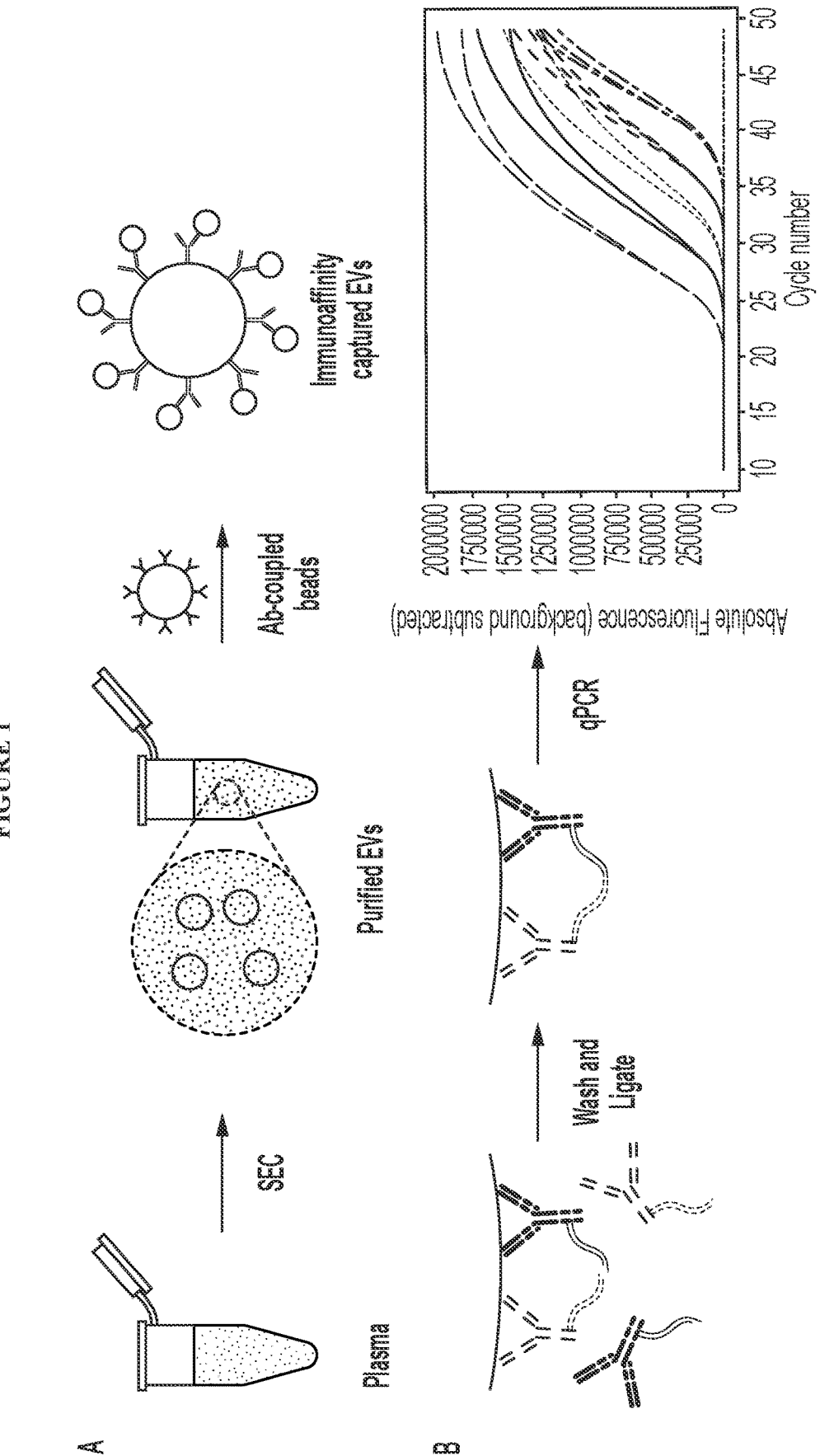
FIG. 1 is a schematic diagram illustrating an exemplary workflow of profiling individual extracellular vesicles (EVs). The figure shows purification of EVs from plasma using size exclusion chromatography (SEC) and immuno-affinity capture of EVs displaying a specific membrane-bound protein marker (Panel A); detection of co-localized target markers (e.g., intravesicular proteins or surface proteins) on captured EVs using a target entity detection assay according to some embodiments described herein (Panel B).

Administering: As used herein, the term "administering" or "administration" typically refers to the administration of a composition to a subject to achieve delivery of an agent that is, or is included in, a composition to a target site or a site to be treated. Those of ordinary skill in the art will be aware of a variety of routes that may, in appropriate circumstances, be utilized for administration to a subject, for example a human. For example, in some embodiments, administration may be parenteral. In some embodiments, administration may be oral. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Amplification: The terms "amplification" and "amplify" refers to a template-dependent process that results in an increase in the amount and/or levels of a nucleic acid molecule relative to its initial amount and/or level. A template-dependent process is generally a process that involves template-dependent extension of a primer molecule, wherein the sequence of the newly synthesized strand of nucleic acid is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

Analyte: As used herein, the term "analyte" refers to an entity, substance, constituent, or complex in a sample to be assayed. In some embodiments, an analyte can be or comprise a biological analyte. In some embodiments, an analyte can be or comprise a chemical analyte. In some embodiments, an analyte can be or comprise a polypeptide or protein. In some embodiments, an analyte can be or comprise a nucleic acid. In some embodiments, an analyte can be or comprise a cell or a microorganism, including a virus, or a fragment or product thereof (including, e.g., but not limited to intracellular molecules, molecules secreted by a cell or microorganism, cell-surface molecules, extracellular vesicle-surface molecules, or membrane-bound cells). In some embodiments, an analyte is an entity comprising at least one target to be detected using technologies described herein (e.g., involving at least 2 detection probes directed to the same target in accordance with the present disclosure). In some embodiments, an analyte is an entity comprising at least two targets or more (including, e.g., at least 2, at least 3, at least 4, or more targets) to be detected using technologies described herein (e.g., involving at least 2 or more detection probes directed to different targets in accordance with the present disclosure). In some embodiments, an analyte can be a single entity or a complex comprising two or more molecular subunits, which may or may not be covalently bound to one another, and/or which may be the same or different. In some embodiments, an analyte can be or comprise a protein complex. Such a complex may be a homo- or hetero-multimer. Aggregates of molecules, e.g. proteins or polypeptides, or nucleic acids (e.g., DNA or RNA) complexed or aggregated with polypeptides or proteins (e.g., regulatory factors such as transcription factors) may also be target analytes.

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated complementarity determining regions (CDRs) or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 95%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody agents can be made by the skilled person using methods and commercially available services and kits known in the art. For example, methods of preparation of monoclonal antibodies are well known in the art and include hybridoma technology and phage display technology. Further antibodies suitable for use in the present disclosure are described, for example, in the following publications: *Antibodies A Laboratory Manual*, Second edition. Edward A. Greenfield. Cold Spring Harbor Laboratory Press (Sep. 30, 2013); *Making and Using Antibodies: A Practical Handbook*, Second Edition. Eds. Gary C. Howard and Matthew R. Kaser. CRC Press (Jul. 29, 2013); *Antibody Engineering: Methods and Protocols*, Second Edition (Methods in Molecular Biology). Patrick Chames. Humana Press (Aug. 21, 2012); *Monoclonal Antibodies: Methods and Protocols* (Methods in Molecular Biology). Eds. Vincent Ossipow and Nicolas Fischer. Humana Press (Feb. 12, 2014); and *Human Monoclonal Antibodies: Methods and Protocols* (Methods in Molecular Biology). Michael Steinitz. Humana Press (Sep. 30, 2013)).

Antibodies may be produced by standard techniques, for example by immunization with the appropriate polypeptide or portion(s) thereof, or by using a phage display library. If polyclonal antibodies are desired, a selected mammal (e.g., mouse, rabbit, goat, horse, etc.) is immunized with an immunogenic polypeptide bearing a desired epitope(s), optionally haptenized to another polypeptide. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Serum from the immunized animal is collected and treated according to known procedures. If serum containing polyclonal antibodies to the desired epitope contains antibodies to other antigens, the polyclonal antibodies can be purified by immunoaffinity chromatography or any other method known in the art. Techniques for producing and processing polyclonal antisera are well known in the art.

Approximately or about: As used herein, the term "approximately" or "about," as applied to one or more values of interest, refers to a value that is similar to a stated reference value. In general, those skilled in the art, familiar within the context, will appreciate the relevant degree of variance encompassed by "about" or "approximately" in that context. For example, in some embodiments, the term "approximately" or "about" may encompass a range of values that are within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Aptamer: As used herein, the term "aptamer" typically refers to a nucleic acid molecule or a peptide molecule that binds to a specific target molecule (e.g., an epitope). In some embodiments, a nucleic acid aptamer may be described by a nucleotide sequence and is typically about 15-60 nucleotides in length. A nucleic acid aptamer may be or comprise a single stranded and/or double-stranded structure. In some embodiments, a nucleic acid aptamer may be or comprise DNA. In some embodiments, a nucleic acid aptamer may be or comprise RNA. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. In some embodiments, a peptide aptamer may be described to have one or more peptide loops of variable sequence displayed by a protein scaffold. Peptide aptamers can be isolated from combinatorial libraries and often subsequently improved by directed mutation or rounds of variable region mutagenesis and selection. Given the extraordinary diversity of molecular shapes that exist within the universe of all possible nucleotide and/or peptide sequences, aptamers may be obtained for a wide array of molecular targets, including proteins and small molecules. In addition to high specificity, aptamers typically have very high affinities for their targets (e.g., affinities in the picomolar to low nanomolar range for proteins or polypeptides). Because aptamers are typically synthetic molecules, aptamers are amenable to a variety of modifications, which can optimize their function for particular applications.

Associated with: Two events or entities are "associated" with one another, as that term is used herein, if the presence, level and/or form of one is correlated with that of the other. For example, a particular biological phenomenon (e.g., expression of a specific biomarker) is considered to be associated with a particular disease, disorder, or condition (e.g., a specific type of cancer and/or stage of cancer), if its presence correlates with incidence of and/or susceptibility of the disease, disorder, or condition (e.g., across a relevant population).

Biological entity: In appropriate circumstances, as will be clear from context to those skilled in the art, the term "biological entity" may be utilized to refer to an entity or component that is present in a biological sample, e.g., in some embodiments derived or obtained from a subject, which, in some embodiments, may be or comprise a cell or an organism, such as an animal or human, or, in some embodiments, may be or comprise a biological tissue or fluid. In some embodiments, a biological entity is or comprises a cell or microorganism, or a fraction, extract, or component thereof (including, e.g., intracellular components and/or molecules secreted by a cell or microorganism). For example, in some embodiments, a biological entity is or comprises a cell. In some embodiments, a biological entity is or comprises an extracellular vesicle. In some embodiments, a biological entity is or comprises a biological analyte (e.g., a metabolite, carbohydrate, protein or polypeptide, enzyme, lipid, organelle, cytokine, receptor, ligand, and any combinations thereof). In some embodiments, a biological entity present in a sample is in a native state (e.g., proteins or polypeptides remain in a naturally occurring conformational structure). In some embodiments, a biological entity is processed, e.g., by isolating from a sample or deriving from a naturally occurring biological entity. For example, a biological entity can be processed with one or more chemical agents such that it is more desirable for detection utilizing technologies provided herein. As an example only, a biological entity may be a cell or extracellular vesicle that is contacted with a fixative agent (e.g., but not limited to methanol and/or formaldehyde) to cause proteins and/or peptides present in the cell or extracellular vesicle to form crosslinks. In some embodiments, a biological entity is in an isolated or pure form (e.g., isolated from a blood or plasma sample). In some embodiments, a biological entity may be present in a complex matrix (e.g., a blood or plasma sample).

Biomarker: The term "biomarker" typically refers to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. In some embodiments, a biomarker may be or comprise a marker for a particular tissue (e.g., but not limited to brain, breast, colon, ovary and/or other tissues associated with a female reproductive system, pancreas, prostate and/or other tissues associated with a male reproductive system, liver, lung, and skin). Such a marker for a particular tissue, in some embodiments, may be specific for a healthy tissue, specific for a diseased tissue, or in some embodiments may be present in a normal healthy tissue and diseased tissue (e.g., a tumor); those skilled in the art, reading the present disclosure, will appreciate appropriate contexts for each such type of biomarker. In some embodiments, a biomarker may be or comprise a cancer-specific marker (e.g., a marker that is specific to a particular cancer). In some embodiments, a biomarker may be or comprise a non-specific cancer marker (e.g., a marker that is present in at least two or more cancers). A non-specific cancer marker may be or comprise, in some embodiments, a generic marker for cancers (e.g., a marker that is typically present in cancers, regardless of tissue types), or in some embodiments, a marker for cancers of a specific tissue (e.g., but not limited to brain, breast, colon, ovary and/or other tissues associated with a female reproductive system, pancreas, prostate and/or other tissues associated with a male reproductive system, liver, lung, and skin). Thus, in some embodiments, a biomarker is predictive; in some embodiments, a biomarker is prognostic; in some embodiments, a biomarker is diagnostic, of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is or comprises a portion of a particular molecule, complex, or structure; e.g., in some embodiments, a biomarker may be or comprise an epitope. In some embodiments, a biomarker is a surface marker (e.g., a surface protein marker) of a biological entity (e.g., an extracellular vesicle). In some embodiments, a biomarker is an intracellular marker. In some embodiments, a biomarker is detected outside of cells, e.g., is secreted or is otherwise generated or present outside of cells, e.g., in a body fluid such as blood, plasma, urine, tears, saliva, cerebrospinal fluid, etc. In some embodiments, a biomarker is intravesicular (e.g., a protein or RNA marker that is present within an extracellular vesicle). In some embodiments, a biomarker may be or comprise a genetic or epigenetic signature. In some embodiments, a biomarker may be or comprise a gene expression signature. In some embodiments, a "biomarker" appropriate for use in accordance with the present disclosure may refer to presence, level, and/or form of a molecular entity (e.g., epitope) present in a target marker. For example, in some embodiments, two or more "biomarkers" as molecular entities (e.g., epitopes) may be present on the same target marker (e.g., a marker protein such as a surface protein present in a biological entity, e.g., an extracellular vesicle).

Blood-derived sample: The term "blood-derived sample," as used herein, refers to a sample derived from a blood sample (i.e., a whole blood sample) of a subject in need thereof. Examples of blood-derived samples include, but are not limited to, blood plasma (including, e.g., fresh frozen plasma), blood serum, blood fractions, plasma fractions, serum fractions, blood fractions comprising red blood cells (RBC), platelets, leukocytes, etc., and cell lysates including fractions thereof (for example, cells, such as red blood cells, white blood cells, etc., may be harvested and lysed to obtain a cell lysate). In some embodiments, a blood-derived sample that is used with methods, systems, and/or kits described herein is a plasma sample.

Cancer: The term "cancer" is used herein to generally refer to a disease or condition in which cells of a tissue of interest exhibit relatively abnormal, uncontrolled, and/or autonomous growth, so that they exhibit an aberrant growth phenotype characterized by a significant loss of control of cell proliferation. In some embodiments, cancer may comprise cells that are precancerous (e.g., benign), malignant, pre-metastatic, metastatic, and/or non-metastatic. In one aspect, the present disclosure provides technologies for detection of cancer. In some embodiments, cancer may be characterized by a solid tumor. In some embodiments, cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, ovarian cancer, breast cancer, glioblastomas, colorectal cancer, gastro-intestinal cancers and nervous system cancers, benign lesions such as papillomas, and the like.

Close proximity: The term "close proximity" as used herein, refers to a distance between two detection probes (e.g. two detection probes in a pair) that is sufficiently close enough such that an interaction between the detection probes (e.g., through respective oligonucleotide domains) is expected to likely occur. For example, in some embodiments, probability of two detection probes interacting with each other (e.g., through respective oligonucleotide domains) over a period of time when they are in sufficiently close proximity to each other under a specified condition (e.g., when detection probes are bound to respective targets in an entity of interest, e.g., extracellular vesicle, is at least 50% or more, including, e.g., at least 60%, at least 70%, at least 80%, at least 90% or more. In some embodiments, a distance between two detection probes when they are in sufficiently close proximity to each other may range between approximately 0.1-1000 nm, or 0.5-500 nm, or 1-250 nm. In some embodiments, a distance between two detection probes when they are in sufficiently close proximity to each other may range between approximately 0.1-10 nm or between approximately 0.5-5 nm. In some embodiments, a distance between two detection probes when they are in sufficiently close proximity to each other may be less than 100 nm or shorter, including, e.g., less than 90 nm, less than 80 nm, less than 70 nm, less than 60 nm, less than 50 nm, less than 40 nm, less than 30 nm, less than 20 nm, less than 10 nm, less than 5 nm, less than 1 nm, or shorter. In some embodiments, a distance between two detection probes when they are in sufficiently close proximity to each other may range between approximately 40-1000 nm or 40 nm-500 nm.

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Complementary: As used herein, the term "complementary" is used in reference to oligonucleotide hybridization related by base-pairing rules. For example, the sequence "C-A-G-T" is complementary to the sequence "G-T-C-A." Complementarity can be partial or total. Thus, any degree of partial complementarity is intended to be included within the scope of the term "complementary" provided that the partial complementarity permits oligonucleotide hybridization. Partial complementarity is where one or more nucleic acid bases is not matched according to the base pairing rules. Total or complete complementarity between nucleic acids is where each and every nucleic acid base is matched with another base under the base pairing rules.

Disease: As used herein, the term "disease" refers to a disorder or condition that typically impairs normal functioning of a tissue or system in a subject (e.g., a human subject) and is typically manifested by characteristic signs and/or symptoms. Examples of diseases that are amenable for detection in accordance with the present disclosure include, but are not limited to autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

Detecting: The term "detecting" is used broadly herein to include appropriate means of determining the presence or absence of an entity of interest or any form of measurement of an entity of interest (e.g., a ligated template) after a sample is contacted with detection probes as described and/or utilized herein. Thus, "detecting" may include determining, measuring, assessing, or assaying the presence or absence, level, amount, and/or location of an entity of interest (e.g., a surface protein biomarker, and/or an intravesicular protein biomarker, and/or an intravesicular RNA biomarker, and/or a form of measurement indicative of aforementioned entity of interest, e.g., a ligated template indicative of a surface protein biomarker and/or an intravesicular protein biomarker, or a PCR amplification product indicative of an intravesicular mRNA) that corresponds to part of a target biomarker signature in any way. Quantitative and qualitative determinations, measurements or assessments are included, including semi-quantitative. Such determinations, measurements or assessments may be relative, for example when an entity of interest (e.g., a surface protein biomarker, and/or an intravesicular protein biomarker, and/or an intravesicular RNA biomarker, and/or a form of measurement indicative of aforementioned entity of interest, e.g., a ligated template indicative of a surface protein biomarker and/or an intravesicular protein biomarker, or a PCR amplification product indicative of an intravesicular mRNA) is being detected relative to a control reference, or absolute. As such, the term "quantifying" when used in the context of quantifying an entity of interest (e.g., a surface protein biomarker, and/or an intravesicular protein biomarker, and/or an intravesicular RNA biomarker, and/or a form of measurement indicative of aforementioned entity of interest, e.g., a ligated template indicative of a surface protein biomarker and/or an intravesicular protein biomarker, or a PCR amplification product indicative of an intravesicular mRNA) can refer to absolute or to relative quantification. Absolute quantification may be accomplished by correlating a detected level of an entity of interest (e.g., a surface protein biomarker, and/or an intravesicular protein biomarker, and/or an intravesicular RNA biomarker, and/or a form of measurement indicative of aforementioned entity of interest, e.g., a ligated template indicative of a surface protein biomarker and/or an intravesicular protein biomarker, or a PCR amplification product indicative of an intravesicular mRNA) to known control standards (e.g., through generation of a standard curve). Alternatively, relative quantification can be accomplished by comparison of detected levels or amounts between two or more different entities of interest (e.g., different surface protein biomarkers, and/or intravesicular protein biomarkers, and/or intravesicular RNA biomarkers) to provide a relative quantification of each of the two or more different entities of interest, i.e., relative to each other.

Detection label: The term "detection label" as used herein refers to any element, molecule, functional group, compound, fragment or moiety that is detectable. In some embodiments, a detection label is provided or utilized alone. In some embodiments, a detection label is provided and/or utilized in association with (e.g., joined to) another agent. Examples of detection labels include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$, etc.), fluorescent dyes, chemiluminescent agents (such as, for example, acridinium esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes, colorimetric labels (such as, for example, dyes, colloidal gold, and the like), biotin, digoxigenin, haptens, and proteins for which antisera or monoclonal antibodies are available.

Detection probe: The term "detection probe" typically refers to a probe directed to detection of a specific target. In accordance with the present disclosure, a detection probe refers to a composition comprising a target binding entity, directly or indirectly, coupled to an oligonucleotide domain, wherein the target binding entity specifically binds to a respective target (e.g., molecular target), and wherein at least a portion of the oligonucleotide domain is designed to permit hybridization with a portion of an oligonucleotide domain of another detection probe for a distinct target. In many embodiments, an oligonucleotide domain appropriate for use in the accordance with the present disclosure comprises a double-stranded portion and at least one single-stranded overhang. In some embodiments, an oligonucleotide domain may comprise a double-stranded portion and a single-stranded overhang at each end of the double-stranded portion.

Double-stranded: As used herein, the term "double-stranded" in the context of oligonucleotide domain is understood by those of skill in the art that a pair of oligonucleotides exist in a hydrogen-bonded, helical arrangement typically associated with, for example, nucleic acid such as DNA. In addition to the 100% complementary form of double-stranded oligonucleotides, the term "double-stranded" as used herein is also meant to refer to those forms which include mismatches (e.g., partial complementarity) and/or structural features as bulges, loops, or hairpins.

Double-stranded complex: As used herein, the term "double-stranded complex" typically refers to a complex comprising at least two or more (including, e.g., 2, 3, 4, 5, 6, 7, 8, 9, 10, 11, 12, 13, 14, 15, 16, 17, 18, 19, 20, or more) detection probes (e.g., as provided and/or utilized herein), each directed to a target (which can be the same target or a distinct target), connected or coupled to one another in a linear arrangement through hybridization of complementary single-stranded overhangs of the detection probes. In some embodiments, such a double-stranded complex may comprise a biological entity (e.g., an extracellular vesicle), wherein respective target binding moieties of the detection probes are simultaneously bound to the biological entity (e.g., extracellular vesicle).

Epitope: As used herein, the term "epitope" includes any moiety that is specifically recognized by an immunoglobulin (e.g., antibody or receptor) binding component or an aptamer. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Extracellular vesicle: As used herein, the term "extracellular vesicle" typically refers to a vesicle outside of a cell, e.g., secreted by a cell. Examples of secreted vesicles include, but are not limited to exosomes, microvesicles, microparticles, ectosomes, oncosomes, and apoptotic bodies. Without wishing to be bound by theory, exosomes are nanometer-sized vesicles (e.g., between 40 nm and 120 nm) of endocytic origin that may form by inward budding of the limiting membrane of multivesicular endosomes (MVEs), while microvesicles typically bud from the cell surface and their size may vary between 50 nm and 1000 nm. In some embodiments, an extracellular vesicle is or comprises an exosome and/or a microvesicle. In some embodiments, a sample comprising an extracellular vesicle is substantially free of apoptotic bodies. In some embodiments, a sample comprising extracellular vesicles may comprise extracellular vesicles shed or derived from one or more tissues (e.g., cancerous tissues and/or non-cancerous or healthy tissues). In some embodiments, an extracellular vesicle in a sample may be shed from or derived from a tissue that is associated with a disease, disorder, or condition. In some embodiments, an extracellular vesicle in a sample may be shed or derived from a tumor of a target cancer; in some embodiments, an extracellular vesicle is shed or derived from a tumor of a non-target cancer. In some embodiments, an extracellular vesicle is shed or derived from a healthy tissue. In some embodiments, an extracellular vesicle is shed or derived from a benign tumor. In some embodiments, an extracellular vesicle is shed or derived from a tissue of a subject with symptoms (e.g., non-specific symptoms) associated with cancer.

Extracellular vesicle-associated membrane-bound polypeptide: As used herein, such a term refers to a polypeptide that is present in the membrane of an extracellular vesicle. In some embodiments, such a polypeptide may be tumor-specific. In some embodiments, such a polypeptide may be tissue-specific (e.g., a tissue that is specific to a target tissue such as skin, lung, pancreas, reproductive system, etc.). In some embodiments, such a polypeptide may be non-specific, e.g., it is present in one or more non-target tumors, and/or in one or more non-target tissues.

Hybridization: As used herein, the term "hybridizing", "hybridize", "hybridization", "annealing", or "anneal" are used interchangeably in reference to pairing of complementary nucleic acids using any process by which a strand of nucleic acid joins with a complementary strand through base pairing to form a hybridization complex. Hybridization and the strength of hybridization (e.g., strength of the association between the nucleic acids) is impacted by various factors including, e.g., the degree of complementarity between the nucleic acids, stringency of the conditions involved, the melting temperature (T) of the formed hybridization complex, and the G:C ratio within the nucleic acids.

Intravesicular protein biomarker: As used herein, the term "intravesicular protein biomarker" refers to a marker indicative of the state (e.g., presence, level, and/or activity) of a polypeptide that is present within a biological entity (e.g., a cell or an extracellular vesicle). In many embodiments, an intravesicular protein biomarker is associated with or present within an extracellular vesicle.

Intravesicular RNA biomarker: As used herein, the term "intravesicular RNA biomarker" refers to a marker indicative of the state (e.g., presence and/or level) of a RNA (e.g., mRNA) that is present within a biological entity (e.g., a cell or an extracellular vesicle). In many embodiments, an intravesicular RNA biomarker is associated with or present within an extracellular vesicle.

Ligase: As used herein, the term "ligase" or "nucleic acid ligase" refers to an enzyme for use in ligating nucleic acids. In some embodiments, a ligase is enzyme for use in ligating a 3'-end of a polynucleotide to a 5'-end of a polynucleotide. In some embodiments, a ligase is an enzyme for use to perform a sticky-end ligation. In some embodiments, a ligase is an enzyme for use to perform a blunt-end ligation. In some embodiments, a ligase is or comprises a DNA ligase.

Ligation: As used herein, the term "ligate", "ligating or "ligation" refers to a method or composition known in the art for joining two oligonucleotides or polynucleotides. A ligation may be or comprise a sticky-end ligation or a blunt-end ligation. In some embodiments, ligation involved in provided technologies is or comprises a sticky-end ligation. In some embodiments, ligation refers to joining a 3' end of a polynucleotide to a 5' end of a polynucleotide. In some embodiments, ligation is facilitated by use of a nucleic acid ligase.

Non-cancer subjects: As used herein, the term "non-cancer subjects" generally refers to subjects who do not have non-benign cancer of interest. For example, in some embodiments, a non-cancer subject is a healthy subject. In some embodiments, a non-cancer subject is a healthy subject of a certain age group. In some embodiments, a non-cancer subject is a subject with a disease, disorder, or condition that is not associated with a target cancer. In some embodiments, a non-cancer subject is a subject having a benign tumor.

Nucleic acid/Oligonucleotide: As used herein, the term "nucleic acid" refers to a polymer of at least 10 nucleotides or more. In some embodiments, a nucleic acid is or comprises DNA. In some embodiments, a nucleic acid is or comprises RNA. In some embodiments, a nucleic acid is or comprises peptide nucleic acid (PNA). In some embodiments, a nucleic acid is or comprises a single stranded nucleic acid. In some embodiments, a nucleic acid is or comprises a double-stranded nucleic acid. In some embodiments, a nucleic acid comprises both single and double-stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long.

Nucleotide: As used herein, the term "nucleotide" refers to its art-recognized meaning. When a number of nucleotides is used as an indication of size, e.g., of an oligonucleotide, a certain number of nucleotides refers to the number of nucleotides on a single strand, e.g., of an oligonucleotide.

Patient: As used herein, the term "patient" refers to any organism who is suffering or at risk of a disease or disorder or condition. Typical patients include animals (e.g., mammals such as mice, rats, rabbits, non-human primates, and/or humans). In some embodiments, a patient is a human. In some embodiments, a patient is suffering from or susceptible to one or more diseases or disorders or conditions. In some embodiments, a patient displays one or more symptoms of a disease or disorder or condition. In some embodiments, a patient has been diagnosed with one or more diseases or disorders or conditions. In some embodiments, a disease or disorder or condition that is amenable to provided technologies is or includes cancer, or presence of one or more tumors. In some embodiments, a patient is receiving or has received certain therapy to diagnose and/or to treat a disease, disorder, or condition.

Polypeptide: The term "polypeptide", as used herein, typically has its art-recognized meaning of a polymer of at least three amino acids or more. Those of ordinary skill in the art will appreciate that the term "polypeptide" is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. In some embodiments, polypeptides may contain L-amino acids, D-amino acids, or both and/or may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof (e.g., may be or comprise peptidomimetics).

Prevent or prevention: As used herein, "prevent" or "prevention," when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Primer: As used herein, the term "primer" refers to an oligonucleotide capable of acting as a point of initiation of synthesis when placed under conditions in which synthesis of a primer extension product which is complementary to a nucleic acid strand is induced (e.g., in the presence of nucleotides and an inducing agent such as DNA polymerase and at a suitable temperature and pH). A primer is preferably single stranded for maximum efficiency in amplification. A primer must be sufficiently long to prime the synthesis of extension products in the presence of the inducing agent. The exact lengths of a primer can depend on many factors, e.g., temperature.

Reference: As used herein, "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. In some embodiments, a reference or control in the context of a reference level of a target refers to a level of a target in a normal healthy subject or a population of normal healthy subjects. In some embodiments, a reference or control in the context of a reference level of a target refers to a level of a target in a subject prior to a treatment. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Risk: As will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Sample: As used herein, the term "sample" typically refers to an aliquot of material obtained or derived from a source of interest. In some embodiments, a sample is obtained or derived from an environmental source (including, e.g., soil, water, air, contact surface, etc.) of interest. In some embodiments, a sample is obtained or derived from a biological source (e.g., a tissue or organism or cell culture) of interest. In some embodiments, a source of interest may be or comprise a cell or an organism, such as an animal or human. In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravesicular fluid (blood plasma), an interstitial fluid, a lymphatic fluid, and/or a transcellular fluid. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., broncheoalveolar, ductal, nasal, ocular, oral, uterine, vaginal, or other washing or lavage). In some embodiments, a biological sample is or comprises a liquid biopsy. In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, a sample is a preparation that is processed by using a semi-permeable membrane or an affinity-based method such antibody-based method to separate a biological entity of interest from other non-target entities. Such a "processed sample" may comprise, for example, in some embodiments extracellular vesicles, while, in some embodiments, nucleic acids and/or proteins, etc., extracted from a sample. In some embodiments, a processed sample can be obtained by subjecting a primary sample to one or more techniques such as amplification or reverse transcription of nucleic acid, isolation and/or purification of certain components, etc.

Selective or specific: The term "selective" or "specific", when used herein with reference to an agent having an activity, is understood by those skilled in the art to mean that the agent discriminates between potential target entities, states, or cells. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of a target-binding moiety for one or more other potential target entities (e.g., competitors). In some embodiments, specificity is evaluated relative to that of a reference specific binding moiety. In some embodiments, specificity is evaluated relative to that of a reference non-specific binding moiety. In some embodiments, a target-binding moiety does not detectably bind to the competing alternative target under conditions of binding to its target entity. In some embodiments, a target-binding moiety binds with higher on-rate, lower off-rate, increased affinity, decreased dissociation, and/or increased stability to its target entity as compared with the competing alternative target(s).

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is biologically active. In some embodiments, suitable small molecules may be identified by methods such as screening large libraries of compounds (Beck-Sickinger & Weber (2001) *Combinational Strategies in Biology and Chemistry* (John Wiley & Sons, Chichester, Sussex); by structure-activity relationship by nuclear magnetic resonance (Shuker et al. (1996) "Discovering high-affinity ligands for proteins: SAR by NMR." *Science* 274:1531-1534); encoded self-assembling chemical libraries (Melkko et al. (2004) "Encoded self-assembling chemical libraries." *Nature Biotechnol.* 22:568-574); DNA-templated chemistry (Gartner et al. (2004) "DNA-templated organic synthesis and selection of a library of macrocycles." *Science* 305:1601-1605); dynamic combinatorial chemistry (Ramstrom & Lehn (2002) "Drug discovery by dynamic combinatorial libraries." *Nature Rev. Drug Discov.* 1:26-36); tethering (Arkin & Wells (2004) "Small-molecule inhibitors of protein-protein interactions: progressing towards the dream." *Nature Rev. Drug Discov.* 3:301-317); and speed screen (Muckenschnabel et al. (2004) "SpeedScreen: label-free liquid chromatography-mass spectrometry-based high-throughput screening for the discovery of orphan protein ligands." *Anal. Biochem.* 324:241-249). In some embodiments, a small molecule may have a dissociation constant for a target in the nanomolar range.

Specific binding: As used herein, the term "specific binding" refers to an ability to discriminate between possible binding partners in the environment in which binding is to occur. A target-binding moiety that interacts with one particular target when other potential targets are present is said to "bind specifically" to the target with which it interacts. In some embodiments, specific binding is assessed by detecting or determining degree of association between a target-binding moiety and its partner; in some embodiments, specific binding is assessed by detecting or determining degree of dissociation of a target-binding moiety-partner complex; in some embodiments, specific binding is assessed by detecting or determining ability of a target-binding moiety to compete an alternative interaction between its partner and another entity. In some embodiments, specific binding is assessed by performing such detections or determinations across a range of concentrations.

Stage of cancer: As used herein, the term "stage of cancer" refers to a qualitative or quantitative assessment of the level of advancement of a cancer. In some embodiments, criteria used to determine the stage of a cancer may include, but are not limited to, one or more of where the cancer is located in a body, tumor size, whether the cancer has spread to lymph nodes, whether the cancer has spread to one or more different parts of the body, etc. In some embodiments, cancer may be staged using the AJCC staging system. The AJCC staging system is a classification system, developed by the American Joint Committee on Cancer for describing the extent of disease progress in cancer patients, which utilizes in part the TNM scoring system: Tumor size, Lymph Nodes affected, Metastases. In some embodiments, cancer may be staged using a classification system that in part involves the TNM scoring system, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present but have not spread to nearby tissue, also called carcinoma in situ, or CIS; CIS is not cancer, but it may become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ (abnormal cells are present but have not spread to nearby tissue); localized (cancer is limited to the place where it started, with no sign that it has spread); regional (cancer has spread to nearby lymph nodes, tissues, or organs): distant (cancer has spread to distant parts of the body); and unknown (there is not enough information to figure out the stage).

Subject: As used herein, the term "subject" refers to an organism from which a sample is obtained, e.g., for experimental, diagnostic, prophylactic, and/or therapeutic purposes. Typical subjects include animals (e.g., mammals such as mice, rats, rabbits, non-human primates, domestic pets, etc.) and humans. In some embodiments, a subject is a human subject. In some embodiments, a subject is suffering from a disease, disorder, or condition (e.g., cancer). In some embodiments, a subject is susceptible to a disease, disorder, or condition (e.g., cancer). In some embodiments, a subject displays one or more symptoms or characteristics of a disease, disorder, or condition (e.g., cancer). In some embodiments, a subject displays one or more non-specific symptoms of a disease, disorder, or condition (e.g., cancer). In some embodiments, a subject does not display any symptom or characteristic of a disease, disorder, or condition (e.g., cancer). In some embodiments, a subject is someone with one or more features characteristic of susceptibility to or risk of a disease, disorder, or condition (e.g., cancer). In some embodiments, a subject is a patient. In some embodiments, a subject is an individual to whom diagnosis and/or therapy is and/or has been administered. In some embodiments, a subject is a subject determined to have a benign tumor or mass. In some embodiments, a subject is an asymptotic subject. Such an symptomatic subject may be a subject at average population risk or with hereditary risk for a disease, disorder, or condition (e.g., a particular cancer). For example, such an asymptomatic subject may be a subject who has a family history of cancer, who has been previously treated for cancer, who is at risk of cancer recurrence after cancer treatment, who is in remission after cancer treatment, and/or who has been previously or periodically screened for the presence of at least one cancer biomarker. Alternatively, in some embodiments, an asymptomatic subject may be a subject who has not been previously screened for cancer, who has not been diagnosed for cancer, and/or who has not previously received cancer therapy. In some embodiments, a subject amenable to provided technologies is an individual selected based on one or more characteristics such as age, race, genetic history, medical history, personal history (e.g., smoking, alcohol, drugs, carcinogenic agents, diet, obesity, physical activity, sun exposure, radiation exposure, exposure to infectious agents such as viruses, and/or occupational hazard).

Suffering from: An individual who is "suffering from" a disease, disorder, and/or condition has been diagnosed with and/or displays one or more symptoms of a disease, disorder, and/or condition.

Surface polypeptide or surface protein: As used interchangeably herein, the terms "surface polypeptide," "surface protein," and "membrane-bound polypeptide" refer to a polypeptide or protein with one or more domains or regions present in and/or on the surface of the membrane of a biological entity (e.g., a cell, an extracellular vesicle, etc.). In some embodiments, a surface protein may comprise one or more domains or regions spanning and/or associated with the plasma membrane of a biological entity (e.g., a cell, an extracellular vesicle, etc.). In some embodiments, a surface protein may comprise one or more domains or regions spanning and/or associated with the plasma membrane of a biological entity (e.g., a cell, an extracellular vesicle, etc.) and also protruding into the intracellular and/or intravesicular space. In some embodiments, a surface protein may comprise one or more domains or regions associated with the plasma membrane of a biological entity (e.g., a cell, an extracellular vesicle, etc.), for example, via one or more non-peptidic linkages. In some embodiments, a surface protein may comprise one or more domains or regions that is/are anchored into either side of plasma membrane of a biological entity (e.g., a cell, an extracellular vesicle, etc.). In some embodiments, a surface protein is associated with or present within an extracellular vesicle. In some embodiments, a surface polypeptide or membrane-bound polypeptide may be associated with or present within an extracellular vesicle from a subject (e.g., an extracellular vesicle obtained or derived from a blood or blood-derived sample of a subject suffering from or susceptible to a disease, disorder, or condition (e.g., cancer)). As will be understood by a skilled artisan, detection of the presence of at least a portion of a surface polypeptide or surface protein on/within extracellular vesicles can facilitate separation and/or isolation of extracellular vesicles from a biological sample (e.g., a blood or blood-derived sample) from a subject. In some embodiments, detection of the presence of a surface polypeptide or surface protein may be or comprise detection of an intravesicular portion (e.g., an intravesicular epitope) of such a surface polypeptide or surface protein. In some embodiments, detection of the presence of a surface polypeptide or surface protein may be or comprise detection of a membrane-spanning portion of such a surface polypeptide or surface protein. In some embodiments, detection of the presence of a surface polypeptide or surface protein may be or comprise detection of an extravesicular portion of such a surface polypeptide or surface protein.

Surface protein biomarker: As used herein, the term "surface protein biomarker" refers to a marker indicative of the state (e.g., presence, level, and/or activity) of a surface protein (e.g., as described herein) of a biological entity (e.g., a cell or an extracellular vesicle). In some embodiments, a surface protein refers to a polypeptide or protein with one or more domains or regions located in or on the surface of the membrane of a biological entity (e.g., a cell or an extracellular vesicle). In some embodiments, a surface protein biomarker may be or comprise an epitope that is present on the interior side (intravesicular) or the exterior side (extravesicular) of the membrane. In some embodiments, a surface protein biomarker is associated with or present in an extracellular vesicle.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder, and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target-binding moiety: In general, the terms "target-binding moiety" and "binding moiety" is used interchangeably herein to refer to any entity or moiety that binds to a target of interest (e.g., molecular target of interest such as a biomarker or an epitope). In many embodiments, a target-binding moiety of interest is one that binds specifically with its target (e.g., a target biomarker) in that it discriminates its target from other potential binding partners in a particular interaction context. In general, a target-binding moiety may be or comprise an entity or moiety of any chemical class (e.g., polymer, non-polymer, small molecule, polypeptide, carbohydrate, lipid, nucleic acid, etc.). In some embodiments, a target-binding moiety is a single chemical entity. In some embodiments, a target-binding moiety is a complex of two or more discrete chemical entities associated with one another under relevant conditions by non-covalent interactions. For example, those skilled in the art will appreciate that in some embodiments, a target-binding moiety may comprise a "generic" binding moiety (e.g., one of biotin/avidin/streptavidin and/or a class-specific antibody) and a "specific" binding moiety (e.g., an antibody or aptamers with a particular molecular target) that is linked to the partner of the generic biding moiety. In some embodiments, such an approach can permit modular assembly of multiple target binding moieties through linkage of different specific binding moieties with a generic binding moiety partner.

Figure 5A:
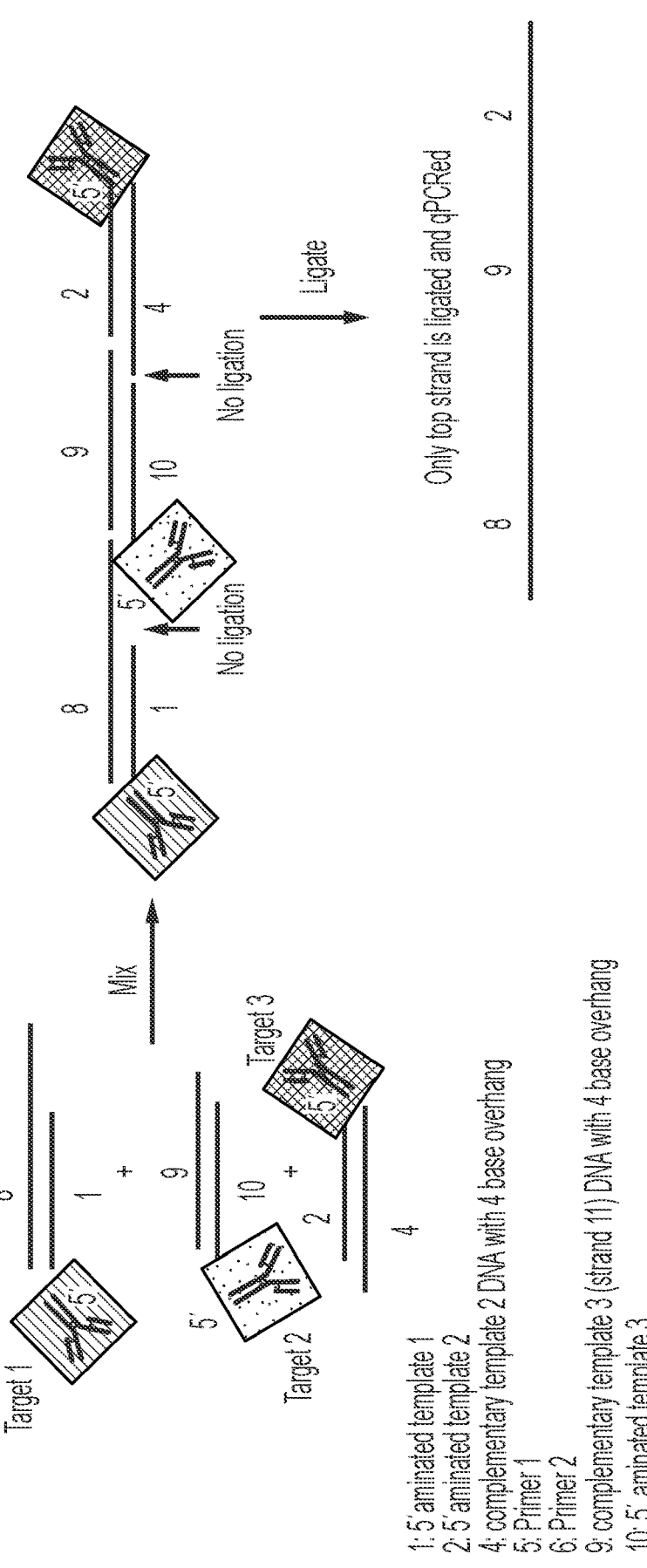
FIG. 5A is a schematic diagram illustrating a target entity detection assay according to some embodiments described herein. The figure shows an exemplary triplex target entity detection system, in which in some embodiments, three or more detection probes, each for a target protein, can be added to a sample comprising a biological entity (e.g., extracellular vesicle). In some embodiments, detection probes each comprise a target binding moiety (e.g., an antibody agent against a target protein) coupled to an oligonucleotide domain, which comprises a double-stranded portion and a single-stranded overhang extended from one end of the oligonucleotide domain. A detection signal is generated when the corresponding single-stranded overhangs of all three or more detection probes hybridize to each other to form a linear double-stranded complex, and ligation of at least one strand of the double-stranded complex occurs, thus allowing a resulting ligated product to be detected.
Figure 5B:
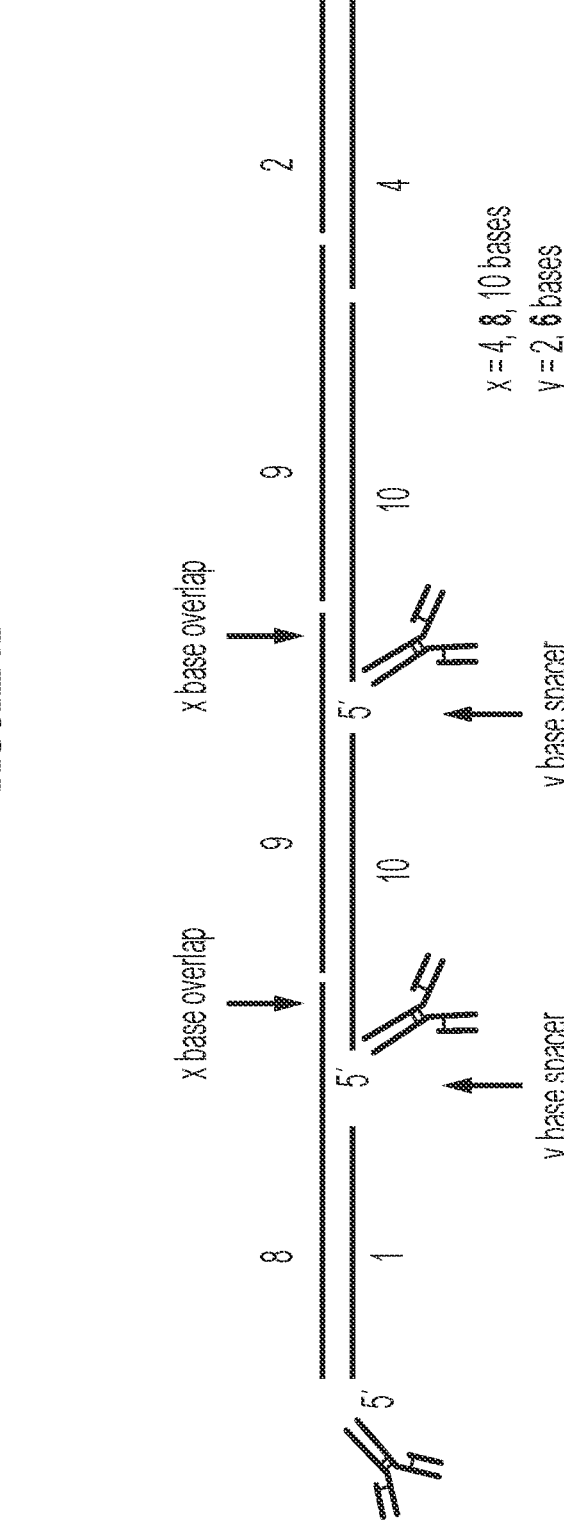
FIG. 5B is a non-limiting example of a double-stranded complex comprising four detection probes connected to each other in a linear arrangement through hybridization of their respective single-stranded overhangs.
Figure 10:
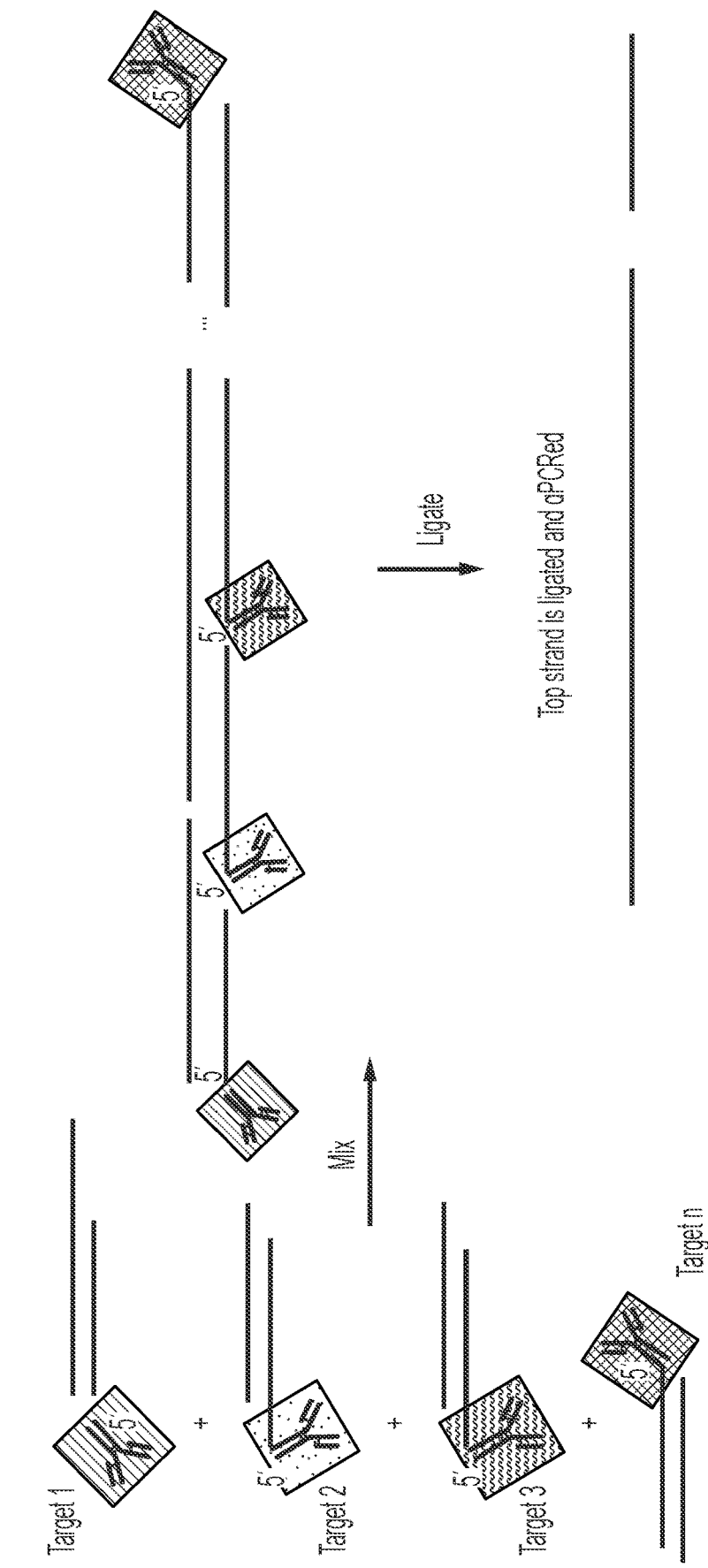
FIG. 10 is a schematic diagram illustrating a target entity detection assay of an exemplary embodiment described herein. In some embodiments, a plurality of detection probes, each for a distinct target, are added to a sample comprising a biological entity (e.g., extracellular vesicle). In some embodiments, detection probes each comprise a target binding moiety (e.g., an antibody agent) coupled to an oligonucleotide domain, which comprises a double-stranded portion and a single-stranded overhang extended from one end of the oligonucleotide domain. A detection signal is generated when all detection probes are localized to the same biological entity (e.g., an extracellular vesicle or analyte) in close proximity such that the corresponding single-stranded overhangs hybridize to form a linear double-stranded complex, and ligation of at least one strand of the resulting linear double-stranded complex occurs, thereby allowing a ligated product to be detected.

Target biomarker signature: The term "target biomarker signature", as used herein, refers to a combination of (e.g., at least 2 or more, including, e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, or more) biomarkers, which combination correlates with a particular biological event or state of interest, so that one skilled in the art will appreciate that it may appropriately be considered to be a "signature" of that event or state. To give but a few examples, in some embodiments, a target biomarker signature may correlate with a particular disease or disease state, and/or with likelihood that a particular disease, disorder or condition may develop, occur, or reoccur. In some embodiments, a target biomarker signature may correlate with a particular disease or therapeutic outcome, or likelihood thereof. In some embodiments, a target biomarker signature may correlate with a specific cancer and/or a stage and/or a subtype thereof. In some embodiments, a target biomarker signature comprises a combination of (e.g., at least 2 or more, including, e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, or more) biomarkers that together are specific for a particular cancer or a subtype and/or a disease stage thereof), though one or more biomarkers in such a combination may be directed to a target (e.g., a surface protein biomarker, an intravesicular protein biomarker, and/or an intravesicular RNA) that is not specific to the cancer. In some embodiments, a combination of biomarkers that constitutes a target biomarker signature may be detected by a plurality of (e.g., at least two or more) pairwise or orthogonal combinations of detection probes, wherein each pair of detection probes may be directed to at least one distinct target. In some embodiments, a combination of biomarkers that constitutes a target biomarker signature may be detected by a set of detection probes that each are designed to hybridize to one another to form a linear complex (see, e.g., as shown in FIGS. 5A-5B, and FIG. 10). For example, in some embodiments, a target biomarker signature may comprise at least one biomarker specific to a particular cancer or a stage and/or subtype thereof (i.e., a cancer-specific target), and may further comprise a biomarker that is not necessarily or completely specific for the cancer (e.g., that may also be found on some or all biological entities such as, e.g., cells, extracellular vesicles, etc., that are not cancerous, are not of the relevant cancer, and/or are not of the particular stage and/or subtype of interest). That is, as will be appreciated by those skilled in the art reading the present specification, so long as a combination of biomarkers utilized in a target biomarker signature is or comprises a plurality of biomarkers that together are specific for the relevant target biological entities of interest (e.g., cancer cells of interest or extracellular vesicles secreted by cancer cells) (i.e., sufficiently distinguish the relevant target biological entities (e.g., cancer cells of interest or extracellular vesicles secreted by cancer cells) for detection from other biological entities not of interest for detection), such a combination of biomarkers is a useful target biomarker signature in accordance with certain embodiments of the present disclosure.

Therapeutic agent: As used interchangeably herein, the phrase "therapeutic agent" or "therapy" refers to an agent or intervention that, when administered to a subject or a patient, has a therapeutic effect and/or elicits a desired biological and/or pharmacological effect. In some embodiments, a therapeutic agent or therapy is any substance that can be used to alleviate, ameliorate, relieve, inhibit, prevent, delay onset of, reduce severity of, and/or reduce incidence of one or more symptoms or features of a disease, disorder, and/or condition. In some embodiments, a therapeutic agent or therapy is a medical intervention (e.g., surgery, radiation, phototherapy) that can be performed to alleviate, relieve, inhibit, present, delay onset of, reduce severity of, and/or reduce incidence of one or more symptoms or features of a disease, disorder, and/or condition.

Threshold level (e.g., cutoff): As used herein, the term "threshold level" refers to a level that are used as a reference to attain information on and/or classify the results of a measurement, for example, the results of a measurement attained in an assay. For example, in some embodiments, a threshold level (e.g., a cutoff) means a value measured in an assay that defines the dividing line between two subsets of a population (e.g., normal and/or non-cancer vs. cancer of interest). Thus, a value that is equal to or higher than the threshold level defines one subset of the population, and a value that is lower than the threshold level defines the other subset of the population. A threshold level can be determined based on one or more control samples or across a population of control samples. A threshold level can be determined prior to, concurrently with, or after the measurement of interest is taken. In some embodiments, a threshold level can be a range of values.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition. In some embodiments, treatment may be administered to a subject at a later-stage of disease, disorder, and/or condition.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

The present disclosure, among other things, provide technologies relating to target entity detection approach based on interaction and/or co-localization of molecules or epitopes on or in individual entities of interest (e.g., biological entities). Such technologies can be useful for detecting entities of interest in various types of samples for different applications and/or purposes. For example, the present disclosure, among other things, provides insights and technologies for achieving effective screening of diseases or disorders (e.g., cancers). In some embodiments, provided technologies are effective for detection of early-stage cancers. In some embodiments, the present disclosure provides technologies for screening subjects at hereditary and average risk for early-stage cancer. In some embodiments, provided technologies are effective even when applied to populations comprising or consisting of asymptomatic or symptomatic individuals (e.g., due to sufficiently high sensitivity and/or low rates of false-positive and/or false-negative results). In some embodiments, provided technologies are effective when applied to populations comprising or consisting of individuals (e.g., asymptomatic or symptomatic individuals) without hereditary risk in developing cancer. In some embodiments, provided technologies are effective when applied to populations comprising or consisting of individuals (e.g., asymptomatic or symptomatic individuals) with hereditary risk in developing cancer. In some embodiments, provided technologies are effective when applied to populations comprising or consisting of individuals susceptible to cancer (e.g., individuals with a known genetic, environmental, or experiential risk, etc.). In some embodiments, provided technologies may be or include one or more compositions (e.g., molecular entities or complexes, systems, cells, collections, combinations, kits, etc.) and/or methods (e.g., of making, using, assessing, etc.), as will be clear to one skilled in the art reading the disclosure provided herein.

In some embodiments, provided technologies provide technical advantages over certain prior technologies including, for example, certain conventional approaches to cancer detection and diagnosis. For example, the present disclosure appreciates that many conventional diagnostic assays, e.g., based on cell-free nucleic acids, circulating tumor cells, protein, serum proteins, and/or bulk analysis of extracellular vesicles, can be time-consuming, costly, and/or lacking sensitivity and/or specificity sufficient to provide a reliable and comprehensive diagnostic assessment. Specifically, the present disclosure, among other things, recognizes that detection of a single cancer-associated biomarker in a biological entity (e.g., extracellular vesicle) or a plurality of cancer-associated biomarkers based on a bulk sample, rather than at a resolution of a single biological entity, typically does not provide sufficient specificity and/or sensitivity in determination of whether a subject from whom the biological entity is obtained is likely to be suffering from or susceptible to cancer. The present disclosure, among other things, provides technologies, including systems, compositions and methods, that solve such problems, including for example by specifically requiring that individual entities for detection be characterized by presence of a combination of targets (e.g., molecular targets). In particular embodiments, the present disclosure teaches technologies that require such individual entities be characterized by presence (e.g., by expression) of a combination (e.g., a set) of molecular targets that is cancer specific (i.e., "target biomarker signature" of a relevant cancer), while biological entities that do not comprise the targeted combination do not produce a detectable signal.

In some embodiments, the present disclosure, among other things, provides insights that screening of asymptotic individuals, e.g., regular screening prior to or otherwise in absence of developed symptom(s), can be beneficial, and even important for effective management (e.g., successful treatment) of cancer. Alternatively or additionally, in some embodiments the present disclosure further provides insights that screening (e.g., regular screening) for different types of cancer (e.g., for a plurality of different cancers) can be beneficial, and even important for effective management (e.g., successful treatment) of cancer. In some embodiments, the present disclosure provides cancer screening systems that can be implemented, for example, to detect cancer, including early-stage cancer, in some embodiments in asymptomatic individuals (e.g., without hereditary risks in cancer). In some embodiments, provided technologies are implemented to achieve regular screening of asymptomatic individuals (e.g., with or without hereditary risk(s) in cancer) and/or for multiple cancers. In some embodiments, provided technologies are implemented to achieve regular screening of symptomatic individuals (E.g., with or without hereditary risk(s) in cancer). In some embodiments, provided technologies achieve detection (e.g., early detection, e.g., in asymptomatic individual(s) and/or population(s)) of one or more features (e.g., incidence, progression, responsiveness to therapy, recurrence, etc.) of a cancer (e.g., of a particular cancer and/or of a plurality of cancers), with sensitivity and/or specificity (e.g., rate of false-positive and/or false-negative results) appropriate to permit useful application of provided technologies to single-time and/or regular (e.g., periodic) assessment. In some embodiments, provided technologies are useful in conjunction with individuals' periodic physical examination. In some embodiments, provided technologies are useful in conjunction with treatment regimen(s); in some embodiments, provided technologies may improve one or more characteristics (e.g., rate of success according to an accepted parameter) of such treatment regimen(s). The present disclosure provides, for example, compositions (e.g., reagents, kits, components, etc.), and methods of providing and/or using them, including strategies that involve testing (e.g., regular testing) of one or more individuals (e.g., asymptomatic individuals and/or individuals suffering from or susceptible to a disease or disorder such as cancer). The present disclosure defines usefulness of such systems and provides compositions and methods for implementing them.

I. Provided Target Entity Detection Systems

The present disclosure provides target entity detection systems for detecting in a sample (e.g., in a biological, environmental, or other sample), in some embodiments at a single entity level, entities of interest (e.g., biological or chemical entities of interest, such as extracellular vesicles or analytes) comprising at least two or more targets (e.g., molecular targets). Those skilled in the art, reading the present disclosure, will recognize that provided target entity detection systems are useful for a wide variety of applications and/or purposes. For example, in some embodiments, provided target entity detection systems may be useful for medical applications and/or purposes. In some embodiments, provided target entity detection systems may be useful to screen (e.g., regularly screen) individuals (e.g., asymptomatic individuals) for a disease or condition (e.g., cancer). In some embodiments, provided target entity detection systems may be useful to screen (e.g., regularly screen) individuals (e.g., asymptomatic individuals) for different types of cancer (e.g., for a plurality of different cancers). In some embodiments, provided target entity detection systems are effective even when applied to populations comprising or consisting of asymptomatic individuals (e.g., due to sufficiently high sensitivity and/or low rates of false-positive and/or false-negative results). In some embodiments, provided target entity detection systems may be useful as a companion diagnostic in conjunction with a disease treatment.

In some embodiments, a target entity detection system includes a plurality of detection probes each for a specific target (e.g., a molecular target or a biomarker of a target biomarker signature). In some embodiments, such a system may comprise at least 2, at least 3, at least 4, at least 5, at least 6, at least 7, at least 8, at least 9, at least 10, at least 15, at least 20, at least 25, at least 30, at least 40, at least 50, or more detection probes each for a specific target (e.g., a molecular target or a biomarker of a target biomarker signature). In some embodiments, such a system may comprise 2-50 detection probes each for a specific target (e.g., a molecular target or a biomarker of a target biomarker signature). In some embodiments, such a system may comprise 2-30 detection probes each for a specific target (e.g., a molecular target or a biomarker of a target biomarker signature). In some embodiments, such a system may comprise 2-25 detection probes each for a specific target (e.g., a molecular target or a biomarker of a target biomarker signature). In some embodiments, such a system may comprise 5-30 detection probes each for a specific target (e.g., a molecular target or a biomarker of a target biomarker signature). In some embodiments, such a system may comprise 5-25 detection probes each for a specific target (e.g., a molecular target or a biomarker of a target biomarker signature). In some embodiments, at least two of such detection probes in a set may be directed to the same target (e.g., the same molecular target or the same biomarker of a target biomarker signature). In some embodiments, at least two of such detection probes in a set may be directed to the same epitope of the same target (e.g., the same molecular target or the same biomarker of a target biomarker signature). In some embodiments, at least two of such detection probes in a set may be directed to different epitopes of the same target (e.g., the same molecular target or the same biomarker of a target biomarker signature).

In some embodiments, detection probes appropriate for use in a target entity detection system provided herein may be used for detection of a single disease or condition, e.g., a particular cancer. In some embodiments, detection probes appropriate for use in a target entity detection system provided herein may permit detection of at least two or more diseases or conditions, e.g., different types of cancers (e.g., skin cancer vs. ovarian cancer), or different subtypes of a particular cancer; and/or different stages of a particular cancer. In some embodiments, detection probes appropriate for use in a target entity detection system provided herein may permit detection of a particular cancer of certain subtypes. By way of example only, in some embodiments for ovarian cancer detection, detection probes appropriate for use in a target entity detection system may permit detection of one or more subtypes of ovarian cancer, including, e.g., but not limited to high-grade serous ovarian cancer, endometrioid ovarian cancer, clear-cell ovarian cancer, low-grade serous ovarian cancer, and/or mucinous ovarian cancer. In some embodiments, detection probes appropriate for use in a target entity detection system provided herein may permit detection of a particular cancer of certain stages, including, e.g., stage I, stage II, stage III, and/or stage IV. Accordingly, in some embodiments, detection probes appropriate for use in a target entity detection system provided herein may comprise a plurality (e.g., at least 2, at least 3, at least 4, at least 5, at least 6, at least 7, at least 8, at least 9, at least 10, or more) of sets of detection probes, wherein each set is directed to detection of a different disease or a different type of disease or condition. For example, in some embodiments, detection probes appropriate for use in a target entity detection system provided herein may comprise a plurality (e.g., at least 2, at least 3, at least 4, at least 5, at least 6, at least 7, at least 8, at least 9, at least 10, or more) of sets of detection probes, wherein in some embodiments, each set is directed to detection of a different type of cancer, or in some embodiments, each set is directed to detection of the same cancer of various subtypes and/or stages.

Detection Probes

In some embodiments, a detection probe as provided and/or utilized herein comprises a target-binding moiety and an oligonucleotide domain coupled to the target-binding moiety. In some embodiments, an oligonucleotide domain coupled to a target-binding moiety may comprise a double-stranded portion and a single-stranded overhang extended from at least one end of the oligonucleotide domain. In some embodiments, an oligonucleotide domain coupled to a target-binding moiety may comprise a double-stranded portion and a single-stranded overhang extended from each end of the oligonucleotide domain.

A. Target-Binding Moieties

A target-binding moiety that is coupled to an oligonucleotide domain is an entity or an agent that specifically binds to a target (e.g., molecular target or a biomarker of a target biomarker signature for a disease, disorder, or condition, e.g., cancer). In some embodiments, a target-binding moiety may have a binding affinity (e.g., as measured by a dissociation constant) for a target (e.g., molecular target) of at least about $10^{-4}$M, at least about $10^{-5}$M, at least about $10^{-6}$M, at least about $10^{-7}$M, at least about $10^{-8}$M, at least about $10^{-9}$M, or lower. Those skilled in the art will appreciate that, in some cases, binding affinity (e.g., as measured by a dissociation constant) may be influenced by non-covalent intermolecular interactions such as hydrogen bonding, electrostatic interactions, hydrophobic and Van der Waals forces between the two molecules. Alternatively or additionally, binding affinity between a ligand and its target molecule may be affected by the presence of other molecules. Those skilled in the art will be familiar with a variety of technologies for measuring binding affinity and/or dissociation constants in accordance with the present disclosure, including, e.g., but not limited to ELISAs, gel-shift assays, pull-down assays, equilibrium dialysis, analytical ultracentrifugation, surface plasmon resonance (SPR), bio-layer interferometry, grating-coupled interferometry, and spectroscopic assays.

In some embodiments, a target-binding moiety may be or comprise an agent of any chemical class such as, for example, a carbohydrate, a nucleic acid, a lipid, a metal, a polypeptide, a small molecule, etc., and/or a combination thereof. In some embodiments, a target-binding moiety may be or comprise an antibody agent and/or an aptamer. In some embodiments, a target-binding moiety is or comprises an antibody agent, e.g., an antibody agent that specifically binds to a target or an epitope thereof, e.g., a biomarker of a target biomarker signature for a disease, disorder, or condition (e.g., cancer) or an epitope thereof. In some embodiments, a target-binding moiety is or comprises an aptamer, e.g., an aptamer that specifically binds to a target or an epitope thereof, e.g., a biomarker of a target biomarker signature for a disease, disorder, or condition (e.g., cancer) or an epitope thereof. In some embodiments, a target may be or comprise a target that is associated with cancer. For example, in some such embodiments, a cancer-associated target can be or comprise a target is associated with more than one cancer (i.e., at least two or more cancers). In some embodiments, a cancer-associated target can be or comprise a target that is typically associated with cancers. In some embodiments, a cancer-associated target can be or comprise a target that is associated with cancers of a specific tissue. In some embodiments, a cancer-associated target can be or comprise a target that is specific to a particular cancer.

In some embodiments, a target-binding moiety recognizes and specifically binds to a target present in a biological entity (including, e.g., but not limited to cells and/or extracellular vesicles). For example, in some embodiments, a target-binding moiety may recognize a tumor-associated antigen or epitope thereof. In some embodiments, a tumor-associated antigen may be or comprise an antigen that is associated with a cancer such as, for example, acute lymphocytic leukemia, acute myeloid leukemia, bile duct cancer, bladder cancer, brain cancer (including, e.g., glioblastoma), breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer. In some embodiments, a target-binding moiety may recognize and specifically bind to a tumor antigen associated with skin cancer (e.g., melanoma). In some embodiments, a target-binding moiety may recognize a tumor antigen associated with lung cancer (e.g., non-small cell lung cancer). In some embodiments, a target-binding moiety may recognize a tumor antigen associated with breast cancer. In some embodiments, a target-binding moiety may recognize a tumor antigen associated with ovarian cancer (e.g., ovarian cancer of epithelial origin such as high-grade serous ovarian cancer).

In some embodiments, a target-binding moiety may specifically bind to an intracellular target. In some embodiments, a target-binding moiety may specifically bind to an intravesicular target, e.g., an intravesicular protein or RNA (e.g., mRNA).

In some embodiments, a target-binding moiety may specifically bind to a surface target. For example, in some embodiments, a target-binding moiety may specifically bind to a surface target that is present on/within a cell surface. In some embodiments, a target-binding moiety may specifically bind to a-surface target that is present on/within extracellular vesicles, e.g., a membrane-bound polypeptide present on/within extracellular vesicles associated with a disease, disorder, or condition (e.g., cancer).

In some embodiments, a target-binding moiety is directed to a biomarker for a specific condition or disease (e.g., cancer), which biomarker is or has been determined, for example, by analyzing a population or library (e.g. tens, hundreds, thousands, tens of thousands, hundreds of thousands, or more) of patient biopsies and/or patient data to identify such a biomarker (e.g., a predictive biomarker).

In some embodiments, a relevant biomarker may be one identified and/or characterized, for example, via data analysis. In some embodiments, for example, a diverse set of data (e.g., in some embodiments comprising one or more of bulk RNA sequencing, single-cell RNA (scRNA) sequencing, mass spectrometry, histology, post-translational modification data, in vitro and/or in vivo experimental data) can be analyzed through machine learning and/or computational modeling to identify biomarkers (e.g., predictive markers) that are highly specific to a disease or condition (e.g., cancer).

In some embodiments, a target-binding moiety is directed to a tissue-specific target, for example, a target that is associated with a specific tissue such as, for example, brain, breast, colon, ovary and/or other tissues associated with a female reproductive system, pancreas, prostate and/or other tissues associated with a male reproductive system, liver, lung, and skin. In some embodiments, such a tissue-specific target may be associated with a normal healthy tissue and/or a diseased tissue, such as a tumor. In some embodiments, a target-binding moiety is directed to a target that is specifically associated with a normal healthy condition of a subject.

In some embodiments, individual target-binding moieties utilized in a plurality of detection probes (e.g., as described and/or utilized herein) are directed to different targets. In some embodiments, such different targets may represent different marker proteins or polypeptides. In some embodiments, such different targets may represent different epitopes of the same marker proteins or polypeptides. In some embodiments, two or more individual target binding moieties utilized in a plurality of detection probes (e.g., as described and/or utilized herein) may be directed to the same target.

In some embodiments, individual target-binding moieties utilized in a plurality of detection probes for detection of a disease, disorder, or condition (e.g., cancer) may be directed to different target biomarkers of a target biomarker signature for a particular disease, disorder, or condition (e.g., a particular cancer). In some embodiments, individual target-binding moieties utilized in a plurality of detection probes for detection of a disease, disorder, or condition (e.g., cancer) may be directed to the same target biomarker of a target biomarker signature for a particular disease, disorder, or condition (e.g., a particular cancer). In some embodiments, such target binding moieties may be directed to the same or different epitopes of the same target biomarker of such a target biomarker signature for a particular disease, disorder, or condition (e.g., a particular cancer).

B. Oligonucleotide Domains

In some embodiments, an oligonucleotide domain for use in accordance with the present disclosure (e.g., that may be coupled to a target-binding moiety) may comprise a double-stranded portion and a single-stranded overhang extended from one or both ends of the oligonucleotide domain. In some embodiments where an oligonucleotide domain comprises a single-stranded overhang extended from each end, a single-stranded overhang is extended from a different strand of a double-stranded portion. In some embodiments where an oligonucleotide domain comprises a single-stranded overhang extended from one end of the oligonucleotide domain, the other end of the oligonucleotide domain may be a blunt end.

In some embodiments involving an oligonucleotide domain, at least one strand of a double-stranded portion comprises a primer site for amplification. In some such embodiments, such a primer site may be located at the end portion of the double stranded portion.

In some embodiments, an oligonucleotide domain may comprise ribonucleotides, deoxyribonucleotides, synthetic nucleotide residues that are capable of participating in Watson-Crick type or analogous base pair interactions, and any combinations thereof. In some embodiments, an oligonucleotide domain is or comprises DNA. In some embodiments, an oligonucleotide domain is or comprises peptide nucleic acid (PNA).

In some embodiments, an oligonucleotide may have a length that is determined, at least in part, for example, by, e.g., the physical characteristics of an entity of interest (e.g., biological entity such as extracellular vesicles) to be detected, and/or selection and localization of molecular targets in an entity of interest (e.g., biological entity such as extracellular vesicles) to be detected. In some embodiments, an oligonucleotide domain of a detection probe is configured to have a length such that when a first detection probe and a second detection probe bind to an entity of interest (e.g., biological entity such as extracellular vesicles), the first single-stranded overhang and the second single-stranded overhang are in sufficiently close proximity to permit interaction (e.g., hybridization) between the single-stranded overhangs. For example, when an entity of interest (e.g., biological entity) is an extracellular vesicle (e.g., an exosome), oligonucleotide domains of detection probes can each independently have a length such that their respective single-stranded overhangs are in sufficiently close proximity to anneal or interact with each other when the corresponding detection probes are bound to the same extracellular vesicle. For example, in some embodiments, oligonucleotide domains of detection probes for use in detecting extracellular vesicles (e.g., an exosome) may each independently have a length of about 20 nm to about 200 nm, about 40 nm to about 500 nm, about 40 nm to about 300 nm, or about 50 nm to about 150 nm. In some embodiments, oligonucleotide domains of detection probes for use in detecting extracellular vesicles (e.g., an exosome) may each independently have a length of about 20 nm to about 200 nm. In some embodiments, lengths of oligonucleotide domains of detection probes in a set can each independently vary to increase and/or maximize the probability of them finding each other when they simultaneously bind to the same entity of interest.

Accordingly, in some embodiments, an oligonucleotide domain for use in technologies provided herein may have a length in the range of about 30 up to about 1000 nucleotides. In some embodiments, an oligonucleotide domain may have a length in the range of about 30 to about 500 nucleotides, from about 30 to about 250 nucleotides, from about 30 to about 200 nucleotides, from about 30 to about 150 nucleotides, from about 40 to about 150 nucleotides, from about 40 to about 125 nucleotides, from about 40 to about 100 nucleotides, from about 50 to about 90 nucleotides, from about 50 to about 80 nucleotides. In some embodiments, an oligonucleotide domain may have a length of at least 30 or more nucleotides, including, e.g., at least 40, at least 50, at least 60, at least 70, at least 80, at least 90, at least 100, at least 250, at least 500, at least 750, at least 1000 nucleotides or more. In some embodiments, an oligonucleotide domain may have a length of no more than 1000 nucleotides or lower, including, e.g., no more than 900, no more than 800, no more than 700, no more than 600, no more than 500, no more than 400, no more than 300, no more than 200, no more than 100, no more than 90, no more than 80, no more than 70, no more than 60, no more than 50, no more than 40 nucleotides or lower. In some embodiments, an oligonucleotide domain may have a length in the range of about 50 nucleotides to about 90 nucleotides. In some embodiments, an oligonucleotide domain may have a length in the range of about 30 nucleotides to about 50 nucleotides. In some embodiments, an oligonucleotide domain may have a length in the range of about 10 nucleotides to about 30 nucleotides.

In some embodiments, an oligonucleotide domain may have a length of about 20 nm to about 500 nm. In some embodiments, an oligonucleotide domain may have a length of about 20 nm to about 400 nm, about 30 nm to about 200 nm, about 50 nm to about 100 nm, about 30 nm to about 70 nm, or about 40 nm to about 60 nm. In some embodiments, an oligonucleotide domain may have a length of at least about 20 nm or more, including, e.g., at least about 30 nm, at least about 40 nm, at least about 50 nm, at least about 60 nm, at least about 70 nm, at least about 80 nm, at least about 90 nm, at least about 100 nm, at least about 200 nm, at least about 300 nm, at least about 400 nm or more. In some embodiments, an oligonucleotide domain may have a length of no more than 1000 nm or lower, including, e.g., no more than 900 nm, no more than 800 nm, no more than 700 nm, no more than 600 nm, no more than 500 nm, no more than 400 nm, no more than 300 nm, no more than 200 nm, no more than 100 nm or lower.

In some embodiments, a double-stranded portion of an oligonucleotide domain for use in technologies provided herein may have a length in the range of about 30 up to about 1000 nucleotides. In some embodiments, a double-stranded portion of an oligonucleotide domain may have a length in the range of about 30 to about 500 nucleotides, from about 30 to about 250 nucleotides, from about 30 to about 200 nucleotides, from about 30 to about 150 nucleotides, from about 40 to about 150 nucleotides, from about 40 to about 125 nucleotides, from about 40 to about 100 nucleotides, from about 50 to about 90 nucleotides, from about 50 to about 80 nucleotides. In some embodiments, a double-stranded portion of an oligonucleotide domain may have a length of at least 30 or more nucleotides, including, e.g., at least 40, at least 50, at least 60, at least 70, at least 80, at least 90, at least 100, at least 250, at least 500, at least 750, at least 1000 nucleotides or more. In some embodiments, a double-stranded portion of an oligonucleotide domain may have a length of no more than 1000 nucleotides or lower, including, e.g., no more than 900, no more than 800, no more than 700, no more than 600, no more than 500, no more than 400, no more than 300, no more than 200, no more than 100, no more than 90, no more than 80, no more than 70, no more than 60, no more than 50, no more than 40 nucleotides or lower. In some embodiments, a double-stranded portion of an oligonucleotide domain may have a length in the range of about 50 nucleotides to about 90 nucleotides. In some embodiments, a double-stranded portion of an oligonucleotide domain may have a length in the range of about 30 nucleotides to about 50 nucleotides. In some embodiments, a double-stranded portion of an oligonucleotide domain may have a length in the range of about 10 nucleotides to about 30 nucleotides.

In some embodiments, a double-stranded portion of an oligonucleotide domain may have a length of about 20 nm to about 500 nm. In some embodiments, a double-stranded portion of an oligonucleotide domain may have a length of about 20 nm to about 400 nm, about 30 nm to about 200 nm, about 50 nm to about 100 nm, about 30 nm to about 70 nm, or about 40 nm to about 60 nm. In some embodiments, a double-stranded portion of an oligonucleotide domain may have a length of at least about 20 nm or more, including, e.g., at least about 30 nm, at least about 40 nm, at least about 50 nm, at least about 60 nm, at least about 70 nm, at least about 80 nm, at least about 90 nm, at least about 100 nm, at least about 200 nm, at least about 300 nm, at least about 400 nm or more. In some embodiments, a double-stranded portion of an oligonucleotide domain may have a length of no more than 1000 nm or lower, including, e.g., no more than 900 nm, no more than 800 nm, no more than 700 nm, no more than 600 nm, no more than 500 nm, no more than 400 nm, no more than 300 nm, no more than 200 nm, no more than 100 nm or lower.

In some embodiments, a double-stranded portion of an oligonucleotide domain is characterized in that when detection probes are connected to each other through hybridization of respective complementary single-stranded overhangs (e.g., as described and/or utilized herein), the combined length of the respective oligonucleotide domains (including, if any, a linker that links a target-binding moiety to an oligonucleotide domain) is long enough to allow respective target binding entities to substantially span the full characteristic length (e.g., diameter) of an entity of interest (e.g., an extracellular vesicle). For example, in some embodiments where extracellular vesicles are entities of interest, a combined length of oligonucleotide domains (including, if any, a linker that links a target-binding moiety to an oligonucleotide domain) of detection probes may be approximately 50 to 200 nm, when the detection probes are fully connected to each other.

In some embodiments, a double-stranded portion of an oligonucleotide domain may comprise a binding site for a primer. In some embodiments, such a binding site for a primer may comprise a nucleotide sequence that is designed to reduce or minimize the likelihood for miss-priming or primer dimers. Such a feature, in some embodiments, can decrease the lower limit of detection and thus increase the sensitivity of systems provided herein. In some embodiments, a binding site for a primer may comprise a nucleotide sequence that is designed to have a similar annealing temperature as another primer binding site.

In some embodiments, a double-stranded portion of an oligonucleotide domain may comprise a nucleotide sequence designed to reduce or minimize overlap with nucleic acid sequences (e.g., DNA and/or RNA sequences) typically associated with genome and/or gene transcripts (e.g., genomic DNA and/or RNA, such as mRNA of genes) of a subject (e.g., a human subject). Such a feature, in some embodiments, may reduce or minimize interference of any genomic DNA and/or mRNA transcripts of a subject that may be present (e.g., as contaminants) in a sample during detection.

In some embodiments, a double-stranded portion of an oligonucleotide domain may have a nucleotide sequence designed to reduce or minimize formation of self-dimers, homo-dimers, or hetero-dimers.

In some embodiments, a single-stranded overhang of an oligonucleotide domain for use in technologies provided herein may have a length of about 2 to about 20 nucleotides. In some embodiments, a single-stranded overhang of an oligonucleotide domain may have a length of about 2 to about 15 nucleotides, from about 2 to about 10 nucleotides, from about 3 to about 20 nucleotides, from about 3 to about 15 nucleotides, from about 3 to about 10 nucleotides. In some embodiments, a single-stranded overhang can have at least 1 to 5 nucleotides in length. In some embodiments, a single-stranded overhang of an oligonucleotide domain may have a length of at least 2 or more nucleotides, including, e.g., at least 3, at least 4, at least 5, at least 6, at least 7, at least 8, at least 9, at least 10, at least 11, at least 12, at least 13, at least 14, at least 15, at least 20 nucleotides, or more. In some embodiments, a single-stranded overhang of an oligonucleotide domain may have a length of no more than 20 nucleotides or lower, including, e.g., no more than 15, no more than 14, no more than 13, no more than 12, no more than 11, no more than 10, no more than 9, no more than 8, no more than 7, no more than 6, no more than 5, no more than 4 nucleotides or lower.

In some embodiments, a single-stranded overhang of an oligonucleotide domain may have a length of about 1 nm to about 10 nm. In some embodiments, a single-stranded overhang of an oligonucleotide domain may have a length of about 1 nm to about 5 nm. In some embodiments, a single-stranded overhang of an oligonucleotide domain may have a length of at least about 0.5 nm or more, including, e.g., at least about 1 nm, at least about 1.5 nm, at least about 2 nm, at least about 3 nm, at least about 4 nm, at least about 5 nm, at least about 6 nm, at least about 7 nm, at least about 8 nm, at least about 9 nm, at least about 10 nm or more. In some embodiments, a single-stranded overhang of an oligonucleotide domain may have a length of no more than 10 nm or lower, including, e.g., no more than 9 nm, no more than 8 nm, no more than 7 nm, no more than 6 nm, no more than 5 nm, no more than 4 nm, no more than 3 nm, no more than 2 nm, no more than 1 nm or lower.

A single-stranded overhang of an oligonucleotide domain is designed to comprise a nucleotide sequence that is complementary to at least a portion of a single-stranded overhang of a second detection probe such that a double-stranded complex comprising a first detection probe and a second detection probe can be formed through hybridization of the complementary single-stranded overhangs. In some embodiments, nucleotide sequences of complementary single-stranded overhangs are selected for optimal ligation efficiency in the presence of an appropriate nucleic acid ligase. In some embodiments, a single-stranded overhang has a nucleotide sequence preferentially selected for efficient ligation by a specific nucleic acid ligase of interest (e.g., a DNA ligase such as a T4 or T7 ligase). For example, such a single-stranded overhang may have a nucleotide sequence of GAGT, e.g., as described in Song et al., "Enzyme-guided DNA sewing architecture" *Scientific Reports* 5:17722 (2015).

When two detection probes couple together through hybridization of respective complementary single-stranded overhangs, their respective oligonucleotide domains comprising the hybridized single-stranded overhangs can, in some embodiments, have a combined length of about 90%-110% or about 95%-105% of a characteristic length (e.g., diameter) of an entity of interest (e.g., a biological entity). For example, in some embodiments when a biological entity is an exosome, the combined length can be about 50 nm to about 200 nm, or about 75 nm to about 150 nm, or about 80 nm to about 120 nm.

C. Coupling Between a Target-Binding Moiety and an Oligonucleotide Domain

An oligonucleotide domain and a target-binding moiety can be coupled together in a detection probe by a covalent linkage, and/or by a non-covalent association (such as, e.g., a protein-protein interaction such as streptavidin-biotin interaction and/or an ionic interaction). In some embodiments, a detection probe appropriate for use in accordance with the present disclosure is a conjugate molecule comprising a target-binding moiety and an oligonucleotide domain, where the two components are typically covalently coupled to each other, e.g., directly through a bond, or indirectly through one or more linkers. In some embodiments, a target-binding moiety is coupled to one of two strands of an oligonucleotide domain by a covalent linkage (e.g., directly through a bond or indirectly through one or more linkers) and/or by a non-covalent association (such as, e.g., a protein-protein interaction such as streptavidin-biotin interaction and/or ionic interaction).

Where linkers are employed, in some embodiments, linkers are chosen to provide for covalent attachment of a target-binding moiety to one or both strands of an oligo-nucleotide domain through selected linkers. In some embodiments, linkers are chosen such that the resulting covalent attachment of a target-binding moiety to one or both strands of an oligonucleotide domain maintains the desired binding affinity of the target-binding moiety for its target. In some embodiments, linkers are chosen to enhance binding specificity of a target-binding moiety for its target. Linkers and/or conjugation methods of interest may vary widely depending on a target-binding moiety, e.g., its size and/or charges. In some embodiments, linkers are biologically inert.

A variety of linkers and/or methods for coupling a target-binding moiety to an oligonucleotide is known to one of ordinary skill in the art and can be used in accordance with the present disclosure. In some embodiments, a linker can comprise a spacer group at either end with a reactive functional group capable of covalent attachment to a target-binding moiety. Examples of spacer groups that can be used in linkers include, but are not limited to, aliphatic and unsaturated hydrocarbon chains (including, e.g., C4, C5, C6, C7, C8, C9, C10, C11, C12, C13, C14, C15, C16, C17, C18, C19, C20, or longer), spacers containing heteroatoms such as oxygen (e.g., ethers such as polyethylene glycol) or nitrogen (polyamines), peptides, carbohydrates, cyclic or acyclic systems that may contain heteroatoms. Non-limiting examples of a reactive functional group to facilitate covalent attachment include nucleophilic functional groups (e.g., amines, alcohols, thiols, hydrazides), electrophilic functional groups (e.g., aldehydes, esters, vinyl ketones, epoxides, isocyanates, maleimides), functional groups capable of cycloaddition reactions, forming disulfide bonds, or binding to metals. In some embodiments, exemplary reactive functional groups, but are not limited to, primary and secondary amines, hydroxamic acids, N-hydroxysuccinimidyl (NHS) esters, dibenzocyclooctyne (DBCO)-NHS esters, azido-NHS esters, azidoacetic acid NHS ester, propargyl-NHS ester, trans-cyclooctene-NHS esters, N-hydroxysuccinim-idyl carbonates, oxycarbonylimidazoles, nitrophenylesters, trifluoroethyl esters, glycidyl ethers, vinylsulfones, maleim-ides, azidobenzoyl hydrazide, N-[4-(p-azidosalicylamino)butyl]-3'-[2'-pyridyldithio]propionamid), bis-sulfosuccinim-idyl suberate, dimethyladipimidate, disuccinimidyltartrate, N-maleimidobutyryloxysuccinimide ester, N-hydroxy sulfo-succinimidyl-4-azidobenzoate, N-succinimidyl [4-azid-ophenyl]-1,3'-dithiopropionate, N-succinimidyl [4-iodo-acetyl]aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and any combi-nations thereof.

In some embodiments, a target-binding moiety (e.g., a target binding antibody agent) is coupled or conjugated to one or both strands of an oligonucleotide domain using N-hydroxysuccinimide (NHS) ester chemistry. NHS esters react with free primary amines and result in stable covalent attachment. In some embodiments, a primary amino group can be positioned at a terminal end with a spacer group, e.g., but not limited to an aliphatic and unsaturated hydrocarbon chain (e.g., a C6 or C12 spacer group).

In some embodiments, a target-binding moiety (e.g., a target binding antibody agent) can be coupled or conjugated to one or both strands of an oligonucleotide domain using a site-specific conjugation method known in the art, e.g., to enhance the binding specificity of conjugated target-binding moiety (e.g., conjugated target binding antibody agent). Examples of a site-specific conjugation method include, but are not limited to coupling or conjugation through a disulfide bond, C-terminus, carbohydrate residue or glycan, and/or unnatural amino acid labeling. In some embodiments where a target-binding moiety is or comprises an antibody agent or a peptide aptamer, an oligonucleotide can be coupled or conjugated to the target-binding moiety via at least one or more free amine groups present in the target-binding moiety. In some embodiments, an oligonucleotide can be coupled or conjugated to a target-binding moiety that is or comprises an antibody agent or a peptide aptamer via at least one or more reactive thiol groups present in the target-binding moiety. In some embodiments, an oligonucleotide can be coupled or conjugated to a target-binding moiety that is or comprises an antibody agent or a peptide aptamer via at least one or more carbohydrate residues present in the target-binding moiety.

In some embodiments, a plurality of oligonucleotides (e.g., at least 2, at least 3, at least 4, at least 5, at least 6, at least 7, at least 8, at least 9, at least ten, or more) can be coupled or conjugated to a target-binding moiety (e.g., a target binding antibody agent).

Exemplary Duplex Target Entity Detection System

In some embodiments, a target entity detection system as provided by the present disclosure (and useful, for example, for detecting, e.g., at a single entity level, entities of interest (e.g., biological entities of interest) comprising at least one or more targets (e.g., molecular targets)) may comprise a first population of first detection probes (e.g., as described and/or utilized herein) for a first target (e.g., a first target biomarker) and a second population of second detection probes (e.g., as described and/or utilized herein) for a second target (e.g., a second target biomarker). In some embodiments, the first target (e.g., first target biomarker) and the second target (e.g., second target biomarker) to which the first detection probes and the second detection probes are directed, respectively, are or comprise the same target (e.g., same target biomarker). In some embodiments, the first target (e.g., first target biomarker) and the second target (e.g., second target biomarker) to which the first detection probes and the second detection probes are directed, respectively, are different targets (e.g., different target biomarkers).

FIGS. 2A-2B illustrate an exemplary duplex target entity detection system for detecting, at a single entity level, an entity of interest (e.g., biological entity such as an extracellular vesicle) comprising (i) at least one target (e.g., a target biomarker of a target biomarker signature for a disease, disorder, or condition, e.g., cancer) which expression level is high enough such that two molecules of the same target are found in close proximity, or (ii) at least two or more distinct targets (e.g., biomarkers of a target biomarker signature for a disease, disorder, or condition, e.g., cancer). A first detection probe comprises a first target-binding moiety (e.g., directed to a target 1, such as a target cancer marker 1) and a first oligonucleotide domain coupled to the first target-binding moiety, the first oligonucleotide domain comprising a first double-stranded portion and a first single-stranded overhang extended from one end of the first oligonucleotide domain. As shown in FIG. 2A, a first oligonucleotide domain may be resulted from hybridization of a longer strand (strand 3) and a shorter strand (strand 1), thereby forming a double-stranded portion and a single-stranded overhang at one end. In some embodiments, a first target-binding moiety (e.g., directed to target 1, such as a target cancer marker 1) is coupled (e.g., covalently coupled) to a 5' end or 3' end of a strand of a first oligonucleotide domain (e.g., strand 1). In some embodiments, a 5' end or 3' end of a strand that is coupled to a first target-binding moiety may be modified with a linker (e.g., as described and/or utilized herein with or without a spacer group). In some embodiments, a 5' end of another strand of a first oligonucleotide domain (e.g., strand 3) has a free phosphate group.

In the embodiment depicted in FIG. 2A, a second detection probe comprises a second target-binding moiety (e.g., directed to a target 2 such as a target cancer marker 2) and a second oligonucleotide domain coupled to the second target-binding moiety, the second oligonucleotide domain comprising a second double-stranded portion and a second single-stranded overhang extended from one end of the second oligonucleotide domain. As shown in FIG. 2A, a second oligonucleotide domain may be resulted from hybridization of a longer strand (strand 4) and a shorter strand (strand 2), thereby forming a double-stranded portion and a single-stranded overhang at one end. In some embodiments, a second target-binding moiety (e.g., directed to a target 2 such as a target cancer marker 2) is coupled (e.g., covalently coupled) to a 5' end of a strand of a second oligonucleotide domain (e.g., strand 2). In some embodiments, a 5' end of a strand that is coupled to a second target-binding moiety may be modified with a linker (e.g., as described and/or utilized herein with or without a spacer group). In some embodiments, a 5' end of another strand of a second oligonucleotide domain (e.g., strand 4) has a free phosphate group.

At least portions of a first single-stranded overhang and a second single-stranded overhang are complementary to each other such that they can hybridize to form a double-stranded complex when they are in sufficiently close proximity, e.g., when a first detection probe and a second detection probe simultaneously bind to the same entity of interest (e.g., biological entity such as extracellular vesicle). In some embodiments, a first single-stranded overhang and a second single-stranded overhang have equal lengths such that when they hybridize to form a double-stranded complex, there is no gap (other than a nick to be ligated) between their respective oligonucleotide domains and each respective target-binding moiety is located at an opposing end of the double-stranded complex. For example, in an embodiment depicted in FIG. 2B, a double-stranded complex forms before ligation occurs, wherein the double-stranded complex comprises a first detection probe and a second detection probe coupled to each other through direct hybridization of their respective single-stranded overhangs (e.g., having 4 nucleotides in length), wherein each respective target-binding moiety (e.g., directed to a target 1 and a target 2, respectively) is present at opposing ends of the double-stranded complex. In such embodiments, both strands of the double-stranded complex (containing a nick between respective oligonucleotide domains) are ligatable, e.g., for amplification and detection. While FIG. 2B shows hybridization of a first detection probe with a second detection probe and does not show binding of such detection probes to an entity of interest (e.g., a biological entity such as an extracellular vesicle), in some embodiments, a double-stranded complex (e.g., before ligation occurs) can comprise an entity of interest (e.g., a biological entity such as an extracellular vesicle), wherein a first target-binding moiety (e.g., directed to a target 1 such as a target cancer marker 1) and a second target-binding moiety (e.g., directed to a target 2 such as a target cancer marker 2) are simultaneously bound to the entity of interest.

In some embodiments, a first target-binding moiety may be directed to a biomarker that is specifically associated with a normal healthy cell and/or tissue (e.g., from which a cancer cell is derived) and a second target-binding moiety may be directed to a biomarker that is associated with more than one cancer (but not present in the normal healthy cell and/or tissue). For example, in some embodiments, a second target-binding moiety may be directed to a generic biomarker for cancers (regardless of tissue types).

In some embodiments, a first target-binding moiety may be directed to a tissue-specific cancer biomarker (e.g., a biomarker that is typically associated with cancers of a specific tissue) and a second target-binding moiety may be directed to a biomarker that is specifically associated with the same tissue of the cancer but in a normal healthy state.

In some embodiments, a first target-binding moiety and a second target-binding moiety may be each directed to a distinct cancer-associated biomarker. For example, in some embodiments, a first target-binding moiety and a second target-binding moiety may be each directed to a biomarker that is associated with a different cancer (e.g., cancers associated with the same tissue or different tissues). In some embodiments, a first target-binding moiety and a second target-binding moiety may be each directed to a biomarker that is associated with the same cancer.

In some embodiments of a duplex target entity detection system for detection of a disease, disorder, or condition (e.g., cancer), a first target-binding moiety of a first detection probe may be directed to a first target surface protein biomarker, while a second target-binding moiety of a second detection probe may be directed to a second target surface protein biomarker. In some embodiments, a first target-binding moiety of a first detection probe may be directed to a first target intravesicular protein biomarker, while a second target-binding moiety of a second detection probe may be directed to a second target intravesicular protein biomarker. In some embodiments, the first target-binding moiety and the second target-binding moiety may be directed to the same or different epitopes of the same target surface protein biomarker or of the same target intravesicular protein biomarker. In some embodiments, the first target-binding moiety and the second target-binding moiety may be directed to the different target surface protein biomarkers or different target intravesicular protein biomarkers.

In some embodiments, the double stranded portion of a first oligonucleotide domain and a second oligonucleotide domain may be the same. In some embodiments, the double stranded portion of a first oligonucleotide domain and a second oligonucleotide domain may be different.

Exemplary Triplex or Multiplex (n≥3) Target Entity Detection System

In some embodiments, a target entity detection system as provided by the present disclosure (and useful, for example, for detecting, e.g., at a single entity level, entities of interest (e.g., biological entities of interest) may comprise n populations of distinct probes (e.g., as described and/or utilized herein), wherein n≥3 (e.g., n=3, 4, 5 or more). For example, in some embodiments when n=3, a target entity detection system may comprise a first detection probe (e.g., as described and/or utilized herein) for a first target, a population of a second detection probe (e.g., as described and/or utilized herein) for a second target, and a population of a third detection probe (e.g., as described and/or utilized herein) for a third target. In some embodiments, the first, second, and third targets are the same target. In some embodiments, the first, second, and third targets are distinct targets. In some embodiments, at least two of the first, second, and third targets are distinct targets.

FIG. 5A illustrates an exemplary triplex target entity detection system for detecting, at a single entity level, an entity of interest (e.g., a biological entity such as an extra-cellular vesicle) comprising at least one or more targets (e.g., molecular targets). A first detection probe comprises a first target-binding moiety (e.g., anti-target 1 antibody agent such as anti-cancer marker 1 antibody agent) and a first oligonucleotide domain coupled to the first target-binding moiety, the first oligonucleotide domain comprising a first double-stranded portion and a first single-stranded overhang extended from one end of the first oligonucleotide domain. As shown in FIG. 5A, a first oligonucleotide domain may be resulted from hybridization of a longer strand (strand 8) and a shorter strand (strand 1), thereby forming a double-stranded portion and a single-stranded overhang at one end. In some embodiments, a first target-binding moiety (e.g., anti-target 1 antibody agent such as anti-cancer marker 1 antibody agent) is coupled (e.g., covalently coupled) to a 5' end of a strand of a first oligonucleotide domain (e.g., strand 1). In some embodiments, a 5' end of a strand that is coupled to a first target-binding moiety may be modified with a linker (e.g., as described and/or utilized herein with or without a spacer group). In some embodiments, a 5' end of another strand of a first oligonucleotide domain (e.g., strand 8) has a free phosphate group.

In the embodiment depicted in FIG. 5A, a second detection probe comprises a second target-binding moiety (e.g., anti-target 3 antibody agent such as anti-cancer marker 3 antibody agent) and a second oligonucleotide domain coupled to the second target-binding moiety, the second oligonucleotide domain comprising a second double-stranded portion and a second single-stranded overhang extended from one end of the second oligonucleotide domain. As shown in FIG. 5A, a second oligonucleotide domain may be resulted from hybridization of a longer strand (strand 4) and a shorter strand (strand 2), thereby forming a double-stranded portion and a single-stranded overhang at one end. In some embodiments, a second target-binding moiety (e.g., anti-target 3 antibody agent such as anti-cancer marker 3 antibody agent) is coupled (e.g., covalently coupled) to a 5' end of a strand of a second oligonucleotide domain (e.g., strand 2). In some embodiments, a 5' end of a strand that is coupled to a second target-binding moiety may be modified with a linker (e.g., as described and/or utilized herein with or without a spacer group). In some embodiments, a 5' end of another strand of a second oligonucleotide domain (e.g., strand 4) has no free phosphate group.

A third detection probe comprises a third target-binding moiety (e.g., anti-target 2 antibody agent such as anti-cancer marker 2 antibody agent) and a third oligonucleotide domain coupled to the third target-binding moiety, the third oligonucleotide domain comprising a third double-stranded portion and a single-stranded overhang extended from each end of the third oligonucleotide domain. For example, a single-stranded overhang is extended from one end of a strand of a third oligonucleotide domain while another single-stranded overhang is extended from an opposing end of a different strand of the third oligonucleotide domain. As shown in FIG. 5A, a third oligonucleotide domain may be resulted from hybridization of portions of two strands (e.g., strands 9 and 10), thereby forming a double-stranded portion and a single-stranded overhang at each end. For example, a single-stranded overhang (3A) is formed at a 5' end of strand 9 of a third detection probe, wherein the '5 end of strand 9 has a free phosphate group. Additionally, a single-stranded overhang (3B) is formed at a 5' end of strand 10 of the same third detection probe and a third target-binding moiety (e.g., anti-target 2 antibody agent such as anti-cancer marker 2 antibody agent) is also coupled (e.g., covalently coupled) to the 5' end of strand 10. In some embodiments, a 5' end of a strand (e.g., strand 10) that is coupled to a third target-binding moiety may be modified with a linker (e.g., as described and/or utilized herein with or without a spacer group).

When all three detection probes are in sufficiently close proximity, e.g., when all three detection probes simultaneously bind to the same entity of interest (e.g., biological entity), (i) at least a portion of a single-stranded overhang (e.g., 3A) of a third detection probe is hybridized to a corresponding complementary portion of a single-stranded overhang of a second detection probe, and (ii) at least a portion of another single-stranded overhang (e.g., 3B) of the third detection probe is hybridized to a corresponding complementary portion of a single-stranded overhang of a first detection probe. As a result, a double-stranded complex comprising all three detection probes coupled to each other in a linear arrangement is formed by direct hybridization of corresponding single-stranded overhangs. See, e.g., FIG. 5A.

In some embodiments involving use of at least three or more (n≥3) detection probes in provided technologies, when single-stranded overhangs of detection probes anneal to each respective partner(s) to form a double-stranded complex, at least (n−2) target-binding moiety/moieties is/are present at internal position(s) of the double-stranded complex. In such embodiments, it is desirable to have internal target binding moieties present in a single strand of the double-stranded complex such that another strand of the double-stranded complex is free of any internal target binding moieties and is thus ligatable to form a ligated template. e.g., for amplification and detection. See, e.g., FIG. 5A (using three detection probes), FIG. 5B (using four detection probes), and FIG. 10 (using n detection probes).

In some embodiments where a strand of a double-stranded complex comprises at least one or more internal target binding moieties, the strand comprises a gap between an end of an oligonucleotide strand of a detection probe to which the internal target-binding moiety is coupled and an end of an oligonucleotide strand of another detection probe. The size of the gap is large enough such that the strand becomes non-ligatable in the presence of a nucleic acid ligase. In some embodiments, the gap may be 2-8 nucleotides in size or 2-6 nucleotides in size. In some embodiments, the gap is 6 nucleotides in size. In some embodiments, the overlap (hybridization region between single-stranded overhangs) can be 2-15 nucleotides in length or 4-10 nucleotides in length. In some embodiments, the overlap (hybridization region between single-stranded overhangs) is 8 nucleotides in length. The size of the gap and/or hybridization region are selected to provide an optimum signal separation from a ligated template (comprising no internal target binding moieties) and non-ligated template (comprising at least one internal target-binding moiety). It should be noted that while FIGS. 5A-5B and FIG. 10 do not show binding of detection probes to an entity of interest (e.g., a biological entity), a double-stranded complex (e.g., before ligation occurs) can comprise an entity of interest (e.g., a biological entity such as extracellular vesicles), wherein at least three or more target binding moieties are simultaneously bound to the entity of interest.

In some embodiments, selection of a combination (e.g., a set) of detection probes (e.g., number of detection probes and/or specific biomarkers) for use in a target entity detection system provided herein (e.g., a duplex, triplex or multiplex target entity detection system described herein) is based on, for example, a desired specificity and/or a desired sensitivity that is deemed to be optimal for a particular application. For example, in some embodiments, a combination of detection probes is selected for detection of cancer (e.g., for stage I, II, III, or IV) such that it provides a specificity of at least 95% or higher, including, e.g., at least 96%, at least 97%, at least 98%, at least 99%, at least 99.5%, at least 99.7%, at least 99.8% or higher. In some embodiments, a combination of detection probes is selected for detection of cancer (e.g., for stage I, II, III, or IV) such that it provides a sensitivity of at least 30% or higher, including, e.g., at least 40%, at least 50%, at least 60%, at least 70%, at least 80%, at least 90%, at least 95% or higher. In some embodiments, a combination of detection probes is selected for detection of cancer (e.g., for stage I, II, III, or IV) such that it provides a positive predictive value of at least 8% or higher, including, e.g., at least 9%, at least 10%, at least 15%, at least 20%, at least 25%, at least 30%, at least 40%, at least 50%, or higher. In some embodiments, a combination of detection probes is selected for detection of cancer (e.g., for stage I, II, III, or IV) such that it provides a limit of detection (LOD) below $1\times10^7$ EV/mL sample or lower, including, e.g., below $7\times10^6$ EV/mL sample, below $6\times10^6$ EV/mL sample, below $5\times10^6$ EV/mL sample, below $4\times10^6$ EV/mL sample, below $3\times10^6$ EV/mL sample, below $2\times10^6$ EV/mL sample, below $1\times10^6$ EV/mL sample, or lower. In some embodiments, such cancer detection assay may be used to detect different cancers, or subtypes and/or stages of a particular cancer. In some embodiments, one or more cancers that may be detected using such a detection assay may comprise one or more of: acute lymphocytic leukemia, acute myeloid leukemia, bile duct cancer, bladder cancer, brain cancer (including, e.g., glioblastoma), breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer. In some embodiments, a detection assay (e.g., ones described herein) may be used to detect skin cancer (e.g., melanoma). In some embodiments, a detection assay (e.g., ones described herein) may be used to detect lung cancer (e.g., non-small cell lung cancer). In some embodiments, a detection assay (e.g., ones described herein) may be used to detect breast cancer. In some embodiments, a detection assay (e.g., ones described herein) may be used to detect ovarian cancer of epithelial origin such as high-grade serous ovarian cancer).

In some embodiments, a combination (e.g., a set) of detection probes, rather than individual detection probes, confers specificity to detection of a disease, disorder, or condition (e.g., a particular cancer and/or a stage of cancer as described herein), for example, one or more individual probes may be directed to a target that itself is not specific to such a disease, disorder, or condition (e.g., cancer). For example, in some embodiments, a useful combination of detection probes in a target entity detection system provided herein (e.g., a duplex, triplex or multiplex target entity detection system described herein) may comprise at least one detection probe directed to a target specific for the relevant disease, disorder, or condition (i.e., a target that is specific to the relevant disease, disorder, or condition), and may further comprise at least one detection probe directed to a target that is not necessarily or completely specific for the relevant disease, disorder, or condition (e.g., that may also be found on some or all cells that are healthy, are not of the particular disease, disorder, or condition, and/or are not of the particular disease stage of interest). That is, as will be appreciated by those skilled in the art reading the present specification, so long as the set of detection probes utilized in accordance with the present invention is or comprises a plurality of individual detection probes that together are specific for detection of the relevant disease, disorder, or condition (i.e., sufficiently distinguish biological entities for detection that are associated with the relevant disease, disorder, or condition from other biological entities not of interest for detection), the set is useful in accordance with certain embodiments of the present disclosure.

In some embodiments, a useful detection probes in a target entity detection system provided herein (e.g., a duplex, triplex or multiplex target entity detection system described herein) may comprise at least one type or more of the following detection probes:

a. a detection probe directed to a biomarker that is specifically associated with a normal healthy cell, extracellular vesicle, and/or tissue (e.g., a normal healthy cell, extracellular vesicle, and/or tissue from which a diseased cell, e.g., a cancer cell, is derived);

b. a detection probe directed to a biomarker that is associated with more than one disease such as, e.g., more than one cancer (but not present in a normal healthy cell, extracellular vesicle, and/or tissue), e.g., directed to a generic biomarker for cancers (regardless of tissues types); and c. a detection probe directed to a tissue-specific disease biomarker (e.g., a tissue-specific cancer biomarker, such as, e.g., a biomarker that is specifically associated with cancers for a specific tissue, e.g., but not limited to brain, breast, colon, ovary and/or other tissues associated with a female reproductive system, pancreas, prostate and/or other tissues associated with a male reproductive system, liver, lung, and skin).

In some embodiments, a useful combination (e.g., a set) of detection probes for detection of cancer may comprise a first detection probe directed to a biomarker that is specifically associated with a normal healthy cell, extracellular vesicle, and/or tissue (e.g., from which a cancer cell is derived) and a second detection probe directed to a biomarker that is associated with more than one cancer (but not present in the normal healthy cell, extracellular vesicle, and/or tissue). For example, in some embodiments, such a second detection probe may be directed to a generic biomarker for cancers (regardless of tissue types).

In some embodiments, a combination of detection probes for detection of cancer may comprise a first detection probe directed to a tissue-specific cancer biomarker (e.g., a biomarker that is typically associated with cancers for a specific tissue) and a second detection probe directed to a biomarker that is specifically associated with the same tissue of the cancer but in a normal healthy state.

In some embodiments, a combination of detection probes for detection of cancer may comprise a first detection probe and a second detection probe each directed to a distinct cancer-associated biomarker. For example, in some embodiments, a first and second detection probe may be each directed to a biomarker that is associated with a different cancer (e.g., cancers associated with the same tissue or different tissues). In some embodiments, a first and second detection probe may be each directed to a biomarker that is associated with the same cancer. In some embodiments, a first and second detection probe may be each directed to a biomarker that is associated with the same cancer of different stages.

In some embodiments, a target entity detection system provided herein (e.g., a duplex, triplex or multiplex target entity detection system described herein) can comprise at least one or more (e.g., at least 2 or more) control probes (in addition to target-specific detection probes, e.g., as described and/or utilized herein, for example, in some embodiments to recognize disease-specific biomarkers such as cancer-specific biomarkers and/or tissue-specific biomarkers). In some embodiments, a control probe is designed such that its binding to an entity of interest (e.g., a biological entity) may facilitate generation of a detection signal. In some embodiments, a control probe is designed such that its binding to an entity of interest (e.g., a biological entity) inhibits (completely or partially) generation of a detection signal ("Inhibitor probe"). For example, in some embodiments, a control probe may be designed to inhibit ligation occurring in a non-target entity. In some embodiments, a control probe may be designed to inhibit amplification of a ligated template from a non-target entity.

In some embodiments, a control probe comprises a control binding moiety and an oligonucleotide domain (e.g., as described and/or utilized herein) coupled to the control binding moiety, the oligonucleotide domain comprising a double-stranded portion and a single-stranded overhang extended from one end of the oligonucleotide domain. A control binding moiety is an entity or moiety that bind to a control reference. In some embodiments, a control reference can be or comprise a biomarker that is preferentially associated with a normal healthy cell or extracellular vesicle. In some embodiments, a control reference can be or comprise a biomarker preferentially associated from a non-target tissue. In some embodiments, inclusion of a control probe can selectively remove or minimize detectable signals generated from false positives (e.g., entities of interest comprising a control reference, optionally in combination with one or more targets to be detected).

Figure 11:
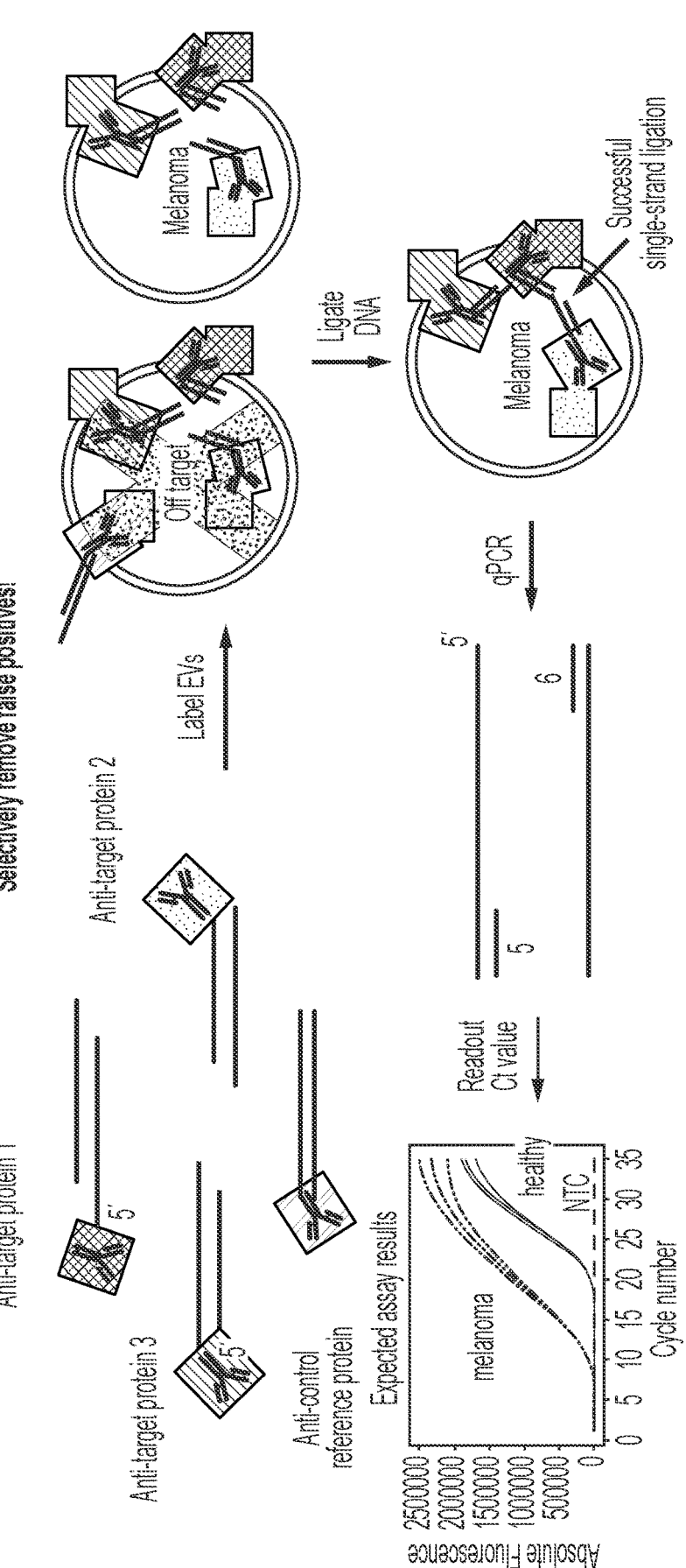
FIG. 11 is a schematic diagram illustrating a target entity detection assay of an exemplary embodiment described herein. In some embodiments, a target entity detection assay utilizes a combination of detection probes, which combination is specific for detection of cancer (e.g., a particular cancer, such as, for example, melanoma, and/or a particular stage of a cancer). In some embodiments, such a combination of detection probes includes at least two or more target-specific detection probes, each directed to a target protein (which in some embodiments may be the same target protein, or in some embodiments may be a distinct protein), and at least one or more control probes, e.g., a negative control probe whose binding inhibits or precludes ligation of detection probes; in some embodiments, a control probe may be directed to, e.g., a protein or peptide that is not associated with cancer such as one which presence in an entity of interest (e.g., a biological entity) is indicative of the entity of interest being negative for a disease, disorder, or condition (e.g., cancer). In some embodiments, such a combination of detection probes is added to a sample comprising a biological entity (e.g., extracellular vesicle or analyte). In some embodiments, detection probes each comprise a target-binding moiety (e.g., an antibody agent or aptamer) coupled to an oligonucleotide domain, which comprises a double-stranded portion and a single-stranded overhang extended from one end of the oligonucleotide domain. A detection signal is generated when all target-specific detection probes (e.g., directed to target protein 1, target protein 2, and target protein 3, respectively), but not a control probe, are localized to the same biological entity (e.g., an extracellular vesicle or analyte) in close proximity. The corresponding single-stranded overhangs of target-specific detection probes hybridize to form a double-stranded complex, and ligation of at least one strand of the resulting double-stranded complex occurs, thereby allowing a ligated product to be detected. For example, even when a control entity (e.g., a biological entity from a healthy subject sample) express all three target proteins, no detection signal can be generated because of the presence of a control protein that is not associated with cancer. However, when a biological entity from a cancer sample (e.g., melanoma) expresses all three target proteins in the absence of a control protein that is not associated with cancer, and the target proteins are present within short enough distances of each other in the same biological entity (e.g., extracellular vesicle or analyte), a detection signal can be generated. In some embodiments, inclusion of a control probe can selectively remove false positives, thereby improving specificity of detection.

For example, as shown in FIGS. 11-12, a target entity detection system (e.g., ones described herein) can comprise a plurality of (e.g., at least 2, at least 3, or more) target-specific detection probes and at least one control probe (e.g., to recognize normal healthy cells or extracellular vesicles and/or cells or extracellular vesicles from non-specific tissues). The oligonucleotide domains of the target-specific detection probes and control probes can be designed and determined such that when a control probe binds to an entity of interest (e.g., a biological entity such as an extracellular vesicle), even binding of at least one or all of target-specific detection probes in the same entity of interest (e.g., biological entity such as an extracellular vesicle) does not necessarily lead to formation of a ligated template. Binding of all target-specific detection probes to a single entity of interest (e.g., biological entity such as an extracellular vesicle) in the absence of a control binding to the same entity of interest results in preferential formation of a ligated template and thus a detectable signal. For illustration purposes only, FIG. 12 shows an exemplary use of a control probe that act as a competitive inhibitor of ligation. For example, in the absence of a control probe (e.g., to recognize normal healthy cells or extracellular vesicles and/or cells or extracellular vesicles from non-specific tissues) binding to an entity of interest (e.g., biological entity), binding of a first target-specific detection probe and a second target-specific probe to the same entity of interest allows them to be in sufficient close proximity to interact with each other through direct hybridization of their respective single-stranded overhangs of the oligonucleotide domains and thereby formation of a ligation template. A control probe can be designed to prevent such hybridization between the target-specific detection probes by competing with at least one of the target-specific detection probes for its respective target binding partner. By way of example only and for illustration purposes only, FIG. 12 shows that one end of a control probe is designed to bind to a target-specific detection probe (e.g., target-specific detection probe 2), while the other end of the control probe is designed to be incapable of interacting with another target-specific detection probe (e.g., target-specific detection probe 1) that would otherwise bind to the former (e.g., target-specific detection probe 2) in the absence of the control probe. In some embodiments, one end of a control probe is designed to be a blunt end such that it is not able to hybridize with a single-stranded overhang of another detection probe. In some embodiments, a 3' end of an oligonucleotide strand (e.g., strand 9 of a control probe as shown in FIG. 12) of a control probe can have a dideoxynucleotide such that no ligation is permissible.

In some embodiments, a control probe can be designed to inhibit amplification of a ligated template from a non-target entity. For illustration purposes only, FIG. 26 shows an exemplary inhibitor probe, which is designed such that its binding to a non-target entity, while allowing ligation with another probe, e.g., a detection probe, inhibits amplification of a ligated template from the non-target entity. In some embodiments, an inhibitor probe may be directed to a non-target, e.g., a marker that is not associated with a target tissue, or a marker that is not associated with a disease, disorder, or condition (e.g., cancer) to be diagnosed. In some such embodiments, an inhibitor probe may be similar to a detection probe (e.g., ones described herein) such that when a detection probe and an inhibitor probe are in close proximity, their single-stranded overhangs are hybridized with each other, thus allowing ligation. However, unlike a detection probe (e.g., ones described herein), at least one strand of the oligonucleotide domain of such an inhibitor probe does not have a primer site, thus prohibiting amplification of any ligated template that may be formed as a result of interaction between a detection probe and an inhibitor probe present in a non-target entity. In the presence of an inhibitor probe binding to a non-target entity (e.g., a biological entity from a different tissue), no detection signal can be generated because the inhibitor probe without a primer site does not permit amplification of a template. In some embodiments, inclusion of such an inhibitor probe can selectively remove false positives, thereby improving specificity of detection.

In some embodiments involving control probe(s) described herein, the length of the oligonucleotide domain used in such control probe(s) can be comparable to or different from the length of the oligonucleotide domain used in detection probes (e.g., ones described herein). For example, in some embodiments, an oligonucleotide domain of a control probe may have a length in the range of about 30 to about 1000 nucleotides. In some embodiments, an oligonucleotide domain of a control probe may have a length in the range of about 30 to about 500 nucleotides, from about 30 to about 250 nucleotides, from about 30 to about 200 nucleotides, from about 30 to about 150 nucleotides, from about 40 to about 150 nucleotides, from about 40 to about 125 nucleotides, from about 40 to about 100 nucleotides, from about 50 to about 90 nucleotides, from about 50 to about 80 nucleotides. In some embodiments, an oligonucleotide domain of a control probe may have a length in the range of about 50 nucleotides to about 90 nucleotides. In some embodiments, an oligonucleotide domain of a control probe may have a length in the range of about 30 nucleotides to about 50 nucleotides. In some embodiments, an oligonucleotide domain of a control probe may have a length in the range of about 10 nucleotides to about 30 nucleotides. One of skilled in the art reading the present disclosure will understand that the length of the oligonucleotide domain can be adjusted to improve the performance of a control probe in a detection assay.

In some embodiments, the present disclosure provides insights, among other things, that detection probes as described or utilized herein may non-specifically bind to a solid substrate surface and some of them may remain in an assay sample even after multiple washes to remove any excess or unbound detection probes; and that such non-specifically bound detection probes may come off from the solid substrate surface and become free-floating in a ligation reaction, thus allowing them to interact with one another to generate a non-specific ligated template that produces an undesirable background signal. Accordingly, in some embodiments, a target entity detection system provided herein (e.g., a duplex, triplex, or multiplex target entity detection described herein) can comprise at least one or more (e.g., at least 2 or more) inhibitor oligonucleotides that are designed to capture residual detection probes that are not bound to an entity of interest but remain as free agents in a ligation reaction, thereby preventing such free-floating detection probes from interacting with other free-floating complementary detection probes to produce an undesirable background signal. In some embodiments, an inhibitor oligonucleotide may be or comprise a single-stranded or double-stranded oligonucleotide comprising a binding domain for a single-stranded overhang of a detection probe (e.g., as described or utilized herein), wherein the inhibitor oligonucleotide does not comprise a primer binding site. The absence of such a primer binding site in an inhibitor oligonucleotide prevents a primer from binding to a non-specific ligated template resulting from ligation of a detectable probe to an inhibitor oligonucleotide, thereby reducing or inhibiting the non-specific ligated template from amplification and/or detection, e.g., by polymerase chain reaction.

In some embodiments, an inhibitor oligonucleotide comprises a binding domain for a single-stranded overhang of a detection probe (e.g., as described or utilized herein), wherein the binding domain is or comprises a nucleotide sequence that is substantially complementary to the single-stranded overhang of the detection probe such that a free, unbound detection probe having a complementary single-stranded overhang can bind to the binding domain of the inhibitor oligonucleotide. In some embodiments, an inhibitor oligonucleotide may have a hairpin at one end. In some embodiments, an inhibitor oligonucleotide may be a single-stranded oligonucleotide comprising at one end a binding domain for a single-stranded overhang of a detection probe, wherein a portion of the single-stranded oligonucleotide can self-hybridize to form a hairpin at another end, e.g., as illustrated in FIG. 18.

In some embodiments, a target entity detection system provided herein (e.g., a duplex, triplex or multiplex target entity detection system described herein) does not comprise a connector oligonucleotide that associates an oligonucleotide domain of a detection probe with an oligonucleotide domain of another detection probe. In some embodiments, a connector oligonucleotide is designed to bridge oligonucleotide domains of any two detection probes that would not otherwise interact with each other when they bind to an entity of interest. In some embodiments, a connector oligonucleotide is designed to hybridize with at least a portion of an oligonucleotide domain of a detection probe and at least a portion of an oligonucleotide domain of another detection probe. A connector oligonucleotide can be single-stranded, double-stranded, or a combination thereof. A connector oligonucleotide is free of any target-binding moiety (e.g., as described and/or utilized herein) or control binding moiety. In at least some embodiments, no connector oligonucleotides are necessary to indirectly connect oligonucleotide domains of detection probes; in some embodiments, such connector oligonucleotides are not utilized, in part because detection probes as provided and/or utilized herein are designed such that their respective oligonucleotide domains have a sufficient length to reach and interact with each other when they are in sufficiently close proximity, e.g., when the detection probes simultaneously bind to an entity of interest (e.g., a biological entity such as an extracellular vesicle).

In some embodiments, a target entity detection system includes (i) a plurality of detection probes (e.g., ones as described herein) each for a specific target (e.g., a molecular target or a biomarker of a target biomarker signature); and (ii) an agent for capturing target entities of interest (e.g., biological entities such as extracellular vesicles). In some embodiments, such a capture agent is or comprises a solid substrate (e.g., ones as described herein, such as, e.g., a magnetic bead in some embodiments) comprising a target-capture moiety conjugated thereto. In some embodiments, a target-capture moiety may be or comprise an antibody agent directed to target entities of interest (e.g., biological entities such as extracellular vesicles).

II. Exemplary Methods of Using Provided Target Entity Detection Systems

Provided target entity detection systems are useful in detecting an entity of interest (e.g., a biological entity such as extracellular vesicles) in a sample (e.g., in a biological, environmental, or other sample) for various applications and/or purposes, e.g., in some embodiments associated with detection of a particular disease, disorder, or condition (e.g., cancer) or a plurality of diseases, disorders, or conditions (e.g., a plurality of cancers). Accordingly, some aspects provided herein relate to methods of using a plurality of (e.g., at least 2, at least 3, or more) detection probes appropriate for use in accordance with the present disclosure. In some embodiments, a method comprises contacting an entity of interest (e.g., a biological entity such as extracellular vesicles) in a sample (e.g., a blood or blood-derived sample from a human subject) with a set of detection probes comprising at least 2 or more (including, e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more) detection probes as described and/or utilized herein. In some embodiments, a method comprises subjecting a sample comprising an entity of interest (e.g., a biological entity such as extracellular vesicles) to a target entity detection system (e.g., as provided herein). A plurality of detection probes (e.g., at least two or more) can be added to a sample comprising an entity of interest (e.g., a biological entity such as extracellular vesicles) at the same time or at different times (e.g., sequentially).

In some embodiments, a set of detection probes that are specific for detection of a particular disease, disorder, or condition (e.g., cancer) may be added to a single assay chamber. In some embodiments, a set of detection probes that are specific for detection of a plurality of diseases, disorders, or conditions (e.g., a plurality of cancers) may be added to a single assay chamber. In some embodiments, a set of detection probes may be divided into a plurality of subsets (e.g., each subset directed to detection of a distinct disease or condition), each subset of which may be added to an aliquot from the same sample. Accordingly, in some embodiments, a sample can be divided into aliquots such that a different set of detection probes (e.g., each directed to detection of a distinct disease or condition) can be added to a different aliquot. In such embodiments, provided technologies can be implemented with one aliquot at a time or multiple aliquots at a time (e.g., for parallel assays to increase throughput).

In some embodiments, amount of detection probes that is added to a sample provides a sufficiently low concentration of detection probes in a mixture to ensure that the detection probes will not randomly come into close proximity with one another in the absence of binding to an entity of interest (e.g., biological entity), at least not to any great or substantial degree. As such, in many embodiments, when detection probes simultaneously bind to the same entity of interest (e.g., biological entity) through the binding interaction between respective targeting binding moieties of the detection probes and the binding sites of an entity of interest (e.g., a biological entity), the detection probes come into sufficiently close proximity to one another to form double-stranded complex (e.g., as described herein). In some embodiments, the concentration of detection probes in a mixture following combination with a sample may range from about 1 fM to 1 μM, such as from about 1 pM to about 1 nM, including from about 1 pM to about 100 nM.

In some embodiments, the concentration of an entity of interest (e.g., a biological entity) in a sample is sufficiently low such that a detection probe binding to one entity of interest (e.g., a biological entity) will not randomly come into close proximity with another detection probe binding to another entity of interest (e.g., biological entity) in the absence of respective detection probes binding to the same entity of interest (e.g., biological entity), at least not to any great or substantial degree. By way of example only, the concentration of an entity of interest (e.g., biological entity) in a sample is sufficiently low such that a first target detection probe binding to a non-target entity of interest (e.g., a non-cancerous biological entity such as an extracellular vesicle comprising a first target) will not randomly come into close proximity with another different target detection probe that is bound to another non-target entity of interest (e.g., a non-cancerous biological entity such as an extracellular vesicle), at least not to any great or substantial degree, to generate a false-positive detectable signal.

In some embodiments, an entity of interest (e.g., biological entity such as an extracellular vesicle) may be captured or immobilized on a solid substrate prior to contacting the entity of interest with detection probes appropriate for use in accordance with the present disclosure. In some embodiments, an entity of interest may be captured on a solid substrate surface by non-specific interaction, including, e.g., adsorption. In some embodiments, an entity of interest may be selectively captured on a solid substrate surface. For example, in some embodiments, a solid substrate surface may be coated with an agent that specifically binds to an entity of interest (e.g., an antibody agent specifically targeting an entity of interest such as extracellular vesicles or cancer-associated extracellular vesicles). In some embodiments, a solid substrate surface may be coated with a member of an affinity binding pair and an entity of interest to be captured may be conjugated to a complementary member of the affinity binding pair. In some embodiments, an exemplary affinity binding pair includes, e.g., but is not limited to biotin and avidin-like molecules such as streptavidin. As will be understood by those of skill in the art, other appropriate affinity binding pairs can also be used to facilitate capture of an entity of interest to a solid substrate surface. In some embodiments, an entity of interest (e.g., biological entity such as extracellular vesicle) may be captured on a solid substrate surface by application of a current, e.g., as described in Ibsen et al. ACS Nano., 11:6641-6651 (2017) and Lewis et al. ACS Nano., 12:3311-3320 (2018), both of which describe use of an alternating current electrokinetic microarray chip device to isolate extracellular vesicles from an undiluted human blood or plasma sample.

A solid substrate may be provided in a form that is suitable for capturing an entity of interest (e.g., biological entity such as extracellular vesicle) and does not interfere with downstream handling, processing, and/or detection. For example, in some embodiments, a solid substrate may be or comprise a bead (e.g., a magnetic bead). In some embodiments, a solid substrate may be or comprise a surface. For example, in some embodiments, such a surface may be a capture surface of an assay chamber (including, e.g., a tube, a well, a microwell, a plate, a filter, a membrane, a matrix, etc.). Accordingly, in some embodiments, a method described herein comprises, prior to contacting an entity of interest (e.g., biological entity) with a plurality of detection probes, capturing or immobilizing the entity of interest on a solid substrate.

In some embodiments, a sample comprising an entity of interest may be processed, e.g., to remove undesirable entities such as cell debris or cells, prior to capturing the entity of interest on a solid substrate surface. For example, in some embodiments, such a sample may be subjected to centrifugation, e.g., to remove cell debris, cells, and/or other particulates. Additionally or alternatively, in some embodiments, such a sample may be subjected to size-exclusion-based purification or filtration. Various size-exclusion-based purification or filtration are known in the art and those skilled in the art will appreciate that in some cases, a sample may be subjected to a spin column purification based on specific molecular weight or particle size cutoff. Those skilled in the art will also appreciate that appropriate molecular weight or particle size cutoff for purification purposes can be selected, e.g., based on the size of the entity of interest (e.g., biological entity such as extracellular vesicle). For example, in some embodiments, size-exclusion separation methods may be applied to samples comprising extracellular vesicles to isolate a fraction of extracellular vesicles that are of a certain size (e.g., 30 nm-1000 nm). In some embodiments, size-exclusion separation methods may be applied to samples comprising extracellular vesicles to isolate a fraction of extracellular vesicles that are greater than 70 nm and no more than 200 nm.

In some embodiments, an entity of interest (e.g., biological entity) in a sample may be processed prior to contacting the entity of interest with a plurality of detection probes described and/or utilized herein. Different sample processing and/or preparation can be performed, e.g., to stabilize targets (e.g., molecular targets) in an entity of interest (e.g., biological entity) to be detected, and/or to facilitate exposure of targets (e.g., molecular targets such as intracellular targets) to detection probes, and/or to reduce non-specific binding of detection probes. Examples of such sample processing and/or preparation are known in the art and include, but are not limited to, crosslinking molecular targets (e.g., fixation), permeabilization of biological entities (e.g., cells or extracellular vesicles), and/or blocking non-specific binding sites.

Following contacting an entity of interest (e.g., biological entity) in a sample with a set of detection probes, such a mixture may be incubated for a period of time sufficient for the detection probes to bind corresponding targets (e.g., molecular targets), if present, in the entity of interest to form a double-stranded complex (e.g., as described herein). In some embodiments, such a mixture is incubated for a period of time ranging from about 5 min to about 5 hours, including from about 30 min to about 2 hours, at a temperature ranging from about 10 to about 50° C., including from about 20° C. to about 37° C.

A double-stranded complex (resulted from contacting an entity of interest such as a biological entity with detection probes) can then be subsequently contacted with a nucleic acid ligase to perform nucleic acid ligation of a free 3' end hydroxyl and 5' end phosphate end of oligonucleotide strands of detection probes, thereby generating a ligated template comprising oligonucleotide strands of at least two or more detection probes. In some embodiments, prior to contacting an assay sample comprising a double-stranded complex with a nucleic acid ligase, at least one or more inhibitor oligonucleotide (e.g., as described herein) can be added to the assay sample such that the inhibitor oligonucleotide can capture any residual free-floating detection probes that may otherwise interact with each other during a ligation reaction.

As is known in the art, ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary. Any known nucleic acid ligase (e.g., DNA ligases) may be employed, including but not limited to temperature sensitive and/or thermostable ligases. Non-limiting examples of temperature sensitive ligases include bacteriophage T4 DNA ligase, bacteriophage T7 ligase, and E. coli ligase. Non-limiting examples of thermostable ligases include Taq ligase, Tth ligase, and Pfu ligase. Thermostable ligase may be obtained from thermophilic or hyperthermophilic organisms, including but not limited to, prokaryotic, eukaryotic, or archael organisms. In some embodiments, a nucleic acid ligase is a DNA ligase. In some embodiments, a nucleic acid ligase can be a RNA ligase.

In some embodiments, in a ligation step, a suitable nucleic acid ligase (e.g., a DNA ligase) and any reagents that are necessary and/or desirable are combined with the reaction mixture and maintained under conditions sufficient for ligation of the hybridized ligation oligonucleotides to occur. Ligation reaction conditions are well known to those of skill in the art. During ligation, a reaction mixture, in some embodiments, may be maintained at a temperature ranging from about 20° C. to about 45° C., such as from about 25° C. to about 37° C. for a period of time ranging from about 5 minutes to about 16 hours, such as from about 1 hour to about 4 hours. In yet other embodiments, a reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 minutes to about 16 hours, such as from about 1 hour to about 10 hours, including from about 2 to about 8 hours.

Detection of such a ligated template can provide information as to whether an entity of interest (e.g., a biological entity) in a sample is positive or negative for targets to which detection probes are directed. For example, a detectable level of such a ligated template is indicative of a tested entity of interest (e.g., a biological entity) comprising targets (e.g., molecular targets) of interest. In some embodiments, a detectable level is a level that is above a reference level, e.g., by at least 10% or more, including, e.g., at least 20%, at least 30%, at least 40%, at least 50%, at least 60%, at least 70%, at least 80%, at least 90% or more. In some embodiments, a reference level may be a level observed in a negative control sample, such as a sample in which an entity of interest comprising such targets is absent. Conversely, a non-detectable level (e.g., a level that is below the threshold of a detectable level) of such a ligated template indicates that at least one of targets (e.g., molecular targets) of interest is absent from a tested entity of interest (e.g., a biological entity). Those of skill in the art will appreciate that a threshold that separates a detectable level from a non-detectable level may be determined based on, for example, a desired sensitivity level, and/or a desired specificity level that is deemed to be optimal for each application and/or purpose. For example, in some embodiments, a specificity of 99.7% may be achieved using a system provided herein, for example by setting a threshold that is three standard deviations above a reference level (e.g., a level observed in a negative control sample, such as, e.g., a sample derived from one or more normal healthy individuals). Additionally or alternatively, those of skill in the art will appreciate that a threshold of a detectable level (e.g., as reflected by a detection signal intensity) may be 1 to 100-fold above a reference level.

In some embodiments, a method provided herein comprises, following ligation, detecting a ligated template, e.g., as a measure of the presence and/or amount of an entity of interest in a sample. In various embodiments, detection of a ligated template may be qualitative or quantitative. As such, in some embodiments where detection is qualitative, a method provides a reading or evaluation, e.g., assessment, of whether or not an entity of interest (e.g., a biological entity) comprising at least two or more targets (e.g., molecular targets) is present in a sample being assayed. In other embodiments, a method provides a quantitative detection of whether an entity of interest (e.g., a biological entity) comprising at least two or more targets (e.g., molecular targets) is present in a sample being assayed, e.g., an evaluation or assessment of the actual amount of an entity of interest (e.g., a biological entity) comprising at least two or more targets (e.g., molecular targets) in a sample being assayed. In some embodiments, such quantitative detection may be absolute or relative.

A ligated template formed by using technologies provided herein may be detected by an appropriate method known in the art. Those of skill in the art will appreciate that appropriate detection methods may be selected based on, for example, a desired sensitivity level and/or an application in which a method is being practiced. In some embodiments, a ligated template can be directly detected without any amplification, while in other embodiments, ligated template may be amplified such that the copy number of the ligated template is increased, e.g., to enhance sensitivity of a particular assay. Where detection without amplification is practicable, a ligated template may be detected in a number of different ways. For example, oligonucleotide domains of detection probes (e.g., as described and/or utilized herein) may have been directly labeled, e.g., fluorescently or radioisotopically labeled, such that a ligated template is directly labeled. For example, in some embodiments, an oligonucleotide domain of a detection probe (e.g., as provided and/or utilized herein) can comprise a detectable label. A detectable label may be a composition detectable by spectroscopic, photochemical, biochemical, immunochemical, electrical, optical or chemical means. Such labels include biotin for staining with labeled Streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{34}$S, $^{14}$C, or $^{32}$P), enzymes (e.g., horseradish peroxidase, alkaline phosphatase and others commonly used in an ELISA), and calorimetric labels such as colloidal gold or colored glass or plastic (e.g., polystyrene, polypropylene, latex, etc.) beads. In some embodiments, a directly labeled ligated template may be size separated from the remainder of the reaction mixture, including unligated directly labeled ligation oligonucleotides, in order to detect the ligated template.

In some embodiments, detection of a ligated template can include an amplification step, where the copy number of ligated nucleic acids is increased, e.g., in order to enhance sensitivity of the assay. The amplification may be linear or exponential, as desired, where amplification can include, but is not limited to polymerase chain reaction (PCR); quantitative PCR, isothermal amplification, nucleic acid sequence-based amplification (NASBA), digital droplet PCR, etc.

Various technologies for achieving PCR amplification are known in the art; those skilled in the art will be well familiar with a variety of embodiments of PCR technologies, and will readily be able to select those suitable to amplify a ligated template generated using technologies provided herein. For example, in some embodiments, a reaction mixture that includes a ligated template is combined with one or more primers that are employed in the primer extension reaction, e.g., PCR primers (such as forward and reverse primers employed in geometric (or exponential) amplification or a single primer employed in a linear amplification). Oligonucleotide primers with which one or more ligated templates are contacted should be of sufficient length to provide for hybridization to complementary template DNA under appropriate annealing conditions. Primers are typically at least 10 bp in length, including, e.g., at least 15 bp in length, at least 20 bp in length, at least 25 bp in length, at least 30 bp in length or longer. In some embodiments, the length of primers can typically range from about 15 to 50 bp in length, from about 18 to 30 bp, or about 20 to 35 bp in length. Ligated templates may be contacted with a single primer or a set of two primers (forward and reverse primers), depending on whether primer extension, linear, or exponential amplification of the template DNA is desired. In addition to the above components, a reaction mixture comprising a ligated template typically includes a polymerase and deoxyribonucleoside triphosphates (dNTPs). The desired polymerase activity may be provided by one or more distinct polymerase enzymes. In preparing a reaction mixture, e.g., for amplification of a ligated template, various constituent components may be combined in any convenient order. For example, an appropriate buffer may be combined with one or more primers, one or more polymerases and a ligated template to be detected, or all of the various constituent components may be combined at the same time to produce the reaction mixture.

III. Detection of Target Combination(s) (e.g., Target Biomarker Signature(s)) in Individual Biological Entities (e.g., Extracellular Vesicles)

In some embodiments, technologies (including, e.g., systems, compositions, and methods) provided herein can be useful for detection of one or more target combinations (e.g., one or more target biomarker signatures for a disease, disorder, or condition, e.g., cancer) in individual biological entities (e.g., extracellular vesicles). In some embodiments, the present disclosure provides technologies (including systems, compositions, and methods) that solve problems of many conventional diagnostic assays, e.g., based on cell-free nucleic acids, serum proteins, and/or bulk analysis of extracellular vesicles, by detecting co-localization of one or more target combinations (e.g., one or more target biomarker signatures) of a disease, disorder, or condition (e.g., cancer) in individual extracellular vesicles. In some embodiments, a target biomarker signature to be detected in accordance with the present disclosure comprises at least one extracellular vesicle-associated membrane-bound polypeptide and at least one target biomarker selected from the group consisting of surface protein biomarkers, internal protein biomarkers, and RNA biomarkers present in extracellular vesicles associated with such a disease, disorder, or condition (e.g., cancer). In some embodiments, such a target biomarker signature may be identified by bioinformatics analysis.

In one aspect, the present disclosure, among other things, provides compositions (e.g., systems and kits) and methods for detection of one or more biomarker signatures in individual biological entities (e.g., extracellular vesicles). In many embodiments, such a target biomarker signature is specific for a disease, disorder, or condition, e.g., cancer. In some embodiments, such target biomarker signatures can be identified by a multi-pronged bioinformatics analysis and biological approach, which for example, in some embodiments involve computational analysis of a diverse set of data, e.g., in some embodiments comprising one or more of sequencing data, expression data, mass spectrometry, histology, post-translational modification data, and/or in vitro and/or in vivo experimental data through machine learning and/or computational modeling.

In some embodiments, a combination of biomarkers (e.g., a target biomarker signature) may be detected by a plurality of (e.g., at least two or more) pairwise or orthogonal combinations of detection probes, wherein each pair of detection probes may be directed to at least one distinct target. In some embodiments, a combination of biomarkers (e.g., a target biomarker signature) may be detected by a set of detection probes that each are designed to hybridize to one another to form a linear complex. In some embodiments, a plurality of (e.g., at least two or more) combinations of biomarkers may be selected for cancer detection. In some embodiments, a plurality of (e.g., at least two or more) combinations of biomarkers may be selected for detection of a specific cancer or its stage and/or subtype thereof. In some embodiments, a plurality of (e.g., at least two or more) orthogonal combinations of biomarkers may be selected for cancer detection. In some embodiments, a plurality of (e.g., at least two or more) orthogonal combinations of biomarkers may be selected for detection of a specific cancer or its stage and/or subtype thereof. In some embodiments, a plurality of (e.g., at least two or more) target biomarker signatures may be selected for cancer detection. In some embodiments, a plurality of (e.g., at least two or more) target biomarker signatures may be selected for detection of a specific cancer or its stage and/or subtype thereof. By way of example only, in some embodiments, at least a Biomarker Combination A and a Biomarker Combination B can be selected for detection of a specific cancer or its stage and/or subtype thereof, wherein the Biomarker Combination A can be or comprise Target 1 and Target 2; and the Biomarker Combination B can be or comprise Target 1 and Target 3. In some embodiments, at least a Biomarker Combination A and a Biomarker Combination B can be selected for detection of a specific cancer or its stage and/or subtype thereof, wherein the Biomarker Combination A can be or comprise Target 1 and Target 2; and the Biomarker Combination B can be or comprise Target 3 and Target 4.

In some embodiments, a target biomarker signature for a disease, disorder, or condition (e.g., cancer) comprises at least one or more (e.g., 1, 2, 3, 4, 5, 6, 7, 8, or more) extracellular vesicle-associated membrane-bound polypeptide (e.g., surface polypeptide present in extracellular vesicles associated with a disease, disorder, or condition (e.g., cancer) and at least one or more (e.g., 1, 2, 3, 4, 5, 6, 7, 8, or more) target biomarkers selected from the group consisting of surface protein biomarker(s), intravesicular protein biomarker(s), and intravesicular RNA biomarker(s), such that the combination of such extracellular vesicle-associated membrane-bound polypeptide(s) and such target biomarker(s) present a target biomarker signature of a disease, disorder, or condition (e.g., cancer), when detected using technologies provided herein (e.g., a target entity detection system described herein), provides (a) high specificity (e.g., greater than 99% or higher such as greater than 99.5%) to minimize the number of false positives, and (b) high sensitivity (e.g., greater than 40%) for a disease, disorder, or condition to be diagnosed (e.g., cancer or early-stage cancer when prognosis is most favorable). In some embodiments, a target biomarker signature of a disease, disorder, or condition (e.g., cancer) comprises at least one extracellular vesicle-associated membrane-bound polypeptide (e.g., surface polypeptide present in extracellular vesicles associated with a disease, disorder, or condition (e.g., cancer) and at least one target biomarker for selected from the group consisting of surface protein biomarker(s), intravesicular protein biomarker(s), and intravesicular RNA biomarker(s), such that the combination of such extracellular vesicle-associated membrane-bound polypeptide(s) and such target biomarker(s) present a target biomarker signature of a disease, disorder, or condition (e.g., cancer), when detected using technologies provided herein (e.g., a target entity detection system described herein), provides a positive predictive value (PPV) of at least 10% or higher, including, e.g., at least 15% or above.

In some embodiments, a target biomarker signature for a disease, disorder, or condition (e.g., cancer) comprises at least one or more (e.g., 1, 2, 3, 4, 5, 6, 7, 8, or more) extracellular vesicle-associated membrane-bound polypeptides and at least one or more (e.g., 1, 2, 3, 4, 5, 6, 7, 8, or more) surface protein biomarkers, wherein the extracellular vesicle-associated membrane-bound polypeptide(s) and surface protein biomarker(s) are distinct.

In some embodiments, a target biomarker signature for a disease, disorder, or condition (e.g., cancer) comprises at least one or more (e.g., 1, 2, 3, 4, 5, 6, 7, 8, or more) extracellular vesicle-associated membrane-bound polypeptides (e.g., ones described herein) and at least one or more (e.g., 1, 2, 3, 4, 5, 6, 7, 8, or more) intravesicular protein biomarkers (e.g., ones described herein). In some such embodiments, the extracellular vesicle-associated membrane-bound polypeptide(s) and the intravesicular protein biomarker(s) can be encoded by the same gene, while the former is expressed in the membrane of the extracellular vesicle and the latter is expressed within the extracellular vesicle. In some such embodiments, the extracellular vesicle-associated membrane-bound polypeptide(s) and the intravesicular protein biomarker(s) can be encoded by different genes.

In some embodiments, a target biomarker signature for a disease, disorder, or condition (e.g., cancer) comprises at least one or more (e.g., 1, 2, 3, 4, 5, 6, 7, 8, or more) extracellular vesicle-associated membrane-bound polypeptides and at least one or more (e.g., 1, 2, 3, 4, 5, 6, 7, 8, or more) intravesicular RNA (e.g., mRNA) biomarkers. In some such embodiments, the extracellular vesicle-associated membrane-bound polypeptide(s) and the intravesicular RNA (e.g., mRNA) biomarker(s) can be encoded by the same gene. In some such embodiments, the extracellular vesicle-associated membrane-bound polypeptide(s) and the intravesicular RNA (e.g., mRNA) biomarker(s) can be encoded by different genes.

IV. Exemplary Methods of Detecting Target Biomarker Signature(s)

In general, the present disclosure provides technologies according to which a target biomarker signature is analyzed and/or assessed in a blood-derived sample comprising extracellular vesicles from a subject in need thereof; in some embodiments, a diagnosis or therapeutic decision is made based on such analysis and/or assessment. One of ordinary skill in the art reading the present disclosure will recognize that various combinations of methods of detecting described herein may be used to detect one or more target biomarker signatures in a sample. For example, in some embodiments, a combination of bulk EV analysis and single-EV profiling analysis may be used to detect one or more target biomarker signatures in a sample. In some embodiments, a single-EV profiling analysis that involves a target entity detection system (e.g., ones as described and/or utilized herein) may be used in combination with one or more methods (e.g., as described herein) for detecting one or more protein- and/or nucleic acid-based biomarkers of a target biomarker signature. In some embodiments, a sample comprising extracellular vesicles may be divided into a plurality of aliquots, which may permit detection of a plurality of (e.g., at least two or more) biomarkers of a target biomarker signature in a single sample using different detection technologies described and/or utilized herein.

For example, in some embodiments, methods of detecting one or more target biomarkers of a target biomarker signature may include methods for detecting one or more markers of a target biomarker signature as proteins. Exemplary protein-based methods of detecting one or more markers include, but are not limited to, proximity ligation assay, mass spectrometry (MS) and immunoassays, such as immunoprecipitation; Western blot; ELISA; immunohistochemistry; immunocytochemistry; flow cytometry; and immuno-PCR. In some embodiments, an immunoassay can be a chemiluminescent immunoassay. In some embodiments, an immunoassay can be a high-throughput and/or automated immunoassay platform.

In some embodiments, methods of detecting one or more markers of a target biomarker signature as proteins in a sample comprise contacting a sample with one or more antibody agents directed to such one or more markers of interest. In some embodiments, such methods also comprise contacting such a sample with one or more detection labels. In some embodiments, antibody agents are labeled with one or more detection labels.

In some embodiments, detecting binding between a biomarker of interest and an antibody agent for the biomarker of interest includes determining absorbance values or emission values for one or more detection agents. For example, the absorbance values or emission values are indicative of amount and/or concentration of biomarker of interest expressed by extracellular vesicles (e.g., higher absorbance is indicative of higher level of biomarker of interest expressed by extracellular vesicles). In some embodiments, absorbance values or emission values for detection agents are above a threshold value. In some embodiments, absorbance values or emission values for detection agents is at least 1.3, at least 1.4, at least 1.5, at least 1.6, at least 1.7, at least 1.8, at least 1.9, at least 2.0, at least 2.5, at least 3.0, at least 3.5 fold or greater than a threshold value. In some embodiments, the threshold value is determined across a population of a control or reference group (e.g., healthy subjects or non-cancer subjects in the context of cancer detection).

In some embodiments, methods of detecting one or more target biomarkers of a target biomarker signature may include methods for detecting one or more markers as nucleic acids. Exemplary nucleic acid-based methods of detecting one or more markers include, but are not limited to, performing nucleic acid amplification methods, such as polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). In some embodiments, a nucleic acid-based method of detecting one or more markers includes detecting hybridization between one or more nucleic acid probes and one or more nucleotides that encode a biomarker of interest. In some embodiments, the nucleic acid probes are each complementary to at least a portion of one of the one or more nucleotides that encode the biomarker of interest. In some embodiments, the nucleotides that encode the biomarker of interest include DNA (e.g., cDNA). In some embodiments, the nucleotides that encode the biomarker of interest include RNA (e.g., mRNA).

In some embodiments, methods of detecting one or more target biomarkers of a target biomarker signature may involve proximity-ligation-immuno quantitative polymerase chain reaction (pliq-PCR). Pliq-PCR can have certain advantages over other technologies to profile EVs. For example, pliq-PCR can have a sensitivity three orders of magnitude greater than other standard immunoassays, such as ELISAs (Darmanis et al., 2010). In some embodiments, a pliq-PCR reaction can be designed to have an ultra-low LOD, which enables to detect trace levels of tumor-derived EVs, for example, down to a thousand EVs per mL.

In some embodiments, methods for detecting one or more target biomarkers of a target biomarker signature may involve other technologies for detecting EVs, including, e.g., Nanoplasmic Exosome (nPLEX) Sensor (Im et al., 2014) and the Integrated Magnetic-Electrochemical Exosome (iMEX) Sensor (Jeong et al., 2016), which have reported LODs of ~$10^3$ and ~$10^4$ EVs, respectively (Shao et al., 2018).

In some embodiments, methods for detecting one or more target biomarkers of a target biomarker signature in extracellular vesicles can involve bulk EV sample analysis.

In some embodiments, methods for detecting one or more target biomarkers of a target biomarker signature in extracellular vesicles can be based on profiling individual EVs (e.g., single-EV profiling assays), which is further discussed in the section entitled "Provided Methods for Profiling Individual Extracellular Vesicles (EVs)" below.

In some embodiments, extracellular vesicles in a sample may be captured or immobilized on a solid substrate prior to detecting one or more target biomarkers of a target biomarker signature in accordance with the present disclosure. In some embodiments, extracellular vesicles may be captured on a solid substrate surface by non-specific interaction, including, e.g., adsorption. In some embodiments, extracellular vesicles may be selectively captured on a solid substrate surface. For example, in some embodiments, a solid substrate surface may be coated with an agent that specifically binds to extracellular vesicles (e.g., an antibody agent specifically targeting extracellular vesicles, e.g., associated with a disease, disorder, or condition, e.g., cancer). In some embodiments, a solid substrate surface may be coated with a member of an affinity binding pair and an entity of interest (e.g., extracellular vesicles) to be captured may be conjugated to a complementary member of the affinity binding pair. In some embodiments, an exemplary affinity binding pair includes, e.g., but is not limited to biotin and avidin-like molecules such as streptavidin. As will be understood by those of skilled in the art, other appropriate affinity binding pairs can also be used to facilitate capture of an entity of interest to a solid substrate surface. In some embodiments, an entity of interest may be captured on a solid substrate surface by application of a current, e.g., as described in Ibsen et al. ACS Nano., 11: 6641-6651 (2017) and Lewis et al. ACS Nano., 12:3311-3320 (2018), both of which describe use of an alternating current electrokinetic microarray chip device to isolate extracellular vesicles from an undiluted human blood or plasma sample.

A solid substrate may be provided in a form that is suitable for capturing extracellular vesicles and does not interfere with downstream handling, processing, and/or detection. For example, in some embodiments, a solid substrate may be or comprise a bead (e.g., a magnetic bead). In some embodiments, a solid substrate may be or comprise a surface. For example, in some embodiments, such a surface may be a capture surface of an assay chamber (including, e.g., a tube, a well, a microwell, a plate, a filter, a membrane, a matrix, etc.). Accordingly, in some embodiments, a method described herein comprises, prior to detecting provided biomarkers in a sample, capturing or immobilizing extracellular vesicles on a solid substrate.

In some embodiments, a sample may be processed, e.g., to remove undesirable entities such as cell debris or cells, prior to capturing extracellular vesicles on a solid substrate surface. For example, in some embodiments, such a sample may be subjected to centrifugation, e.g., to remove cell debris, cells, and/or other particulates. Additionally or alternatively, in some embodiments, such a sample may be subjected to size-exclusion-based purification or filtration. Various size-exclusion-based purification or filtration are known in the art and those skilled in the art will appreciate that in some cases, a sample may be subjected to a spin column purification based on specific molecular weight or particle size cutoff. Those skilled in the art will also appreciate that appropriate molecular weight or particle size cutoff for purification purposes can be selected, e.g., based on the size of extracellular vesicles. For example, in some embodiments, size-exclusion separation methods may be applied to samples comprising extracellular vesicles to isolate a fraction of extracellular vesicles that are of a certain size (e.g., greater than 30 nm and no more than 1000 nm, or greater than 70 nm and no more than 200 nm). Typically, extracellular vesicles may range from 30 nm to several micrometers in diameter. See, e.g., Chuo et al., "Imaging extracellular vesicles: current and emerging methods" *Journal of Bio-*

*medical Sciences* 25: 91 (2018), which provides information of sizes for different extracellular vesicle (EV) subtypes: migrasomes (0.5-3 μm), microvesicles (0.1-1 μm), oncosomes (1-10 μm), exomeres (<50 nm), small exosomes (60-80 nm), and large exosomes (90-120 nm). In some embodiments, size-exclusion separation methods may be applied to samples comprising extracellular vesicles to isolate specific EV subtype(s).

In some embodiments, extracellular vesicles in a sample may be processed prior to detecting one or more target biomarkers of a target biomarker signature for a disease, disorder, or condition, e.g., cancer. Different sample processing and/or preparation can be performed, e.g., to stabilize targets (e.g., target biomarkers) in extracellular vesicles to be detected, and/or to facilitate exposure of targets (e.g., intravesicular proteins and/or RNA such as mRNA) to a detection assay (e.g., as described herein), and/or to reduce non-specific binding. Examples of such sample processing and/or preparation are known in the art and include, but are not limited to, crosslinking molecular targets (e.g., fixation), permeabilization of biological entities (e.g., cells or extracellular vesicles), and/or blocking non-specific binding sites.

In one aspect, the present disclosure provides a method for detecting whether a target biomarker signature of a disease, disorder, or condition such as, e.g., cancer is present or absent in a biological sample from a subject in need thereof, which may be in some embodiments a blood-derived sample comprising extracellular vesicles. In some embodiments, such a method comprises (a) detecting, in a biological sample such as a blood-derived sample (e.g., a plasma sample) from a subject, biological entities of interest (including, e.g., extracellular vesicles) expressing a target biomarker signature of a disease, disorder, or condition such as, e.g., cancer; and (b) comparing sample information indicative of the level of the target biomarker signature-expressing biological entities of interest (e.g., extracellular vesicles) in the biological sample (e.g., blood-derived sample) to reference information including a reference threshold level. In some embodiments, a reference threshold level corresponds to a level of biological entities of interest (e.g., extracellular vesicles) that express such a target biomarker signature in comparable samples from a population of reference subjects, e.g., non-cancer subjects. In some embodiments, exemplary non-cancer subjects include healthy subjects (e.g., healthy subjects of specified age ranges, such as e.g., ages 20-30, or ages 30-40, or ages 40-50, or ages 50-60, or ages 60-70, or above age 70 or higher), subjects with non-cancer related health diseases, disorders, or conditions (including, e.g., subjects having symptoms of inflammatory bowel diseases or disorders), subjects having benign tumors or masses, and combinations thereof.

In some embodiments, a sample is determined to have extracellular vesicles expressing a target biomarker signature (e.g., ones described herein) when it shows an elevated level of target biomarker signature-expressing extracellular vesicles relative to a reference threshold level (e.g., ones described herein). In some embodiments, a sample is determined to be positive for target biomarker signature-expressing extracellular vesicles if its level is at least 30% or higher, including, e.g., at least 40%, at least 50%, at least 60%, at least 70%, at least 80%, at least 90%, at least 95% or higher, as compared to a reference threshold level. In some embodiments, a sample is determined to be positive for target biomarker signature-expressing extracellular vesicles if its level is at least 2-fold or higher, including, e.g., at least 3-fold, at least 4-fold, at least 5-fold, at least 6-fold, at least 7-fold, at least 8-fold, at least 9-fold, at least 10-fold, at least 50-fold, at least 100-fold, at least 250-fold, at least 500-fold, at least 750-fold, at least 1000-fold, at least 2500-fold, at least 5000-fold, or higher, as compared to a reference threshold level.

In some embodiments, a binary classification system may be used to determine whether a sample is positive for target biomarker signature-expressing extracellular vesicles. For example, in some embodiments, a sample is determined to be positive for target biomarker signature-expressing extracellular vesicles if its level is at or above a reference threshold level, e.g., a cutoff value. In some embodiments, such a reference threshold level (e.g., a cutoff value) may be determined based on a log-normal distribution around healthy subjects (e.g., of specified age ranges) and selection of the number of standard deviations (SDs) (e.g., at least 1.5, at least 1.6, at least 1.7, at least 1.8, at least 1.9, at least 2, at least 2.1, at least 2.2, at least 2.3, at least 2.4, at least 2.5, at least 2.6, at least 2.7, at least 2.8, at least 2.9, at least 3, at least 3.1, at least 3.2, at least 3.3, at least 3.4, at least 3.5, at least 3.6 or higher SDs) necessary to achieve the specificity of interest (e.g., at least 95% or higher specificity [including, e.g., at least 96%, at least 97%, at least 98%, at least 99%, or higher specificity] such as in some embodiments at least 99.8% specificity), e.g., based on prevalence of a disease, disorder, or condition such as a certain cancer.

The present disclosure, among other things, also provides technologies for determining whether a subject as having or being susceptible to a disease, disorder, or condition such as, e.g., cancer. For example, in some embodiments, when a blood-derived sample from a subject in need thereof shows a level of target biomarker signature-expressing extracellular vesicles that is at or above a reference threshold level, e.g., cutoff value, then the subject is classified as having or being susceptible to a disease, disorder, or condition such as, e.g., cancer. In some such embodiments, a reference threshold level (e.g., cutoff value) may be determined based on a log-normal distribution around healthy subjects (e.g., of specified age ranges) and selection of the number of standard deviations (SDs) (e.g., at least 1.5, at least 1.6, at least 1.7, at least 1.8, at least 1.9, at least 2, at least 2.1, at least 2.2, at least 2.3, at least 2.4, at least 2.5, at least 2.6, at least 2.7, at least 2.8, at least 2.9, at least 3, at least 3.1, at least 3.2, at least 3.3, at least 3.4, at least 3.5, at least 3.6 or higher SDs) necessary to achieve the specificity of interest (e.g., at least 95% or higher specificity [including, e.g., at least 96%, at least 97%, at least 98%, at least 99%, or higher specificity] such as in some embodiments at least 99.8% specificity), e.g., based on prevalence of a disease, disorder, or condition such as a certain cancer. In some embodiments, when a blood-derived sample from a subject in need thereof shows an elevated level of target biomarker signature-expressing extracellular vesicles relative to a reference threshold level, then the subject is classified as having or being susceptible to a disease, disorder, or condition such as, e.g., cancer. In some embodiments, a subject in need thereof is classified as having or being susceptible to a disease, disorder, or condition such as, e.g., cancer when such a subject's blood-derived sample shows a level of target biomarker signature-expressing extracellular vesicles that is at least 30% or higher, including, e.g., at least 40%, at least 50%, at least 60%, at least 70%, at least 80%, at least 90%, at least 95% or higher, as compared to a reference threshold level. In some embodiments, a subject in need thereof is classified as having or being susceptible to a disease, disorder, or condition such as, e.g., cancer when such a subject's blood-derived sample shows a level of target biomarker signature-expressing extracellular vesicles that is at least 2-fold or higher, including, e.g., at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, at least 250-fold, at least 500-fold, at least 750-fold, at least 1000-fold, or higher, as compared to a reference threshold level. When a blood-derived sample from a subject in need thereof shows a comparable level (e.g., within 10-20%) to a reference threshold level, then the subject is classified as not likely to have or as not likely to be susceptible to a disease, disorder, or condition such as, e.g., cancer. In some such embodiments, a reference threshold level corresponds to a level of extracellular vesicles that express a target biomarker signature in comparable samples from a population of reference subjects, e.g., non-cancer subjects. In some embodiments, exemplary non-cancer subjects include healthy subjects (e.g., healthy subjects of specified age ranges, such as e.g., below 20 (e.g., including infants), ages 20-30, or ages 30-40, or ages 40-50, or ages 50-60, or ages 60-70, or above age 70 or higher), subjects with non-cancer related health diseases, disorders, or conditions (including, e.g., subjects having symptoms of inflammatory bowel diseases or disorders), subjects having benign tumors or masses, and combinations thereof.

V. Provided Methods for Profiling Individual Extracellular Vesicles (EVs)

In some embodiments, assays for profiling individual extracellular vesicles (e.g., single EV profiling assays) can be used to detect one or more target biomarker signatures for one or more diseases, disorders, or conditions (e.g., cancers). For example, in some embodiments, such an assay may involve (i) a capture assay through targeting one or more markers of a target biomarker signature for a disease, disorder, or condition (e.g., cancer) and (ii) one or more detection assays for at least one or more additional provided markers of such a target biomarker signature, wherein such a capture assay is performed prior to such a detection assay.

In some embodiments, a capture assay is performed to selectively capture extracellular vesicles from a blood or blood-derived sample (e.g., plasma sample) of a subject in need thereof. In some embodiments, a capture assay is performed to selectively capture extracellular vesicles of a certain size range, and/or certain characteristic(s), for example, extracellular vesicles associated with a disease, disorder, or condition (e.g., cancer). In some such embodiments, prior to a capture assay, a blood or blood-derived sample may be pre-processed to remove non-extracellular vesicles, including, e.g., but not limited to soluble proteins and interfering entities such as, e.g., cell debris. For example, in some embodiments, extracellular vesicles are purified from a blood or blood-derived sample of a subject using size exclusion chromatography. In some such embodiments, extracellular vesicles can be directly purified from a blood or blood-derived sample using size exclusion chromatography, which in some embodiments may remove at least 90% or higher (including, e.g., at least 93%, 95%, 97%, 99% or higher) of soluble proteins and other interfering agents such as, e.g., cell debris.

In some embodiments, a capture assay comprises a step of contacting a blood or blood-derived sample with at least one capture agent comprising a target-capture moiety that binds to at least one biomarker of a target biomarker signature for a disease, disorder, or condition (e.g., cancer). In some embodiments, a capture assay may be multiplexed, which comprises a step of contacting a blood or blood-derived sample with a set of capture agents, each capture agent comprising a target-capture moiety that binds to a distinct biomarker of a target biomarker signature for a disease, disorder, or condition (e.g., cancer). In some embodiments, a target-capture moiety is directed to an extracellular vesicle-associated membrane-bound polypeptide.

In some embodiments, such a target-capture moiety may be immobilized on a solid substrate. Accordingly, in some embodiments, a capture agent employed in a capture assay is or comprises a solid substrate comprising at least one or more (e.g., 1, 2, 3, 4, 5, or more) target-capture moiety conjugated thereto, each target-capture moiety directed to an extracellular vesicle-associated membrane-bound polypeptide (e.g., ones as described and/or utilized herein). A solid substrate may be provided in a form that is suitable for capturing extracellular vesicles and does not interfere with downstream handling, processing, and/or detection. For example, in some embodiments, a solid substrate may be or comprise a bead (e.g., a magnetic bead). In some embodiments, a solid substrate may be or comprise a surface. For example, in some embodiments, such a surface may be a capture surface of an assay chamber (including, e.g., a tube, a well, a microwell, a plate, a filter, a membrane, a matrix, etc.). In some embodiments, a capture agent is or comprises a magnetic bead comprising a target-capture moiety conjugated thereto.

In some embodiments, a detection assay is performed to detect one or more biomarkers of a target biomarker signature (e.g., ones that are different from ones targeted in a capture assay) in extracellular vesicles that are captured by a capture assay (e.g., as described above). In some embodiments, a detection assay may comprise immuno-PCR. In some embodiments, an immuno-PCR may involve at least one probe targeting a single biomarker of a target biomarker signature. In some embodiments, an immuno-PCR may involve a plurality of (e.g., at least two, at least three, at least four, or more) probes directed to different epitopes of the same biomarker of a target biomarker signature. In some embodiments, an immuno-PCR may involve a plurality of (e.g., at least two, at least three, at least four, or more) probes, each directed to a different biomarker of a target biomarker signature.

In some embodiments, a detection assay may comprise reverse transcription polymerase chain reaction (RT-PCR). In some embodiments, an RT-PCR may involve at least one primer/probe set targeting a single biomarker of a target biomarker signature. In some embodiments, an RT-PCR may involve a plurality of (e.g., at least two, at least three, at least four, or more) primer/probe sets, each set directed to a different biomarker of a target biomarker signature.

In some embodiments, a detection assay may comprise a proximity-ligation-immuno quantitative polymerase chain reaction (pliq-PCR), for example, to determine co-localization of biomarker proteins of a target biomarker signature within extracellular vesicles (e.g., captured extracellular vesicles that express at least one extracellular vesicle-associated membrane-bound polypeptide).

In some embodiments, a detection assay employs a target entity detection system described herein (e.g., as described in the section entitled "Provided Target Entity Detection Systems"), which is, in part, based on interaction and/or co-localization of a target biomarker signature in individual extracellular vesicles. For example, such a target entity detection system can detect in a sample (e.g., in a biological, environmental, or other sample), in some embodiments at a single entity level, entities of interest (e.g., biological or chemical entities of interest, such as extracellular vesicles or analytes) comprising at least one or more (e.g., at least two or more) targets (e.g., molecular targets). Those skilled in the art, reading the present disclosure, will recognize that provided target entity detection systems are useful for a wide variety of applications and/or purposes, including, e.g., for detection of a disease, disorder, or condition (e.g., cancer). For example, in some embodiments, provided target entity detection systems may be useful for medical applications and/or purposes. In some embodiments, provided target entity detection systems may be useful to screen (e.g., regularly screen) individuals (e.g., asymptomatic individuals) for a disease or condition (e.g., cancer). In some embodiments, provided target entity detection systems may be useful to screen (e.g., regularly screen) individuals (e.g., asymptomatic individuals) for different types of cancer. In some embodiments, provided target entity detection systems are effective even when applied to populations comprising or consisting of asymptomatic individuals (e.g., due to sufficiently high sensitivity and/or low rates of false-positive and/or false-negative results). In some embodiments, provided target entity detection systems may be useful as a companion diagnostic in conjunction with a disease treatment (e.g., treatment of a disease, disorder, or condition such as, e.g., cancer).

In some embodiments, a plurality of (e.g., at least two or more) detection assays may be performed to detect a plurality of biomarkers (e.g., at least two or more) of one or more target biomarker signatures (e.g., ones that are different from ones targeted in a capture assay) in extracellular vesicles, e.g., ones that are captured by a capture assay (e.g., as described above). In some embodiments, a plurality of detection assays may comprise (i) a provided target entity detection system or a system described herein (e.g., as described in the section entitled "Provided Target Entity Detection Systems"); and (ii) immuno-PCR. In some embodiments, a plurality of detection assays may comprise (i) a provided target entity detection system or a system described herein (e.g., as described in the section entitled "Provided Target Entity Detection Systems"); and (ii) RT-PCR.

VI. Uses

In some embodiments, technologies provided herein can be applied to a sample of interest comprising a biological entity to be assayed. In some embodiments, technologies described herein may be used to screen a sample for the presence or absence of a combination (e.g., a set) of targets. Accordingly, provided technologies can be used in various research and/or medical applications. Examples of such applications include, but are not limited to study of interactions of molecules (e.g., proteins, transcription factors, and/or nucleic acid molecules) within a complex, screening of patients for a specific disease or condition, monitoring recurrence and/or progression of a disease or condition, selecting therapy for a patient suffering from a disease or condition, and/or evaluating and/or monitoring efficacy of a treatment administered to a subject in need thereof. Examples of diseases that can be detected or screened by technologies described herein include, but are not limited to autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

In some embodiments, one or more target biomarker signatures for a disease, disorder, or condition (e.g., cancer) can be detected in a sample comprising biological entities (including, e.g., cells, circulating tumor cells, cell-free DNA, extracellular vesicles, etc.) using methods of detecting and/or assays as described herein. In some embodiments, one or more target biomarker signatures for a disease, disorder, or condition (e.g., cancer) can be detected in a sample comprising extracellular vesicles using methods of detecting and/or assays as described herein.

In some embodiments, a sample may be or comprise a biological sample. In some embodiments, a biological sample can be derived from a blood or blood-derived sample of a subject (e.g., a human subject) in need of such an assay. In some embodiments, a biological sample can be or comprise a primary sample (e.g., a tissue or tumor sample) from a subject (e.g., a human subject) in need of such an assay. In some embodiments, a biological sample can be processed to separate one or more entities of interest (e.g., biological entity) from non-target entities of interest, and/or to enrich one or more entities of interest (e.g., biological entity). In some embodiments, an entity of interest present in a sample may be or comprise a biological entity, e.g., a cell or an extracellular vesicle (e.g., an exosome). In some embodiments, such a biological entity (e.g., extracellular vesicle) may be processed or contacted with a chemical reagent, e.g., to stabilize and/or crosslink targets (e.g., provided target biomarkers) to be assayed in the biological entity and/or to reduce non-specific binding with detection probes. In some embodiments, a biological entity is or comprises a cell, which may be optionally processed, e.g., with a chemical reagent for stabilizing and/or crosslinking targets (e.g., molecular targets) and/or for reducing non-specific binding. In some embodiments, a biological entity is or comprises an extracellular vesicle (e.g., an exosome), which may be optionally processed, e.g., with a chemical reagent for stabilizing and/or crosslinking targets (e.g., molecular targets) and/or for reducing non-specific binding.

In some embodiments, technologies provided herein can be useful for managing patient care, e.g., for one or more individual subjects and/or across a population of subjects. By way of example only, in some embodiments, provided technologies may be utilized in screening, which for example, may be performed periodically, such as annually, semi-annually, bi-annually, or with some other frequency as deemed to be appropriate by those skilled in the art. In some embodiments, such a screening may be temporally motivated or incidentally motivated. For example, in some embodiments, provided technologies may be utilized in temporally-motivated screening for one or more individual subjects or across a population of subjects (e.g., asymptomatic subjects) who are older than a certain age (e.g., over 20, 25, 30, 35, 40, 45, 50, 55, 60, 65, 70, 75, 80, or older). As will be appreciated by those skilled in the art, in some embodiments, the screening age and/or frequency may be determined based on, for example, but not limited to prevalence of a disease, disorder, or condition (e.g., cancer). In some embodiments, provided technologies may be utilized in incidentally-motivated screening for individual subjects who may have experienced an incident or event that motivates screening for a particular disease, disorder, or condition (e.g., cancer). For example, in some embodiments, an incidental motivation relating to determination of one or more indicators of a disease, disorder, or condition (e.g., cancer) or susceptibility thereto may be or comprise, e.g., an incident based on their family history (e.g., a close relative such as blood-related relative was previously diagnosed for such a disease, disorder, or condition such as cancer), identification of one or more risk factors for a disease, disorder, or condition (e.g., cancer) and/or prior incidental findings from genetic tests (e.g., genome sequencing), and/ or imaging diagnostic tests (e.g., ultrasound, computerized tomography (CT) and/or magnetic resonance imaging (MRI) scans), development of one or more signs or symptoms characteristic of a particular disease, disorder, or condition (e.g., in the context of cancer, a persistent cough potentially indicative of lung cancer; a lump in breast tissue potentially indicative of breast cancer; gastrointestinal (GI) tract bleeding potentially indicative of GI cancer; abnormal bleeding during a woman's period potentially indicative of ovarian cancer, etc.) and/or other incidents or events as will be appreciated by those skilled in the art.

In some embodiments, provided technologies for managing patient care can inform treatment and/or payment (e.g., reimbursement for treatment) decisions and/or actions. For example, in some embodiments, provided technologies can provide determination of whether individual subjects have one or more indicators of risk, incidence, or recurrence of a disease disorder, or condition (e.g., cancer), thereby informing physicians and/or patients when to provide/receive therapeutic or prophylactic recommendations and/or to initiate such therapy in light of such findings. In some embodiments, such individual subjects may be asymptomatic subjects, who may be temporally-motivated or incidentally-motivated screened at a regular frequency (e.g., annually, semi-annually, bi-annually, or other frequency as deemed to be appropriate by those skilled in the art).

Additionally or alternatively, in some embodiments, provided technologies can inform physicians and/or patients of treatment selection, e.g., based on findings of specific responsiveness biomarkers (e.g., cancer responsiveness biomarkers). In some embodiments, provided technologies can provide determination of whether individual subjects are responsive to current treatment, e.g., based on findings of changes in one or more levels of molecular targets associated with a disease, thereby informing physicians and/or patients of efficacy of such therapy and/or decisions to maintain or alter therapy in light of such findings. In some embodiments, provided technologies can provide determination of whether individual subjects are likely to be responsive to a recommended treatment, e.g., based on findings of molecular targets (e.g., a target biomarker signature for a disease, disorder, or condition) that predict therapeutic effects of a recommended treatment on individual subjects, thereby informing physicians and/or patients of potential efficacy of such therapy and/or decisions to administer or alter therapy in light of such findings.

In some embodiments, provided technologies can inform decision making relating to whether health insurance providers reimburse (or not), e.g., for (1) screening itself (e.g., reimbursement available only for periodic/regular screening or available only for temporally- and/or incidentally-motivated screening); and/or for (2) initiating, maintaining, and/ or altering therapy in light of findings by provided technologies. For example, in some embodiments, the present disclosure provides methods relating to (a) receiving results of a screening that employs provided technologies and also receiving a request for reimbursement of the screening and/or of a particular therapeutic regimen; (b) approving reimbursement of the screening if it was performed on a subject according to an appropriate schedule (based on, e.g., screening age such as older than a certain age, e.g., over 20, 25, 30, 35, 40, 45, 50, 55, 60, 65, 70, 75, 80, or older, and/or screening frequency such as, e.g., every 3 months, every 6 months, every year, every 2 years, every 3 years or at some other frequencies) or response to a relevant incident and/or approving reimbursement of the therapeutic regimen if it represents appropriate treatment in light of the received screening results; and, optionally (c) implementing the reimbursement or providing notification that reimbursement is refused. In some embodiments, a therapeutic regimen is appropriate in light of received screening results if the received screening results detect a biomarker that represents an approved biomarker for the relevant therapeutic regimen (e.g., as may be noted in a prescribing information label and/or via an approved companion diagnostic).

Alternatively or additionally, the present disclosure contemplates reporting systems (e.g., implemented via appropriate electronic device(s) and/or communications system (s)) that permit or facilitate reporting and/or processing of screening results (e.g., as generated in accordance with the present disclosure), and/or of reimbursement decisions as described herein. Various reporting systems are known in the art; those skilled in the art will be well familiar with a variety of such embodiments, and will readily be able to select those suitable for implementation.

EXEMPLARY USES

A. Detection of Cancer Incidence or Recurrence

The present disclosure, among other things, recognizes that detection of a single cancer-associated biomarker in a biological entity (e.g., extracellular vesicle) or a plurality of cancer-associated biomarkers based on a bulk sample, rather than at a resolution of a single biological entity (e.g., individual extracellular vesicles), typically does not provide sufficient specificity and/or sensitivity in determination of whether a subject from whom the biological entity is obtained is likely to be suffering from or susceptible to cancer. The present disclosure, among other things, provides technologies, including compositions and/or methods, that solve such problems, including for example by specifically requiring that an entity (e.g., an extracellular vesicle) for detection be characterized by presence of a combination of targets. For example, in some embodiments, technologies provided herein are useful for characterization of an entity (e.g., an extracellular vesicle) by presence of a combination of at least two or more targets. For example, in some such embodiments, at least two or more targets may be detected involving a provided target entity detection system. Alternatively, in some such embodiments, at least one target may be detected by a capture assay (e.g., as described and/or utilized herein), while at least one another target may be detected by a detection assay, e.g., involving a target entity detection system described and/or utilized herein. In particular embodiments, the present disclosure teaches technologies that require such an entity (e.g., an extracellular vesicle) be characterized by presence (e.g., by expression) of a combination of molecular targets that is specific to cancer (i.e., "target biomarker signature" of a relevant cancer, e.g., cancer), while biological entities (e.g., extracellular vesicles) that do not comprise the targeted combination (e.g., target biomarker signature) do not produce a detectable signal. Accordingly, in some embodiments, technologies provided herein can be useful for detection of risk, incidence, and/or recurrence of cancer in a subject. For example, in some embodiments, a combination of two or more detection probes (e.g., ones described herein) directed to at least one or more targets (including, e.g., at least 2, at least 3, at least 4, at least 5, at least 6, at least 7, at least 8, at least 9, at least 10, at least 15, at least 20, or more targets) are selected for detection of a specific cancer or various cancers. In some embodiments, a specific combination of detection probes (e.g., ones described herein) directed to at least one or more targets (including, e.g., at least 2, at least 3, at least 4, at least 5, at least 6, at least 7, at least 8, at least 9, at least 10, at least 15, at least 20, or more targets) of a target biomarker signature for detection of cancer(s) can be determined by analyzing a population or library (e.g. tens, hundreds, thousands, tens of thousands, hundreds of thousands, or more) of cancer patient biopsies and/or patient data to identify such a predictive combination. In some embodiments, a relevant combination of biomarkers may be one identified and/or characterized, for example, via data analysis. In some embodiments, for example, a diverse set of cancer-associated data (e.g., in some embodiments comprising one or more of bulk RNA sequencing, single-cell RNA (scRNA) sequencing, mass spectrometry, histology, post-translational modification data, in vitro and/or in vivo experimental data) can be analyzed through machine learning and/or computational modeling to identify a combination of predictive markers that is highly specific to cancer. In some embodiments, a combination of predictive markers to distinguish stages of cancer can be determined in silico based on comparing and analyzing diverse data (e.g., in some embodiments comprising bulk RNA sequencing, scRNA sequencing, mass spectrometry, histology, post-translational modification data, in vitro and/or in vivo experimental data) relating to different stages of cancer. For example, in some embodiments, technologies provided herein can be used to distinguish cancer subjects from non-cancer subjects, including, e.g., healthy subjects, subjects diagnosed with benign tumors or masses, and subjects with non-cancer-related diseases, disorders, and/or conditions (e.g., subjects with inflammatory bowel diseases or disorders). In some embodiments, technologies provided herein can be useful for early detection of cancer, e.g., detection of cancer of stage I or stage II. In some embodiments, technologies provided herein can be useful to distinguish melanoma stages I, II, III, and IV from each other and healthy patients. In some embodiments, technologies provided herein can be useful to distinguish lung adenocarcinoma stages I, II, III, and IV from each other and healthy patients. In some embodiments, technologies provided herein can be useful to distinguish colorectal cancer stages I, II, III, and IV from each other and healthy patients. In some embodiments, technologies provided herein can be useful to distinguish ovarian cancer stages I, II, III, and IV from each other and healthy patients. In some embodiments, technologies provided herein can be useful for detection of one or more cancer subtypes. By way of example only, in some embodiments, technologies provided herein can be useful for detection of one or more ovarian cancer subtypes, including, e.g., high-grade serous ovarian cancer, endometrioid ovarian cancer, clear-cell ovarian cancer, low-grade serous ovarian cancer, or mucinous ovarian cancer. In some embodiments, technologies provided herein can be useful for screening subjects at hereditary risk or average risk for early-stage cancer.

In some embodiments, technologies provided herein can be useful for screening a subject for risk, incidence, or recurrence of a specific cancer in a single assay. For example, in some embodiments, technologies provided herein is useful for screening a subject for risk, incidence, or recurrence of breast cancer. In some embodiments, technologies provided herein is useful for screening a subject for risk, incidence, and/or recurrence of lung cancer (e.g., but not limited to non-small cell lung cancer). In some embodiments, technologies provided herein is useful for screening for risk, incidence, or recurrence of skin cancer (e.g., but not limited to melanoma). In some embodiments, technologies provided herein is useful for screening a subject for risk, incidence, or recurrence of ovarian cancer. In some embodiments, technologies provided herein can be used to screen a subject for risk or incidence of a specific cancer or a plurality of (e.g., at least 2, at least 3, or more) cancers in a single assay. For example, in some embodiments, technologies provided herein can be used to screen a subject for a plurality of cancers in a single assay, wherein in some embodiments, cancers to be screened can be selected from the group consisting of acute lymphocytic leukemia, acute myeloid leukemia, bile duct cancer, bladder cancer, brain cancer (including, e.g., glioblastoma), breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer.

In some embodiments, provided technologies can be used periodically (e.g., every year, every two years, every three years, etc.) to screen a human subject for cancer (e.g., early-stage cancer) or cancer recurrence. In some embodiments, a human subject amenable to such screening may be an infant, a child, an adult or an elderly individual. In some embodiments, a human subject amenable to such screening may have an age of about 2 years old to 80 years old, or about 12 years old to about 70 years old, or about 18 years old to about 65 years old. In some embodiments, a human subject amenable to such screening may be an elderly subject, e.g., age 65 above, age 70 above, at least 75 above, at least 80, or above. In some embodiments, a human subject amenable to such screening may have an age of about 50 or above. In some embodiments, a human subject amenable to such screening may have an age of 50 or less. In some embodiments, a human subject amenable to such screening may have an age over 35.

In some embodiments, a subject that is amenable to provided technologies for detection of incidence or recurrence of cancer may be an asymptomatic human subject and/or across an asymptomatic population. Such an asymptomatic subject and/or an asymptomatic population may be subject(s) who has/have a family history of cancer (e.g., subjects having one or more first-degree relatives with a history of cancer), who has been previously treated for cancer, who is at risk of cancer recurrence after cancer treatment, who is in remission after cancer treatment, and/or who has been previously or periodically screened for cancer, e.g., by screening for the presence of at least one cancer biomarker. Alternatively, in some embodiments, an asymptomatic subject may be a subject who has not been previously screened for cancer, who has not been diagnosed for cancer, and/or who has not previously received cancer therapy. In some embodiments, an asymptomatic subject may be a subject with a benign tumor or tissue mass. In some embodiments, an asymptomatic subject may be a subject who is susceptible to cancer (e.g., at an average population risk or with hereditary risk for cancer).

In some embodiments, a subject or population of subjects that are amenable to provided technologies for detection of cancer may be selected based on one or more characteristics such as age, race, genetic history, medical history, personal history (e.g., smoking, alcohol, drugs, carcinogenic agents, diet, obesity, physical activity, sun exposure, radiation exposure, exposure to infectious agents such as viruses, and/or occupational hazard). For example, in some embodiments, a subject or population of subjects that are amenable to provided technologies for detection of cancer may be a subject (e.g., a human subject) or a population of subjects determined to have one or more germline mutations in one or more cancer-associated genes, including, e.g., but not limited to BRCA1, BRCA2, and TP53, and combinations thereof.

In some embodiments, a subject or population of subjects that are amenable to provided technologies for detection of cancer may be a subject or a population of subjects diagnosed with an imaging-confirmed tissue mass.

In some embodiments, a subject or population of subjects that are amenable to provided technologies for detection of cancer may be a subject or a population of subjects at hereditary risk for cancer before undergoing a risk-reducing surgical intervention.

In some embodiments, a subject or population of subjects that are amenable to provided technologies for detection of cancer may be a subject or a population of subjects with one or more non-specific symptoms of cancer. In some embodiments, exemplary non-specific symptoms of cancer may include, e.g., but not limited to coughing, difficulty in swallowing, tiredness, loss of appetite, abdominal pain, weight loss, etc., In some embodiments, a subject or population of subjects that are amenable to provided technologies for detection of cancer may be a subject or a population of subjects of Asians, African Americans, Caucasians, Native Hawaiians or other Pacific Islanders, Hispanics or Latinos, American Indian or Alaska natives, non-Hispanic black, or non-Hispanic white. In some embodiments, a subject or population of subjects that are amenable to provided technologies for detection of cancer may be a subject of any race and/or any ethnicity.

In some embodiments, technologies provided herein can be used in combination with other diagnostics assays including, e.g., but not limited to (i) an individual's annual physical examination, (ii) a genetic assay to screen blood plasma for genetic mutations in circulating tumor DNA and/or protein biomarkers linked to cancer; (iii) an assay involving immunofluorescent staining to identify cell phenotype and marker expression, followed by amplification and analysis by next-generation sequencing; and (iv) germline and somatic mutation assays (e.g., BRCA1 and/or BRCA2), or assays involving cell-free tumor DNA, liquid biopsy, serum protein and cell-free DNA, and/or circulating tumor cells.

B. Selection of Therapy (e.g., Cancer Therapy)

In some embodiments, provided technologies can be used for selecting an appropriate treatment for a patient (e.g., a patient suffering from or susceptible to cancer). For example, some embodiments provided herein relate to a companion diagnostic assay for classification of patients for therapy (e.g., cancer and/or adjunct treatment) which comprises assessment in a patient sample (e.g., a blood or blood-derived sample from a patient, e.g., a cancer patient) of a selected combination of stratification and/or responsiveness biomarkers using technologies provided herein. Based on such an assay outcome, patients who are determined to be more likely to respond to a therapy (e.g., a cancer therapy and/or an adjunct therapy) can be administered such a therapy, or patients who are determined to be non-responsive to a specific such therapy can be administered a different therapy.

C. Evaluation of Treatment Efficacy (e.g., Cancer Treatment Efficacy)

In some embodiments, technologies provided herein can be used for monitoring and/or evaluating efficacy of a therapy administered to a patient (e.g., cancer patient). For example, a blood or blood-derived sample can be collected from a patient (e.g., a cancer patient) prior to or receiving a therapy (e.g., an anti-cancer therapy) at a first time point to detect or measure a combination of biomarkers that is specific for the patient's disease, disorder, or condition. In some embodiments, a blood or blood-derived sample can be collected from a cancer patient prior to or receiving an anti-cancer therapy at a first time point to detect or measure tumor burdens, e.g., by detecting presence or amount of extracellular vesicles comprising a selected combination of biomarkers that is specific to detection of cancer. After a period of treatment, a second blood or blood-derived sample can be collected from the same patient to detect changes in such disease-specific biomarker(s). For example, in some such embodiments, a second blood or blood-derived sample can be collected after a period of treatment from the same cancer patient to detect changes in tumor burdens, e.g., by detecting absence or reduction in amount of extracellular vesicles comprising a selected combination of biomarkers that is specific to detection of cancer. By monitoring levels and/or changes in disease-specific biomarkers and/or tumor burdens over the course of treatment, appropriate course of action, e.g., increasing or decreasing the dose of a therapeutic agent, and/or administering a different therapeutic agent, can be taken.

VII. Kits

Also provided are kits that find use in practicing technologies as described above. In some embodiments, a kit comprises a plurality of detection probes (e.g., as described and/or utilized herein). In some embodiments, a provided kit may comprise two or more (e.g., 3, 4, 5, 6, 7, 8, 9, 10, 11, 12, 13, 14, 15, 16, 17, 18, 19, 20 or more) detection probes. In some embodiments, individual detection probes may be directed at different targets. In some embodiments, two or more individual detection probes may be directed to the same target. In some embodiments, a provided kit comprises two or more different detection probes directed at different targets, and optionally may include at least one additional detection probe also directed at a target to which another detection probe is directed. In some embodiments, a provided kit comprises a plurality of subsets of detection probes, each of which comprises two or more detection probes directed at the same target. In some embodiments, a plurality of detection probes may be provided as a mixture in a container. In some embodiments, multiple subsets of detection probes may be provided as individual mixtures in separate containers. In some embodiments, each detection probe is provided individually in a separate container.

In some embodiments, a kit for cancer detection comprises: (a) a capture agent comprising a target-capture moiety directed to an extracellular vesicle-associated membrane-bound polypeptide; and (b) a set of detection probes, which set comprises at least two detection probes each directed to a target biomarker of a target biomarker signature for cancer, wherein the detection probes each comprise: (i) a target binding moiety directed the target biomarker of the target biomarker signature for cancer; and (ii) an oligonucleotide domain coupled to the target binding moiety, the oligonucleotide domain comprising a double-stranded portion and a single-stranded overhang portion extended from one end of the oligonucleotide domain, wherein the single-stranded overhang portions of the at least two detection probes are characterized in that they can hybridize to each other when the at least two detection probes are bound to the same extracellular vesicle. In these embodiments, such a target biomarker signature for cancer comprises: at least one extracellular vesicle-associated membrane-bound polypeptide and at least one target biomarker selected from the group consisting of: surface protein biomarkers, intravesicular protein biomarkers, and intravesicular RNA biomarkers, wherein when the at least one target biomarker is selected from one or more of the surface protein biomarkers, the selected surface protein biomarker(s) and the at least one extracellular vesicle-associated membrane-bound polypeptide are different.

In some embodiments, a target binding moiety of at least two detection probes provided in a kit is each directed to the same target biomarker of a target biomarker signature. In some such embodiments, an oligonucleotide domain of such at least two detection probes are different.

In some embodiments, a target binding moiety of at least two detection probes provided in a kit is each directed to a distinct target biomarker of a target biomarker signature.

In some embodiments, a kit may comprise at least one chemical reagent such as a fixation agent, a permeabilization agent, and/or a blocking agent.

In some embodiments, a kit may comprise one or more nucleic acid ligation reagents (e.g., a nucleic acid ligase such as a DNA ligase and/or a buffer solution).

In some embodiments, a kit may comprise at least one or more amplification reagents such as PCR amplification reagents. In some embodiments, a kit may comprise one or more nucleic acid polymerases (e.g., DNA polymerases), one or more pairs of primers, nucleotides, and/or a buffered solution.

In some embodiments, a kit may comprise a solid substrate for capturing an entity (e.g., biological entity) of interest. For example, such a solid substrate may be or comprise a bead (e.g., a magnetic bead). In some embodiments, such a solid substrate may be or comprise a surface. In some embodiments, a surface may be or comprise a capture surface (e.g., an entity capture surface) of an assay chamber, such as, e.g., a filter, a matrix, a membrane, a plate, a tube, a well (e.g., but not limited to a microwell), etc. In some embodiments, a surface (e.g., a capture surface) of a solid substrate can be coated with a capture agent (e.g., polypeptide or antibody agent) for an entity (e.g., biological entity) of interest.

In some embodiments, a set of detection probes provided in a kit may be selected for diagnosis of a specific cancer (including, e.g., but not limited to acute lymphocytic leukemia, acute myeloid leukemia, bile duct cancer, bladder cancer, brain cancer, breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer).

In some embodiments, a kit may comprise a plurality of sets of detection probes, wherein each set of detection probes is directed for detection of a specific cancer and comprises at least 2 or more detection probes. For example, such a kit can be used to screen a subject for various cancers (including, e.g., but not limited to acute lymphocytic leukemia, acute myeloid leukemia, bile duct cancer, bladder cancer, brain cancer, breast cancer, cervical cancer, chronic lymphocytic leukemia, chronic myeloid leukemia, colorectal cancer, endometrial cancer, esophageal cancer, gastrointestinal cancer, Hodgkin lymphoma, kidney cancer, liver cancer, lung cancer, multiple myeloma, non-Hodgkin lymphoma, ovarian cancer, pancreatic cancer, prostate cancer, sarcomas, skin cancer, and stomach cancer) in a single assay.

In some embodiments, kits provided herein may include instructions for practicing methods described herein. These instructions may be present in kits in a variety of forms, one or more of which may be present in the kits. One form in which these instructions may be present is as printed information on a suitable medium or substrate, e.g., a piece or pieces of paper on which the information is printed, in the packaging of kits, in a package insert, etc. Yet another means may be a computer readable medium, e.g., diskette, CD, USB drive, etc., on which instructional information has been recorded. Yet another means that may be present is a website address which may be used via the internet to access instructional information. Any convenient means may be present in the kits.

In some embodiments where kits are for use as companion diagnostics, such kits can include instructions for identifying patients that are likely to respond to a therapeutic agent (e.g., identification of biomarkers that are indicative of patient responsiveness to the therapeutic agent). In some embodiments, such kits can comprise a therapeutic agent for use in tandem with the companion diagnostic test.

Other features of the invention will become apparent in the course of the following description of exemplary embodiments, which are given for illustration of the invention and are not intended to be limiting thereof.

EXEMPLIFICATION

Example 1: Detection of Two or More Targets (e.g., Molecular Targets) Present in Single Biological Entities The present Example describes synthesis of detection probes for different targets each comprising a target-binding moiety and an oligonucleotide domain (comprising a double-stranded portion and a single stranded overhang) coupled to the target-binding moiety. The present Example further demonstrates that use of such detection probes to detect the presence or absence of biological entities comprising two or more targets (which targets may be same or distinct).

In some embodiments, a detection probe can comprise a double-stranded oligonucleotide with an antibody agent specific to a target protein at one end and a single stranded overhang at another end. When two or more detection probes are bound to the same biological entity (e.g., a cell or an extracellular vesicle), the single-stranded overhangs of the detection probes are in close proximity such that they can hybridize to each other to form a double-stranded complex, which can be subsequently ligated and amplified for detection.

While this study employed two detection probes, each for a specific target (e.g., molecular target), three or more detection probes, each for a specific target (e.g., molecular target), may also be used. Further, compositions and methods described in this Example can be extended to applications in different biological samples (e.g., comprising extracellular vesicles) other than biological cells that were used as a model biological entity in this Example.

In some embodiments, an entity detection assay utilizes two detection probes, each recognizing a target (e.g., in some embodiments, each recognizing a distinct cancer-specific epitope, or in some embodiments, one recognizing a biomarker that is specifically associated with a normal cell and/or tissue, while another recognizing a generic biomarker for cancers; or in come embodiments, both recognizing the same target). For example, paired double-stranded template DNAs are utilized, each of which has specific single-stranded 5' overhangs (e.g., four-base 5' overhangs) complementary to the 5' overhang on its partner. Each antibody agent specific to a target epitope (e.g., cancer epitope) is conjugated to one of the two double-stranded DNA templates. When antibodies bind their target epitopes, the sticky ends (e.g., single stranded overhangs) of the respective DNA templates are able to hybridize. These sticky ends are then ligated together by a DNA ligase (e.g., T7 ligase), prior to PCR amplification. For hybridization between the two DNA templates to occur, the two antibodies need to be in close proximity to each other (e.g., within 50 to 60 nm, the length of the DNA linker and antibody agent). Any templates that bind but remain unhybridized/ligated will not produce PCR product, as shown in FIG. 2A.

In this Example, a duplex system of two antibodies and two primers (with EvaGreen fluorescent dye as a labeling probe) shown in FIG. 2A was used. While a fluorescent dye was used in this Example as a labeling probe, other detectable labels that are known to label nucleic acid or oligonucleotides can also be used. Target 1 (e.g., target protein 1) and Target 2 (e.g., target protein 2) were chosen such that they are generally not co-expressed in any other cell type but in cells of a particular cancer, e.g., melanoma, albeit there may be exceptions that can be accounted for by adding a third target (e.g., a third target protein) to the cancer (e.g., melanoma) fingerprint. To assess a duplex system (e.g., ones described herein), an experiment was conducted on two melanoma cell lines, SK-MEL-1 and MeWo, and one negative control colorectal cancer cell line, T84. As shown in Table 1, T84s are a colorectal cell line that express Target protein 1 and Target protein 2 at very low levels. Conversely, SK-MEL-1 and MeWo are melanoma cell lines that express Target protein 1 and Target protein 2 at high levels. As described herein, it should be noted that "Transcript per million" or "TPM" refers to normalization for RNA-sequencing, which means "for every 1,000,000 RNA molecules in the RNA-sequencing sample, x comes from a gene transcript as specified."

TABLE 1

| Cell lines gene expression (transcripts per million/ TPM) | | | |
|---|---|---|---|
| Gene | SK-MEL-1 (melanoma) | MeWo (melanoma) | T84 (colorectal cancer) |
| Target protein 1 | +++ | +++ | − |
| Target protein 2 | + | ++ | − |

Exemplary Methods

Oligonucleotides

In some embodiments, oligonucleotides can have the following sequence structure and modifications:

Strand 1:
/5AmMC12/CAGTCTGACTCACCACTCGT-TAATCGTCGCTGCTACCCTTGACATCCGTG ACTGGCTAGACAGAGGTGT (SEQ ID NO: 1), wherein /5AmMC12/ refers to an amine group (e.g., a primary amino group) linked to the 5' oligonucleotide terminus via a 12-carbon spacer Strand 2:
/5AmMC12/CACCAGACCTACGAAGTCCAT-AGCCTTGCCTGATTAGCCACTGTCCAGTT TGGCTCCTGGTCTCACTAG (SEQ ID NO: 2), wherein /5AmMC12/ refers to an amine group (e.g., a primary amino group) linked to the 5' oligonucleotide terminus via a 12-carbon spacer Strand 3:

/5Phos/GAGTACACCTCTGTCTAGCCAGTCACG-GATGTCAAGGGTAGCAGCGACGATT AACGAGTGGTGAGTCAGACTG (SEQ ID NO: 3), wherein /5Phos/ refers to a phosphate group linked to the 5' oligonucleotide terminus Strand 4:

/5Phos/ACTCCTAGTGAGACCAGGAGC-CAAACTGGACAGTGGCTAATCAGGCAAGGCT ATGGACTTCGTAGGTCTGGTG (SEQ ID NO: 4), wherein /5Phos/ refers to a phosphate group linked to the 5' oligonucleotide terminus Strand 5:

CAGTCTGACTCACCACTCGT (SEQ ID NO: 5)

Strand 6:

CACCAGACCTACGAAGTCCA (SEQ ID NO: 6)

Poly T:

TTTTTTTTTTTTTTTTTTTTTTTTTTTTT (SEQ ID NO: 7)

Verification of Ligation and Amplification

To verify if DNA templates ligate and can be amplified by PCR, pairs of strands 1 and 3 and of strands 2 and 4 were hybridized. Hybridized strands 1+3 and 2+4 were then ligated using a DNA ligase (e.g., a T7 or T4 ligase), and qPCR was performed using EvaGreen fluorescent dye and strands 5 and 6 as primers.

To hybridize the DNA, a 500 pM, equal volume amount of strand 1 and 3 and strand 2 and 4 were melted in a thermocycler, for example, using the following protocol: 95° C. for 10 seconds, 65° C. for 30 seconds, hold at 4° C. After making the DNA double-stranded, a DNA ligation (e.g., using a T4 and T7 ligase) was performed, e.g., using 9 uL of the hybridized 250 pM DNA in a 20 uL reaction. Negative controls received no ligase but contained the same buffer. Ligation was performed in a thermocycler, e.g., at 25° C. for 20 minutes. The product post-ligation (as well as samples without ligase) underwent qPCR, e.g., using Luna master mix without the reverse transcriptase (RT). All qPCR reactions were done in triplets and a passive reference (e.g., ROX) was used to normalize the qPCR signals. Data was then analyzed and graphed.

Antibody Agent-DNA Conjugation

To conjugate an oligonucleotide (e.g., hybridized strands 1 and 3 and hybridized strands 2 and 4) to a target-binding moiety (e.g., an antibody agent against a target protein), pairs of single strands were hybridized to form a double-stranded oligonucleotide with a single-stranded overhang at one end and then a target-binding moiety (e.g., an antibody agent against a target protein) was conjugated to the double-stranded oligonucleotide at another end, e.g., using a commercial DNA-oligonucleotide conjugation kit (e.g., Abcam, ab218260).

To hybridize two single-stranded DNAs to form a double-stranded DNA, 50 uL of 100 uM equal molar and volume DNA was subject to a thermal cycling, e.g., using the following protocol: 1. Heat to 95° C. and maintain the temperature for 2 min. 2. Cool to 25° C. over 45 min by dropping 5° C. every 3 mins until 25° C. 3. Hold at 4° C. Using the 50 uM double-stranded DNA product, a plurality of double-stranded DNA (e.g., five strands of double-stranded DNA) was annealed to each antibody agent.

Cell Culture

Cells can be cultured using any methods known in the art. For example, T84 cells were grown in 1:1 Dulbecco's modified Eagle Medium (DMEM): Ham's F12 medium with 5% exosome-free fetal bovine serum (FBS) and 50 units of Penicillin/streptomycin per mL. SK-MEL-1 and MeWo cells were both grown in Eagle's minimum essential medium (EMEM) with 10% exosome-free FBS and 50 units of Penicillin/streptomycin per mL. All cell lines were maintained at 5% $CO_2$ and 37° C. and the passage number was below 15.

Cell Fixation and Blocking

Cells can be fixed, permeabilized, and blocked using any methods known in the art. For example, prior to fixation, adherent T84 and MeWo cells were detached from their substrate, e.g., using TrypLE protease. SK-MEL-1 are weakly adherent and can be liberated from the flask substrate, e.g., by shaking the flask. Once in solution, the cells were pelleted at 300 rcf for 5 minutes at room temperature. The cells were washed once in 10 mL 1×PBS and pelleted as above. Each cell line was then fixed and permeabilized. For example, cells can be simultaneously fixed and permeabilized in ice-cold methanol and incubated at –25° C. for at least 20 minutes. Prior to blocking, the cells were rehydrated by first pelleting at 1000 rcf for 2 minutes (once fixed, they can withstand greater g-forces), then washed once in 1×PBS. The washed and rehydrated pellets were then resuspended in a blocking buffer.

Antibody Agent-DNA Conjugate Labeling and Washing of Cell Lines

Each of the three methanol-fixed cell lines (SK-MEL-1, MeWo, and T84) were divided into three aliquots in 1.5 mL Protein Lo Bind Eppendorf tubes in 1 mL of a blocking buffer to block non-specific binding, prior to the addition of the DNA-conjugated antibodies. The three tubes, for each of the three cell lines, were devised to have one that contained no antibody agent, one that contained DNA-conjugated antibodies (one for Target protein 1 and another for Target protein 2) at 1 ug/mL, and one that contained DNA-conjugated antibodies (one for Target protein 1 and another for Target protein 2) at 10 ng/mL. The antibodies were prediluted in a blocking buffer prior to addition to the 1 mL of blocked cells and the antibody agent-DNA conjugates were incubated with cells for 30 minutes. After antibody incubation, the cells were washed, e.g., four times in 1 mL of 1×PBS by centrifuging at 1,000 rcf at room temperature for 2 minutes.

Ligation and qPCR of Labeled Cells

DNA ligation (e.g., T7 ligation) of the blocked, labeled, and washed cells was done, e.g., using the following protocol: 1. A DNA ligase master mix was made to resuspend the cells after the final wash in a volume of 50 uL. The DNA ligase master mix contained, e.g., 5% (v/v) T7 ligase, 50% (v/v) 2×T7 Ligase buffer, and 45% (v/v) nuclease-free water. 2. After resuspending each of the cell lines in 50 uL of DNA ligase master mix, the cell-ligase mix was placed in a thermocycler, e.g., at 25° C. for 20 mins. 3. A qPCR master mix was made, e.g., using a 500 nM concentration of primers (e.g., strand 5 and 6), 1× EvaGreen fluorescent dye, and Luna qPCR master mix to achieve a final reaction volume of 25 uL. 4. About 8 uL of cell-ligase product was added to each of the 25 uL qPCR reactions. 5. A qPCR was performed, e.g., in a 96-well plate, for example, using the following PCR protocol: hold at 95° C. for 1 min, perform 50 cycles of 95° C. for 10 seconds and 60° C. for 30 seconds, and standard melt curve. The rate of temperature change was chosen to be standard (e.g., 2° C. per second). All qPCR reactions were done in triplets and a passive reference (e.g., ROX) was used to normalize the qPCR signals. Data was then analyzed and graphed.

Results

Interpretation of qPCR Plots qPCR plots identify the Ct (cycle threshold) for which the fluorescent signal from EvaGreen intercalating with double-stranded DNA increases beyond background. Since a non-specific dye for any type of double-stranded DNA was used, no template controls (NTCs) will come up after around 35 cycles from the amplification of primer dimers. Moreover, any small amount of template that gets into the PCR reaction will lead to a Ct value that is lower than expected Ct value, which is what happens when the NTC has a Ct value below 30 (a Ct value lower than 30 for a NTC occurred in FIG. 4. Such a contamination can be controlled, e.g., by performing the amplification with a hybridization probe, resulting in fluorescence only when the template is amplified (or a labeling probe or detection label can be hydrolyzed).

Ligase is Required for Amplification

The presence of ligase was necessary to achieve a qPCR signal above primer-dimer background, as shown in FIG. 3. Moreover, the T7 and T4 ligase produced a similar Ct value and consistent results.

The qPCR Results are Consistent

As shown in FIG. 4, the group without any antibody agent had high Ct values (~33+) across cell lines. Conversely, the group labeled with 1 ug/mL of antibody agent had a Ct value as low as 18. The cell line with the strongest signal were the MeWos, followed by the SK-MEL-1 and T84 cell lines. This observed result is consistent with the MeWos expressing Target protein 1 and Target protein 2 the most, the SK-MEL-1 expressing Target protein 1 and Target protein 2 the second most, and the T84 cell line expressing Target protein 1 and Target protein 2 the least. Lastly, a lower concentration of antibody agent (10 ng/ml) has much higher Ct values, similar to those of the no antibody agent controls.

Discussion

A duplex system (e.g., ones described above) is demonstrated to identify co-localized Target protein 1 and Target protein 2 in cell lines. First, the template ligates and is amplifiable, as shown in FIG. 3. Second, after conjugating these DNA templates to two different antibodies and staining cell lines, an expression-dependent signal was observed. Namely, the MeWo cell line expresses the highest level of Target protein 1 and Target protein 2 (Table 1) and commensurately has the strongest Target protein 1 and Target protein 2 signals, the SK-MEL-1 cell line expresses Target protein 1 and Target protein 2 about 4.4 times lower than MeWo and has a weaker signal, and the T84 cell line expresses no to very little Target protein 1 and Target protein 2 and has the weakest signal. The negative T84 cells also have high Ct values, consistent with non-specific background. However, T84 at 1 ug/mL of antibody agent still has one Ct value as low as 23. This Ct value is an outlier to the two other Ct values of 27 and could be from clumping of the cells or from other non-specific priming interactions or contamination. In some embodiments, the difference between the strongest and weakest signals can be increased by performing more thorough washes.

While a duplex system (e.g., ones described above) is demonstrated herein to accurately identify cells expressing Target protein 1 and Target protein 2, such a system can also be used to identify other biological entities (e.g., extracellular vesicles) comprising Target protein 1 and Target protein 2. For example, extracellular vesicles can be captured onto solid substrates (e.g., silica beads) prior to fixation and any downstream processing.

Example 2: Detection of Three or More Targets (e.g., Molecular Targets) Present in Single Biological Entities The present Example describes synthesis of detection probes for three targets each comprising a target-binding moiety and an oligonucleotide domain (comprising a double-stranded portion and a single stranded overhang) coupled to the target-binding moiety. The present Example further demonstrates that three double-stranded oligonucleotides (each having a single-stranded overhang) can be used in a mixture to ligate and amplify, showing that when such double-stranded oligonucleotides are conjugated to antibodies, a triplex system, e.g., as shown in FIG. 5A, can be performed to identify three targets (e.g., molecular targets) all localized in the same biological entity (e.g., individual extracellular vesicles). In some embodiments, such three targets may be the same targets. In some embodiments, such three targets may be distinct targets. In some embodiments, at least two of such three targets may be the same targets.

Exemplary Methods

Oligonucleotides

In some embodiments, oligonucleotides can have the following sequence structure and modifications:

Strand 1:

/5AmMC12/CAGTCTGACTCACCACTCGT-TAATCGTCGCTGCTACCCTTGACATCCGTG ACTGGCTAGACAGAGGTGT (SEQ ID NO: 1), wherein /5AmMC12/ refers to an amine group (e.g., a primary amino group) linked to the 5' oligonucleotide terminus via a 12-carbon spacer Strand 2:

/5AmMC12/CACCAGACCTACGAAGTCCAT-AGCCTTGCCTGATTAGCCACTGTCCAGTT TGGCTCCTGGTCTCACTAG (SEQ ID NO: 2), wherein /5AmMC12/ refers to an amine group (e.g., a primary amino group) linked to the 5' oligonucleotide terminus via a 12-carbon spacer Strand 4 (No 5' Phosphate):

/5'ACTCCTAGTGAGACCAGGAGC-CAAACTGGACAGTGGCTAATCAGGCAAGGC-TAT GGACTTCGTAGGTCTGGTG (SEQ ID NO: 4)

Strand 5:

CAGTCTGACTCACCACTCGT (SEQ ID NO: 5)

Strand 6:

CACCAGACCTACGAAGTCCA (SEQ ID NO: 6)

Strand 8:

/5Phos/TTCCAACTAT/CCAACTAT/CTAT/+TTTTTT/ TT+ACACCTCTGTCTAGCCAGTCA CGGATGT-CAAGGGTAGCAGCGACGATTAACGAGTGGT-GAGTCAGACTG (various embodiments disclosed as SEQ ID NOS 8-13), wherein /5Phos/ refers to a phosphate group linked to the 5' oligonucleotide terminus Strand 9:

/5Phos/GAGTGTGAGGATGTCAGTGTGTCTC/TT/ CCAA (various embodiments disclosed as SEQ ID NOS 14-16), wherein /5Phos/ refers to a phosphate group linked to the 5' oligonucleotide terminus Strand 10:

/5AmMC12/ATAGTTGGAAGAGACACACTGA-CATCCTCAC (SEQ ID NO: 17), wherein /5AmMC12/ refers to an amine group (e.g., a primary amino group) linked to the 5' oligonucleotide terminus via a 12-carbon spacer Note: the "/" indicates variants of a given strand of DNA. Three different lengths of strands 8 and 9 with two different gaps in strands 8 were chosen.

Verification of Ligation and Amplification

To verify if DNA templates ligate and can be amplified by PCR, pairs of strands 1 and 8, of strands 9 and 10, and of strands 2 and 4 were hybridized. Hybridized strands 1+8, 9+10, and 2+4 were then ligated using a DNA ligase (e.g., a T7 or T4 ligase), and qPCR was performed using EvaGreen fluorescent dye and strands 5 and 6 as primers.

To hybridize the DNA, a 1 uM, equal volume amount of strand 1 and 8, strand 9 and 10, and strand 2 and 4 were melted in a thermocycler, for example, using the following protocol: 95° C. for 10 seconds, 65° C. for 30 seconds, hold at 4° C. After making the DNA double-stranded, a DNA ligation (e.g., using a T4 and T7 ligase) was performed, e.g., using 9 uL of the hybridized 100 nM DNA in a 20 uL reaction. Negative controls received no ligase but contained the same buffer. Ligation was performed in a thermocycler, e.g., at 25° C. for 20 minutes. The product post-ligation (or without ligase) was then subjected to qPCR, e.g., using TaqMan Fast Advanced master mix. A qPCR was performed, e.g., in a 96-well plate, for example, using the following PCR protocol: hold at 50° C. for 2 mins, hold at 95° C. for 2 mins, perform 55 cycles of 95° C. for 5 seconds and 60° C. for 15 seconds, and perform a standard melt curve. All qPCR reactions were done in triplets and a passive reference (e.g., ROX) was used to normalize the qPCR signals. Data was then analyzed and graphed.

Results

Ligase is Required for a Robust Ct Value

The presence of ligase is necessary to produce a robust Ct value, as shown in FIG. 6.

All Three Templates are Required for a Strong Signal

Each pair of the three template DNAs were ligated in reaction, as shown in FIGS. 7 to 9. With only two of the three strands, the signal is approximately 13 to 14 Ct values weaker. These findings show that a triplex DNA system can be amplified, with all three strands required for a robust signal.

Example 3: Detection of Two or More Targets Present in Single Extracellular Vesicles The present Example demonstrates that a duplex system and a triplex system as described in Examples 1 and 2, respectively, are useful for detecting a different type of biological entities (e.g., extracellular vesicles) for the presence of a combination (e.g., a set) of targets, and not biological entities (e.g., extracellular vesicles) with at least one of the targets missing. The present Example also describes synthesis of detection probes for individual targets each comprising a target-binding moiety and an oligonucleotide domain (comprising a double-stranded portion and a single stranded overhang) coupled to the target-binding moiety.

To assess the performance of a duplex system in detection for extracellular vesicles comprising two targets (e.g., molecular targets), in some embodiments, a different combination of target biomarkers than described in Example 1 was used. In some embodiments, a detectable probe such as EvaGreen fluorescent dye used in Example 1 was substituted with a hydrolysis probe. In some embodiments, Target marker A was a generic marker for extracellular vesicles. In some embodiments, Target marker B is expressed only in normal skin and melanoma, but not in other cancers. As shown in Table 2, T84 is a colorectal cell line that does not detectably (under conditions of this assay) express Target marker B but expresses Target marker A at a lower level than the MeWo cells. Conversely, the MeWo melanoma cell line expresses both Target marker A and Target marker B at high levels.

TABLE 2

| Cell line-derived extracellular vesicle gene expression (transcripts per million/TPM) | | |
| --- | --- | --- |
| Target | MeWo (TPM) | T84 (TPM) |
| Target marker A | ++++ | +++ |
| Target marker B | +++ | − |

To assess the performance of a triplex system in detection for extracellular vesicles comprising three target biomarkers, three target markers were utilized, each of which is expressed at a higher level in MeWo cells over T84 cells or is expressed highly in MeWos and not at all in T84s. In this present Example, a combination of three target markers were selected such that at least one of the target markers is not detectably expressed (under conditions of this assay) in T84 extracellular vesicles.

TABLE 3

| Cell line-derived extracellular vesicle gene expression transcripts per million/TPM) | | |
| --- | --- | --- |
| Target | MeWo (TPM) | T84 (TPM) |
| Target marker A | ++++ | +++ |
| Target marker C | ++++ | + |
| Target marker D | +++ | +++ |

Exemplary Methods

Oligonucleotides

In some embodiments, oligonucleotides can have the following sequence structure and modifications. It is noted that the strand numbers below correspond to the numerical values associated with strands shown in FIGS. 2A and 5A.

Strand 1:
/5AmMC12/CAGTCTGACTCACCACTCGT-TAATCGTCGCTGCTACCCTTGACATCCGTG ACTGGCTAGACAGAGGTGT (SEQ ID NO: 1), wherein /5AmMC12/ refers to an amine group (e.g., a primary amino group) linked to the 5' oligonucleotide terminus via a 12-carbon spacer Strand 2:
/5AmMC12/CACCAGACCTACGAAGTCCAT-AGCCTTGCCTGATTAGCCACTGTCCAGTT TGGCTCCTGGTCTCACTAG (SEQ ID NO: 2), wherein /5AmMC12/ refers to an amine group (e.g., a primary amino group) linked to the 5' oligonucleotide terminus via a 12-carbon spacer Strand 3:
/5Phos/GAGTACACCTCTGTCTAGCCAGTCACG-GATGTCAAGGGTAGCAGCGACGATT AACGAGTGGTGAGTCAGACTG (SEQ ID NO: 3), wherein /5Phos/ refers to a phosphate group linked to the 5' oligonucleotide terminus Strand 4:
/5Phos/ACTCCTAGTGAGACCAGGAGC-CAAACTGGACAGTGGCTAATCAGGCAAGGCT ATGGACTTCGTAGGTCTGGTG (SEQ ID NO: 4), wherein /5Phos/ refers to a phosphate group linked to the 5' oligonucleotide terminus Strand 4 (No 5' Phosphate when Used in a Triplex System):
/5'ACTCCTAGTGAGACCAGGAGC-CAAACTGGACAGTGGCTAATCAGGCAAGGC-TAT GGACTTCGTAGGTCTGGTG (SEQ ID NO: 4)

Strand 5:
CAGTCTGACTCACCACTCGT (SEQ ID NO: 5)

Strand 6:
CACCAGACCTACGAAGTCCA (SEQ ID NO: 6)

Poly T:
TTTTTTTTTTTTTTTTTTTTTTTTTTTTTT (SEQ ID NO: 7)

Strand 8:
/5Phos/CCAACTATTTTTTA-CACCTCTGTCTAGCCAGTCACGGATGT-CAAGGGTAGCA GCGACGATTAACGAGTGGT-GAGTCAGACTG (SEQ ID NO: 9), wherein /5Phos/ refers to a phosphate group linked to the 5' oligonucleotide terminus Strand 9:
/5Phos/GAGTGTGAGGATGTCAGTGTGTCTCTT (SEQ ID NO: 15), wherein /5Phos/ refers to a phosphate group linked to the 5' oligonucleotide terminus Strand 10:
/5AmMC12/ATAGTTGGAAGAGACACACTGA-CATCCTCAC (SEQ ID NO: 17), wherein /5AmMC12/ refers to an amine group (e.g., a primary amino group) linked to the 5' oligonucleotide terminus via a 12-carbon spacer Antibody-DNA Conjugation For a duplex system, in some embodiments, an oligonucleotide comprising strands 1 and 3 was conjugated to a target-binding moiety specific to Target marker A, while an oligonucleotide comprising strands 2 and 4 was conjugated to a target-binding moiety specific to Target marker B. In some embodiments, a method for conjugating a target-binding moiety (e.g., antibody agent) to an oligonucleotide as described in Example 1 was used to anneal approximately two strands of double-stranded DNA to each target-binding moiety (e.g., antibody agent).

For a triplex system, in some embodiments, an oligonucleotide comprising strands 1 and 8 was conjugated to a target-binding moiety specific to Target marker C; an oligonucleotide comprising strands 10 and 9 was conjugated to a target-binding moiety specific to Target marker A; and an oligonucleotide domain comprising strands 2 and 4 (where strand 4 does not have a free 5' phosphate) was conjugated to a target-binding moiety specific to Target marker D. In some embodiments, a method for conjugating a target-binding moiety (e.g., antibody agent) to an oligonucleotide as described in Example 1 was used to anneal approximately two strands of double-stranded DNA to each target-binding moiety (e.g., antibody agent).

Cell Culture

T84 cells were grown in 1:1 Dulbecco's modified Eagle Medium (DMEM): Ham's F12 medium with 5% exosome-free fetal bovine serum (FBS) and 50 units of Penicillin/streptomycin per mL. MeWo cells were both grown in Eagle's minimum essential medium (EMEM) with 10% exosome-free FBS and 50 units of Penicillin/streptomycin per mL. All cell lines were maintained at 5% $CO_2$ and 37° C. and the passage number was below 20.

Purification of Extracellular Vesicles from Cell Culture Medium

In some embodiments, MeWo and T84 cells were grown in their respective media until they reached ~80% confluency. The cell culture medium was collected and spun at 300×rcf for 5 minutes at room temperature (RT) to removes cells and debris. The supernatant was then collected and frozen at −80° C.

Prior to use, the frozen supernatant stored at −80° C. was thawed and then clarified of cells and large (e.g., greater than 1 micron in diameter) cellular fragments. The thawed supernatant was clarified using centrifugation.

In some embodiments, the clarified spent medium (e.g., ~500 uL) was run through a size-exclusion purification column. Nanoparticles having a size range of about 65 nm to about 200 nm were collected for each sample.

Extracellular Vesicle Biotinylation

In some embodiments, the protein concentration of the purified extracellular vesicles was measured, e.g., using the NanoDrop, following the manufacturer's instructions. This measurement was used to calculate the amount of biotin to add to each sample. Following the manufacturer's instructions, the extracellular vesicles were biotinylated, e.g., using a EZ-link Micro NHS-PEG4-biotinylation kit. After the biotin was added to the sample it was shaken for 45 minutes. Excess biotin was removed using two consecutive 5 mL, 40 kDa MWCO column spins (e.g., from Zeba™).

Particle Counts

Particle counts were obtained, e.g., using a SpectroDyne particle counting instrument using the TS400 chips, to measure nanoparticle range between 65 and 200 nm.

Capture or Immobilization of Biotinylated Extracellular Vesicles onto Streptavidin-Coated 96-Well Plates In some embodiments, equal numbers of biotinylated extracellular vesicles were added, e.g., in triplicate for each sample condition assayed, to a streptavidin-coated capture surface (e.g., wells of a 96-well plate). The plate was incubated and shaken at room temperature for a period of time.

Extracellular Vesicle Fixation

In some embodiments, an appropriate concentration of formaldehyde (in 1×PBS) was added to extracellular vesicles captured on a streptavidin-coated surface. The fixed extracellular vesicles were then washed for use in subsequent steps.

Sample Blocking and Extracellular Vesicle Permeabilization

A sample comprising fixed extracellular vesicles was mixed with a blocking buffer. In some embodiments, a blocking buffer may comprise Triton X-100 or saponin and salmon sperm DNA at appropriate concentrations in a buffered solution such as a phosphate-free buffer (e.g., Low-Cross-Buffer® from Candor Bioscience).

Detection Probe Binding

Detection probes (e.g., at a concentration of about 0.5 ug/mL to about 3.5 ug/ml based on the amount of antibody agent) was added to a sample comprising extracellular vesicles (e.g., intact extracellular vesicles that are fixed, blocked, and optionally permeabilized). The mixture is then incubated under conditions such that detection probes bind to extracellular vesicles comprising target biomarkers.

Post-Binding Washes

In some embodiments, samples were washed in an appropriate buffer.

Ligation

After the wash to remove unbound detection probes, detection probe-bound extracellular vesicles (captured on a solid substrate surface) were contacted with a ligation mix. The mixtures were incubated for 20 minutes at RT.

PCR

Following ligation, detection probe-bound extracellular vesicles (captured on a solid substrate surface) were contacted with a PCR mix. PCR was performed, e.g., on the Quant Studio 3, with the following exemplary PCR protocol: hold at 95° C. for 1 minute, perform 50 cycles of 95° C. for 5 seconds and 62° C. for 15 seconds, and standard melt curve. The rate of temperature change was chosen to be standard (2° C. per second). All qPCRs were done in doublets or triplets and ROX was used as the passive reference to normalize the qPCR signals. Data was then downloaded from the Quant Studio 3 machine and analyzed and plotted in Python 3.7.

Results

Figure 13A:
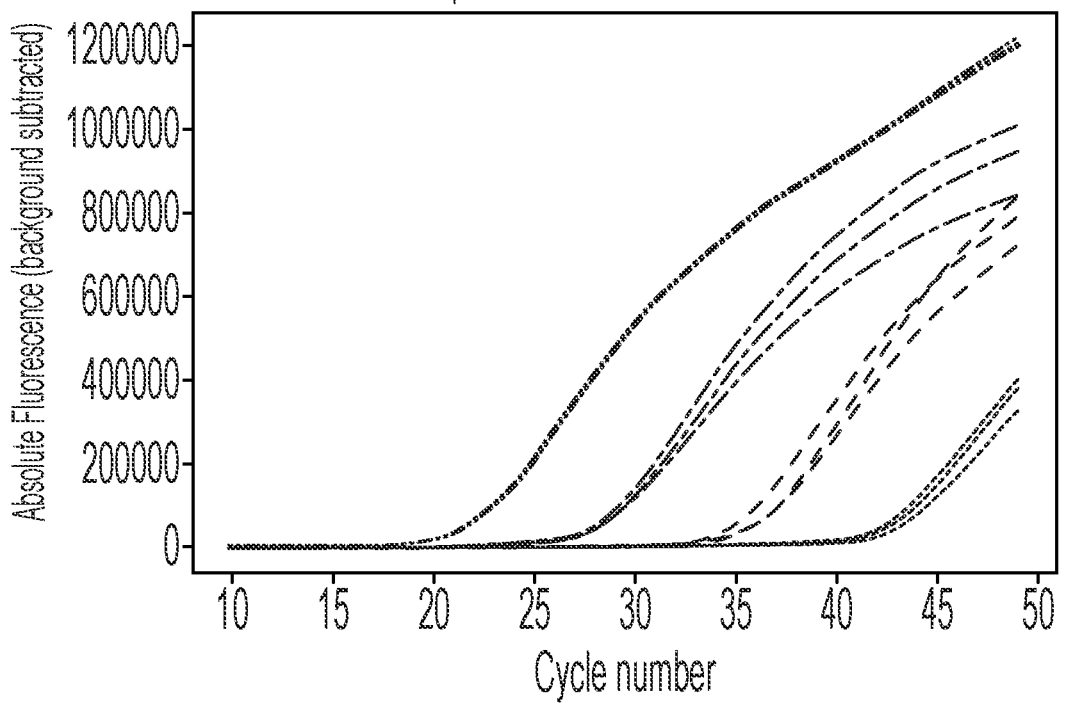

The results of the qPCR, shown in FIGS. 13A and 13B, demonstrate that extracellular vesicles containing a target biomarker signature (e.g., a protein-expression pattern) are detectable and distinguishable from extracellular vesicles that do not have such a target biomarker signature using systems (e.g., duplex and/or triplex systems) described herein. The differential gene expression of the parent cell lines was readily identifiable in the respective cell line-derived extracellular vesicles using systems (e.g., duplex and/or triplex systems) described herein. MeWo cells and extracellular vesicles derived therefrom express higher levels of each of the target markers (Target marker A and Target marker B for a duplex system; Target marker A, Target marker C, and Target marker D for a triplex system) than T84 cells and extracellular vesicles derived therefrom. Therefore, MeWo extracellular vesicles had subsequently lower Cts (~6 Ct lower) than that obtained from T84 extracellular vesicles in both the duplex and triplex assays performed in this Example. These results are consistent with the mRNA expression in each cell line, as shown in Tables 2-3.

Discussion

This present Example shows that a duplex system to identify co-localized Target marker A and Target marker B works at the level of labeling extracellular vesicles, where an expression-dependent signal is observed. Specifically, MeWo cells and extracellular vesicles derived therefrom express higher levels of both Target marker A and Target marker B, relative to T84 cells and extracellular vesicles derived therefrom (Table 2) and thus a stronger signal was produced in samples containing MeWo extracellular vesicles.

The present Example also shows that a triplex system to identify a combination of Target marker A, Target marker C, and Target marker D works at the level of extracellular vesicles, where an expression-dependent signal is observed. The MeWo cells and extracellular vesicles derived therefrom express higher levels of all three markers as compared to those expressed in T84 cells and extracellular vesicles derived therefrom. In particular, one of the target markers (Target marker A) was not expressed in T84 cells and extracellular vesicles derived therefrom. This greater expression in the MeWo extracellular vesicles of these three markers results in a substantially stronger signal compared to the T84 extracellular vesicles ($2^6$ is about 64 times stronger).

Without wishing to be bound by theory, in some embodiments, non-specific binding of target-binding moiety (e.g., antibody agent) of detection probes may contribute to noise signals detected in T84 samples (as compared to no-template negative controls). Accordingly, in some embodiments, a sample comprising extracellular vesicles may be treated to reduce or minimize non-specific binding of detection probes.

Example 4: Cancer Detection Using an Exemplary System to Detect Cancer-Associated Extracellular Vesicles in Patient Plasma Samples The present Example demonstrates that systems described herein can be useful for detecting target biological entities in a complex sample matrix (e.g., a plasma sample from a subject). For example, target biological entities (e.g., cancer-associated extracellular vesicles) were spiked into a plasma sample (e.g., from a human subject) and signals of ligated templates were detected in samples comprising target biological entities in a concentration-dependent manner.

The present Example also demonstrates that systems described herein can be useful for cancer detection. Specifically, the present Example shows that systems described herein are useful for distinguishing extracellular vesicles of cancer patients from those of normal healthy subjects. In addition, the present Example shows that such a cancer detection assay provides high sensitivity and/or specificity.

While this present Example used samples (e.g., plasma samples) obtained from lung adenocarcinoma patients to demonstrate the capability of systems described herein to detect cancer-associated extracellular vesicles, one of those skill in the art reading the present disclosure will appreciate that such systems described herein can be used to detect other types of cancer using different appropriate combination of at least two or more target markers. Further, one of those skill in the art reading the present disclosure will appreciate that such systems described herein can be also useful for diagnosing different stages of a cancer using an appropriate set of at least two or more target markers.

The capabilities as demonstrated in the present Example are not limited to a duplex system (i.e., comprising a set of two distinct detection probes specific to a target biological entity) evaluated in this present Example. It will be apparent to one of those skill in the art reading the present disclosure that other systems described herein (e.g., a triplex or n-plex system comprising a set of at least three or more distinct detection probes) can be also useful for detecting target biological entities in complex sample matrices, e.g., for cancer detection. Those skilled in the art reading the present disclosure will also appreciate that inclusion of additional detection probes for different targets, in some embodiments, would increase specificity and/or sensitivity of a detection assay.

Spike-in experiment: In one aspect, ability of a duplex system to detect extracellular vesicles in a complex sample matrix was assessed. For example, cancer-associated extracellular vesicles (EVs) were spiked into plasma samples of subjects (e.g., human subjects). The spiked plasma samples were then purified to isolate EVs. The isolated or purified EVs can be captured or adsorbed on a solid substrate surface (e.g., a PCR plate) prior to performing a duplex system assay (e.g., as described herein). In some embodiments, cancer-associated extracellular vesicles were obtained from HCC- 4006, a lung adenocarcinoma cell line. In some embodiments, cancer-associated extracellular vesicles were obtained from SK-MEL1, a melanoma cell line.

In this spike-in experiment, four exemplary different combinations of biomarkers were assessed in a duplex system assay. In addition, a hydrolysis probe were substituted for a detectable fluorophore label SYBR green. The four exemplary different combinations are shown below:

Target marker A+Target marker B (combination markers utilized in this assay for detection of melanoma-associated extracellular vesicles)

Target marker E+Target marker F (combination markers utilized in this assay for detection of lung adenocarcinoma-associated extracellular vesicles)

Target marker E+Target marker A (combination markers utilized in this assay for detection of lung adenocarcinoma-associated extracellular vesicles)

Target marker G+Target marker F (combination markers utilized in this assay for detection of lung adenocarcinoma-associated extracellular vesicles)

Table 4 below summarizes expression of various target markers in different cancer-associated extracellular vesicles. It is noted that the Combination 5 in Table 4 was not evaluated in the spike-in experiment but was used in an experiment (as described below) to screen patient samples.

TABLE 4

The transcript per million (TPM) scores for five combinations, as expressed in lung adenocarcinoma cell line (HCC4006) and melanoma cell line (SKMEL1).

| Combination | Target marker | HCC4006 | SKMEL1 |
|---|---|---|---|
| 1 | Target maker A | High | High |
| | Target marker B | Low | High |
| 2 | Target marker E | High | Low |
| | Target marker F | High | Low |
| 3 | Target marker E | High | Low |
| | Target marker A | High | High |
| 4 | Target marker G | High | Low |
| | Target marker F | High | Low |
| 5 | Target marker E | High | Low |
| | Target marker H | High | Low |

Target marker E, Target marker F, Target marker G, and Target marker H are more highly expressed in lung adenocarcinoma than in other tissues. It should be noted that Target marker E is also expressed elsewhere in healthy tissues, but generally at lower levels than in LUAD. As discussed in Example 3, Target marker B is expressed more highly in melanoma than in other tissues, which was used in this present Example as a positive control for melanoma-associated extracellular vesicles. Target marker A, as discussed in Example 3, is a generic marker for extracellular vesicles because of its presence in many types of extracellular vesicles.

Healthy vs stage IV lung adenocarcinoma (LUAD) plasma experiment: In another aspect, ability of a duplex system to discriminate between extracellular vesicles in plasma samples of healthy and stage IV LUAD patients was assessed. For example, extracellular vesicles were purified or isolated from plasma samples of stage IV LUAD patients and of age and gender matched healthy subjects, which were then profiled using a set of at least two or more detection probes, e.g., directed to Combination 3 or Combination 5 as shown in Table 4 above.

Exemplary Methods

Oligonucleotides

In some embodiments, oligonucleotides can have the following sequence structure and modifications. It is noted that the strand numbers below correspond to the numerical values associated with strands shown in FIG. 2A.

Strand 1:
/5AmMC12/CAGTCTGACTCACCACTCGT-TAATCGTCGCTGCTACCCTTGACATCCGTG ACTGGCTAGACAGAGGTGT (SEQ ID NO: 1), wherein /5AmMC12/ refers to an amine group (e.g., a primary amino group) linked to the 5' oligonucleotide terminus via a 12-carbon spacer Strand 2:
/5AmMC12/CACCAGACCTACGAAGTCCAT-AGCCTTGCCTGATTAGCCACTGTCCAGTT TGGCTCCTGGTCTCACTAG (SEQ ID NO: 2), wherein /5AmMC12/ refers to an amine group (e.g., a primary amino group) linked to the 5' oligonucleotide terminus via a 12-carbon spacer Strand 3:
/5Phos/GAGTACACCTCTGTCTAGCCAGTCACG-GATGTCAAGGGTAGCAGCGACGATT AACGAGTGGTGAGTCAGACTG (SEQ ID NO: 3), wherein /5Phos/ refers to a phosphate group linked to the 5' oligonucleotide terminus Strand 4:
/5Phos/ACTCCTAGTGAGACCAGGAGC-CAAACTGGACAGTGGCTAATCAGGCAAGGCT ATGGACTTCGTAGGTCTGGTG (SEQ ID NO: 4), wherein /5Phos/ refers to a phosphate group linked to the 5' oligonucleotide terminus Strand 5:
CAGTCTGACTCACCACTCGT (SEQ ID NO: 5)

Strand 6:
CACCAGACCTACGAAGTCCA (SEQ ID NO: 6)

Antibody Agent-DNA Conjugation

In some embodiments, conjugation of an antibody agent to an oligonucleotide is performed to minimize or avoid alteration in the antigen binding portion of the antibody agent. In some embodiments, an oligonucleotide is or comprises hybridized strands 1 and 3 or hybridized strands 2 and 4. In some embodiments, an antibody agent can be conjugated to an oligonucleotide using the method as described in Examples 1 and 3. In some embodiments, an antibody agent can be conjugated to an oligonucleotide via a free amine group of the antibody agent. In some embodiments, an antibody agent can be conjugated to an oligonucleotide via a reactive thiol group of the antibody agent. In some embodiments, an antibody agent can be conjugated to an oligonucleotide via a carbohydrate residue present in the antibody agent.

Cell Culture

SK-MEL-1 cells were grown in Eagle's minimum essential medium (EMEM) with 10% exosome-free FBS and 50 units of Penicillin/streptomycin per mL. HCC-4006 cells were grown in Roswell Park Memorial Institute (RPMI 1640) with 10% exosome-free FBS and 50 units of Penicillin/streptomycin per mL. All cell lines were maintained at 5% $CO_2$ and 37° C. and the passage number was below 20.

Purification of Extracellular Vesicles from Cell Culture Medium

In some embodiments, SK-MEL-1 and HCC4006 cells were grown in their respective media until they reached ~80% confluency. The cell culture medium was collected and spun at 300×rcf for 5 minutes at room temperature (RT) to remove cells and debris. The supernatant was then collected and frozen at −80° C.

Prior to use, the frozen supernatant stored at –80° C. was thawed and then clarified of cells and large (e.g., greater than 1 micron diameter) cellular fragments.

In some embodiments, the clarified spent medium (e.g., ~500 uL) was run through a size-exclusion purification column. Nanoparticles having a size range of about 65 nm to about 200 nm were collected for each sample.

Addition of Cell Line-Derived Extracellular Vesicles to Normal Plasma Samples

For the spike-in study, different volumes (e.g., 50, 100, and 400 uL) of purified SK-MEL-1 and HCC-4006 extracellular vesicles at the same concentration of approximately 3e10 nanoparticles greater than 80 nm in diameter per mL, for example, as measured on the SpectraDyne nCS1 TS400 cartridge, were spiked into plasma from healthy patient BL3 ("BL3 plasma"). Starting with 500 uL of BL3 plasma, different volumes (e.g., 0 uL, 50 uL, 100 uL, or 400 uL) of purified cell line-derived extracellular vesicles were added. A buffered solution, e.g., PBS, was then added such that each sample reaches a volume of 900 uL prior to purification of extracellular vesicles. An exemplary protocol for extracellular vesicle purification from a plasma sample was described in the "Extracellular vesicle purification from healthy and stage IV plasma" section below, with the exception that the post-size exclusion column purification extracellular vesicles were concentrated down to 400 uL, diluted to about 3e9 nanoparticles per mL greater than 80 nm in diameter in ELISA capture buffer, and plated into a PCR plate at 30 uL.

Extracellular Vesicle Purification from Healthy and Stage IV Plasma

In some embodiments, plasma extracellular vesicles were subjected to clarification and were afterwards immediately loaded onto size exclusion purification columns. Nanoparticles having a size range of about 65 nm to about 200 nm were collected for each sample.

Particle Counts

Particle counts were performed as described in Example 3.

Capture or Immobilization of Extracellular Vesicles to PCR Plate Wells

In some embodiments, extracellular vesicles were captured onto PCR plates. For example, a surface coated with an antibody targeting cancer extracellular vesicles can be used to selectively capture cancer extracellular vesicles. Another example is biotinylation of extracellular vesicles and capture on a streptavidin (e.g., from BioTez) coated PCR well.

Extracellular Vesicle Fixation

In some embodiments, an appropriate concentration of formaldehyde (in 1×PBS) was added to extracellular vesicles adsorbed on a PCR plate surface. The fixed extracellular vesicles were then washed for use in subsequent steps.

Sample Blocking and Extracellular Vesicle Permeabilization

A sample comprising fixed extracellular vesicles was mixed with a blocking buffer. In some embodiments, a blocking buffer comprises Triton X-100 and salmon sperm DNA at appropriate concentrations in a buffered solution such as a phosphate-free buffer (e.g., LowCross-Buffer® from Candor Bioscience).

Detection Probe Binding

Detection probes (e.g., at a concentration of about 1 ug/ml based on the amount of antibody agent) was added to a sample comprising extracellular vesicles (e.g., intact extracellular vesicles that are fixed, blocked, and optionally permeabilized). The mixture is then incubated under conditions such that detection probes bind to extracellular vesicles comprising target biomarkers.

Post-Binding Washes

In some embodiments, samples were washed, e.g., multiple times, in an appropriate buffer.

Ligation

After the wash to remove unbound detection probes, detection probe-bound extracellular vesicles (captured on a solid substrate surface) were contacted with a ligation mix. The mixtures were incubated for 20 minutes at RT.

PCR

Following ligation, detection probe-bound extracellular vesicles (captured on a solid substrate surface) were contacted with a PCR mix. PCR was performed, e.g., on the Quant Studio 3, with the following exemplary PCR protocol: hold at 95° C. for 1 minute, perform 50 cycles of 95° C. for 5 seconds and 62° C. for 15 seconds, and standard melt curve. The rate of temperature change was chosen to be standard (2° C. per second). All qPCRs were done in doublets or triplets and ROX was used as the passive reference to normalize the qPCR signals. Data was then downloaded from the Quant Studio 3 machine and analyzed and plotted in Python 3.7.

Results and Discussion

Spike-In Experiment

Raw qPCR plots for each of four different combinations of detection probes (directed to different combinations of target markers as shown in Table 4) were obtained (data not shown) and then analyzed to generate delta Ct plots (as shown in FIGS. 14A-14D), with the BL3 plasma sample (healthy plasma sample) taken as the zero baseline.

Figure 14A:
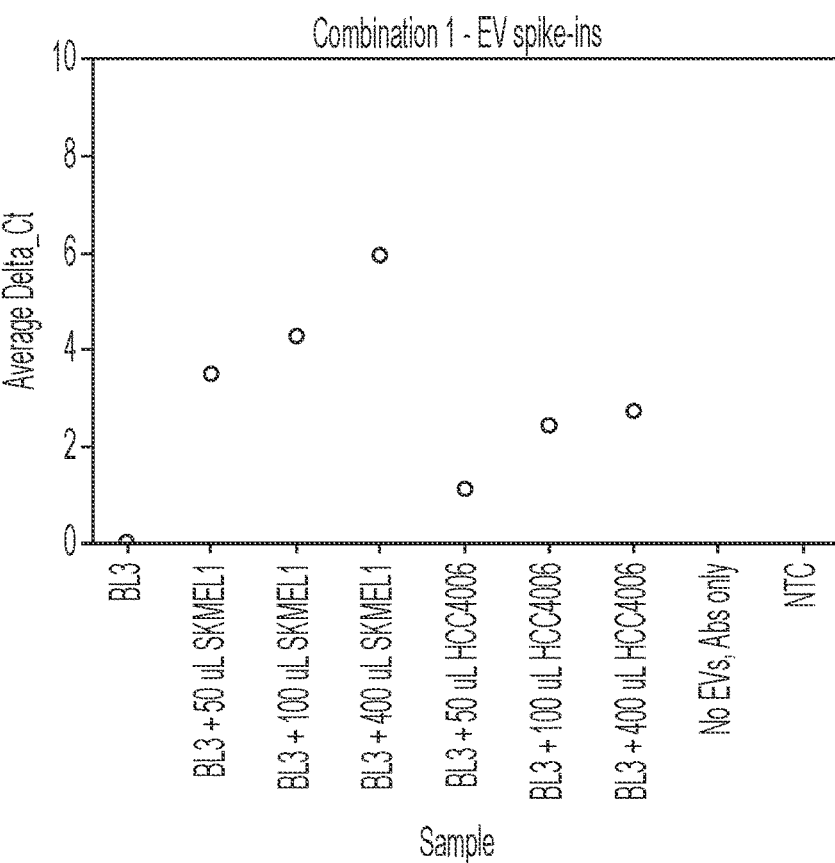
Figure 14B:
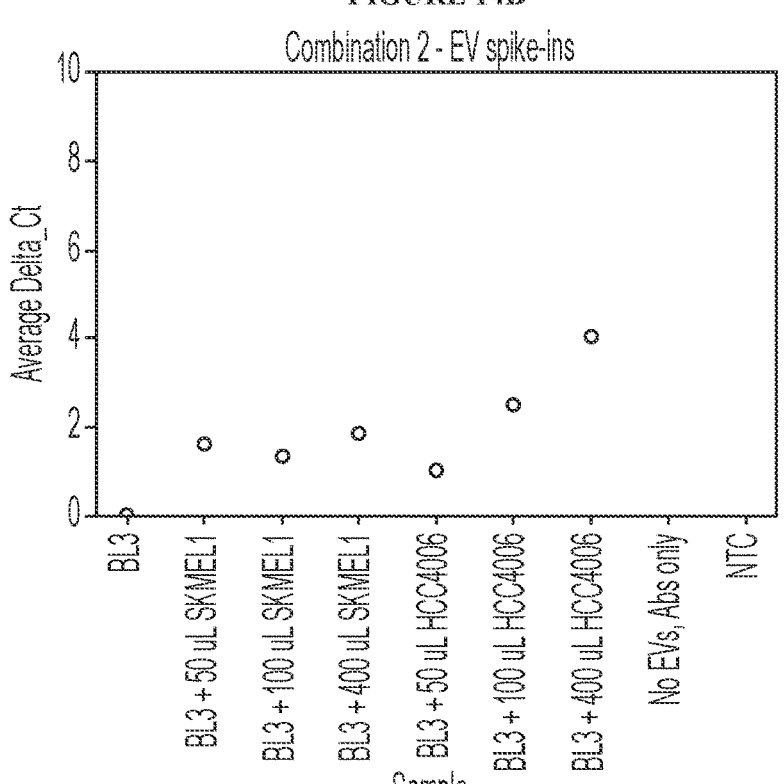

Combination 1 (shown in Table 4) generated the largest delta Ct (FIG. 14A) for all SK-MEL-1 extracellular vesicle concentrations, because Target marker B of Combination 1 is expressed mostly in SK-MEL-1 but not in lung adenocarcinoma such as HCC4006. The delta Ct values for SK-MEL-1 extracellular vesicle plasma samples were higher than that of HCC4006 extracellular vesicle plasma samples, thus indicating that systems using detection probes directed to this combination marker can be used to detect melanoma. Combination 2 (shown in Table 4) generated the larger delta Ct (FIG. 14B) for the higher concentrations (100 uL and 400 uL) of HCC4006 extracellular vesicles. Combination 3 (shown in Table 4) generated largest delta Ct (FIG. 14C) for plasma samples containing lung adenocarcinoma extracellular vesicles HCC4006. The delta Ct values for HCC4006 extracellular vesicle plasma samples were higher than that of SK-MEL-1 extracellular vesicle plasma samples, thus indicating that systems using detection probes directed to this combination marker can be used to detect lung adenocarcinoma. Combination 4 (shown in Table 4) did not show strong signals for all levels of HCC4006 extracellular vesicles (FIG. 14D).

The spike-in experiment simulated melanoma and lung adenocarcinoma patient plasma samples to evaluate the utility of different combinations of biomarkers for cancer screening. As discussed above, Combination 1 was capable of distinguishing between all levels of SK-MEL-1 extracellular vesicle spiked plasma and all other samples tested, as shown in FIG. 14A. Given Combination 1 provided the strongest signals for SK-MEL-1 spiked samples, those of skill in the art reading the disclosure will appreciate that systems described herein, e.g., with detection probes directed to target markers in Combination 1, can be sensitive and specific for melanoma when screening patient samples.

As discussed above, Combination 3 had the strongest signal (FIG. 14C) for all three concentrations of HCC4006 spike ins, which made it the best candidate to test on lung adenocarcinoma patient samples.

Figure 15A:
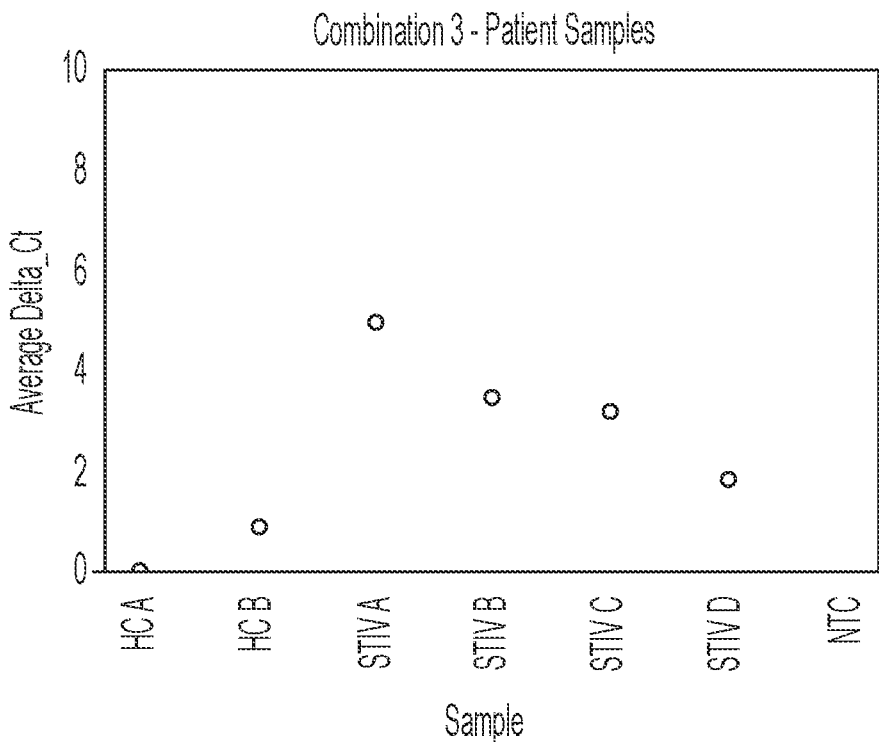
FIGS. 15A-15C are graphs showing experimental data obtained from assaying extracellular vesicles in plasma samples obtained from Stage IV lung adenocarcinoma patients and normal healthy subjects using an exemplary duplex detection assay with detection probes directed to a combination of Target marker E and Target marker A (Combination 3 as shown in Table 4).
Figure 15B:
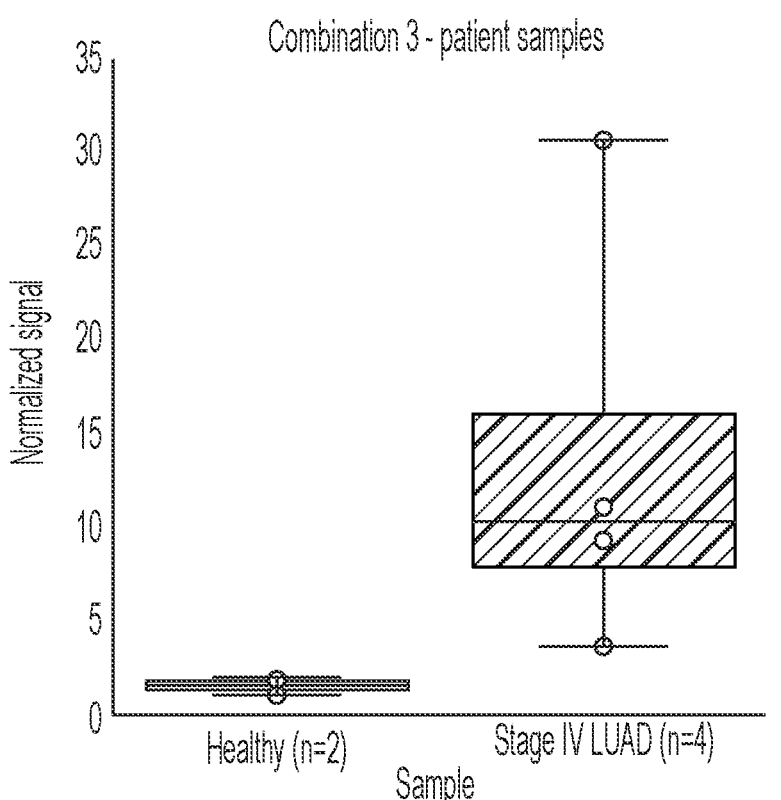
Figure 15C:
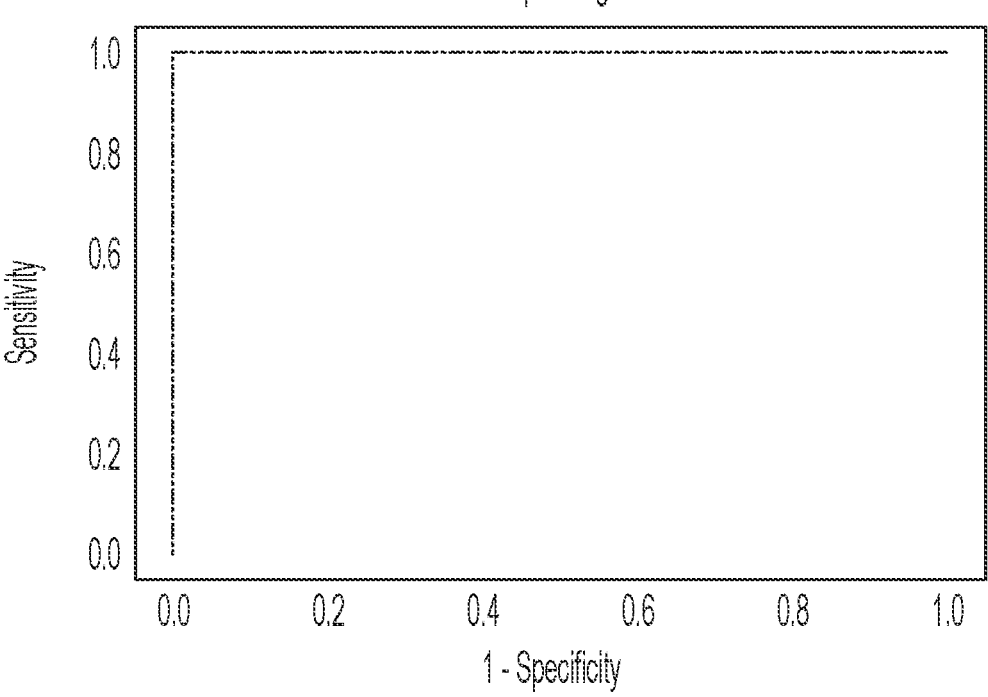

Combination 3 and Combination 5 in Healthy Control and Lung Adenocarcinoma (LUAD) Patient Plasma Samples In view of the strong signals detected in HCC4006 extracellular vesicle spike-in plasma samples using Combination 3, Combination 3 was selected to assess LUAD patient plasma samples. As shown in FIGS. 15A-15C, Combination 3 was able to distinguish between the LUAD patient samples (STIV samples) and healthy controls (HC samples) with very high sensitivity and specificity. FIG. 15C shows that in some embodiments, such an assay can provide 100% sensitivity and 100% specificity.

Figure 16A:
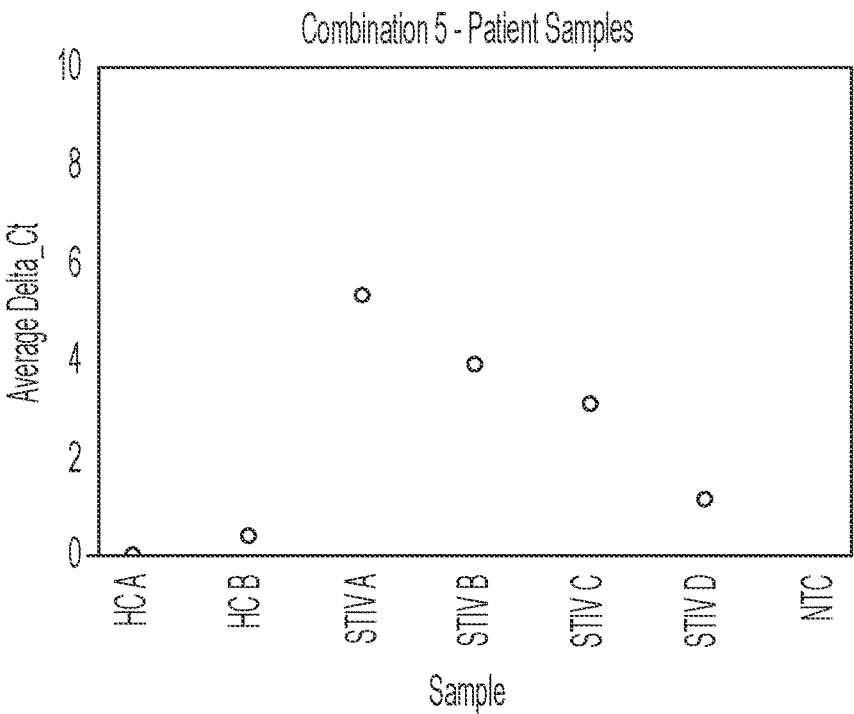
FIGS. 16A-16C are graphs showing experimental data obtained from assaying extracellular vesicles in plasma samples obtained from Stage IV lung adenocarcinoma patients and normal healthy subjects using an exemplary duplex detection assay with detection probes directed to a combination of Target marker E and Target marker H (Combination 5 as shown in Table 4).
Figure 16B:
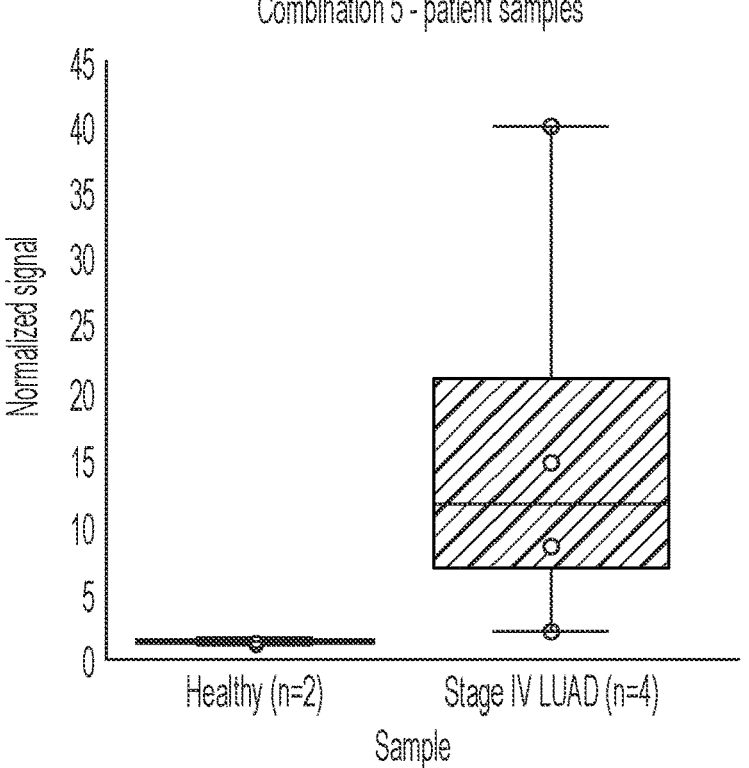
Figure 16C:
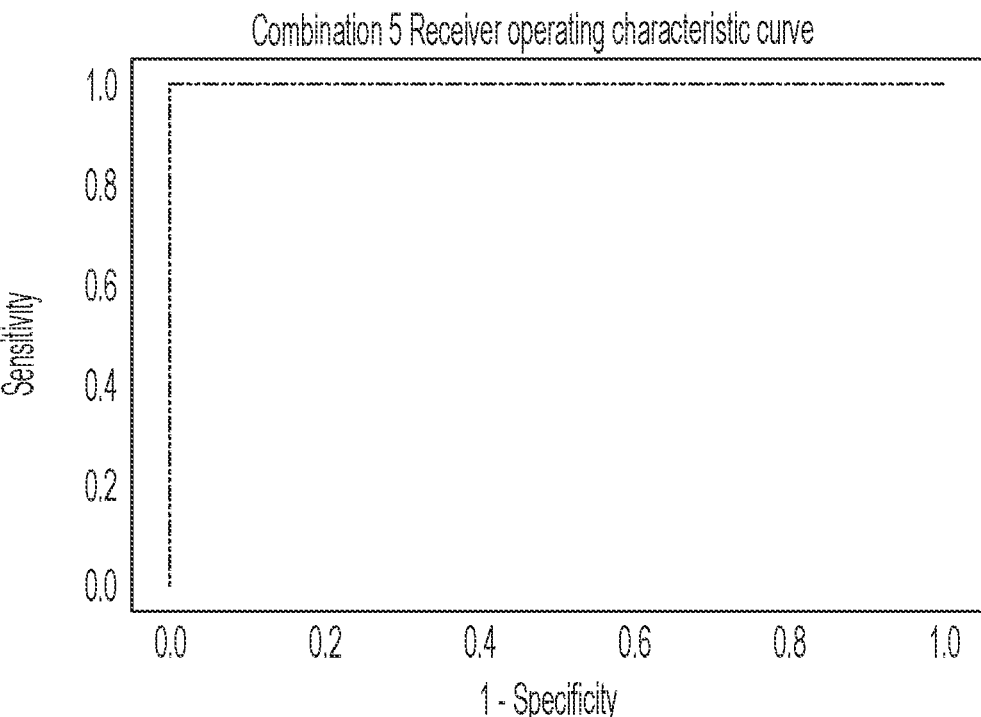

In addition to Combination 3, Combination 5 (as shown in Table 4) was also selected to assess LUAD patient plasma samples. As shown in FIGS. 16A-16C, Combination 5 was able to distinguish between the LUAD patient samples (STIV samples) and healthy controls (HC samples) with very high sensitivity and specificity. FIG. 16C shows that in some embodiments, such an assay can provide 100% sensitivity and 100% specificity.

Figure 17:
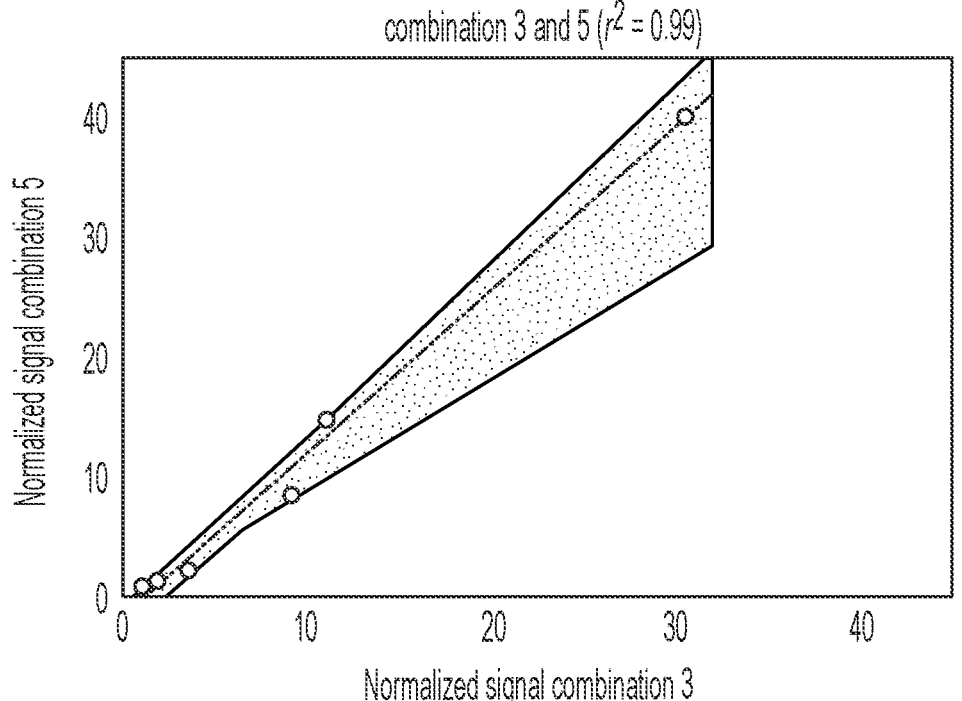
FIG. 17 shows a correlation between normalized signals obtained using Combination 3 markers and Combination 5 markers as shown in FIG. 15B and FIG. 16B, respectively.

Interestingly, there was a very high correlation ($r^2=0.99$) between the normalized signal for Combination 3 and 5, as shown in FIG. 17, indicating the consistency of results presented herein. For example, the intensity of the signal in sample STIV A was consistently the greatest among other LUAD sample signals, which may provide prognostic value in portending treatment response.

The findings presented herein show that systems and methods involving detection probes (e.g., as described herein) directed to appropriate combinations of biomarkers are useful to differentiate different types of cancer patients (e.g., lung adenocarcinoma patients vs. melanoma patients) or to differentiate cancer patients from normal healthy subjects.

In some embodiments, systems and methods described herein can be used to identify stage of cancer (e.g., Stage I, Stage II, Stage III, and Stage IV).

Example 5: Detection of Individual Extracellular Vesicles Associated with Cancer The present Example describes synthesis of detection probes for targets (e.g., target biomarker(s)) each comprising a target-binding moiety and an oligonucleotide domain (comprising a double-stranded portion and a single stranded overhang) coupled to the target-binding moiety. The present Example further demonstrates that use of such detection probes to detect the presence or absence of biological entities (e.g., extracellular vesicles) comprising two or more distinct targets.

In some embodiments, a detection probe can comprise a double-stranded oligonucleotide with an antibody agent specific to a target cancer biomarker at one end and a single stranded overhang at another end. When two or more detection probes are bound to the same biological entity (e.g., an extracellular vesicle), the single-stranded overhangs of the detection probes are in close proximity such that they can hybridize to each other to form a double-stranded complex, which can be subsequently ligated and amplified for detection.

While this study employed two detection probes, each directed to the same target biomarker, a skilled artisan reading the present disclosure will understand when two detection probes are directed to different target biomarkers, or when three or more detection probes, each for a distinct target protein, are used. Further, compositions and methods described in this Example can be extended to applications in different biological samples (e.g., comprising extracellular vesicles).

The present Example shows experimental data from certain experiments demonstrating technologies provided herein are capable of detecting cancer (e.g., ovarian cystadenocarcinoma) in patient samples using a target biomarker combination for cancer (Cancer marker 1 and Cancer marker 2, e.g., in some embodiments, using Cancer marker 1 as a capture target with detection probes directed to Cancer marker 2). The first experiment demonstrated the detection of two different cancer cell-line-derived-extracellular vesicles (CLD-EVs) in PBS using a duplex system assay described herein. See, for example, FIG. 19.

Figure 21:
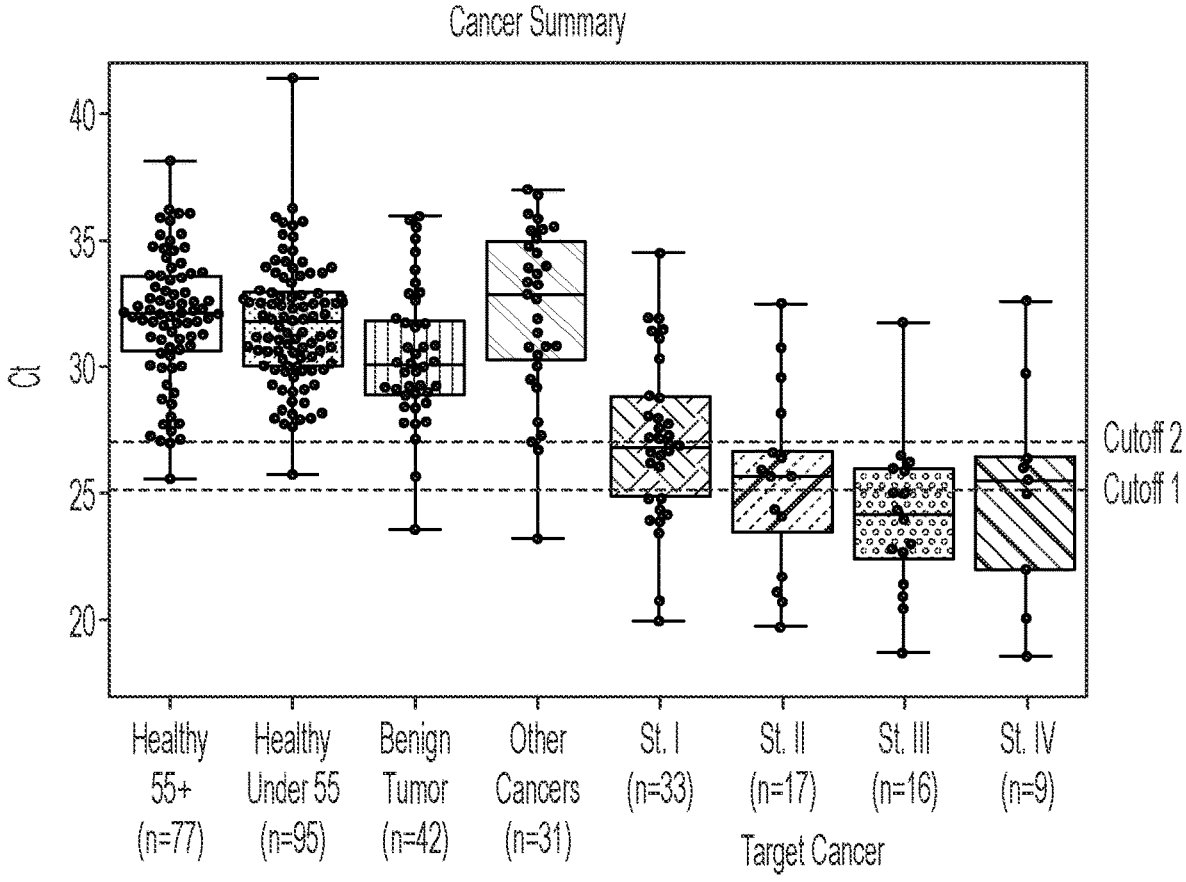
FIG. 21 is a graph showing performance of an exemplary assay for detection of a target cancer involving a duplex system (e.g., as described in FIG. 1 or FIGS. 2A-2B) based on cancer marker 1 capture with cancer marker 2+cancer maker 2 antibody probes, at two different cutoffs. Cutoff 1 pertains to a 99.8% specificity and Cutoff 2 pertains to a 98% specificity.
Figure 22:
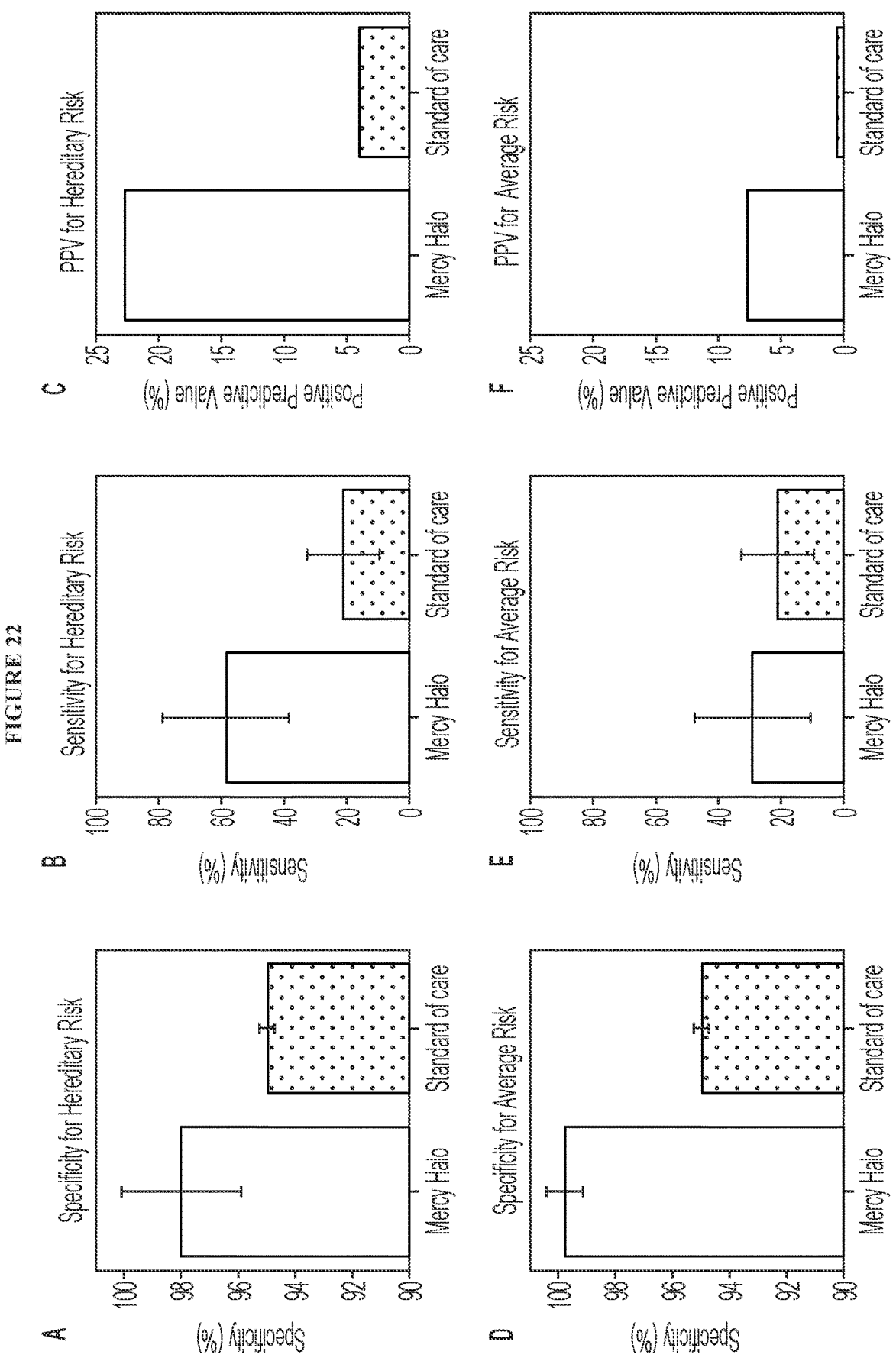
FIG. 22 is a set of data showing performance of an exemplary assay for detection of a target cancer compared to the current standard of care for the target cancer: serum protein and/or imaging. The specificity (Panels A and D), sensitivity (Panels B and E), and positive predictive value (Panels C and F) were compared for screening subjects at hereditary risk (Panels A, B, and C), and average risk (Panels D, E, and F) for the target cancer.

With such a duplex system assay capable of detecting CLD-EVs, a study containing patient samples from cancer of each stage (Stage I-IV) and/or subtypes and from various control groups (e.g., healthy subjects, subjects with benign tumors, and non-target cancers) was performed. Please see Example 6 and FIGS. 21-22 showing performance of an exemplary duplex system assay for detection of cancer (e.g., ovarian cancer).

Overview of an Exemplary Assay

In some embodiments, a target entity detection system described herein is a duplex system. In some embodiments, such a duplex system, e.g., as illustrated in FIG. 2A, utilizes two antibodies that each recognize a different epitope. Paired double-stranded template DNAs are also utilized in qPCR, each of which has specific four-base 5' overhangs complementary to the 5' overhang on its partner. Each antibody is conjugated with one of the two double-stranded DNA templates. When the antibodies bind their target epitopes, the sticky ends of the respective templates can hybridize. These sticky ends are then ligated together by T7 ligase, prior to PCR amplification. For hybridization between the two DNA templates to occur, the two antibodies need to be bound close enough to each other (within 50 to 60 nm, the length of the DNA linker and antibody). Any templates that bind but remain unligated will not produce PCR product, as shown in FIG. 2A.

Healthy Controls Versus Stage I, II, III, and IV Cancer Patient Plasma:

Plasma samples from healthy controls and cancer patients (e.g., patients having ovarian cancer) were processed to obtain purified extracellular vesicles, which were interrogated using an exemplary assay as described below.

Purified EVs were captured using magnetic beads covalently conjugated with anti-Cancer marker 1 antibodies. The EVs captured by the beads were profiled using a set of two detection probes, each comprising an antibody directed to Cancer marker 2 and a distinct oligonucleotide domain (e.g., ones as described herein).

The biomarker combination of Cancer marker 1 and Cancer marker 2 was carefully selected to minimize cross-reactivity with healthy-tissue-derived extracellular vesicles. The cross-reactivity of such a biomarker combination with healthy tissues was bioinformatically predicted, in part, by using a heatmap of differentially expressed mRNAs in a target cancer, e.g., ovarian cystadenocarcinoma. Thus, different combinations of markers can be predicted to be much more abundant on the surface of cancer-associated extracellular vesicles than on the surface of extracellular vesicles from healthy tissues.

TABLE 5

| Genes | The transcript expression scores for the following biomarker combination, as expressed in certain cancer cell lines vs. negative control cell line (e.g., non-cancer line) | | |
| --- | --- | --- | --- |
| | Positive Cell Line 1 | Positive Cell Line 2 | Negative Cell Line |
| Cancer marker 1 | +++ | + | − |
| Cancer marker 2 | +++ | + | − |

Exemplary Methods

Oligonucleotides

In some embodiments, oligonucleotides can have the following sequence structure and modifications. It is noted that the strand numbers below correspond to the numerical values associated with strands shown in FIG. 2A.

Strand 1 v1:

/5AzideN/CAGTCTGACACAGCAGTCGT-TAATCGTCGCTGCTACCCTTGACATCCGTGA CTGGCTAGACAGAGGTGT (SEQ ID NO: 18), where /5AzideN/ refers to an azide group linked to the 5' oligonucleotide terminus via a NHS ester linker, or /5AmMC12/CAGTCTGACACAGCAGTCGT-TAATCGTCGCTGCTACCCTTGACATCCGTG ACTGGCTAGACAGAGGTGT (SEQ ID NO: 18), where /5AmMC12/ refers to an amine group (e.g., a primary amino group) linked to the 5' oligonucleotide terminus via a 12-carbon spacer, or /5ThiolMC6/ CAGTCTGACACAGCAGTCGT-TAATCGTCGCTGCTACCCTTGACATCCGT GACTGGCTAGACAGAGGTGT (SEQ ID NO: 18), where /5ThiolMC6/ refers to a thiol linked to the 5' oligonucleotide terminus via a 6-carbon spacer.

Strand 2 v1:

/5AzideN/GACCTGACCTACAGTGACCAT-AGCCTTGCCTGATTAGCCACTGTCCAGTTT GGCTCCTGGTCTCACTAG (SEQ ID NO: 19), where /5AzideN/ refers to an azide group linked to the 5' oligonucleotide terminus via a NHS ester linker, or /5AmMC12/GACCTGACCTACAGTGACCAT-AGCCTTGCCTGATTAGCCACTGTCCAGTT TGGCTCCTGGTCTCACTAG (SEQ ID NO: 19), where /5AmMC1/ refers to an amine group (e.g., a primary amino group) linked to the 5' oligonucleotide terminus via a 12-carbon spacer, or /5ThiolMC6/ GACCTGACCTACAGTGACCATAGCCTTGCCT-GATTAGCCACTGTCCAGT TTGGCTCCTGGTCT-CACTAG (SEQ ID NO: 19), where /5ThiolMC6/ refers to a thiol linked to the 5' oligonucleotide termi-nus via a 6-carbon spacer Strand 3 v1:

/5Phos/GAGTACACCTCTGTCTAGCCAGTCACG-GATGTCAAGGGTAGCAGCGACGATT AACGACTGCTGTGTCAGACTG (SEQ ID NO: 20), wherein /5Phos/ refers to a phosphate group linked to the 5' oligonucleotide terminus Strand 4 v1:

/5Phos/ACTCCTAGTGAGACCAGGAGC-CAAACTGGACAGTGGCTAATCAGGCAAGGCT ATGGTCACTGTAGGTCAGGTC (SEQ ID NO: 21), wherein /5Phos/ refers to a phosphate group linked to the 5' oligonucleotide terminus Strand 5 v1:

CAGTCTGACACAGCAGTCGT (SEQ ID NO: 22)

Strand 6 v1:

GACCTGACCTACAGTGACCA (SEQ ID NO: 23)

Strand 7 (Probe) v1:

/56-FAM/TGGCTAGAC/ZEN/ AGAGGTGTACTCCTAGTGAGA/3IABkFQ/ (SEQ ID NO: 24), wherein /56-FAM/ refers to a fluorescein (e.g., 6-FAM) at the 5' oligonucleotide terminus; and /3IABkFQ/ refers to a fluorescein quencher at the 3' oligonucleotide terminus In some embodiments, oligonucleotides can have the following sequence structure and modifications. It is noted that the strand numbers below correspond to the numerical values associated with strands shown in FIG. 2A.

Strand 1 v2:

/5AzideN/CAGTCTGACTCACCACTCGT-TAATCGTCGCTGCTACCCTTGACATCCGTGA CTGGCTAGACAGAGGTGT (SEQ ID NO: 1), where /5AzideN/ refers to an azide group linked to the 5' oligonucleotide terminus via a NHS ester linker, or /5AmMC12/CAGTCTGACTCACCACTCGT-TAATCGTCGCTGCTACCCTTGACATCCGTG ACTGGCTAGACAGAGGTGT (SEQ ID NO: 1), where /5AmMC12/ refers to an amine group (e.g., a primary amino group) linked to the 5' oligonucleotide terminus via a 12-carbon spacer, or /5ThiolMC6/ CAGTCTGACTCACCACTCGT-TAATCGTCGCTGCTACCCTTGACATCCGTG ACTGGCTAGACAGAGGTGT (SEQ ID NO: 1), where /5ThiolMC6/ refers to a thiol linked to the 5' oligonucleotide terminus via a 6-carbon spacer Strand 2 v2:

/5AzideN/CACCAGACCTACGAAGTCCAT-AGCCTTGCCTGATTAGCCACTGTCCAGTTT GGCTCCTGGTCTCACTAG (SEQ ID NO: 2), where /5AzideN/ refers to an azide group linked to the 5' oligonucleotide terminus via a NHS ester linker, or /5AmMC12/CACCAGACCTACGAAGTCCAT-AGCCTTGCCTGATTAGCCACTGTCCAGTT TGGCTCCTGGTCTCACTAG (SEQ ID NO: 2), where /5AmMC1/ refers to an amine group (e.g., a primary amino group) linked to the 5' oligonucleotide terminus via a 12-carbon spacer, or /5ThiolMC6/ CACCAGACCTACGAAGTCCATAGCCTTGCCT-GATTAGCCACTGTCCAGT TTGGCTCCTGGTCT-CACTAG (SEQ ID NO: 2), where /5ThiolMC6/ refers to a thiol linked to the 5' oligonucleotide terminus via a 6-carbon spacer Strand 3 v2:

/5Phos/GAGTACACCTCTGTCTAGCCAGTCACG-GATGTCAAGGGTAGCAGCGACGATT AACGAGTGGTGAGTCAGACTG (SEQ ID NO: 3), wherein /5Phos/ refers to a phosphate group linked to the 5' oligonucleotide terminus Strand 4 v2:

/5Phos/ACTCCTAGTGAGACCAGGAGC-CAAACTGGACAGTGGCTAATCAGGCAAGGCT ATGGACTTCGTAGGTCTGGTG (SEQ ID NO: 4), wherein /5Phos/ refers to a phosphate group linked to the 5' oligonucleotide terminus Strand 5 v2:

CAGTCTGACTCACCACTCGT (SEQ ID NO: 5)

Strand 6 v2:

CACCAGACCTACGAAGTCCA (SEQ ID NO: 25)

Strand 7 (Probe) v2:

/56-FAM/TGGCTAGAC/ZEN/
AGAGGTGTACTCCTAGTGAGA/3IABkFQ/ (SEQ
ID NO: 24), wherein /56-FAM/ refers to a fluorescein
(e.g., 6-FAM) at the 5' oligonucleotide terminus; and
/3IABkFQ/ refers to a fluorescein quencher at the 3'
oligonucleotide terminus Antibody-Oligonucleotide (e.g., Antibody-DNA) Conjugation:

60 ug aliquots of an antibody directed to a target marker
(e.g., Cancer marker 2) was conjugated with hybridized
strands 1+3 and 2+4, for example, using copper-free click
chemistry. The first step was to prepare DBCO-functionalized
antibodies to participate in the conjugation reaction
with azide-modified oligonucleotide domain (e.g., DNA
domain). This began with reacting the antibodies with the
DBCO-PEG5-NHS heterobifunctional cross linker. The
reaction between the NHS ester and available lysine groups
was allowed to take place at room temperature for 2 hours,
after which unreacted crosslinker was removed using centrifugal
ultrafiltration. To complete the conjugation, azide-
modified oligonucleotide domain (e.g., DNA domain) and
the DBCO-functionalized antibodies was allowed to react
overnight at room temperature.

Cell Culture

Negative control cells (e.g., non-target cancer cells such
as melanoma cells or healthy cells) were grown in Eagle's
Minimum Essential Medium (EMEM) with 10% exosome-
free FBS and 50 units of penicillin/streptomycin per mL.
Cancer cells (e.g., ovarian cancer cells) were grown in
Roswell Park Memorial Institute (RPMI 1640) with 10%
exosome-free FBS and 50 units of penicillin/streptomycin
per mL. Exemplary cancer cell lines that may be useful to
develop an assay for detection of cancer (e.g., ones as
described herein) include, but are not limited to, A2780,
Caov-3, COV413A, ES2, OVCAR-3, OV90, PA-1, SK-OV-
3, SW 626, TOV-112, and cells lines described in Ince et al.,
"Characterization of twenty-five ovarian tumor cell lines
that phenocopy primary tumours" Nature Communications
6:7419 (2015). All cell lines were maintained at 5% $CO_2$ and
37° C. and the passage number was below 20.

Purification of Extracellular Vesicles from Cell Culture
Medium

In some embodiments, cancer cells (e.g., ovarian cancer
cells) and negative control cells were grown in their respec-
tive media until they reached ~80% confluence. The cell
culture medium was collected and spun at 300×rcf for 5
minutes at room temperature (RT) to removes cells and
debris. The supernatant was then collected and frozen at
−80° C.

Prior to use, the frozen supernatant stored at −80° C. was
thawed and then clarified of cells and large (e.g., greater than
1 micron in diameter) cellular fragments. The thawed super-
natant was clarified using centrifugation.

In some embodiments, the clarified cell culture medium
(e.g., ~500 uL) was run through a size-exclusion purification
column. Nanoparticles having a size range of about 65 nm
to about 1000 nm were collected for each sample. In some
embodiments, a smaller particle range may be desirable.

Particle Counts:

Particle counts were obtained, e.g., using a SpectroDyne
particle counting instrument using the TS400 chips, to
measure nanoparticle range between 65 and 1000 nm. In
some embodiments, a smaller particle range may be desir-
able.

Whole-Plasma Clarification:

Prior to EVs purification, samples were blinded by per-
sonnel who would not participate in sample-handling. The
patient-identification information was only revealed after
the experiment was completed to enable data analysis. 1 mL
aliquots of whole plasma were removed from storage at
−80° C. and subjected to three clarification spins to remove
cells, platelets, and debris.

Size-Exclusion Chromatography Purification of EVs from
Clarified Plasma:

Each clarified plasma sample was run through a single-
use, size-exclusion purification column to isolate the EVs.
Nanoparticles having a size range of about 65 nm to about
1000 nm were collected for each sample. In some embodi-
ments, smaller particle range may be desirable.

Capture-Antibody Conjugation to Magnetic-Capture Beads:

Antibodies were conjugated to magnetic beads. Briefly,
beads were weighed in a sterile environment and resus-
pended in buffer. Antibodies were mixed with the function-
alized beads and the conjugation reaction took place with
end-over-end mixing. The beads were washed several times
using the wash buffer provided by the conjugation kit and
were stored at 4° C. in the provided storage buffer.

Direct Capture of Purified Plasma EVs Using Antibody-
Conjugated Magnetic Beads:

For EV capture, a diluted sample of purified plasma EVs
were incubated with magnetic beads conjugated with anti-
bodies directed to an EV target (e.g., Cancer marker 1) for
an appropriate time period, e.g., at room temperature.

Binding of Antibody-Oligonucleotide Conjugates to EVs
Bound on Magnetic Capture Beads:

Antibody-oligonucleotide conjugates ("antibody
probes"), directed to an EV target (e.g., Cancer marker 2)
that is different from the one used in an EV capture assay
(e.g., one described above), were diluted in an appropriate
buffer at their optimal concentrations. Antibody probes were
allowed to interact with a sample comprising EVs bound on
magnetic capture beads.

Post-Binding Washes:

In some embodiments, samples were washed, e.g., mul-
tiple times, in an appropriate buffer.

Ligation:

After the wash to remove unbound antibody-oligonucle-
otide conjugates, the beads with bound extracellular vesicles
and bound antibody-oligonucleotide conjugates were con-
tacted with a ligation mix. The mixtures were incubated for
20 minutes at RT.

PCR:

Following ligation, the beads with bound extracellular
vesicles and bound antibody-oligonucleotide conjugates
were contacted with a PCR mix. PCR was performed in a
96-well plate, e.g., on the Quant Studio 3, with the following
exemplary PCR protocol: hold at 95° C. for 1 minute,
perform 50 cycles of 95° C. for 5 seconds and 62° C. for 15
seconds. The rate of temperature change was chosen to be
standard (2° C. per second). A single qPCR reaction was
perform for each experimental replicate and ROX was used
as the passive reference to normalize the qPCR signals. Data
was then downloaded from the Quant Studio 3 machine and
analyzed and plotted in Python 3.7.

Data Analysis:

In some embodiments, a binary classification system can
be used for data analysis. In some embodiments, signals
from a detection assay may be normalized based on a
reference signal. For example, in some embodiments, nor-
malized signals for a single antibody duplex were calculated
by choosing a reference sample. In some embodiments, the
equations used to calculate the normalized signal for an arbitrary sample i are given below, where $\text{Signal}_{max}$ is the signal from the highest concentration cell-line EVs standard.

$$\Delta Ct_i = Ct_{ref} - Ct_i$$

$$\text{Signal}_i = 2^{\Delta Ct_i}$$

$$\text{Norm Signal}_i = \frac{\text{Signal}_i}{\text{Signal}_{max}}$$

Representative Results

In Vitro Cell Line Experiments

Purified cell-line EVs were diluted to an optimal concentration in an appropriate buffer and captured using Cancer marker 1-functionalized beads (1 mL replicates). Captured EVs were analyzed using a pair of antibody probes each directed to Cancer marker 2. Representative qPCR data and $\Delta Ct$ values are provided in FIG. 19. The data show that the tested biomarker combination (e.g., in combination with an exemplary assay such as, e.g., as described in the present Example and illustrated in FIGS. 1-2B) is capable of distinguishing cancer-derived EVs from the negative control cell line, with a signal strength that is well-correlated with the expression of the two markers (see Table 5).

Pilot Cancer Patient Plasma Study

Figure 20:
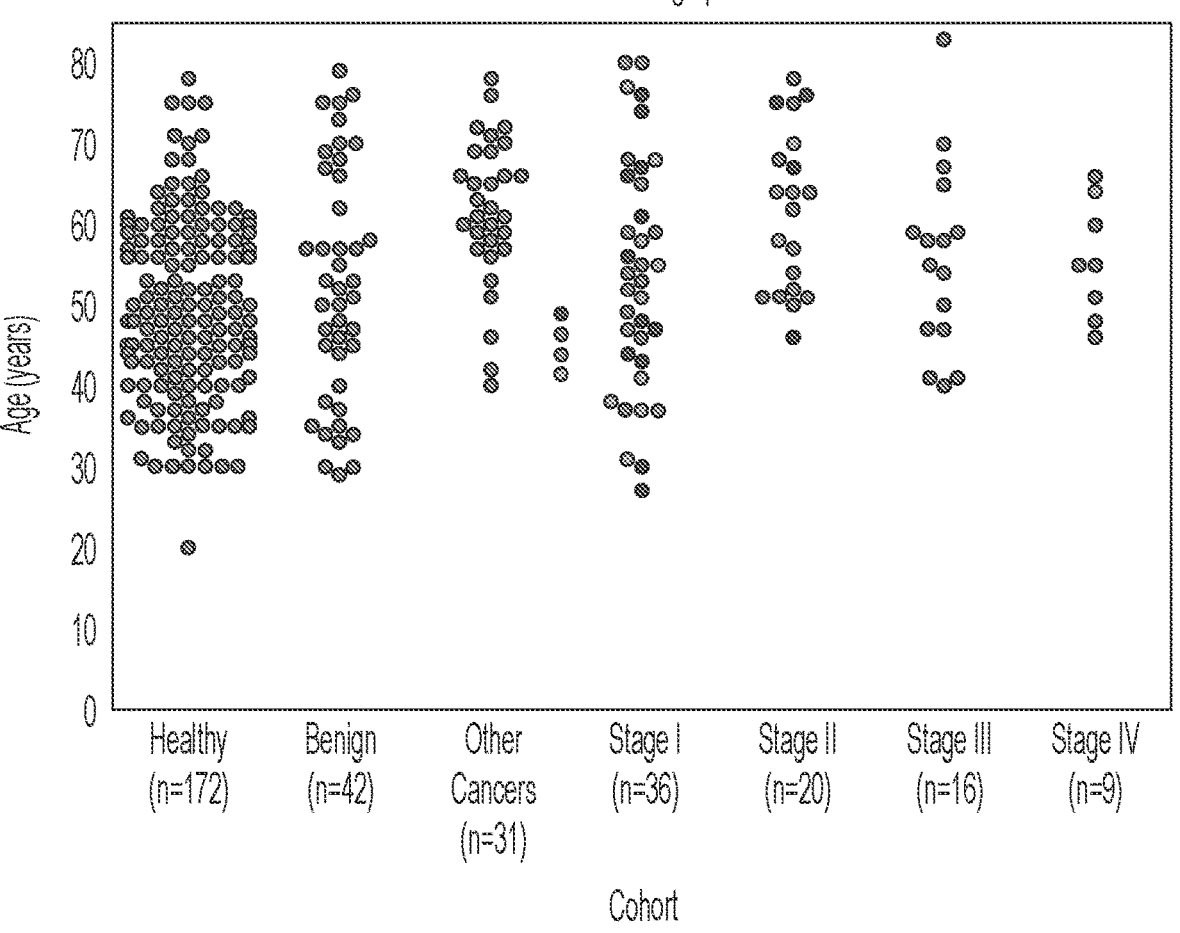
FIG. 20 is a graph showing demographics of patients included in a cancer patient plasma sample study, which shows age and cohort size for the patient cohort evaluated by the exemplary assay.

The demographics of cancer patients (e.g., ovarian cancer patients) included in a pilot study are provided in FIG. 20. Care was taken to match age and gender as closely as possible across the different sample cohorts.

One milliliter of patient sample plasma was clarified as described above and EVs were purified using size-exclusion chromatography. EVs were captured using anti-Cancer marker 1 magnetic beads. EVs captured by the anti-Cancer marker 1 magnetic beads were profiled using antibody probes directed to Cancer marker 2. Please see Example 6 and FIGS. 21-22 showing performance of an exemplary duplex system assay for detection of cancer (e.g., ovarian cancer).

Discussion

Figure 2:
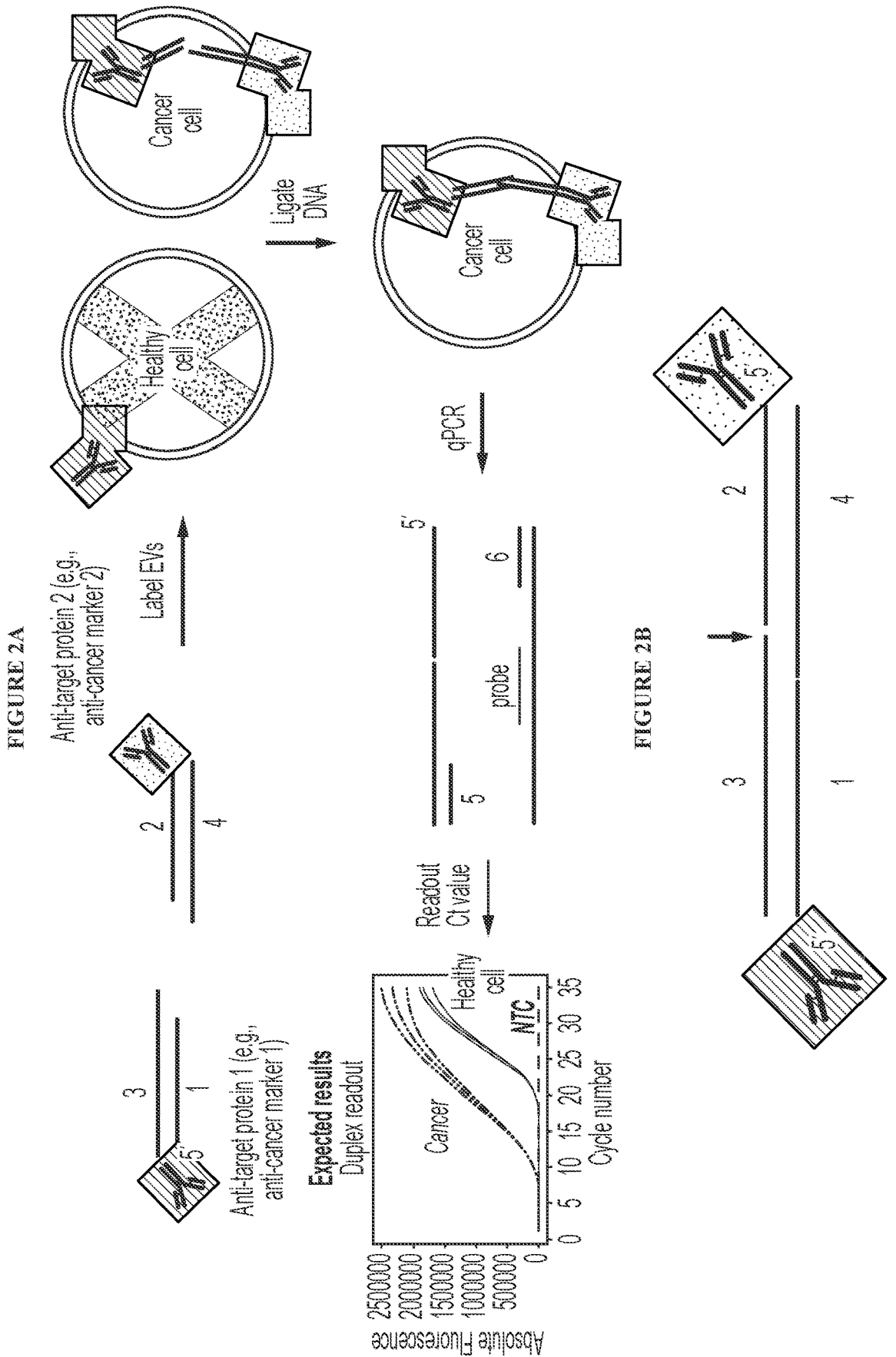
FIGS. 2A-2B are schematic diagrams illustrating a target entity detection assay according to some embodiments described herein.

The present Example demonstrates that a capture assay (e.g., as utilized and/or described herein) directed to a first target biomarker, in combination with a duplex detection assay (e.g., as described in the present Example and illustrated in FIGS. 1-2B) directed to a second target biomarker, such that the combination of the first target biomarker and the second target biomarker is specific for detection of a target cancer, is capable of detecting early-stage cancer (e.g., ovarian cystadenocarcinoma) with >99.5% specificity.

In some embodiments, a dendron, which can add up to 16 strands of oligonucleotide domain (e.g., DNA) per antibody, can be used instead of one or two strands of DNA per antibody, for example, to enhance signal-to-noise.

Example 6: Development of a Cancer Liquid Biopsy Assay

The present Example describes development of a cancer liquid biopsy assay, for example, for screening hereditary-and average-risk subjects. Despite being the fifth largest killer of women among all cancers (Howlader et al., 2019), there is currently no recommended ovarian cancer screening tool for average-risk women. This is due, in part, to the poor performance of proposed ovarian cancer screening technologies. Given the incidence of ovarian cancer in average-risk women, inadequate test specificities (<99.5%) result in false-positive results that outnumber true positives by more than an order of magnitude. This places a significant burden on the healthcare system and on the women being screened as false-positive results lead to additional tests, unnecessary surgeries, and emotional/physical distress (Buys et al., 2011). As a result, it may be desirable to develop an ovarian cancer screening test that may exhibit two features to provide clinical utility: (1) ultrahigh specificity (>99.5%) to minimize the number of false positives, and (2) high sensitivity (>40%) for stage I and II ovarian cancer when prognosis is most favorable. The development of such a test has the potential to save tens of thousands of lives each year.

Several different biomarker classes have been studied for an ovarian cancer liquid biopsy assay including circulating tumor DNA (ctDNA), circulating tumor cells (CTCs), bulk proteins, and extracellular vesicles (EVs). EVs are particularly promising due to their abundance and stability in the bloodstream relative to ctDNA and CTCs, suggesting improved sensitivity for early-stage cancers. Moreover, EVs contain cargo (e.g., proteins, RNA, metabolites) that originated from the same cell, providing superior specificity over bulk protein measurements. While the diagnostic utility EVs has been studied, much of this work has pertained to bulk EV measurements or low-throughput single-EV analyses.

This present Example describes one aspect of an exemplary approach for early-stage cancer detection through the profiling of individual extracellular vesicles (EVs) in human plasma using technologies as described and/or utilized herein. EVs, including exosomes and microvesicles, contain co-localized proteins, RNAs, metabolites, and other compounds representative of their cell of origin (Kosaka et al., 2019). The detection of co-localized markers within a single EV can enable the identification of cell type with ultrahigh specificity, including the ability to distinguish cancer cells from normal tissues. As opposed to other cancer diagnostic approaches that rely on cell death for biomarkers to enter the blood (i.e., cfDNA), EVs are released at a high rate by functioning cells. Single cells have been shown to release as many as 10,000 EVs per day in vitro (Balaj et al., 2011). In addition, it is widely accepted that cancer cells release EVs at a higher rate than healthy cells (Bebelman et al. 2018).

In one aspect, cancer-associated biomarkers for use in a detection assay (e.g., as described and/or utilized herein) include genes that are upregulated in cancer versus healthy tissues, which for example, can be identified using Applicant's proprietary bioinformatic biomarker discovery process. Using an exemplary individual EV assay (see, e.g., illustrated in FIG. 1 or 2A-2B and/or described herein), co-localization of such biomarkers on an individual vesicle is detected, indicating that the grouping of biomarkers originated from the same cell. This provides superior specificity to bulk biomarker measurements, including bulk EV assays, given that many upregulated cancer biomarkers are expressed by one or more healthy tissues. In some embodiments, the present disclosure provides technologies with ultrahigh specificity that is particularly helpful as a cancer screening test, for example, ovarian cancer for which the prevalence of disease is low and a high positive-predictive value (>10%) is required (Seltzer et al., 1995).

Biomarker Discovery

In some embodiments, a biomarker discovery process leverages bioinformatic analysis of large databases and an understanding of the biology of cancer (e.g., ovarian cancer) and extracellular vesicles.

Individual Extracellular Vesicle Analysis

The detection of tumor-derived EVs in the blood requires an assay that has sufficient selectivity and sensitivity to detect relatively few tumor-derived EVs per milliliter of plasma in a background of 10 billion EVs from a diverse range of healthy tissues. The present disclosure, among other things, provides technologies that address this challenge. For example, in some embodiments, an assay for individual extracellular vesicle analysis is illustrated in FIG. 1, which is performed in three key steps as outlined below:

1. EVs are purified from patient plasma using size-exclusion chromatography (SEC), which removes greater than 99% of soluble proteins and other interfering compounds.

2. Tumor-specific EVs are captured using antibody-functionalized magnetic beads specific to a membrane-bound protein.

3. A modified version of proximity-ligation-immuno quantitative polymerase chain reaction (pliq-PCR) is performed to determine the co-localization of additional protein biomarkers contained on or within the captured EVs.

In many embodiments of a modified version of a pliq-PCR assay, two or more different antibody-oligonucleotide conjugates are added to the EVs captured by the antibody-functionalized magnetic bead and the antibodies subsequently bind to their protein targets. The oligonucleotides are composed of dsDNA with single-stranded overhangs that are complementary, and thus, capable of hybridizing when in close proximity (i.e., when the corresponding protein targets are located on the same EV). After washing away unbound antibody-oligonucleotide species, adjacently bound antibody-oligonucleotide species are ligated using a standard DNA ligase reaction. Subsequent qPCR of the ligated template strands enables the detection and relative quantification of co-localized protein species. In some embodiments, two to twenty distinct antibody-oligonucleotide probes can be incorporated into such an assay, e.g., involving a provided target entity detection system.

pliq-PCR has numerous advantages over other technologies to profile EVs. For example, pliq-PCR has a sensitivity three orders of magnitude greater than other standard immunoassays, such as ELISAs (Darmanis et al., 2010). The ultra-low LOD of a well-optimized pliq-PCR reaction enables detection of trace levels of tumor-derived EVs, down to a thousand EVs per mL. This compares favorably with other emerging EV analysis technologies, including the Nanoplasmic Exosome (nPLEX) Sensor (Im et al., 2014) and the Integrated Magnetic-Electrochemical Exosome (iMEX) Sensor (Jeong et al., 2016), which have reported LODs of ~$10^3$ and ~$10^4$ EVs, respectively (Shao et al., 2018). Moreover, in some embodiments, a modified version of pliq-PCR approach does not require complicated equipment and can uniquely detect the co-localization of multiple biomarkers on individual EVs.

In some embodiments, to further improve the sensitivity and specificity of an individual EV profiling assay, other classes of EV biomarkers include mRNA and intravesicular proteins (in addition to EV surface proteins) can be identified and included in an assay.

Preliminary Work

Through preliminary studies, a workflow is developed in which biomarker candidates are validated to be present in EVs and capable of being detected by commercially available antibodies or mRNA primer-probe sets. For a given biomarker of interest, one or more cell lines expressing (positive control) and not expressing the biomarker of interest (negative control) can be cultured to harvest their EVs through concentrating their cell culture media and performing purification to isolate nanoparticles having a size range of interest (e.g., using SEC). Typically, extracellular vesicles may range from 30 nm to several micrometers in diameter. See, e.g., Chuo et al., "Imaging extracellular vesicles: current and emerging methods" *Journal of Biomedical Sciences* 25:91 (2018), which provides information of sizes for different extracellular vesicle (EV) subtypes: migrasomes (0.5-3 μm), microvesicles (0.1-1 μm), oncosomes (1-10 μm), exomeres (<50 nm), small exosomes (60-80 nm), and large exosomes (90-120 nm). In some embodiments, nanoparticles having a size range of about 30 nm to 1000 nm may be isolated for detection assay. In some embodiments, specific EV subtype(s) may be isolated for detection assay.

Through a proprietary biomarker discovery process, two membrane-bound protein biomarkers that are upregulated in cancer (e.g., ovarian cancer) versus healthy tissues were identified and used in proof-of-concept experiments in cell-line EVs and cancer patient samples.

To detect assay signal from EVs that contain co-localized Cancer marker 1 and Cancer marker 2, which combination is specific detection of cancer (e.g., ovarian cancer), in some embodiments, an assay configuration involving immunoaffinity capture directed to Cancer marker 1 and two distinct antibody-oligonucleotide probes directed to Cancer marker 2 was developed.

Purified cell-line EVs were captured using anti-Cancer marker 1-functionalized magnetic beads. FIG. 19 (Panel A) provides representative qPCR traces for two positive control cell lines and one negative control cell line, for example. The data demonstrate the influence of gene expression on assay signal, in which the higher expressing cell line exhibited a 36-fold increase ($2^{5.2}$) in signal relative to the lower expressing cell line. These results demonstrate that in some embodiments, a single EV profiling assay (e.g., ones described herein) is capable of detecting co-localized membrane-bound protein markers on single EVs with very high sensitivity.

Following the validation of a cancer detection assay involving a combination of a capture assay and a detection assay (e.g., as illustrated in FIGS. 1 and 2A-2B or described herein) with cancer cell-line EVs, a pilot study (eventually expanded to 320 patient samples) was performed on cancer patient plasma samples (e.g., ovarian cancer patient plasma samples) using an optimized and operator-blinded assay protocol. All plasma samples were purchased from the same source, were processed according to the same blood collection protocol, and patient samples were collected prior to the initiation of any treatment (i.e., treatment naïve). The patient cohorts included in the study of this Example are described in FIG. 20.

The results of this clinical pilot study are provided in FIG. 21. Specificity was determined by assuming a log-normal distribution around all healthy controls (n=172) and setting a cutoff at 2.879 standard deviations above the mean (Cutoff 1) for 99.8% specificity and 2.055 standard deviations above the mean (Cutoff 2) for 98% specificity. By way of example only, in the context of ovarian cancer, a specificity of 99.8% was used to evaluate the PPV for screening average-risk women where a prevalence of 5.7 per 10,000 women was used. The 98% specificity cutoff was used to calculate the PPV for screening hereditary-risk women where the prevalence is approximately 1 per 100 women. These separate cutoffs were established to account for the difference in false-positive tolerance among different patient populations.

These results demonstrate that in some embodiments, a single EV profiling assay (e.g., as described herein) has great potential for being used as a cancer screening test. In some embodiments, the sensitivity of such an assay may be increased, for example, by including one or more sets of detection probes (e.g., as described herein) directed to additional biomarker(s). In some embodiments, such biomarker(s) may include, e.g., but are not limited to membrane-bound proteins and intravesicular mRNAs/proteins.

Figure 23:
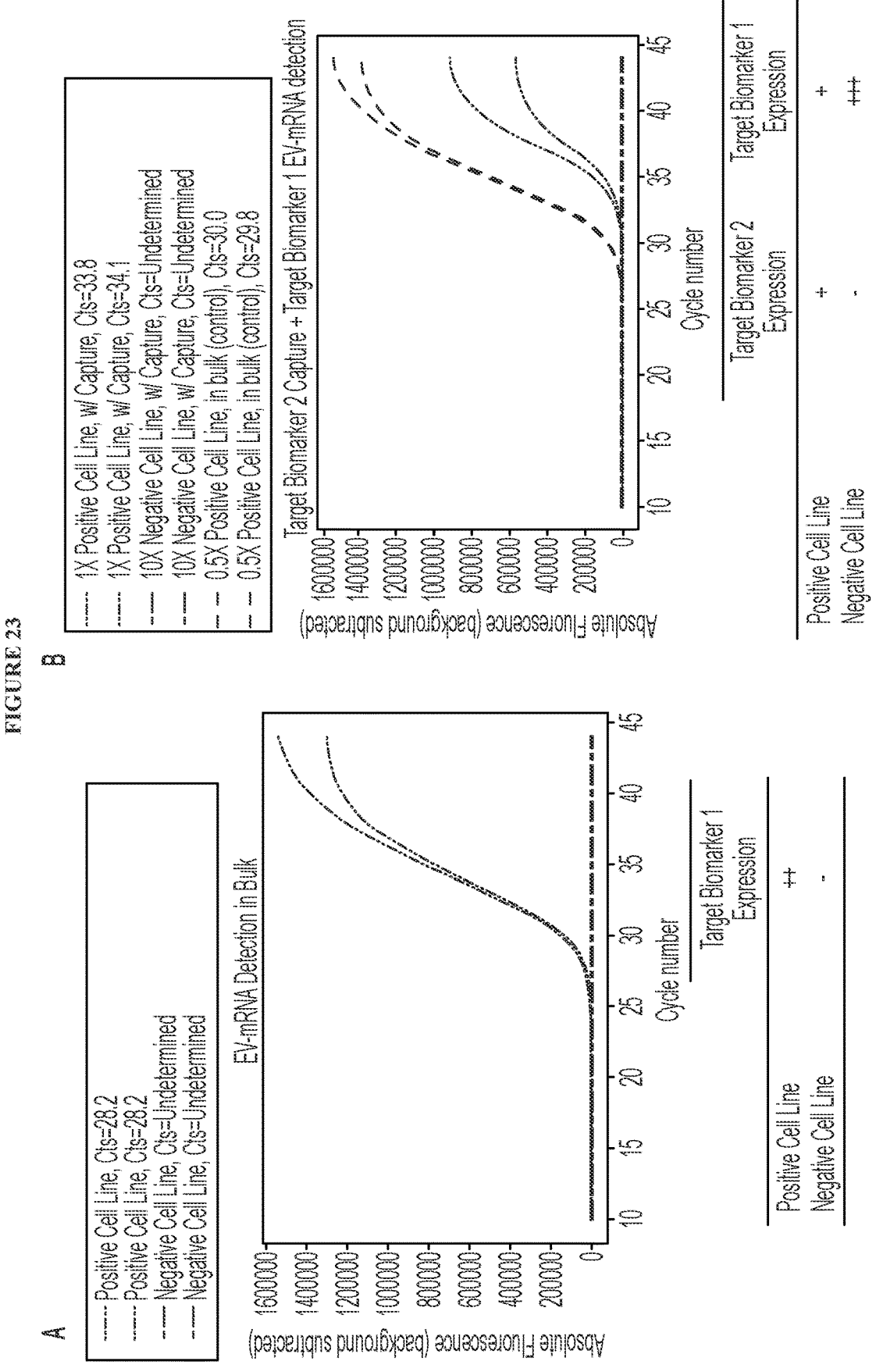
FIG. 23 is a set of graphs showing detection of target biomarker 1 mRNA in EVs from cancer cell-lines vs. negative control cell lines. (Panel A) Detection of target biomarker 1 mRNA in bulk EVs using RT-qPCR. (Panel B) Detection of target biomarker 1 mRNA in EVs that were captured using anti-target biomarker 2 functionalized beads compared to EVs in bulk.

In some embodiments, it was demonstrated the feasibility of EV-mRNA detection using purified cell-line EVs in bulk, as shown in FIG. 23 (Panel A) for the detection of a transcript associated with a target cancer. Through immunoaffinity capture of a membrane bound protein marker, this approach enables the detection of two co-localized biomarkers. Moreover, EV-mRNA detection requires a simpler protocol because RT-qPCR can be performed directly after immunoaffinity capture. mRNA detection using EVs was demonstrated in FIG. 23 (Panel B), where EVs were first captured using anti-EV marker 1 modified magnetic beads and EV marker 2 mRNA was detected. Both positive and negative cell lines express EV marker 2, however, only the positive cell line expresses EV marker 1. Selective detection of the positive cell line, was demonstrated, even at an order of magnitude higher concentration of negative cell line EVs with such a detection system.

In some embodiments, a cancer liquid biopsy assay for detection of a target biomarker signature (comprising a plurality of target biomarkers) in individual EVs comprises: (a) an immunoaffinity capture assay (e.g., as described herein) directed to at least one or more target biomarkers ("capture biomarker(s)"); and (b) a detection assay comprising a target entity detection system described herein (e.g., as illustrated in FIG. 2A) directed to at least one or more target biomarkers of a target biomarker signature that are distinct from the capture biomarker(s). In some embodiments, such a detection assay may further comprise an EV-mRNA detection assay (e.g., as described above) directed to one or more target biomarkers of such a target biomarker signature.

Example 7: Effect of Length of an Oligonucleotide Domain of Detection Probes on Assay Signal The present Example describes synthesis of detection probes for targets (e.g., target biomarker(s)) each comprising a target-binding moiety and an oligonucleotide domain of various lengths (comprising a double-stranded portion and a single stranded overhang) coupled to the target-binding moiety. The present Example further demonstrates that the length of an oligonucleotide domain of detection probes can impact the performance of a target entity detection system (e.g., ones described herein) and/or methods using the same.

To evaluate the effect of an oligonucleotide domain length on performance (e.g., assay signal) of a target entity detection system (e.g., a duplex target entity detection system described herein), detection probes having antibody agents conjugated to oligonucleotide domains of three different lengths (described below) were synthesized:

Length 1 ("Long"): 69-73 nucleotides (69-nucleotide long double-stranded portion with a single-stranded overhang of 4 nucleotides in length)

Length 2 ("Medium"): 40-44 nucleotides (40-nucleotide long double-stranded portion with a single-stranded overhang of 4 nucleotides in length)

Length 3 ("Short"): 20-24 nucleotides (20-nucleotide long double-stranded portion with a single-stranded overhang of 4 nucleotides in length)

Two cell line extracellular vehicles (EVs) were used as positive controls for this experiment: HCC4006 and T84. The negative control for this experiment was capture beads without EVs. EVs were captured using anti-Target 1-functionalized magnetic beads and assay signal was generated using anti-Target 1 and anti-Target 2 detection probes. Table 6 summarizes the expression of these proteins in cell line EVs.

TABLE 6

| The transcript per million (TPM) scores, as expressed in HCC4006 and T84 cell lines. | | | |
|---|---|---|---|
| Combination | Targets | HCC4006 Expression | T84 Expression |
| 1 | Target 1 | ++++ | ++ |
| | Target 2 | + | +++ |

Exemplary Methods

Oligonucleotides

In some embodiments, oligonucleotides can have the following sequence structure and modifications. It is noted that the strand numbers below correspond to the numerical values associated with strands shown in FIG. 2A. It is also noted that the oligonucleotide functionalization can be switched from one functional group to another functional group (e.g., from amine to azide to thiol, etc.).

In some embodiments, below provides an exemplary set of oligonucleotides to form an oligonucleotide domain of Length 1 ("Long"):

Strand 1v1:
/5AmMC12/CAGTCTGACTCACCACTCGT-TAATCGTCGCTGCTACCCTTGACATCCGTG ACTGGCTAGACAGAGGTGT (SEQ ID NO: 1), wherein /5AmMC12/ refers to an amine group (e.g., a primary amino group) linked to the 5' oligonucleotide terminus via a 12-carbon spacer; or Strand 2v1:
/5AmMC12/CACCAGACCTACGAAGTCCAT-AGCCTTGCCTGATTAGCCACTGTCCAGTT TGGCTCCTGGTCTCACTAG (SEQ ID NO: 2), wherein /5AmMC12/ refers to an amine group (e.g., a primary amino group) linked to the 5' oligonucleotide terminus via a 12-carbon spacer Strand 3v1:
/5Phos/GAGTACACCTCTGTCTAGCCAGTCACG-GATGTCAAGGGTAGCAGCGACGATT AACGAGTGGTGAGTCAGACTG (SEQ ID NO: 3), wherein /5Phos/ refers to a phosphate group linked to the 5' oligonucleotide terminus Strand 4v1:
/5Phos/ACTCCTAGTGAGACCAGGAGC-CAAACTGGACAGTGGCTAATCAGGCAAGGCT ATGGACTTCGTAGGTCTGGTG (SEQ ID NO: 4), wherein /5Phos/ refers to a phosphate group linked to the 5' oligonucleotide terminus In some embodiments, below provides an exemplary set of oligonucleotides to form an oligonucleotide domain of Length 1 ("Long"):

Strand 1v2:
/5AmMC12/CAGTCTGACACAGCAGTCGT-TAATCGTCGCTGCTACCCTTGACATCCGTG ACTGGCTAGACAGAGGTGT (SEQ ID NO: 18), wherein /5AmMC12/ refers to an amine group (e.g., a primary amino group) linked to the 5' oligonucleotide terminus via a 12-carbon spacer; or Strand 2v2:
/5AmMC12/GACCTGACCTACAGTGACCAT-AGCCTTGCCTGATTAGCCACTGTCCAGTT TGGCTCCTGGTCTCACTAG (SEQ ID NO: 19), wherein /5AmMC12/ refers to an amine group (e.g., a primary amino group) linked to the 5' oligonucleotide terminus via a 12-carbon spacer Strand 3v2:
/5Phos/GAGTACACCTCTGTCTAGCCAGTCACG-GATGTCAAGGGTAGCAGCGACGATT AACGACTGCTGTGTCAGACTG (SEQ ID NO: 20), wherein /5Phos/ refers to a phosphate group linked to the 5' oligonucleotide terminus Strand 4v2:
/5Phos/ACTCCTAGTGAGACCAGGAGC-CAAACTGGACAGTGGCTAATCAGGCAAGGCT ATGGTCACTGTAGGTCAGGTC (SEQ ID NO: 21), wherein /5Phos/ refers to a phosphate group linked to the 5' oligonucleotide terminus In some embodiments, below provides an exemplary set of oligonucleotides to form an oligonucleotide domain of Length 2 ("Medium"):

Strand 1v1-Medium:
/5AmMC12/CAGTCTGACTCAC-CACTCGTGACTGGCTAGACAGAGGTGT (SEQ ID NO: 26), wherein /5AmMC12/ refers to an amine group (e.g., a primary amino group) linked to the 5' oligonucleotide terminus via a 12-carbon spacer Strand 2v1-Medium:
/5AmMC12/CACCAGACCTACGAAGTCCAT-TGGCTCCTGGTCTCACTAG (SEQ ID NO: 27), wherein /5AmMC12/ refers to an amine group (e.g., a primary amino group) linked to the 5' oligonucleotide terminus via a 12-carbon spacer Strand 3v1-Medium:
/5Phos/GAGTACACCTCTGTCTAGCCAGT-CACGAGTGGTGAGTCAGACTG (SEQ ID NO: 28), wherein /5Phos/ refers to a phosphate group linked to the 5' oligonucleotide terminus Strand 4v1-Medium:
/5Phos/ACTCCTAGTGAGACCAGGAGC-CAATGGACTTCGTAGGTCTGGTG (SEQ ID NO: 29), wherein /5Phos/ refers to a phosphate group linked to the 5' oligonucleotide terminus In some embodiments, below provides an exemplary set of oligonucleotides to form an oligonucleotide domain of Length 2 ("Medium"):

Strand 1v2-Medium:
/5AmMC12/ CAGTCTGACACAGCAGTCGTGACTGGCTA-GACAGAGGTGT (SEQ ID NO: 30), wherein /5AmMC12/ refers to an amine group (e.g., a primary amino group) linked to the 5' oligonucleotide terminus via a 12-carbon spacer Strand 2v2-Medium:
/5AmMC12/GACCTGACCTACAGTGACCAT-TGGCTCCTGGTCTCACTAG (SEQ ID NO: 31), wherein /5AmMC12/ refers to an amine group (e.g., a primary amino group) linked to the 5' oligonucleotide terminus via a 12-carbon spacer Strand 3v2-Medium:
/5Phos/GAGTACACCTCTGTCTAGCCAGT-CACGACTGCTGTGTCAGACTG (SEQ ID NO: 32), wherein /5Phos/ refers to a phosphate group linked to the 5' oligonucleotide terminus Strand 4v2-Medium:
/5Phos/ACTCCTAGTGAGACCAGGAGCCAATGGT-CACTGTAGGTCAGGTC (SEQ ID NO: 33), wherein /5Phos/ refers to a phosphate group linked to the 5' oligonucleotide terminus In some embodiments, below provides an exemplary set of oligonucleotides to form an oligonucleotide domain of Length 3 ("Short"):

Strand 1v1-Short:
/5AmMC12/CAGTCTGACTCACCACTCGT (SEQ ID NO: 5), wherein /5AmMC12/ refers to an amine group (e.g., a primary amino group) linked to the 5' oligonucleotide terminus via a 12-carbon spacer Strand 2v1-Short:
/5AmMC12/CACCAGACCTACGAAGTCCA (SEQ ID NO: 6), wherein /5AmMC12/ refers to an amine group (e.g., a primary amino group) linked to the 5' oligonucleotide terminus via a 12-carbon spacer Strand 3v1-Short:
/5Phos/GAGTACGAGTGGTGAGTCAGACTG (SEQ ID NO: 34), wherein /5Phos/ refers to a phosphate group linked to the 5' oligonucleotide terminus Strand 4v1-Short:
/5Phos/ACTCTGGACTTCGTAGGTCTGGTG (SEQ ID NO: 35), wherein /5Phos/ refers to a phosphate group linked to the 5' oligonucleotide terminus In some embodiments, below provides an exemplary set of oligonucleotides to form an oligonucleotide domain of Length 3 ("Short"):

Strand 1v2-Short:
/5AmMC12/CAGTCTGACACAGCAGTCGT (SEQ ID NO: 22), wherein /5AmMC12/ refers to an amine group (e.g., a primary amino group) linked to the 5' oligonucleotide terminus via a 12-carbon spacer Strand 2v2-Short:
/5AmMC12/GACCTGACCTACAGTGACCA (SEQ ID NO: 23), wherein /5AmMC12/ refers to an amine group (e.g., a primary amino group) linked to the 5' oligonucleotide terminus via a 12-carbon spacer Strand 3v2-Short:
/5Phos/GAGTACGACTGCTGTGTCAGACTG (SEQ ID NO: 36), wherein /5Phos/ refers to a phosphate group linked to the 5' oligonucleotide terminus Strand 4v2-Short:
/5Phos/ACTCTGGTCACTGTAGGTCAGGTC (SEQ ID NO: 37), wherein /5Phos/ refers to a phosphate group linked to the 5' oligonucleotide terminus Strand 5v1:
CAGTCTGACACAGCAGTCGT (SEQ ID NO: 38)

Strand 6v1:
GACCTGACCTACAGTGACCA (SEQ ID NO: 23)

Strand 5v2:
CAGTCTGACTCACCACTCGT (SEQ ID NO: 5)

Strand 6v2:
CACCAGACCTACGAAGTCCA (SEQ ID NO: 25)

Antibody-Oligonucleotide (e.g., Antibody-DNA) Conjugation:

Antibodies directed to a desirable target were conjugated to oligonucleotides as described in prior Examples. One of those skill in the art will appreciate that other known conjugation methods can be used to form antibody-oligonucleotide conjugates.

Cell Culture

HCC-4006 cells were grown in Roswell Park Memorial Institute (RPMI 1640) with 10% exosome-free FBS and 50 units of Penicillin/streptomycin per mL. T84 cells were grown in 1:1 Dulbecco's modified Eagle Medium (DMEM):

Ham's F12 medium with 5% exosome-free fetal bovine serum (FBS) and 50 units of Penicillin/streptomycin per mL. All cell lines were maintained at 5% CO2 and 37° C. and the passage number was below 20.

Purification of Extracellular Vesicles from Cell Culture Medium

In some embodiments, cells were grown in their respective media until they reached ~80% confluence. The cell culture medium was collected and spun at 300×rcf for 5 minutes at room temperature (RT) to removes cells and debris. The supernatant was then collected and frozen at −80° C.

Prior to use, the frozen supernatant stored at −80° C. was thawed and then clarified of cells and large (e.g., greater than 1 micron in diameter) cellular fragments. The thawed supernatant was clarified using centrifugation.

In some embodiments, the clarified cell culture medium (e.g., ~500 uL) was run through a size-exclusion purification column. Nanoparticles having a size range of about 65 nm to about 1000 nm were collected for each sample. In some embodiments, a smaller particle range may be desirable.

Particle Counts:

Particle counts were obtained, e.g., using a SpectroDyne particle counting instrument using the TS400 chips, to measure nanoparticle range between 65 and 1000 nm. In some embodiments, a smaller particle range may be desirable, for example between 65 and 200 nm.

Capture-Antibody Conjugation to Magnetic-Capture Beads:

Antibodies were conjugated to magnetic beads. Briefly, beads were weighed in a sterile environment and resuspended in buffer. Antibodies were mixed with the functionalized beads and the conjugation reaction took place with end-over-end mixing. The beads were washed several times using the wash buffer provided by the conjugation kit and were stored at 4° C. in the provided storage buffer.

Direct Capture of Purified Plasma EVs Using Antibody-Conjugated Magnetic Beads:

For EV capture, a diluted sample of cell line EVs were incubated with magnetic beads conjugated with antibodies directed to an EV target (e.g., Target 1) for an appropriate time period, e.g., at room temperature.

Binding of Antibody-Oligonucleotide Conjugates to EVs Bound on Magnetic Capture Beads:

Antibody-oligonucleotide conjugates ("antibody probes"), directed to an EV target (e.g., Target 2) that is different from the one used in an EV capture assay (e.g., one described above), were diluted in an appropriate buffer at their optimal concentrations. Antibody probes were allowed to interact with a sample comprising EVs bound on magnetic capture beads.

Post-Binding Washes:

In some embodiments, samples were washed, e.g., multiple times, in an appropriate buffer.

Ligation:

After the wash to remove unbound antibody-oligonucleotide conjugates, the beads with bound extracellular vesicles and bound antibody-oligonucleotide conjugates were contacted with a ligation mix. The mixtures were incubated for 20 minutes at RT.

PCR:

Following ligation, the beads with bound extracellular vesicles and bound antibody-oligonucleotide conjugates were contacted with a PCR mix. PCR was performed in a 96-well plate, e.g., on the Quant Studio 3, with the following exemplary PCR protocol: hold at 95° C. for 1 minute, perform 50 cycles of 95° C. for 5 seconds and 62° C. for 15 seconds. The rate of temperature change was chosen to be standard (2° C. per second). A single qPCR reaction was perform for each experimental replicate and ROX was used as the passive reference to normalize the qPCR signals. Data was then downloaded from the Quant Studio 3 machine and analyzed and plotted in Python 3.7.

Representative Results

Figure 25:
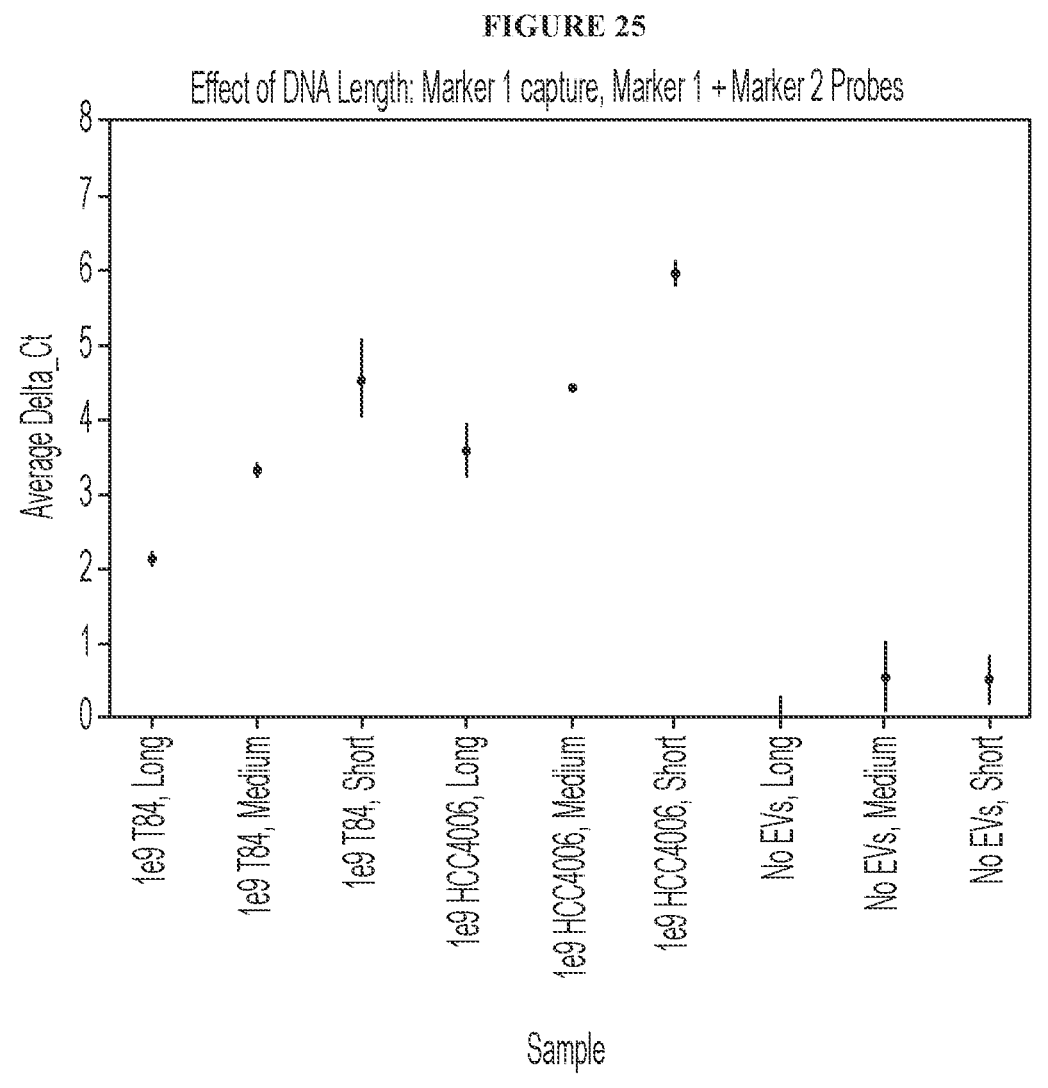

The raw qPCR plot for the oligonucleotide domain length experiment is provided in FIG. 24 and the corresponding delta Ct data are provided in FIG. 25. The data demonstrate that for this biomarker combination, a reduction in oligonucleotide length results in a stronger assay signal. Reducing the DNA length from 69-73 nucleotides to 20-24 nucleotides caused an increase in signal of about 2.5 Ct. Moreover, the shorter DNA length did not significantly increase the assay background signal (No EVs data), causing less than a 1 Ct increase in background.

Discussion

In this experiment, reducing the oligonucleotide length resulted in an increase in assay signal from immunoaffinity-captured EVs. The short oligonucleotide resulted in a signal ~2.5 Ct stronger than the long oligonucleotide with only a small increase in assay background (<1 Ct). However, without wishing to be bound by theory, this observation may not be applicable to certain biomarker combinations. In some embodiments, a shorter DNA length may be more desirable when Target 1 and Target 2 can interact with each other to form homodimers and/or heterodimers, and/or are present in close proximity on the membranes of EVs. In some embodiments, a longer DNA length may be more desirable when Target 1 and Target 2 do not interact with each other and/or are present sparsely on the membranes of EVs. Accordingly, these results demonstrate that oligonucleotide length may be configured to improve the performance of the target entity detection system and/or assay described herein.

Example 8: Use of Inhibitor Probe(s) in Combination with Detection Probes in a Target Entity Detection System The present Example describes synthesis of detection probes for targets (e.g., target biomarker(s)) each comprising a target-binding moiety and an oligonucleotide domain (comprising a double-stranded portion and a single stranded overhang) coupled to the target-binding moiety. The present Example also describes synthesis of inhibitor probes for non-targets (e.g., ones that are not associated with a target entity and/or are not associated with a disease, disorder, or condition). The present Example demonstrates that adding an oligonucleotide domain (e.g., comprising a double-stranded DNA portion) without a primer site can prevent amplification of a ligated template that is generated from a non-target entity. The present Example also demonstrates that conjugating such an oligonucleotide domain (without a primer site) to a target-binding entity directed to a non-target entity (e.g., a cross-reactive target) can reduce background signal from non-target entities, thereby increasing signal-to-noise ratio of target entity detection assays described herein. In some embodiments, the present Example demonstrates that conjugating such an oligonucleotide domain (comprising a double-stranded DNA portion without a primer site, for example, as illustrated in FIG. 26) to a target-binding entity (e.g., an antibody agent) directed to a non-target entity (e.g., a cross-reactive target) can reduce background signal from non-target entities (e.g., extracellular vesicles from a non-target tissue), thereby increasing signal-to-noise ratio of target entity detection assays described herein to detect target entities (e.g., extracellular vesicles from a target tissue). In some such embodiments, use of such inhibitor probes in combination with target-specific detection probes can be useful for detection of cancer-specific extracellular vesicles.

Experiment 1: Assessment of inhibitor probes without target-binding moieties in solution: First, the relative number of ligation templates produced by a 600 pM concentration (or 1200 pM in the case of the 2× inhibitor strands) of the following solutions of DNA were evaluated. It is noted that the numbers below refer to strand numbers corresponding to the numerical values associated with strands shown in FIG. 26. The "i" designates a strand of an inhibitor probe. It is also noted that the oligonucleotide functionalization can be switched from one functional group to another functional group (e.g., from amine to azide to thiol, etc.).

1. (1+3)
2. (2+4)
3. (1i+3i)
4. (2i+4i)
5. (1+3)+(2+4)
6. (1+3)+(2i+4i)—as shown in FIG. 26
7. (1i+3i)+(2+4)
8. (1i+3i)+(2i+4i)
9. (1+3)+(2+4)+(1i+3i)
10. (1+3)+(2+4)+(2i+4i)
11. (1+3)+(2+4)+2X(1i+3i)
12. (1+3)+(2+4)+2X(2i+4i)
13. (1+3)+(2+4)+(1i+3i)+(2i+4i)

Exemplary DNA strand sequences are provided in the Exemplary Methods section below. Double stranded DNA (e.g., (1+3), (2+4), etc.) was prepared by annealing the appropriate single stranded sequences together.

Each double-stranded DNA or combination of double-stranded DNAs were incubated at a 600 pM concentration in 30 μL of T4 ligase solution, following the manufacture's recommended time and temperature of 20 minutes at room temperature. Following ligation, 5 μL of the ligase mix was transferred to 25 μL of PCR mix in duplicates, containing TaqMan Advanced Master Mix (Thermo), primers, EvaGreen, DMSO, and water. The PCR mix was analyzed by a standard qPCR protocol and the relative abundance of amplifiable transcript was measured.

Exemplary Methods

Oligonucleotides

In some embodiments, oligonucleotides can have the following sequence structure and modifications. As noted above, the strand numbers below correspond to the numerical values associated with strands shown in FIG. 26. The oligonucleotide functionalization can be switched from one functional group to another functional group (e.g., from amine to azide to thiol, etc.).

I. Oligonucleotides for Oligonucleotide Domains of Detection Probes

In some embodiments, an exemplary set of oligonucleotides to form oligonucleotide domains of detection probes is provided below.

Strand 1:
/5AmMC12/CAGTCTGACTCACCACTCGT-TAATCGTCGCTGCTACCCTTGACATCCGTG ACTGGCTAGACAGAGGTGT (SEQ ID NO: 1), wherein /5AmMC12/ refers to an amine group (e.g., a primary amino group) linked to the 5' oligonucleotide terminus via a 12-carbon spacer Strand 2:
/5AmMC12/CACCAGACCTACGAAGTCCAT-AGCCTTGCCTGATTAGCCACTGTCCAGTT TGGCTCCTGGTCTCACTAG (SEQ ID NO: 2), wherein /5AmMC12/ refers to an amine group (e.g., a primary amino group) linked to the 5' oligonucleotide terminus via a 12-carbon spacer Strand 3:
/5Phos/GAGTACACCTCTGTCTAGCCAGTCACG-GATGTCAAGGGTAGCAGCGACGATT AACGAGTGGTGAGTCAGACTG (SEQ ID NO: 3), wherein /5Phos/ refers to a phosphate group linked to the 5' oligonucleotide terminus Strand 4:
/5Phos/ACTCCTAGTGAGACCAGGAGC-CAAACTGGACAGTGGCTAATCAGGCAAGGCT ATGGACTTCGTAGGTCTGGTG (SEQ ID NO: 4), wherein /5Phos/ refers to a phosphate group linked to the 5' oligonucleotide terminus Strand 5:
CAGTCTGACTCACCACTCGT (SEQ ID NO: 5)

Strand 6:
CACCAGACCTACGAAGTCCA (SEQ ID NO: 6)

In some embodiments, any exemplary set of oligonucleotides of various lengths as described in Example 7 can be used to form oligonucleotide domains of detection probes.

II. Oligonucleotides for Oligonucleotide Domains of Inhibitor Probes

In some embodiments, inhibitor probes having oligonucleotide domains (without a primer site) of three different lengths (described below) can be synthesized:

Length 1 ("Long"): 69-73 nucleotides (69-nucleotide long double-stranded portion with a single-stranded overhang of 4 nucleotides in length)

Length 2 ("Medium"): 40-44 nucleotides (40-nucleotide long double-stranded portion with a single-stranded overhang of 4 nucleotides in length)

Length 3 ("Short"): 20-24 nucleotides (20-nucleotide long double-stranded portion with a single-stranded overhang of 4 nucleotides in length)

In some embodiments, below provides an exemplary set of oligonucleotides to form an oligonucleotide domain of Length 1 ("Long") for inhibitor probes:

Strand 1i:
/5AmMC12/GCACACACCT-CATCGTCTTGTAATCGTCGCTGCTACCCTTGA-CATCCGTG ACTGGCTAGACAGAGGTGT (SEQ ID NO: 39), wherein /5AmMC12/ refers to an amine group (e.g., a primary amino group) linked to the 5' oligonucleotide terminus via a 12-carbon spacer Strand 2i:
/5AmMC12/CACAATCTCGAC-CACGCAAGTAGCCTTGCCTGATTAGC-CACTGTCCAGTT TGGCTCCTGGTCTCACTAG (SEQ ID NO: 40), wherein /5AmMC12/ refers to an amine group (e.g., a primary amino group) linked to the 5' oligonucleotide terminus via a 12-carbon spacer Strand 3i:
/5Phos/GAGTACACCTCTGTCTAGCCAGTCACG-GATGTCAAGGGTAGCAGCGACGATT ACAA-GACGATGAGGTGTGTGC (SEQ ID NO: 41), wherein /5Phos/ refers to a phosphate group linked to the 5' oligonucleotide terminus Strand 4i:

/5Phos/ACTCCTAGTGAGACCAGGAGC-CAAACTGGACAGTGGCTAATCAGGCAAGGCT ACTTGCGTGGTCGAGATTGTG (SEQ ID NO: 42), wherein /5Phos/ refers to a phosphate group linked to the 5' oligonucleotide terminus In some embodiments, below provides an exemplary set of oligonucleotides to form an oligonucleotide domain of Length 2 ("Medium") for inhibitor probes:

Strand 1i-Medium:

/5AmMC12/GCACACACCT-CATCGTCTTGGACTGGCTAGACAGAGGTGT (SEQ ID NO: 43), wherein /5AmMC12/ refers to an amine group (e.g., a primary amino group) linked to the 5' oligonucleotide terminus via a 12-carbon spacer Strand 2i-Medium:

/5AmMC12/CACAATCTCGAC-CACGCAAGTTGGCTCCTGGTCTCACTAG (SEQ ID NO: 44), wherein /5AmMC12/ refers to an amine group (e.g., a primary amino group) linked to the 5' oligonucleotide terminus via a 12-carbon spacer Strand 3i-Medium:

/5Phos/GAGTACACCTCTGTCTAGCCAGTCCAA-GACGATGAGGTGTGTGC (SEQ ID NO: 45), wherein /5Phos/ refers to a phosphate group linked to the 5' oligonucleotide terminus Strand 4i-Medium:

/5Phos/ACTCCTAGTGAGACCAGGAGC-CAACTTGCGTGGTCGAGATTGTG (SEQ ID NO: 46), wherein /5Phos/ refers to a phosphate group linked to the 5' oligonucleotide terminus In some embodiments, below provides an exemplary set of oligonucleotides to form an oligonucleotide domain of Length 3 ("Short") for inhibitor probes:

Strand 1i-Short:

/5AmMC12/GCACACACCTCATCGTCTTG (SEQ ID NO: 47), wherein /5AmMC12/ refers to an amine group (e.g., a primary amino group) linked to the 5' oligonucleotide terminus via a 12-carbon spacer Strand 2i-Short:

/5AmMC12/CACAATCTCGACCACGCAAG (SEQ ID NO: 48), wherein /5AmMC12/ refers to an amine group (e.g., a primary amino group) linked to the 5' oligonucleotide terminus via a 12-carbon spacer Strand 3i-Short:

/5Phos/GAGTCAAGACGATGAGGTGTGTGC (SEQ ID NO: 49), wherein /5Phos/ refers to a phosphate group linked to the 5' oligonucleotide terminus Strand 4i-Short:

/5Phos/ACTCCTTGCGTGGTCGAGATTGTG (SEQ ID NO: 50), wherein /5Phos/ refers to a phosphate group linked to the 5' oligonucleotide terminus Experiment 2: Assessment of inhibitor probes in cell line EVs: For this experiment, cell line EVs were captured using magnetic beads conjugated to an EV capture agent, e.g., an antibody directed to a surface protein of EVs (Marker 1). Assay signal was generated using a duplex target entity detection system comprising two detection probes each directed to a target, Marker 2 (which can be the same target for both probes, or a different target for each probe), with and without the addition of an inhibitor probe directed to a non-target (Marker 3).

TABLE 7

| The transcript per million (TPM) scores, as expressed in a certain cell line. | | |
|---|---|---|
| Biomarker combination | Genes | Cell Line Expression |
| Marker 1 Capture | Target 1 | ++ |
| Marker 2 + Marker 2 Probes | Target 2 | ++ |
| Marker 3 Inhibitor Probes | Target 3 | +++ |

Antibody-Oligonucleotide (e.g., Antibody-DNA) Conjugation:

Antibodies directed to a desirable target were conjugated to oligonucleotides as described in prior Examples. One of those skill in the art will appreciate that other known conjugation methods can be used to form antibody-oligonucleotide conjugates.

Capture-Antibody Conjugation to Magnetic-Capture Beads:

Antibodies were conjugated to magnetic beads as described in prior Examples.

Direct Capture of Purified Cell Line EVs Using Antibody-Conjugated Magnetic Beads:

For EV capture, a diluted sample of cell line EVs were incubated with magnetic beads conjugated with antibodies directed to an EV target (e.g., Target 1) for an appropriate time period, e.g., at room temperature.

Binding of Antibody-Oligonucleotide Conjugates to EVs Bound on Magnetic Capture Beads:

Antibody-oligonucleotide conjugates ("Marker 2+Marker 2 Probes"; also known as "Antibody probes"), directed to an EV target (e.g., Target 2) that is different from the one used in an EV capture assay (e.g., one described above), were diluted in an appropriate buffer at their optimal concentrations. Antibody probes were allowed to interact with a sample comprising EVs bound on magnetic capture beads. In addition, inhibitor probes were also added to the mixture, allowing to interact with the sample comprising EVs bound on magnetic capture beads.

Post-Binding Washes:

In some embodiments, samples were washed, e.g., multiple times, in an appropriate buffer.

Ligation:

After the wash to remove unbound antibody-oligonucleotide conjugates, the beads with bound extracellular vesicles and bound antibody-oligonucleotide conjugates were contacted with a ligation mix. The mixtures were incubated for 20 minutes at RT.

PCR:

Following ligation, the beads with bound extracellular vesicles and bound antibody-oligonucleotide conjugates were contacted with a PCR mix. PCR was performed in a 96-well plate, e.g., on the Quant Studio 3, with the following exemplary PCR protocol: hold at 95° C. for 1 minute, perform 50 cycles of 95° C. for 5 seconds and 62° C. for 15 seconds. The rate of temperature change was chosen to be standard (2° C. per second). A single qPCR reaction was perform for each experimental replicate and ROX was used as the passive reference to normalize the qPCR signals. Data was then downloaded from the Quant Studio 3 machine and analyzed and plotted in Python 3.7.

Representative Results and Discussion

Figure 28:
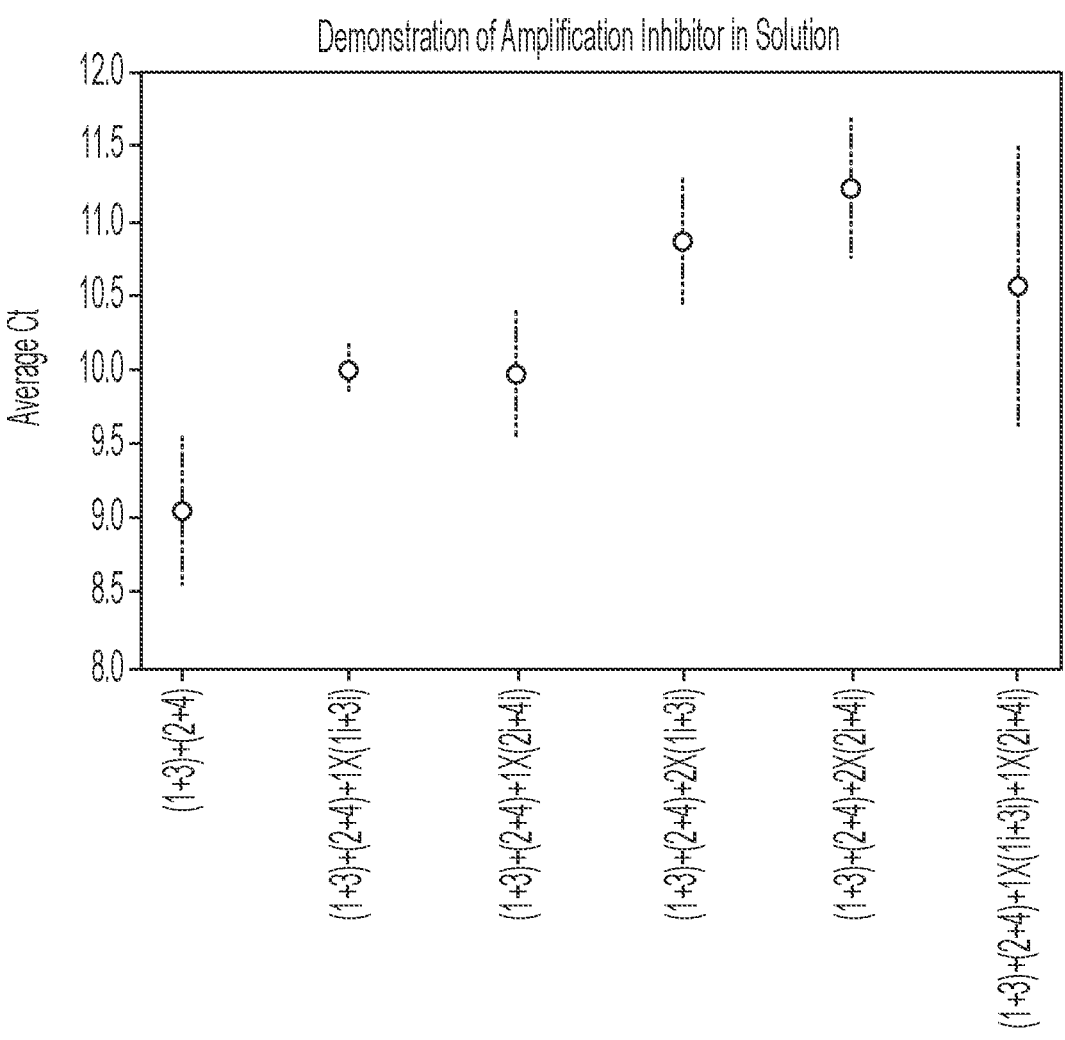
FIG. 28 is a graph showing qPCR detection of a ligated template in solution with and without inhibitor probes as indicated: (1+3)+(2+4) strands; (1+3)+(2+4)+1X(1i+3i) strands; (1+3)+(2+4)+1X(2i+4i) strands; (1+3)+(2+4)+2X (1i+3i) strands; (1+3)+(2+4)+2X(2i+4i) strands; and (1+3)+(2+4)+1X(1i+3i)+1X(2i+4i) strands.

Experiment 1: Assessment of inhibitor probes (without target-binding moieties) in solution: Raw qPCR data are shown in FIG. 27. As shown in FIG. 28, there was a concentration dependent increase in Ct value with each inhibitor probe (without target-binding moieties). Addition of the inhibitor probe at the same concentration (600 pM) resulted in a signal reduction of approximately 1Ct. Further addition of inhibitor probe (without target-binding moieties) reduced the signal by one more Ct. Addition of both inhibitor probes (each without target-binding moieties) at the same time slightly reduces the effect relative to a single inhibitor probe (without target-binding moieties) at a 2× concentration. Without wishing to be bound by theory, this is likely due to ligation taking place between strands of inhibitor probes, which prevents the strands from inhibiting the amplification reaction. These data demonstrate that the oligonucleotide domains of inhibitor probes can successfully prevent amplification upon ligation.

Figure 29:
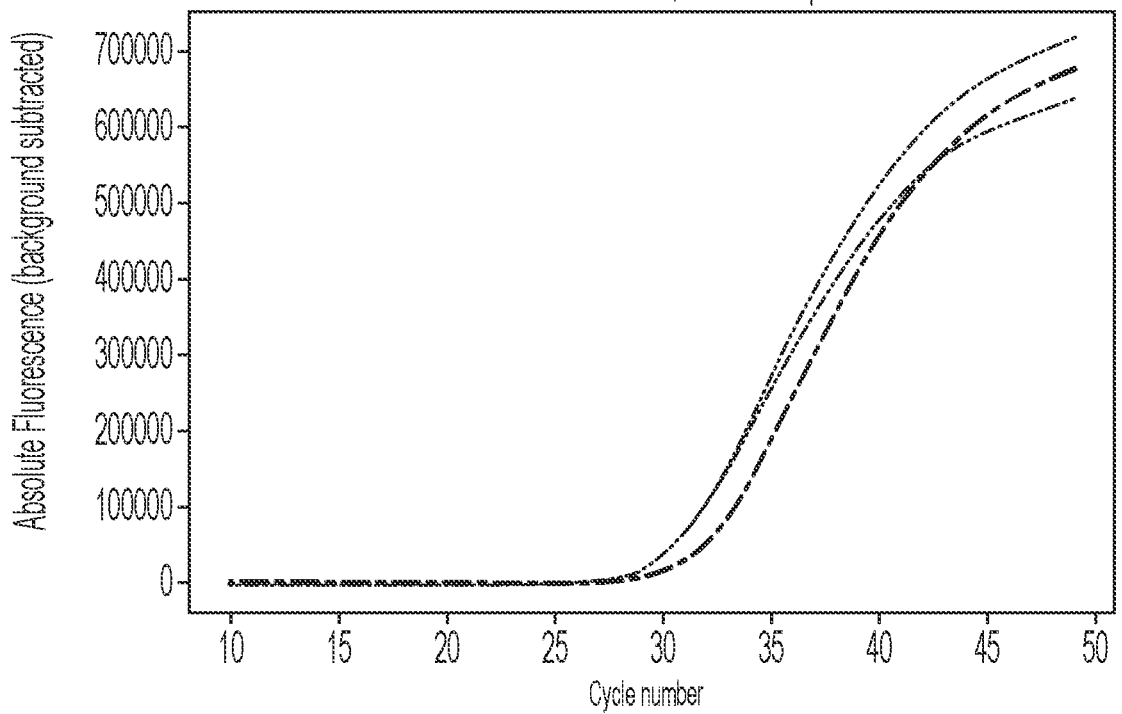
FIG. 29 is a graph showing raw qPCR data generated from assaying cell line EVs using an exemplary duplex detection assay with detection probes in the presence or absence of an inhibitor probe (e.g., as illustrated in FIG. 26).

Experiment 2: Assessment of inhibitor probes in cell line EVs: The cell line data in FIG. 29 demonstrate that the addition of an inhibitor probe comprising a target-binding moiety (e.g., an antibody agent) conjugated to an oligonucleotide domain without a primer site (e.g., comprising a double stranded DNA portion without a primer site) can successfully and selectively attenuate assay signal. Without wishing to be bound by theory, the modest reduction in signal is likely a consequence of the homodimeric nature of Target 2. Given that a large portion of the assay signal may be originating from Target 2 dimers (which by nature are in close proximity), the effect of the inhibitor probe against Target 3 may have a reduced effect. Nevertheless, these data prove that one can selectively reduce and/or eliminate signal from cross-reacting tissues within a target entity detection assay (e.g., as described herein) by deploying inhibitor probes. For example, this is outlined by the example in Table 8 below.

TABLE 8

Use of inhibitor probes to eliminate cross-reacting tissues.

| Tissue | Marker 1 | Marker 2 | Marker 3 | Probe Condition | Assay Signal |
|---|---|---|---|---|---|
| Tissue of interest | Positive | Positive | Negative | Without inhibitor | Positive |
| | | | | With inhibitor probe | Positive |
| Cross-reacting tissue | Positive | Positive | Positive | Without inhibitor probe | Positive |
| | | | | With inhibitor probe | Negative |

REFERENCES CITED

Balaj, L., Lessard, R., Dai, L., Cho, Y. J., Pomeroy, S. L., Breakefield, X. O. and Skog, J., 2011. Tumour microvesicles contain retrotransposon elements and amplified oncogene sequences. *Nature communications*, 2, p. 180.

Bebelman, M. P., Smit, M. J., Pegtel, D. M., and Baglio, S. R., 2018. Biogenesis and function of extracellular vesicles in cancer. *Pharmacology & Therapeutics*, 188, pp. 1-11.

Buys, S. S., Partridge, E., Black, A., Johnson, C. C., Lamerato, L., Isaacs, C., Reding, D. J., Greenlee, R. T., Yokochi, L. A., Kessel, B. and Crawford, E. D., 2011. Effect of screening on ovarian cancer mortality: the Prostate, Lung, Colorectal and Ovarian (PLCO) cancer screening randomized controlled trial. *Jama*, 305(22), pp. 2295-2303.

Darmanis, S., Nong, R. Y., Hammond, M., Gu, J., Alderborn, A., Vänelid, J., Siegbahn, A., Gustafsdottir, S., Ericsson, O., Landegren, U. and Kamali-Moghaddam, M., 2010. Sensitive plasma protein analysis by microparticle-based proximity ligation assays. *Molecular & cellular proteomics*, 9(2), pp. 327-335.

Howlader N, Noone A M, Krapcho M, Miller D, Brest A, Yu M, Ruhl J, Tatalovich Z, Mariotto A, Lewis D R, Chen H S, Feuer E J, Cronin K A (eds). SEER Cancer Statistics Review, 1975-2016, National Cancer Institute. Bethesda, MD, https://seer.cancer.gov/csr/1975_2016/, based on November 2018 SEER data submission, posted to the SEER web site, April 2019.

Im, H., Shao, H., Park, Y. I., Peterson, V. M., Castro, C. M., Weissleder, R. and Lee, H., 2014. Label-free detection and molecular profiling of exosomes with a nano-plasmonic sensor. *Nature biotechnology*, 32(5), p. 490.

Jeong, S., Park, J., Pathania, D., Castro, C. M., Weissleder, R. and Lee, H., 2016. Integrated magneto-electrochemical sensor for exosome analysis. *ACS nano*, 10(2), pp. 1802-1809.

Shao, H., Im, H., Castro, C. M., Breakefield, X., Weissleder, R. and Lee, H., 2018. New technologies for analysis of extracellular vesicles. *Chemical reviews*, 118(4), pp. 1917-1950.

Sun, L., Brentnall, A., Patel, S., Buist, D. S., Bowles, E. J., Evans, D. G. R., Eccles, D., Hopper, J., Li, S., Southey, M. and Duffy, S., 2019. A cost-effectiveness analysis of multigene testing for all patients with breast cancer. *JAMA oncology*.

Torre, L. A., Trabert, B., DeSantis, C. E., Miller, K. D., Samimi, G., Runowicz, C. D., Gaudet, M. M., Jemal, A. and Siegel, R. L., 2018. Ovarian cancer statistics, 2018. *CA: a cancer journal for clinicians*, 68(4), pp. 284-296.

EQUIVALENTS

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

What is claimed is:

1. A method of detecting co-localization of proteins, the method comprising steps of:

capturing an extracellular vesicle (EV) with a capture agent that binds to a first protein on a surface of the EV;

contacting the captured EV with (a) a first probe comprising a first oligonucleotide linked to a first ligand that binds to a second protein on the EV surface, wherein the first oligonucleotide comprises a first double-stranded portion and a first single-stranded overhang, and (b) a second probe comprising a second oligonucleotide linked to a second ligand that binds to a third protein on the EV surface, wherein the second oligonucleotide comprises a second double-stranded portion and a second single-stranded overhang, and the overhangs are complementary to each other and can thereby hybridize when the probes are bound to their respective proteins and in proximity, wherein the second and third proteins are different;

ligating the hybridized first and the second oligonucleotides to form a ligated template; and measuring co-localization of the second and third proteins on the EV surface by detecting levels of the ligated template.

2. The method of claim 1, wherein the first oligonucleotide comprises a first double-stranded portion and a first single-stranded overhang and the second oligonucleotide comprises a second double-stranded portion and a second single-stranded overhang, and wherein the second single-stranded overhang comprises a nucleotide sequence complementary to at least a portion of the first single-stranded overhang and can thereby hybridize to the first single-stranded overhang.

3. The method of claim 2, wherein when the probes are bound to their respective proteins on the extracellular vesicles, the first single-stranded overhang and the second single-stranded overhang hybridize to form a double-stranded complex.

4. The method of claim 3, further comprising contacting the double-stranded complex with a nucleic acid ligase to generate the ligation product.

5. The method of claim 4, wherein the nucleic acid ligase is selected from the group comprising a T4 DNA ligase and a T7 DNA ligase.

6. The method of claim 4, wherein the step of detecting levels of a ligation product further comprises a step of amplifying the ligation product and detecting the presence of the ligation product.

7. The method of claim 6, wherein the step of amplifying is performed by quantitative polymerase chain reaction.

8. The method of claim 1, wherein the extracellular vesicles are immobilized on a solid substrate during the step of capturing.

9. The method of claim 8, wherein the solid substrate is a bead.

10. The method of claim 8, wherein the solid substrate is coated with the capture agent.

* * * * *